(12) United States Patent
Ressemann et al.

(10) Patent No.: US 12,318,201 B2
(45) Date of Patent: Jun. 3, 2025

(54) SYSTEMS AND METHODS FOR USING PORTABLE COMPUTER DEVICES HAVING EYE-TRACKING CAPABILITY

(71) Applicant: EarliTec Diagnostics, Inc., Decatur, GA (US)

(72) Inventors: Thomas Ressemann, Bloomington, MN (US); Sreeni Narayanan, Lincolnshire, IL (US); Ella Swanson-Hysell, Saint Paul, MN (US); Steven Shifke, Atlanta, GA (US)

(73) Assignee: EarliTec Diagnostics, Inc., Plymouth, MN (US)

( * ) Notice: Subject to any disclaimer, the term of this patent is extended or adjusted under 35 U.S.C. 154(b) by 2 days.

(21) Appl. No.: 18/589,822

(22) Filed: Feb. 28, 2024

(65) Prior Publication Data

US 2024/0398302 A1    Dec. 5, 2024

Related U.S. Application Data

(60) Provisional application No. 63/604,647, filed on Nov. 30, 2023, provisional application No. 63/506,211, filed on Jun. 5, 2023.

(51) Int. Cl.

| | |
|---|---|
| *A61B 5/16* | (2006.01) |
| *A61B 3/11* | (2006.01) |
| *A61B 3/113* | (2006.01) |
| *A61B 3/14* | (2006.01) |
| *A61B 3/18* | (2006.01) |

(Continued)

(52) U.S. Cl.
CPC ............. *A61B 5/163* (2017.08); *A61B 3/113* (2013.01); *A61B 3/14* (2013.01); *A61B 5/0022* (2013.01); *A61B 5/168* (2013.01); *A61B 5/6898* (2013.01); *A61B 5/742* (2013.01); *G06T 7/0012* (2013.01); *G06T 7/246* (2017.01); *G06T 7/73* (2017.01);
(Continued)

(58) Field of Classification Search
CPC ......... A61B 5/163; A61B 5/0022; A61B 3/14; A61B 3/0041; A61B 3/0025; A61B 3/18; A61B 3/113; G16H 5/00; G16H 40/67; G16H 50/20; G06T 7/0012; G02B 2027/0178
USPC ......................................................... 600/588
See application file for complete search history.

(56) References Cited

U.S. PATENT DOCUMENTS

| | | |
|---|---|---|
| 6,670,963 B2 | 12/2003 | Osberger |
| 7,556,377 B2 | 7/2009 | Beymer et al. |

(Continued)

OTHER PUBLICATIONS

Frazier et al., "Development and validation of objective and quantitative eye tracking-based measures of autism risk and symptom levels," Journal of the American Academy of Child & Adolescent Psychiatry, Nov. 2018, 57(11):858, 18 pages.

(Continued)

*Primary Examiner* — Boniface N Nganga
(74) *Attorney, Agent, or Firm* — Fish & Richardson P.C.

(57) ABSTRACT

Embodiments described herein include portable devices having user-detection equipment, such as eye-tracker devices or other sensors, and computer systems including such portable devices or the data collected from such devices (such as eye-tracking data and/or other multi-modal data such as facial expressions, verbal expression, and/or physical movements). Some examples of the systems include can provide useful assessments for developmental disorders and can generate prescriptive treatment plans having individual time lengths for different treatment-specific skill areas during a period of time.

20 Claims, 56 Drawing Sheets

(51) Int. Cl.
*A61B 5/00* (2006.01)
*G06T 7/00* (2017.01)
*G06T 7/246* (2017.01)
*G06T 7/73* (2017.01)
*G16H 15/00* (2018.01)
*G16H 40/67* (2018.01)
*G16H 50/20* (2018.01)

(52) U.S. Cl.
CPC ... *G16H 40/67* (2018.01); *G06T 2207/10048* (2013.01); *G06T 2207/30041* (2013.01)

(56) References Cited

U.S. PATENT DOCUMENTS

| | | |
|---|---|---|
| 7,819,818 B2 | 10/2010 | Ghajar |
| 7,922,670 B2 | 4/2011 | Jones et al. |
| 8,229,229 B2 | 7/2012 | Ferguson |
| 8,343,067 B2 | 1/2013 | Jones et al. |
| 8,371,693 B2 | 2/2013 | Ebisawa |
| 8,434,867 B2 | 5/2013 | Helfman et al. |
| 8,551,015 B2 | 10/2013 | Jones et al. |
| 8,668,337 B2 | 3/2014 | Waldorf et al. |
| 8,714,982 B2 | 5/2014 | Wimsatt |
| 8,808,195 B2 | 8/2014 | Tseng et al. |
| 9,050,035 B2 | 6/2015 | Yao et al. |
| 9,239,956 B2 | 1/2016 | Hein |
| 9,265,416 B2 | 2/2016 | Klin et al. |
| 9,314,157 B2 | 4/2016 | Yao et al. |
| 9,463,132 B1 | 10/2016 | Simmons |
| 9,510,752 B2 | 12/2016 | Klin et al. |
| 9,538,947 B2 | 1/2017 | Mori et al. |
| 9,629,543 B2 | 4/2017 | Agichtein et al. |
| 9,854,966 B2 | 1/2018 | Otero-Millan et al. |
| 9,861,307 B2 | 1/2018 | Klin et al. |
| 9,936,916 B2 | 4/2018 | Sahin et al. |
| 9,962,119 B2 | 5/2018 | Macknik et al. |
| 10,010,284 B2 | 7/2018 | Khaligh-Razavi et al. |
| 10,016,130 B2 | 7/2018 | Ganesan et al. |
| 10,016,156 B2 | 7/2018 | Klin et al. |
| 10,022,049 B2 | 7/2018 | Klin et al. |
| 10,052,057 B2 | 8/2018 | Klin et al. |
| 10,117,569 B2 | 11/2018 | Shudo et al. |
| 10,149,643 B2 | 12/2018 | Shudo et al. |
| 10,159,408 B2 | 12/2018 | Shudo |
| 10,165,176 B2 | 12/2018 | Frahm et al. |
| 10,165,940 B2 | 1/2019 | Simmons |
| 10,176,299 B2 | 1/2019 | Torres et al. |
| 10,201,274 B2 | 2/2019 | Samadami et al. |
| 10,226,172 B2 | 3/2019 | Simmons |
| 10,413,176 B2 | 9/2019 | Mori et al. |
| 10,537,276 B2 | 1/2020 | Macknik et al. |
| 10,602,972 B2 | 3/2020 | Super |
| 10,610,165 B2 | 4/2020 | Samadani |
| 10,617,295 B2 | 4/2020 | Klin et al. |
| 10,643,741 B2 | 5/2020 | Gross et al. |
| 10,694,942 B2 | 6/2020 | Agichtein et al. |
| 10,729,321 B2 | 8/2020 | Samadani et al. |
| 10,863,902 B2 | 12/2020 | Samadani et al. |
| 10,885,719 B1 | 1/2021 | Ravindran et al. |
| 10,936,059 B2 | 3/2021 | Stoner |
| 10,966,605 B2 | 4/2021 | Komogortsev |
| 10,966,669 B2 | 4/2021 | Samadani |
| 11,141,095 B2 | 10/2021 | Samadani et al. |
| 11,158,403 B1 | 10/2021 | Sapiro et al. |
| 11,207,011 B2 | 12/2021 | Gross et al. |
| 11,393,564 B2 | 7/2022 | Gross et al. |
| 11,666,259 B1 | 6/2023 | Narayan et al. |
| 11,903,711 B2 | 2/2024 | Narayanan et al. |
| 2007/0136102 A1 | 6/2007 | Rodgers |
| 2008/0147488 A1 | 6/2008 | Tunick |
| 2010/0056875 A1 | 3/2010 | Schoenberg et al. |
| 2011/0242486 A1 | 10/2011 | Ebisawa |
| 2012/0178064 A1 | 7/2012 | Katz |
| 2014/0253876 A1 | 9/2014 | Klin et al. |
| 2014/0287398 A1 | 9/2014 | Singh |
| 2014/0323901 A1 | 10/2014 | Kim |
| 2015/0157235 A1 | 6/2015 | Jelen et al. |
| 2015/0223731 A1 | 8/2015 | Sahin |
| 2015/0282705 A1 | 10/2015 | Aivtal |
| 2016/0195924 A1 | 7/2016 | Weber et al. |
| 2016/0262613 A1 | 9/2016 | Klin et al. |
| 2017/0049362 A1 | 2/2017 | Macknik et al. |
| 2017/0055825 A1 | 3/2017 | Tumlinson |
| 2018/0008141 A1 | 1/2018 | Krueger |
| 2018/0063220 A1 | 3/2018 | Dhanabalan et al. |
| 2018/0357552 A1 | 12/2018 | Campos et al. |
| 2019/0029585 A1 | 1/2019 | Geva |
| 2019/0043618 A1 | 2/2019 | Vaughn et al. |
| 2019/0239790 A1 | 8/2019 | Gross |
| 2019/0324532 A1 | 10/2019 | Aleem et al. |
| 2020/0107767 A1 | 4/2020 | Anson |
| 2020/0146611 A1 | 5/2020 | Macknik et al. |
| 2020/0352499 A1 | 11/2020 | Frazier |
| 2021/0000340 A1 | 1/2021 | Klin et al. |
| 2021/0015416 A1 | 1/2021 | Wang |
| 2021/0200310 A1 | 7/2021 | Eash et al. |
| 2021/0259602 A1 | 8/2021 | Kissine |
| 2021/0259603 A1 | 8/2021 | Kissine |
| 2021/0321955 A1 | 10/2021 | Samadani |
| 2022/0061724 A1 | 3/2022 | Gross et al. |
| 2023/0397863 A1 | 12/2023 | Narayan et al. |
| 2023/0397864 A1 | 12/2023 | Narayan et al. |
| 2023/0397865 A1 | 12/2023 | Narayan et al. |

OTHER PUBLICATIONS

PCT International Search Report and Written Opinion in International Appln. No. PCT/US2023/024967, mailed on Sep. 28, 2023, 15 pages.

PCT International Search Report and Written Opinion in International Appln. No. PCT/US2024/017707, mailed on Jul. 25, 2024, 14 pages.

Rusch, "Combining fMRI and Eye-tracking for the Study of Social Cognition," Neuroscience Insights, Dec. 16, 2021, vol. 16, 4 pages.

Movie Playlist Data

| timestamp_system_us | media_name |
|---|---|
| 36140926 8522 | CenterStim |
| 36141198 5722 | 0075PEER |
| 36143143 9717 | CenterStim |
| 36143421 6413 | 0076PEER |
| 36146152 4245 | CenterStim |
| 36146428 8903 | CCTL |
| 36146619 9665 | CCTR |
| 36146800 9587 | CCBL |
| 36146981 7708 | CCCC |
| 36147163 2348 | CCBR |
| 36147343 4754 | CenterStim |
| 36147630 7507 | 0079PEER |

(a)

Eye-Tracking Data

| timestamp_tobii_us | timestamp_system_us | EyeTrack DataX1 | ... | EyeTrack Data Xn |
|---|---|---|---|---|
| 8989455873 | 36126609 8581 | −38.446266 | ... | 10.881472 |
| 8989485796 | 36126612 8504 | −38.430622 | ... | 10.7505 |
| 8989515576 | 36126615 8284 | −38.456818 | ... | 10.9184475 |
| ... | | | | |

Evaluation for Autism Spectrum Disorder (ASD)

1322 → Detailed Individual Test Results

An individual's looking behavior metrics quantify how much of their looking behavior aligned with age expected looking behavior during moments that have been identified by expert clinicians as being relevant to a special skill area...

1324 →

| Relevant Skill Area | Example Video Scene | Typical Looking Behavior (Group) | | Ben's Looking Behavior |
|---|---|---|---|---|
| Manding | | | | Ben attended to 29% of moments relevant to manding. |
| Listener responding | | | | Ben attended to 37% of moments relevant to listener responding. |
| Joint Attention | | | | Ben attended to 32% of moments relevant to joint attention. |

Receive, at a network-connected server, a request for an assessment result of a patient based on session data of the patient, the session data being collected during presentation of a data collection playlist of visual stimuli to the patient in a session, at least one visual scene of the data collection playlist being annotated with at least one of a plurality of skill areas associated with visual scenes of the data collection playlist

1404

Output, by the network-collected server, the assessment result of the patient, the assessment result comprising, for each of one or more specific skill areas of the plurality of skill areas, behavior data of the patient with respect to moments relevant to the specific skill area in the session, each of the moments corresponding to a respective visual scene of the visual scenes of the data collection playlist

EarliPoint
Evaluation for Autism Spectrum Disorder (ASD) — 1601

1602
PATIENT INFORMATION
| | |
|---|---|
| Patient Name: | NAME |
| Date of Birth: | MM/DD/YYYY |
| Patient Age at Evaluation: | 2 years 0 months |

1604
SESSION INFORMATION
| | |
|---|---|
| Testing Organization: | NAME |
| Prescribing Clinician: | NAME |
| Session Date: | MM/DD/YYYY |
| Results Prepared: | MM/DD/YYYY / 14:31:36 |
| Device Operator: | NAME |
| Device Name: | NAME |

1606
Narrative Results Summary

Ben is a 24-month-old child referred for an EarliPoint Evaluation for Autism Spectrum Disorder. Ben's evaluation took place on XX/XX/XX at CHOA where his results are consistent with a diagnosis of ASD.

Assessment Results:
1. Results are consistent with a diagnosis of Autism Spectrum Disorder. — 1607
2. A Social Disability Index score of -7.2 indicates a high concern for social disability.
3. A Verbal Ability Index score of 23 indicates less advanced verbal ability than typical age-matched peers.
4. A Nonverbal Learning Index score of 78 indicates more advanced nonverbal learning skills than typical age-matched peers.

1608

Clinician Comments

Clinician Signature

EarliPoint
Evaluation for Autism Spectrum Disorder (ASD)

1612

| Diagnostic Assessment Results | Criteria Met for ASD |
|---|---|
| | Ben's looking behaviors are consistent with a diagnosis of ASD |

1614

EarliPoint Severity Measures

1614a — Social Disability Index

Ben's score of -7.2 indicates a high concern for social disability.

1614b — Verbal Ability Index

Ben's score of 23 indicates less advanced verbal ability than typical age-matched peers.

1614c — Nonverbal Learning Index

Ben's score of 78 indicates more advanced nonverbal learning skills than typical age-matched peers.

1616

Correlation with ADOS-2 Measures (see page 3)
- Ben's EarliPoint Social Disability Index score of -7.2 correlates to a moderate-to-severe level of concern on the ADOS-2.

1618

Correlation with Mullen Scales of Early Learning Measures (see pages 4-5)
- Ben's EarliPoint Verbal Ability Index score of 23 correlates to a Mullen verbal age equivalent of approximately 6 months, which is less than his chronological age of 24 months.
- Ben's EarliPoint Nonverbal Learning Index score of 78 correlates to a Mullen nonverbal age equivalent of approximately 29 months, which is greater than his chronological age of 24 months.

EarliPoint
Evaluation for Autism Spectrum Disorder (ASD)

Detailed Individual Test Results  1622

EarliPoint Social Disability Index

The EarliPoint test is clinically validated as a tool to aid clinicians in the diagnosis and assessment of young children with ASD and to measure an individual child's strengths and vulnerabilities on three indices. The first index, the EarliPoint Social Disability Index, quantifies how a child looks at social information in the environment.

The EarliPoint Social Disability Index proxies the Autism Diagnostic Observation Schedule, 2nd Edition (ADOS-2)[1]. The figures below show how the EarliPoint Social Disability Index correlates to the ADOS-2 Total Score. The ADOS-2 categorizes scores in terms of level of concern, from 'moderate-to-severe', to 'mild-to-moderate', or 'little-to-no'[2,3]. While higher scores on the ADOS-2 indicate more concern about social disability, lower and more negative EarliPoint Social Disability scores indicate more concern about social disability.

1623

> Ben scored -7.2 on the Social Disability Index, indicating a high concern for social disability.
>
> This score correlates to a moderate-to-severe level of concern on the ADOS-2.

1624

EarliPoint Social Disability Index Correlation to ADOS-2 Total Score

1628a — Age 16-20 months OR nonverbal
1628b — Age 21+ months with 5+ words 1626   1625   1628

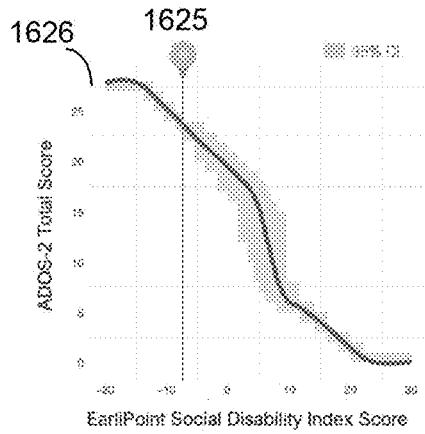
EarliPoint Social Disability Index Score

Ben's Social Disability Index Score of -7.2 corresponds to an ADOS-2 Total Score of 24 (95% confidence interval of 23 - 25).

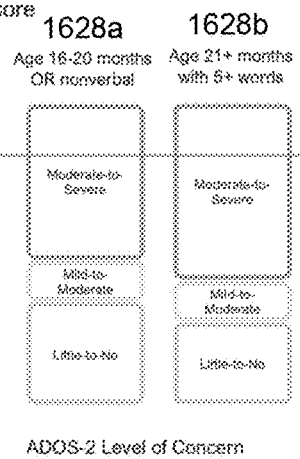
ADOS-2 Level of Concern

The ADOS-2 concern ranges are dependent on the child's age and whether the child is nonverbal (has less than five words) or has some words (five or more)[4].

EarliPoint
Evaluation for Autism Spectrum Disorder (ASD)

Detailed Individual Test Results *(continued)*   1632

EarliPoint Verbal Ability Index

A young child's language skills are acquired through interaction: through paying attention to what other people are doing, saying, and feeling.

The EarliPoint Verbal Ability Index is clinically validated as a tool to measure a child's strengths and vulnerabilities in verbal abilities, quantifying how a child looks at communicative cues and language-related information in the environment and proxying verbal age equivalent scores on the *Mullen Scales of Early Learning*[1]. The figure below shows how the EarliPoint Verbal Ability Index correlates to the Mullen Verbal Age Equivalent. Higher scores indicate more advanced verbal abilities.

1633 ➤ Ben scored 23 on the Verbal Ability Index, indicating less advanced verbal ability than typical age-matched peers.

This score correlates to a Mullen verbal age equivalent of approximately 6 months. This is less than his chronological age of 24 months, indicating less advanced verbal ability than typical age-matched peers.

1634
EarliPoint Verbal Ability Index Correlation to Mullen Verbal Age Equivalent 1636   1638

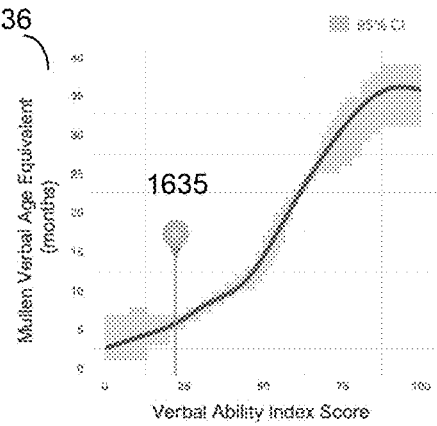
1635
Verbal Ability Index Score

Ben's Verbal Ability Index Score of 23 corresponds to a Mullen Verbal Age Equivalent of 6 months (95% confidence interval of 5 – 7 months).

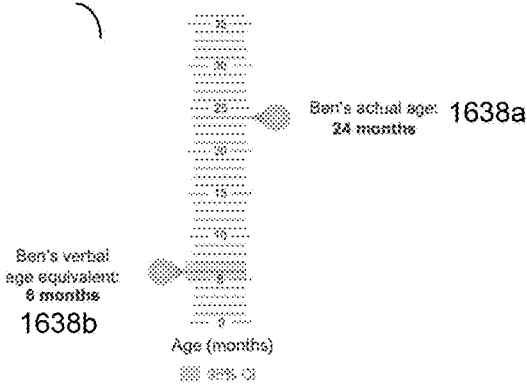
Ben's actual age: 24 months  1638a
Ben's verbal age equivalent: 6 months  1638b
Age (months)

Ben's verbal age equivalent is less than his actual age, indicating less advanced verbal ability than typical age-matched peers.

EarliPoint
Evaluation for Autism Spectrum Disorder (ASD)

Detailed Individual Test Results *(continued)*  1642

EarliPoint Nonverbal Learning Index

When a young child pays attention to the way in which events and actions happen over time, they acquire problem-solving skills, and their looking behavior reflects these skills.

The EarliPoint Nonverbal Learning Index is clinically validated as a tool to measure a child's strengths and vulnerabilities in early learning and cognitive skills, quantifying how a child looks at cause-and-effect sequences over time. The EarliPoint Nonverbal Learning index proxies nonverbal age equivalent scores on the *Mullen Scales of Early Learning*[1]. The figure below shows how the EarliPoint Nonverbal Learning Index correlates to the Mullen Nonverbal Age Equivalent. Higher scores indicate more advanced nonverbal learning skills.

1643 ➤ Ben scored 78 on the Nonverbal Learning Index, indicating more advanced nonverbal learning skills than typical age-matched peers.

This score correlates to a Mullen nonverbal age equivalent of approximately 29 months. This is greater than his chronological age of 24 months, indicating more advanced nonverbal learning skills than typical age-matched peers.

1644

EarliPoint Nonverbal Learning Index Correlation to Mullen Nonverbal Age Equivalent

1646

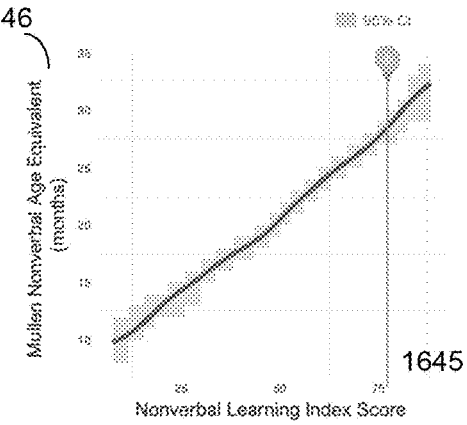

Nonverbal Learning Index Score  1645

Ben's Nonverbal Learning Index Score of 78 corresponds to a Mullen Nonverbal Age Equivalent of 29 months (95% confidence interval of 27 – 30 months).

1648

Ben's nonverbal age equivalent: 29 months
1648b

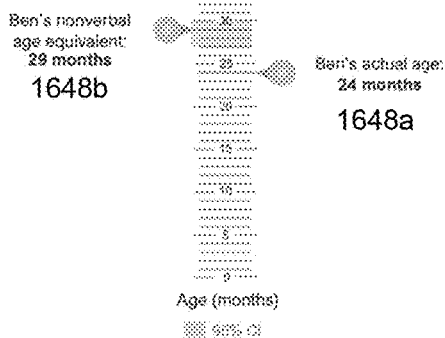

Ben's actual age: 24 months
1648a

Age (months)

Ben's nonverbal age equivalent is greater than his actual age, indicating more advanced nonverbal learning skills than typical age-matched peers.

EarliPoint
Evaluation for Autism Spectrum Disorder (ASD)

1652

Visualizing Individual Test Results

When watching video scenes of social interaction, typically developing children spend the majority of their time focusing on the same scene content at the same moments in time. This behavior — when different individual children look at the same content at the same time, responding in the same way to salient social information – is known as entrainment: children's looking behavior is entrained to salient social information. The EarliPoint test compares an individual child's looking behavior to clinically validated reference standards at each moment (Fig. 1).

1654

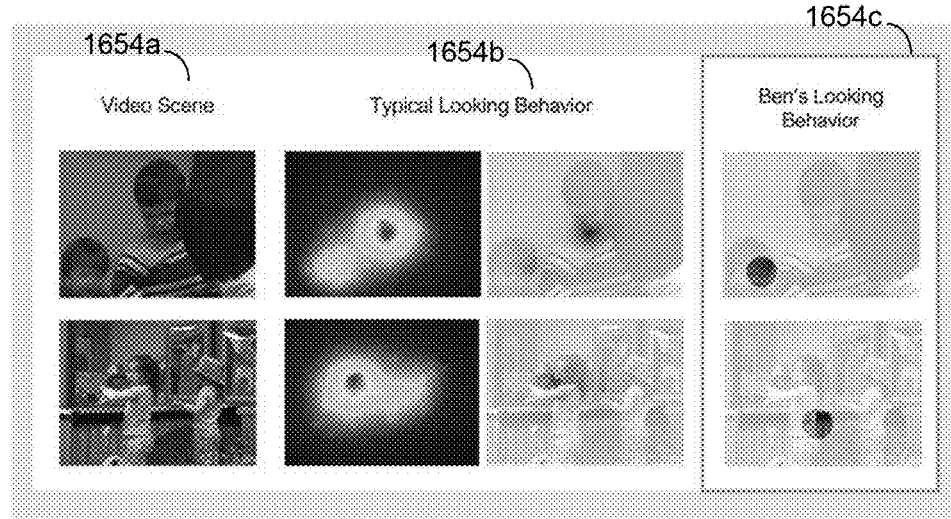

1654a Video Scene  1654b Typical Looking Behavior  1654c Ben's Looking Behavior

1656 *Fig. 1 Comparison of reference standard looking behavior with patient data. Images show a still image of the social scene content (left), the age-expected reference standard typical looking behavior (middle panels), and this patient's data (right).*

1657

The EarliPoint Attentional Funnel

Compiling moment-by-moment looking behavior over many social scenes (Fig. 2) shows the focus of typically developing children largely converging on the same content at the same moments in time. Represented by the narrow, red area on the salience map, these points of convergence create Attentional Funnels (Fig. 3). During the test, a child's attention, whether inside or outside of the funnel (Fig. 4), is analyzed to determine the presence or absence of ASD together with individual measures of social disability, verbal ability, and nonverbal learning.

1658

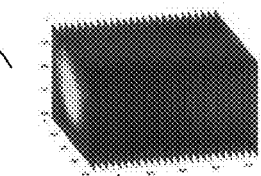 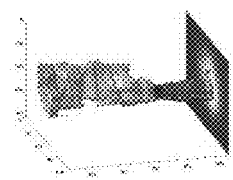 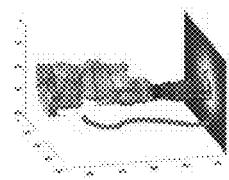

*Fig. 2 Moment-by-Moment Eye-Gaze Measurement*   *Fig. 3 Attentional Funnel for Typically Developing Children*   *Fig. 4 Deviation from Attentional Funnel*

Receive, at a network-connected server, a request for an evaluation result of a patient based on session data of the patient, the session data being collected during presentation of a data collection playlist of visual stimuli to the patient in a session for evaluating a development disorder of the patient

1754

Output, by the network-connected server, the evaluation result of the patient, the evaluation result including: i) respective scores of developmental disorder indexes associated with the development disorder for the patient, and ii) for each of the developmental disorder indexes, a result of a correlation between the respective score of the developmental disorder index and a corresponding reference assessment measure

FIG. 17B

SYSTEMS AND METHODS FOR USING PORTABLE COMPUTER DEVICES HAVING EYE-TRACKING CAPABILITY

CROSS-REFERENCE TO RELATED PATENT APPLICATIONS

This application claims the benefit of U.S. Provisional Application No. 63/506,211, filed Jun. 5, 2023, and the U.S. Provisional Application No. 63/604,647, filed Nov. 30, 2023, the contents of which are incorporated by reference herein.

TECHNICAL FIELD

This disclosure relates generally to portable devices having user-detection equipment such as an eye-tracking sensor, and interconnected devices for using eye-tracking data and/or other multi-modal data such as facial expressions, verbal expression, and/or physical movements.

BACKGROUND

Computer systems have been used to gather eye-tracking data from users, such as young patients in a clinical setting, for purposes of gathering objective data of user responses to stimuli. In some cases, the objective data can be indicative of developmental disorders such as an autism spectrum disorder (ASD). Various attempts by treatment providers (e.g., pediatricians or other medical professionals) to assess the severity of ASD in patients can diverge considerably in terms of objective assessment tools and experience of the particular treatment provider. In some circumstances, the use of traditional "best practice" tools by a treatment provider achieves rather poor sensitivity and specificity to the conditions, especially for toddlers or other young patients. Furthermore, treatment providers can often lack adequate tools for objectively measuring progress in these conditions over time, especially very early in a patient's life.

SUMMARY

The present disclosure describes portable devices having user-detection equipment, such as eye-tracker devices or other sensors, and computer systems including such portable devices or the data collected from such devices (such as eye-tracking data and/or other multi-modal data such as facial expressions, verbal expression, and/or physical movements).

For example, some systems described herein may optionally be implemented with improved portable devices that achieve improved objective measurements and added convenience to both a treatment provider and a patient, such as a toddler or other young patient. In some embodiments, the system includes at least two separate portable computing devices, e.g., an operator-side portable device and at least one patient-side portable device that is integrated with an eye-tracking device (or an eye-tracker device or an eye-tracker). In particular examples described below, these portable devices can be differently equipped yet both wirelessly interact with a network-connected server platform to advantageously gather session data in a manner that is comfortable and less intrusive for the patient while also adding improved flexibility of control for the treatment provider. Optionally, the session data gathered via the patient-side portable device (e.g., using analysis of eye-tracking data generated in response to display of predetermined, age-appropriate visual stimuli) can be promptly analyzed for purposes of outputting at the operator-side portable device a result interface displaying at least one index based on objective factors. In some versions described herein, the system can be used to provide objective and comparative assessments indicative of developmental, cognitive, social, or mental abilities or disabilities, including Autism Spectrum Disorder (ASD).

Some examples described herein can implement specific skill areas (and/or skills) monitoring for developmental assessment, including but not limited to, annotating visual stimuli (e.g., movies or videos) for moment-by-moment skill relevance, customizing data collection playlist (e.g., according to targeted skill areas selected by users), implementing annotated skill visualization and analytics sections in a diagnostic/monitoring report, customizing a monitoring report with targeted skill areas that can be automatically selected or selected by users when starting a session or viewing a diagnostic result), providing an interactive dashboard for users (e.g., treatment providers or clinicians or patient's guardians such as parents) to explore any skill areas and visualization of behaviors of a patient and a reference group, and/or capturing multi-modal data (e.g., audios/videos of social interaction showing facial expressions, verbal expressions, and/or physical movements) during a data collection session, where the multi-modal data can be used in conjunction with eye-tracking data for developmental assessment.

One aspect of the present disclosure features a system using at least one portable computing device with eye-tracking capability. The system includes: a portable eye-tracker console including a display screen and an eye-tracker device mounted adjacent to the display screen such that both the display screen and the eye-tracker device are oriented toward a patient, where the eye-tracker device is configured to collect eye-tracking coordinate data of the patient while a predetermined sequence of stimulus videos is presented on the display screen during a session; a portable computing device having a touchscreen display interface and being spaced apart from, and portable to different locations relative to, the portable eye-tracker console; and a network-connected server that wirelessly receives session data of the session from the portable eye-tracker console and includes a web portal that exports an evaluation result including a graphic correlation of a numeric disability index score correlated to a reference assessment measure. The network-connected server is configured to wirelessly connect with both the portable eye-tracker console and the portable computing device such that, subsequent to the portable computing device wirelessly communicating with the portable eye-tracker console via the network-connected server to control activation of the session present the predetermined sequence of stimulus videos on the display screen of the portable eye-tracker console, the portable eye-tracker console wirelessly communicates to the network-connected server the session data including the eye-tracking coordinate data in timestamp relationship with information of the predetermined sequence of stimulus videos displayed by the portable eye-tracker console during the session.

In some implementations, the system includes multiple portable eye-tracker consoles that contemporaneously wirelessly communicate with the network-connected server.

In some implementations, the eye-tracker device includes one or more eye-tracking sensors mechanically assembled adjacent to a periphery of the display screen.

In some implementations, each of the one or more eye-tracking sensors includes: an illumination source configured to emit detection light, and a camera configured to capture eye movement data including at least one of pupil or corneal reflection or reflex of the detection light from the illumination source. The eye-tracking sensor is configured to convert the eye movement data into a data stream that contains information of at least one of pupil position, a gaze vector for each eye, or gaze point, and the eye-tracking data of the patient includes a corresponding data stream of the patient.

In some implementations, the detection light includes an infrared light, and the camera includes an infrared-sensitive camera. While the predetermined sequence of stimulus videos is presented on the display screen oriented to the patient during the session, a caregiver that carries the patient wears a pair of eyeglasses having a filter configured to filter the infrared light, such that the camera captures only eye movement data of the patient.

In some implementations, the eye-tracker device includes at least one image acquisition device configured to capture images of at least one eye of the patient, while the predetermined sequence of stimulus videos is presented on the display screen oriented to the patient during the session, and the eye-tracker device is configured to generate corresponding eye-tracking data of the patient based on the captured images of the at least one eye of the patient.

In some implementations, the system further includes at least one recording device assembled on the portable eye-tracker console and configured to collect at least one of image data, audio data, or video data associated with the patient while the predetermined sequence of stimulus videos is presented on the display screen oriented to the patient during the session, and the session data includes the at least one of image data, audio data, or video data.

In some implementations, the portable eye-tracker console includes: a housing configured to hold the display screen and the eye-tracker device and a base coupled to the housing through one or more joints. The base is rotatable around the one or more joints to adjust a relative position or angle between the display screen and the patient during the session.

In some implementations, the network-connected server provides the web portal accessible by the portable computing device, and the network-connected server is configured to output a developmental analysis report including the developmental analysis data of the patient on a user interface of the web portal to the portable computing device.

In some implementations, the network-connected server is configured to: receive treatment data associated with the patient, the treatment data including at least one of previous developmental analysis data of the patient, previous treatment plans for the patient, or reference treatment data of other patients; and generate a prescriptive treatment plan for the patient based on the treatment data associated with the patient and developmental analysis data of the patient using artificial intelligence.

Another aspect of the present disclosure features a computer-implemented method, including: obtaining, at a network-connected server, a treatment plan of developmental disorder for a patient, the treatment plan having individual time lengths for different treatment-specific skill areas during a period of time, the treatment plan having a specific treatment plan format, where the network-connected server is configured to process data associated with a default treatment plan format; and parsing, at the network-connected server, the treatment plan with the specific treatment plan format to determine treatment data for the patient, the treatment data being consistent with the default treatment plan format.

In some implementations, the computer-implemented method further includes: receiving, at the network-connected server, an input for selecting a treatment plan format from a plurality of treatment plan formats presented on a user interface, where the plurality of treatment plan formats are different from each other.

In some implementations, the plurality of treatment plan formats are different from each other in at least one of skill area names, prompting approaches, treatment or training materials, reinforcement approaches, or data collection approaches.

In some implementations, parsing the treatment plan with the specific treatment plan format includes: parsing the treatment plan with the specific treatment plan format based on the selected treatment plan format and the default treatment plan format.

In some implementations, the plurality of treatment plan formats include two or more of EarliPoint, the Early Start Denver Model (ESDM), Early Social Interaction (ESI), Discrete Trial Training (DTT), Joint Attention Symbolic Play Engagement Regulation (JASPER), and Project of Improving Parents As Communication Teachers (Project ImPACT).

In some implementations, obtaining the treatment plan of developmental disorder for the patient includes: uploading the treatment plan with the specific treatment plan format from a repository at the network-connected server or a storage medium.

In some implementations, the treatment data includes at least one of: respective time lengths of the different treatment-specific skill areas during the period of time, respective percentages of time lengths of the different treatment-specific skill areas during the period of time, respective attendance percentages of the different treatment-specific skill areas over a series of sessions, respective attendance percentage changes of the different treatment-specific skill areas between at least two most recent sessions, or relationships between the respective percentages of time lengths and the respective attendance percentage changes of the different treatment-specific skill areas.

In some implementations, the computer-implemented method further includes: receiving, at the network-connected server, an input for selecting a treatment plan format from a plurality of treatment plan formats presented on a user interface, where the plurality of treatment plan formats are different from each other; and generating, at the network-connected server, a new treatment plan based on the treatment data for the patient and the selected treatment plan format.

In some implementations, the computer-implemented method further includes: transmitting, by the network-connected server, the new treatment plan with the selected treatment plan format to a computing device or an external server.

In some implementations, the computer-implemented method further includes: generating, at the network-connected server, evaluation data of developmental disorder for the patient based on eye-tracking session data of the patient. Generating the new treatment plan is based on the evaluation data of developmental disorder for the patient.

In some implementations, the computer-implemented method further includes: determining, at the network-connected server, a particular treatment plan format for the new treatment plan for the patient among the plurality of treatment plan formats; and presenting a visual indication on the particular treatment plan format among the plurality of treatment plan formats in the user interface, the visual indication indicating a recommendation of the particular treatment plan format for the new treatment plan for the patient.

In some implementations, the computer-implemented method further includes: receiving, at the network-connected server, a selection of a targeted session from a list of sessions on a user interface of a web portal on the network-connected server; in response to receiving the selection of the targeted session, popping up a window for selecting targeted skill areas from a plurality of skill areas listed in the window; automatically selecting one or more targeted skill areas from the plurality of skill areas based on the treatment data, where the different treatment-specific skill areas include the one or more targeted skill areas; and running the targeted session based on the selected one or more targeted skill areas.

In some implementations, the computer-implemented method further includes: presenting, at the network-connected server, input fields of the treatment plan on a user interface of a web portal on the network-connected server; receiving, at the network-connected server, an input for one of the input fields of the treatment plan on the user interface; and updating, at the network-connected server, the treatment plan based on the input for the one of the input fields.

In some implementations, the different treatment-specific skill areas include one or more of manding, listener responding, turn-taking, joint attention, tact, and play.

In some implementations, the computer-implemented method further includes: receiving, at the network-connected server, an input for selecting a third party system from a plurality of third party systems presented on a user interface; and retrieving, by the network-connected server, data relevant to the patient from the selected third party system after establishing a connection between the network-connected server and the selected third party system, where the data relevant to the patient includes at least one of previous clinical data of the patient, previous treatment data of the patient, or reference data of other patients.

In some implementations, the computer-implemented method further includes: generating, at the network-connected server, a new treatment plan for the patient based on the treatment data and the data relevant to the patient.

Another aspect of the present disclosure features a computer-implemented method, including: receiving, at a network-connected server, a request for an evaluation result of a patient based on session data of the patient, the session data being collected during presentation of a data collection playlist of visual stimuli to the patient in a session for evaluating a development disorder of the patient; and outputting, by the network-connected server, the evaluation result of the patient. The evaluation result includes: respective scores of developmental disorder indexes associated with the development disorder for the patient, and for each of the developmental disorder indexes, a result of a correlation between the respective score of the developmental disorder index and a corresponding reference assessment measure.

In some implementations, the result of the correlation includes at least one of: a summary describing the correlation, or a graphical presentation of the correlation.

In some implementations, the evaluation result further includes at least one of: an assessment result indicating whether the patient has the developmental disorder, or indication information of each of the respective scores of the developmental disorder indexes.

In some implementations, the developmental disorder indexes include at least one of social disability index, verbal ability index, or nonverbal learning index.

In some implementations, the corresponding reference assessment measure for the respective score of the social disability index includes ADOS-2 measure, the corresponding reference assessment measure for the respective score of the verbal ability index includes Mullen Verbal Age Equivalent, and the corresponding reference assessment measure for the respective score of the nonverbal learning index includes Mullen Nonverbal Age Equivalent.

In some implementations, at least one visual scene of the data collection playlist is annotated with at least one of a plurality of skill areas associated with visual scenes of the data collection playlist. The evaluation result includes, for each of one or more specific skill areas of the plurality of skill areas, behavior data of the patient with respect to moments relevant to the specific skill area in the session, each of the moments corresponding to a respective visual scene of the visual scenes of the data collection playlist.

In some implementations, the behavior data includes an attendance percentage defined as a ratio between a number of moments which the patient attends to relevant scene contents in the visual stimuli and a total number of moments which the patient is watching the visual stimuli.

In some implementations, the evaluation result includes a contour of a distribution map of behavior data of a reference group, the behavior data of the reference group being based on reference session data collected during presentation of the data collection playlist of visual stimuli to each person of the reference group. The evaluation result can also include, for each of the one or more specific skill areas, a representative visual scene, the representative visual scene highlighting one or more attendance areas in a predetermined region for the reference group, or the representative visual scene highlighting the attendance area of the patient in the session.

In some implementations, the evaluation result includes at least one of: a first graphical presentation of moment-by-moment measurement of the patient's looking behavior during the session, or a second graphical presentation of attentional funnel of a reference group and the patient's attention during the session.

Another aspect of the present disclosure features a computer-implemented method, including: initiating a session for a patient by establishing a communication with an operator-side computing device and a patient-side portable tablet computing device, the patient-side portable tablet computing device being integrated with an eye-tracker device; sequentially presenting visual scenes of a data collection playlist of visual stimuli on a screen of the patient-side portable tablet computing device to the patient while collecting eye-tracking data of the patient using the eye-tracker device; and transmitting session data of the session to a network-connected server the session data including the eye-tracking data of the patient collected in the session. Collecting the eye-tracking data of the patient using the eye-tracker device includes: capturing at least one of images of eyes of the patient or positions of the eyes of the patient, where the eye-tracking data is determined based on the captured at least one of the images of the eyes or the positions of the eyes of the patient.

In some implementations, the eye-tracker device is configured to: determine eye-movement data based on the captured at least one of the images of the eyes or the positions of the eyes of the patient, and convert the eye-movement data of the patient into the eye-tracking data that includes information associated with at least one of pupil position, gaze vector of each eye, or gaze point.

In some implementations, collecting the eye-tracking data of the patient using the eye-tracker device further includes: capturing first eye-movement data of the eyes of the patient by measuring reflected light from the eyes of the patient.

In some implementations, the eye-tracker device includes: at least one eye-tracking unit configured to capture the first eye-movement data of the eyes of the patient; and at least one image acquisition unit configured to capture the at least one of the images of eyes of the patient or the positions of the eyes of the patient.

In some implementations, the eye-tracker device is configured to: determine second eye-movement data based on the captured at least one of the images of the eyes or the positions of the eyes of the patient, and determine the eye-tracking data based on the first eye-movement data and the second eye-movement data.

In some implementations, the eye-tracker device is configured to: convert the first eye-movement data into first eye-tracking data, determine second eye-movement data based on the captured at least one of the images of the eyes or the positions of the eyes of the patient, convert the second eye-movement data into second eye-tracking data, and determine the eye-tracking data based on the first eye-tracking data and the second eye-tracking data.

In some implementations, the computer-implemented method further includes: collecting at least one of image data, audio data, or video data collected by one or more recording devices while the visual scenes of the data collection playlist of visual stimuli are sequentially presented, where the one or more recording device are assembled in at least one of the patient-side computing device or external to the patient-side computing device. The session data includes the at least one of image data, audio data, or video data.

Another aspect of the present disclosure features an apparatus including: at least one processor; and one or more memories storing instructions that, when executed by the at least one processor, cause the at least one processor to perform any one of the computer-implemented methods as disclosed herein.

Another aspect of the present disclosure features one or more non-transitory computer-readable media storing instructions that, when executed by at least one processor, cause the at least one processor to perform any one of the computer-implemented methods as disclosed herein.

Another aspect of the present disclosure features a computer-implemented method, comprising: receiving, at a network-connected server, a request for an assessment result of a patient based on session data of the patient, the session data being collected during presentation of a data collection playlist of visual stimuli to the patient in a session, where at least one visual scene of the data collection playlist is annotated with at least one of a plurality of skill areas associated with visual scenes of the data collection playlist; and outputting, by the network-collected server, the assessment result of the patient, the assessment result comprising, for each of one or more specific skill areas of the plurality of skill areas, behavior data of the patient with respect to moments relevant to the specific skill area in the session, each of the moments corresponding to a respective visual scene of the visual scenes of the data collection playlist.

In some embodiments, the behavior data comprises an attendance percentage defined as a ratio between a number of moments which the patient attends to relevant scene contents in the visual stimuli and a total number of moments which the patient is watching the visual stimuli.

In some embodiments, the session data comprises eye-tracking data of the patient. The computer-implemented method further comprises: determining the total number of moments which the patient is watching the visual stimuli based on the eye-tracking data of the patient, and determining the number of moments which the patient attends to the relevant scene contents based on the eye-tracking data of the patient.

In some embodiments, the computer-implemented method of further comprises: determining, at a moment in the session, an attendance area of the patient to be within a predetermined region; and determining the moment to be one of the number of moments which the patient attends to a relevant scene content.

In some embodiments, the predetermined region corresponds to a contour of a distribution map of behavior data of a reference group, the behavior data of the reference group being based on reference session data collected during presentation of the data collection playlist of visual stimuli to each person of the reference group.

In some embodiments, a value of the contour of the distribution map corresponds to a cutoff threshold.

In some embodiments, the assessment result further comprises the distribution map of the behavior data of the reference group.

In some embodiments, the assessment result further comprises at least one of: for each of the one or more specific skill areas, a representative visual scene, the representative visual scene highlighting one or more attendance areas in the predetermined region for the reference group, or the representative visual scene highlighting the attendance area of the patient in the session.

In some embodiments, the assessment result further comprises at least one of: for each of the one or more specific skill areas, behavior data of one or more preceding sessions of the patient, or a comparison between the behavior data of the session and the behavior data of the one or more preceding sessions of the patient.

In some embodiments, the assessment result comprises a graph showing, for each of the one or more specific skill areas, the behavior data of the session and the behavior data of the one or more preceding sessions of the patient.

In some embodiments, the computer-implemented method further comprises: selecting the one or more specific skill areas from the plurality of skill areas for the assessment result of the patient.

In some embodiments, selecting the one or more specific skill areas from the plurality of skill areas comprises at least one of: selecting a specific skill area with reliable data among the plurality of skill areas, selecting a popularly requested skill area among the plurality of skill areas, selecting a skill area with a particularly high, low, or representative score among the plurality of skill areas, where a score represents an attendance percentage of the patient, selecting a skill area that is previously selected as a targeted skill area in the session, selecting a skill area that is selected for customizing the assessment result, or selecting a skill area that is previously selected in a previous session of the patient or a previous assessment result of the patient.

In some embodiments, the computer-implemented method comprises: receiving, through a web portal on the network-connected server, a session request to launch the session; presenting a list of sessions on a user interface of the web portal; and receiving a selection of the session from the list of sessions on the user interface.

In some embodiments, the computer-implemented method further comprises: in response to receiving the selection of the session, popping up a window for selecting targeted skill areas from the plurality of skill areas listed in the window, receiving a user input to select one or more targeted skill areas in the window, and running the session based on the selected one or more targeted skill areas, where the selected one or more targeted skill areas comprise the one or more specific skill areas.

In some embodiments, the computer-implemented method comprise: adjusting the data collection playlist of visual stimuli based on the selected one or more targeted skill areas.

In some embodiments, adjusting the data collection playlist of visual stimuli comprises at least one of: prioritizing visual scenes related to the selected one or more targeted skill areas in the data collection playlist, enriching additional visual scenes related to the selected one or more targeted skill areas in the data collection playlist, or reducing or removing visual scenes unrelated to the selected targeted skill areas in the data collection playlist.

In some embodiments, prioritizing the visual scenes related to the selected one or more targeted skill areas comprises at least one of: arranging the visual scenes related to the selected one or more targeted skill areas at a beginning of the data collection playlist, arranging the visual scenes related to the selected one or more targeted skill areas in an order of weighted correlation values to the selected one or more targeted skill areas, or selecting only the visual scenes related to the selected one or more targeted skill areas in the data collection playlist.

In some embodiments, receiving the user input comprises: receiving the user input from an operator-side computing device in communication with the network-connected server through the web portal. In some embodiments, the computer-implemented method further comprises: establishing a communication between the operator-side computing device with a patient-side computing device through the network-connected server, and transmitting information of the adjusted data collection playlist of visual stimuli to the patient-side computing device, such that the adjusted data collection playlist of visual stimuli is presented on a display screen of the patient-side computing device to the patient in the session.

In some embodiments, the computer-implemented method further comprises: receiving the session data of the patient from a patient-side computing device for the patient once the session is completed, where the session data of the patient is collected by the patient-side computing device during the session; and generating the behavior data of the patient by processing the session data of the patient based on reference data of a reference group and the one or more specific skill areas.

In some embodiments, the computer-implemented method further comprises: loading reference data of a reference group, the reference data being based on behavior data of the reference group that is based on reference session data collected during presentation of the data collection playlist of visual stimuli and the one or more specific skill areas.

In some embodiments, the reference data of the reference group comprises at least one of: for each of the one or more specific skill areas, specific visual scenes relevant to the specific skill area, each of the specific visual scenes highlighting one or more attendance areas of the reference group, or a distribution map of the behavior data of the reference group for each of the specific visual scenes.

In some embodiments, the reference data comprises: for each of the one or more specific skill areas and for each of the specific visual scenes, a contour in the distribution map representing a threshold for determining whether or not the patient attends to a relevant scene content of the specific visual scene. The computer-implemented method further comprises at least one of: determining that the patient attends to the relevant scene content of the specific visual scene if an attendance area of the patient is within a predetermined region corresponding to the contour, or determining that the patient fails to attend to the relevant scene content of the specific visual scene if an attendance area of the patient is out of the predetermined region.

In some embodiments, the behavior data of the patient comprises an attendance percentage defined as a ratio between a number of moments which the patient attends to relevant scene contents and a total number of moments which the patient is watching the visual stimuli. The computer-implemented method can further comprise: determining, at a moment in the session, an attendance area of the patient to be within the predetermined region; and determining the moment to be one of the number of moments which the patient attends to a relevant scene content.

In some embodiments, the behavior data of the patient comprises a result of comparison between an attendance percentage of the patient and a threshold attendance percentage of the reference group. The result of comparison can include at least one of: a ratio between the attendance percentage of the patient and the threshold attendance percentage of the reference group, or a relationship between the attendance percentage of the patient and the threshold attendance percentage of the reference group.

In some embodiments, receiving the request comprises: receiving, from a computing device, a user input on a user interface of a web portal of the network-connected server, the user input indicating the request, the user interface being presented on a display screen of the computing device.

In some embodiments, the user interface comprises at least one of a first user interface element for viewing a default evaluation report, a second user interface element for customizing an evaluation report, or a third user interface element for launching an interactive dashboard with the assessment result.

In some embodiments, the computer-implemented method further comprises: in response to a selection for the second user interface element, popping up a window on the user interface for selecting targeted skill areas in the evaluation report; receiving a second user input for selecting one or more targeted skill areas in the window; and generating the evaluation report based on the selected one or more targeted skill areas, where the one or more targeted skill areas comprise the one or more specific skill areas in the assessment result.

In some embodiments, the computer-implemented method further comprises: in response to a selection for the third user interface element, presenting the interactive dashboard in the user interface, where the interactive dashboard comprises a sub-window for selecting one of a list of skill areas for interaction.

In some embodiments, the computer-implemented method further comprises: in response to receiving a selection of a particular targeted skill area from the list of skill areas, presenting at least one of: a change of an attendance percentage of the patient for the particular targeted skill area over a series of sequential sessions, a change of a ratio between the attendance percentage of the patient and the threshold attendance percentage of the reference group, a change of a relationship between the attendance percentage of the patient and the threshold attendance percentage of the reference group, or for each of a plurality of visual scenes relevant to the particular target skill area, a first scene highlighting one or more attendance areas of a reference group in the visual scene and a second scene highlighting an attendance area of the patient in the visual scene.

In some embodiments, the plurality of visual scenes are overlaid with each other in the user interface, and the interactive dashboard comprises a sliding user interface element for selecting each of the plurality of visual scenes.

In some embodiments, the computer-implemented method further comprises: storing, at the network-connected server, annotation data of visual scenes of the data collection playlist of visual stimuli, the annotation data specifying respective specific skill areas associated with the visual scenes; and storing, at the network-connected server, reference data of a reference group, the reference data being based on behavior data that is based on reference session data collected during presentation of the data collection playlist of visual stimuli.

In some embodiments, the session data comprises at least one of: eye-tracking data collected by an eye-tracking device assembled in a patient-side computing device in communication with the network-connected server, or at least one of image data, audio data, or video data collected by one or more recording devices, where the one or more recording devices are assembled in at least one of the patient-side computing device or external to the patient-side computing device.

Another aspect of the present disclosure features a computer-implemented method, comprising: accessing, by a computing device, a web portal at a network-connected server; receiving, by the computing device, a user input on a user interface of the web portal, the user input for requesting an assessment result of a patient based on session data of the patient, the session data being collected during presentation of a data collection playlist of visual stimuli to the patient in a session, where at least one visual scene of the data collection playlist is annotated with at least one of a plurality of skill areas associated with visual scenes of the data collection playlist; presenting, by the computing device, the assessment result on a display screen of the computing device, the assessment result comprising, for each of one or more specific skill areas of the plurality of skill areas, behavior data of the patient with respect to moments relevant to the specific skill area in the session, each of the moments corresponding to a respective visual scene of the visual scenes of the data collection playlist.

In some embodiments, the computer-implemented method further comprises: establishing a wireless connection with a patient-side computing device that is integrated with an eye-tracking device; and presenting the user interface to communicate with the patient-side computing device for acquisition of the session data of the patient.

Another aspect of the present disclosure features a computer-implemented method, comprising: initiating a session for a patient by establishing a communication with an operator-side computing device and a patient-side portable tablet computing device, the patient-side portable tablet computing device being integrated with an eye-tracking device; sequentially presenting visual scenes of a data collection playlist of visual stimuli on a screen of the patient-side portable tablet computing device to the patient while collecting eye-tracking data of the patient using the eye-tracking device, where at least one visual scene of the data collection playlist is annotated with at least one of a plurality of skill areas associated with the visual scenes of the data collection playlist; and transmitting session data of the session to a network-connected server the session data comprising the eye-tracking data of the patient collected in the session.

In some embodiments, the data collection playlist comprises visual scenes relevant to one or more specific skill area of the plurality of skill areas that are prioritized in the data collection playlist.

In some embodiments, the computer-implemented method further comprises: collecting at least one of image data, audio data, or video data collected by one or more recording devices while the visual scenes of the data collection playlist of visual stimuli are sequentially presented, where the one or more recording device are assembled in at least one of the patient-side computing device or external to the patient-side computing device, where the session data comprises the at least one of image data, audio data, or video data.

Another aspect of the present disclosure features a system for development assessment via eye tracking, including: a patient-side mobile computing device including a screen for presenting visual stimuli to a patient; an eye-tracking device mounted with the patient-side mobile computing device and oriented at a fixed positioned relative to the screen of the patient-side mobile computing device to collect eye-tracking data of the patient while the visual stimuli are presented to the patient on the screen of the patient-side mobile computing device; and an operator-side mobile computing device configured to present a user interface that controls activation of the visual stimuli presented to the patient on the screen of the patient-side mobile computing device.

In some embodiments, the operator-side computing mobile device and the patient-side mobile computing device are configured to communicate with each other via a wireless connection. In some embodiments, the operator-side mobile computing device and the patient-side mobile computing device are configured to wirelessly communicate with each other via a network-connected server. In some embodiments, the network-connected server includes a cloud computing system or a cloud server implemented in a cloud environment.

In some embodiments, the patient-side mobile computing device is configured to transmit data to the network-connected server, the data including eye-tracking data of the patient collected in a session while presenting the visual stimuli from a list of predetermined visual stimuli are presented to the patient.

In some embodiments, the patient-side mobile computing device is configured to automatically transmit the data in response to completion of all visual stimuli in the list of predetermined visual stimuli being presented in the session. In some embodiments, the patient-side mobile computing device is configured to transmit the data in response to receiving a completion indication from the operator-side mobile computing device or the network-connected server. In some embodiments, the operator-side mobile computing device or the network-connected server is configured to generate the completion indication in response to a determination that the session ends or receipt of an input indicating a completion of the session.

In some embodiments, the data includes information of the list of predetermined visual stimuli and the eye-tracking data of the patient collected in the session. In some embodiments, the patient-side computing mobile device is configured to transmit the data in two files that include a first file including the eye-tracking data of the patient and associated timestamp information and a second file including the information of the list of the visual stimuli. In some embodiments, the associated timestamp information for the eye-tracking data includes timestamps when the eye-tracking data are generated or collected, and the information of the list of predetermined visual stimuli includes timestamps when individual visual stimuli in the list are presented.

In some embodiments, the operator-side mobile computing device is configured to access a web portal in the network-connected server. In some embodiments, the operator-side mobile computing device is configured to communicate with one or more patient-side computing devices through the web portal in the network-connected server. In some embodiments, the user interface of the operator-side mobile computing device includes at least one of information of one or more patients associated with the operator, information of one or more patient-side computing devices associated with the operator, or information of the operator.

In some embodiments, the patient-side mobile computing device is configured to display connection information including an access code on the screen of the patient-side mobile computing device in response to connecting to the network-connected server. In some embodiments, the operator-side mobile computing device is configured to connect with the patient-side computing device by receiving an input of the connection information including the access code at the user interface. In some embodiments, the user interface of the operator-side mobile computing device presents a request for the connection information in response to receiving a selection of the patient-side mobile computing device among the one or more patient-side computing devices presented in the user interface.

In some embodiments, the operator-side mobile computing device is configured to present the user interface of an operator application running on one of the operator-side computing device or the network-connected server. In some embodiments, the operator application is configured to: present a user interface element for a start of desensitization in the user interface; and in response to a selection of the user interface element, transmit a command to the patient-side computing device to play visual desensitization information.

In some embodiments, the patient-side mobile computing device is configured to: in response to receiving the command, play the visual desensitization information on the screen of the patient-side mobile computing device to the patient, and control the eye-tracking device not to collect eye-tracking data of the patient while displaying the visual desensitization information on the screen.

In some embodiments, the operator application is configured to present the user interface for the operator to set up a session for the patient by selecting the patient among a list of patients or creating a profile for the patient, while the visual desensitization information is displayed on the screen of the patient-side mobile computing device.

In some embodiments, the operator application is configured to display in the user interface an instruction to adjust a position of the eye-tracking device relative to the patient or a position of the patient relative to the patient-side mobile computing device based on a sensed position of the eye-tracking device relative to at least one eye of the patient. In some embodiments, the sensed position is determined based on image data of the at least one eye of the patient captured by using an image acquisition device that is included with or adjacent to the eye-tracking device. In some embodiments, the sensed position is determined by the patient-side mobile computing device or the operator application.

In some embodiments, the operator application is configured to transmit a command to the patient-side mobile computing device for a calibration between the patient and the eye-tracking device, in response to one of: a selection of a user interface element for calibration in the user interface, or determining that a session for the patient is setup.

In some embodiments, the patient-side mobile computing device is configured to: in response to receiving the command, sequentially present one or more calibration targets at one or more predetermined locations of the screen of the patient-side mobile computing device, while capturing eye-tracking calibration data of the patient using the eye-tracking device.

In some embodiments, the patient-side mobile computing device is configured to: for each of the one or more calibration targets, process the captured eye-tracking calibration data of the patient to determine a position of a corresponding visual fixation of the patient for the calibration target; and compare the position of the corresponding visual fixation of the patient to a corresponding predetermined location where the calibration target is presented on the screen; determine whether the calibration target is calibrated for the patient based on a result of the comparison.

In some embodiments, the patient-side mobile computing device is configured to determine the calibration is completed in response to determining that the one or more calibration targets are calibrated. In some embodiments, the patient-side mobile computing device is configured to: in response to determining that a calibration target fails to be calibrated, re-calibrate the calibration target.

In some embodiments, the patient-side mobile computing device is configured to play desensitization information between presenting two adjacent calibration targets. In some embodiments, the operator application is configured to: in response to receiving an indication that the calibration is completed, start to validate the calibration. In some embodiments, the patient-side mobile computing device is configured to: in response to receiving a request for validating the calibration, present at least one additional calibration target on the screen, while capturing additional eye-tracking calibration data of the patient using the eye-tracking device; and process the captured additional eye-tracking calibration data of the patient to determine a position of a corresponding visual fixation of the patient for the at least one additional calibration target.

In some embodiments, the patient-side mobile computing device is configured to: compare the position of the corresponding visual fixation of the patient for the at least one additional calibration target to a corresponding predetermined location where the at least one additional calibration target is presented on the screen; and determine whether the calibration is validated based on a result of the comparison.

In some embodiments, the operator application is configured to: simultaneously present, in the user interface, the at least one additional calibration target at the corresponding predetermined location and at least one representation of the corresponding visual fixation of the patient at the determined position of the corresponding visual fixation of the patient for the at least one additional calibration target; and presenting a first user interface element for validation of the calibration and a second user interface element for re-calibration in the user interface.

In some embodiments, the operator application is configured to transmit a command to the patient-side computing device for data collection, in response to one of: a selection of a user interface element for staring the data collection, or determining that the calibration is completed or validated.

In some embodiments, the patient-side mobile computing device is configured to: in response to receiving the command, sequentially present a list of predetermined visual stimuli on the screen of the patient-side mobile computing device to the patient, while capturing eye-tracking data of the patient using the eye-tracking device.

In some embodiments, the patient-side mobile computing device is configured to: before presenting each of the list of predetermined visual stimuli, present a centering target on the screen of the patient-side mobile computing device to the patient. In some embodiments, the patient-side mobile computing device is configured to: perform a calibration of the patient to the eye-tracking device between presenting two adjacent visual stimuli among the list of predetermined visual stimuli. In some embodiments, the eye-tracking data collected in performing the calibration is used for at least one of recalibrating the eye-tracking data of the patient or for determining a calibration accuracy.

In some embodiments, the operator application is configured to present, in the user interface, at least one of a progress indicator that keeps updating throughout presenting the list of predetermined visual stimuli, a user interface element for skipping a visual stimulus among the list of predetermined visual stimuli, information of a visual stimulus already presented or being presented, or information of a visual stimulus to be presented.

In some embodiments, the network-connected server is configured to provide a diagnostic result of the patient based on the eye-tracking data of the patient, the diagnostic result includes at least one index value associated with developmental disorder. In some embodiments, the operator-side mobile computing device is configured to present the diagnostic result in the user interface.

In some embodiments, the visual stimuli are predetermined based on at least an age of the patient or a condition of the patient. In some embodiments, each of the visual stimuli includes at least one of a static visual stimulus, a dynamic visual stimulus, a pre-recorded visual stimulus, a pre-recorded audiovisual stimulus, a live visual stimulus, a live audiovisual stimulus, a two-dimensional stimulus, or a three-dimensional stimulus. In some embodiments, each of the visual stimuli is normed for eliciting specific eye movement responses with greater than 95% statistical confidence. In some embodiments, each of the visual stimuli is configured to elicit eye movement responses to discrete spatial-temporal locations with greater than 95% statistical confidence.

In some embodiments, the eye-tracking device is connected with the patient-side mobile computing device through a wired connection. In some embodiments, the eye-tracking device and the screen are housed together in a holder. In some embodiments, the patient-side mobile computing device includes a screen holder that retains the screen and the eye-tracking device in the fixed position relative to the screen.

In some embodiments, the eye-tracking device includes one or more eye-tracking units arranged in one or more locations adjacent to a peripheral of the screen. In some embodiments, at least one of the patient-side mobile computing device or the operator-side mobile computing device is a tablet computing device. In some embodiments, the operator-side computing device is configured to communicate with the patient-side mobile computing device via a bi-directional communication.

Another aspect of the present disclosure features an apparatus including: a patient-side computing device including a screen for presenting visual stimuli to a patient, and an eye-tracking device integrated with the patient-side computing device and configured to collect eye-tracking data of the patient while the visual stimuli are presented to the patient on the screen of the patient-side computing device. The patient-side computing device includes the patient-side computing device as described above.

Another aspect of the present disclosure features an apparatus including the operator-side computing device as described above.

Another aspect of the present disclosure features an apparatus including: at least one processor; and at least one non-transitory memory coupled to the at least one processor and storing programming instructions for execution by the at least one processor to perform operations including: establishing a wireless connection with a patient-side computing device that is integrated with an eye-tracking device; and presenting a user interface to communicate with the patient-side computing device for acquisition of eye-tracking data of a patient.

In some embodiments, the operations further include: accessing a web portal of a network-connected server, where the wireless connection is established through the web portal. In some embodiments, the operations further include: presenting in the user interface a diagnostic result based on the eye-tracking data of the patient.

Another aspect of the present disclosure features a computer-implemented method of development assessment via eye tracking. The computer-implemented method includes: initiating a session for a patient by establishing a communication with an operator-side computing device and a patient-side computing device, the patient-side computing device being integrated with an eye-tracking device; sequentially presenting a list of predetermined visual stimuli on a screen of the patient-side computing device to the patient, while collecting eye-tracking data of the patient using the eye-tracking device; and transmitting session data of the session to a network-connected server, the session data including the eye-tracking data of the patient collected in the session.

In some embodiments, at least one of the operator-side computing device or the patient-side computing device is a portable device. In some embodiments, establishing the communication includes: establishing a wireless connection between the operator-side computing device and the patient-side computing device.

In some embodiments, establishing the wireless connection between the operator-side computing device and the patient-side computing device includes: accessing, by the operator-side computing device, a web portal at the network-connected server; and in response to receiving a selection of the patient-side computing device in the web portal, wirelessly connecting the operator-side computing device to the patient-side computing device. In some embodiments, establishing the wireless connection between the operator-side computing device and the patient-side computing device includes: displaying, by the patient-side computing device, connection information on the screen of the patient-side computing device; and in response to receiving an input of the connection information by the operator-side computing device, establishing the wireless connection between the operator-side computing device and the patient-side computing device.

In some embodiments, the computer-implemented method further includes: after establishing the communication, displaying visual desensitization information on the screen of the patient-side computing device to the patient. In some embodiments, the computer-implemented method further includes: controlling the eye-tracking device not to collect eye-tracking data of the patient while displaying the visual desensitization information.

In some embodiments, the computer-implemented method further includes: while displaying the visual desensitization information, accessing, by the operator-side computing device, a web portal at the network-connected server to set up the session for the patient. In some embodiments, setting up the session includes one of selecting the patient among a list of patients or creating a profile for the patient at the network-connected server. In some embodiments, the computer-implemented method further includes determining a relative position between the eye-tracking device and at least one eye of the patient; and displaying an instruction to adjust a position of the eye-tracking device or a position of the patient on a user interface of the operator-side computing device.

In some embodiments, the computer-implemented method further includes: in response to determining that the relative location at least one eye of the patient is at a predetermined location in a detection area of the eye-tracking device, determining that the patient is aligned with the eye-tracking device.

In some embodiments, the computer-implemented method further includes: calibrating the patient to the eye-tracking device by displaying one or more calibration targets on the screen of the patient-side computing device to the patient.

In some embodiments, calibrating the patient to the eye-tracking device includes: sequentially presenting each of the one or more calibration targets at a corresponding predetermined location of the screen of the patient-side computing device, while capturing eye-tracking calibration data of the patient using the eye-tracking device; for each of the one or more calibration targets, processing the captured eye-tracking calibration data of the patient to determine a position of a corresponding visual fixation of the patient for the calibration target; comparing the position of the corresponding visual fixation of the patient with the corresponding predetermined location where the calibration target is presented; and determining whether the calibration target is calibrated to the eye-tracking device based on a result of the comparing.

In some embodiments, calibrating the patient to the eye-tracking device further includes: in response to determining that a deviation between the position of the corresponding visual fixation of the patient with the corresponding predetermined location is smaller than or equal to a predetermined threshold, determining that the calibration target is calibrated and displaying a next calibration target, or in response to determining that the deviation is greater than the predetermined threshold, determining that the calibration target fails to be calibrated and re-displaying the calibration target for calibration.

In some embodiments, the computer-implemented method further includes: after calibrating the patient to the eye-tracking device, validating the calibration with one or more new calibration targets. In some embodiments, validating the calibration includes: sequentially presenting each of the one or more new calibration targets at a corresponding predetermined location of the screen of the patient-side computing device, while capturing eye-tracking calibration data of the patient using the eye-tracking device; and processing the captured eye-tracking calibration data of the patient to determine a position of a corresponding visual fixation of the patient for each of the one or more new calibration targets.

In some embodiments, validating the calibration includes: simultaneously presenting, on a user interface of the operator-side computing device, the one or more new calibration targets at one or more corresponding predetermined locations and representations of the one or more corresponding visual fixations of the patient at the determined one or more positions; and in response to receiving an indication to validate a result of the calibrating, determining that the calibration is validated, or in response to receiving an indication to invalidate the result of the calibrating, starting to re-calibrate the patient to the eye-tracking device.

In some embodiments, validating the calibration includes: determining a number of new calibration targets that each passes a calibration based on the position of the corresponding visual fixation of the patient and the corresponding predetermined position; and if the number or an associated percentage is greater than or equal to a predetermined threshold, determining that the calibration is validated, or if the number or the associated percentage is smaller than the predetermined threshold, determining that the calibration is invalidated and starting to re-calibrate the patient to the eye-tracking device.

In some embodiments, sequentially presenting the list of predetermined visual stimuli on the screen of the patient-side computing device to the patient includes: before presenting each of the list of predetermined visual stimuli, presenting a centering target on the screen of the patient-side computing device to the patient.

In some embodiments, sequentially presenting the list of predetermined visual stimuli on the screen of the patient-side computing device to the patient includes: performing a calibration of the patient to the eye-tracking device between presenting two adjacent visual stimuli among the list of predetermined visual stimuli, where the eye-tracking data collected in performing the calibration is used for at least one of calibrating the eye-tracking data of the patient or for determining a calibration accuracy.

In some embodiments, the computer-implemented method further includes: presenting, on a user interface of the operator-side computing device, at least one of: a progress indicator that keeps updating throughout presenting the list of predetermined visual stimuli, information of visual stimuli already presented or being presented, information of visual stimuli to be presented, or a user interface element for skipping a visual stimulus among the list of predetermined visual stimuli.

In some embodiments, transmitting the session data of the session to the network-connected server includes: automatically transmitting, by the patient-side computing device, the session data of the session to the network-connected server, in response to one of: determining a completion of presenting the list of predetermined visual stimuli on the screen, or receiving a completion indication of the session from the operator-side computing device.

In some embodiments, the session data includes information related to the presented list of predetermined visual stimuli. In some embodiments, the information related to the presented list of predetermined visual stimuli includes names of presented predetermined visual stimuli and associated timestamps when the predetermined visual stimuli are presented.

In some embodiments, the session data includes the eye-tracking data and associated timestamps when the eye-tracking data are generated or collected. In some embodiments, the session data is stored in a first file storing the eye-tracking data of the patient and a second file storing the information related to the presented list of predetermined visual stimuli.

Another aspect of the present disclosure features a computer-implemented method for development assessment using eye-tracking data by a network-connected server. the computer-implemented method includes: receiving session data of multiple sessions, the session data of each session including eye-tracking data of a corresponding patient in the session; processing the session data of the multiple sessions in parallel to generate processed session data for the multiple sessions; and for each session of the multiple sessions, analyzing the processed session data of the session based on corresponding reference data to generate an assessment result for the corresponding patient in the session.

In some embodiments, the computer-implemented method further includes: loading the corresponding reference data for the multiple sessions in parallel with processing the session data of the multiple sessions.

In some embodiments, the network-connected server includes a plurality of processing cores. Processing the session data of the multiple sessions in parallel includes using a first plurality of processing cores to process the session data of the multiple sessions in parallel and using a second, different plurality of processing cores to load the corresponding reference data for the multiple sessions, a number of the first plurality of processing cores being larger than a number of the second plurality of processing cores.

In some embodiments, analyzing the processed session data of the multiple sessions based on the loaded corresponding reference data for the multiple sessions includes: using the plurality of processing cores including the first plurality of processing cores and the second plurality of processing cores.

In some embodiments, analyzing the processed session data of the multiple sessions based on the loaded corresponding reference data for the multiple sessions includes at least one of: comparing the processed session data of the session to the corresponding reference data, inferring the assessment result for the corresponding patient from the processed session data using the corresponding reference data, or using at least one of a statistical model or an artificial intelligence (AI) model. In some embodiments, the corresponding reference data includes historical eye-tracking data or results for patients having substantially same age or condition as the corresponding patient.

In some embodiments, the computer-implemented method further includes: generating the assessment result based on previous session data of the corresponding patient. In some embodiments, the computer-implemented method includes: for each session of the multiple session, assigning a respective container for the session, and, in the respective container, processing the session data of the session and analyzing the processed session data of the session based on the corresponding model data to generate the assessment result for the corresponding patient in the session.

In some embodiments, the eye-tracking data is associated with a list of predetermined visual stimuli presented to the patient while the eye-tracking data is collected in the session, and where the session data includes information associated with the list of predetermined visual stimuli in the session.

In some embodiments, the computer-implemented method further includes: linking the eye-tracking data of the session with the list of predetermined visual stimuli in the session. In some embodiments, linking the eye-tracking data of the session with the list of predetermined visual stimuli in the session includes: in the respective container, breaking up the eye-tracking data into multiple portions based on the information associated with the list of predetermined visual stimuli, each portion of the eye-tracking data being associated with one of a respective predetermined visual stimulus or a corresponding calibration.

In some embodiments, processing the session data of the session includes processing portions of the eye-tracking data associated with respective predetermined visual stimulus based on information of the respective predetermined visual stimulus.

In some embodiments, the computer-implemented method further includes: in the respective container, recalibrating portions of eye-tracking data associated with respective predetermined visual stimulus based on at least one portion of eye-tracking data associated with the corresponding calibration.

In some embodiments, the computer-implemented method further includes: in the respective container, determining a calibration accuracy using at least one portion of eye-tracking data associated with the corresponding calibration and a plurality of predetermined locations where a plurality of calibration targets are presented in the corresponding calibration.

In some embodiments, receiving the session data of the multiple sessions includes: receiving, through a web portal, the session data of the multiple sessions from a plurality of computing devices associated with corresponding entities. In some embodiments, the computer-implemented method further includes: in response to receiving session data of a session, adding a file pointer for the session data of the session in a processing queue to be processed. In some embodiments, the computer-implemented method further includes: storing the session data of the session using the file pointer for the session in a database; and retrieving the session data of the session from the database using the file pointer for the session.

In some embodiments, the computer-implemented method further includes: for each entity, storing session data from one or more computing devices associated with the entity in a respective repository. In some embodiments, the respective repository for the entity includes at least one of: information of the entity, information of one or more operators or operator-side computing devices associated with the entity, information of one or more patient-side computing devices associated with the entity, information of one or more sessions conducted in the entity, information of one or more patients associated with the entity, or history information of the respective repository.

In some embodiments, the respective repository is included in a NoSQL database. In some embodiments, the respective repository is isolated from one or more other repositories and inaccessible by one or more other entities.

In some embodiments, the computer-implemented method further includes: dynamically adjusting resources of the network-connected server based on a number of computing devices that access the network-connected server.

In some embodiments, the computer-implemented method further includes: replicating data of a first data center to a second data center; and in response to determining that the first data center is inaccessible, automatically directing traffic to the second data center. In some embodiments, each of the first data center and the second data center includes at least one of a web portal accessible for the operator-side computing device, an operator application, or an application layer for data processing and data analysis.

In some embodiments, the computer-implemented method further includes: storing same data in multiple data centers, where the data includes application data for entities and information associated with the eye-tracking data.

In some embodiments, the computer-implemented method further includes: associating the generated assessment result with the corresponding patient in the session; and generating an assessment report for the corresponding patient.

In some embodiments, the computer-implemented method further includes: outputting assessment results or assessment reports to be presented at a user interface of the operator-side computing device. In some embodiments, the assessment report includes at least one of: information of the corresponding patient, information of an entity performing the session for the corresponding patient, information of a calibration accuracy in the session, information of session data collection, or the assessment result for the corresponding patient.

In some embodiments, the assessment result indicates a likelihood that the corresponding patient has a developmental, cognitive, social, or mental disability or ability. In some embodiments, the assessment result indicates a likelihood that the corresponding patient has an Austin Spectrum Disorder (ASD) or a non-ASD. In some embodiments, the assessment result includes a respective score for each of one or more of social disability index, verbal ability index, nonverbal ability, social adaptiveness index, and social communication index.

In some embodiments, the assessment result includes at least one of: a visualization of the eye-tracking data overlaid on corresponding visual stimulus stills from socially relevant moments, an animation visualizing the eye-tracking data overlaid on corresponding visual stimulus stills from socially relevant moments, a visualization of aggregated reference data from a plurality of reference patients matched with a corresponding patient on one or more patient attributes, or annotations describing at least one of a visual stimulus content or eye-gaze patterns.

In some embodiments, the corresponding patient has an age in a range from 5 months to 7 years, including an age in a range from 5 months to 43 months or 48 months, an age in a range from 16 to 30 months, an age in a range from 18 months to 36 months, an age in a range from 16 months to 48 months, or an age in a range from 16 months to 7 years.

Another aspect of the present disclosure features a system, including: at least one processor; and one or more memories storing instructions that, when executed by the at least one processor, cause the at least one processor to perform a computer-implemented method as described herein.

Another aspect of the present disclosure features one or more non-transitory computer-readable media storing instructions that, when executed by at least one processor, cause the at least one processor to perform a computer-implemented method as described herein.

One or more of the embodiments described herein can achieve a number of technical effects and advantages. In a first example, some embodiments can provide a convenient, miniaturized, and effective computing system for advantageously gathering eye-tracking data and subsequently communicating such data for analysis and diagnostic results. The computing system may include at least two separate portable computing devices, e.g., an operator-side portable device and at least one patient-side portable device that is integrated with an eye-tracking device. These portable devices can be equipped differently (different peripherals or equipment, different user interfaces, and the like) and can be wirelessly connected, without physical connection, to one another or to a network-connected server platform (which, in turn, provides communication between the operator-side portable device and the patient-side portable device). For example, an operator may use the operator-side portable device to calibrate the eye-tracking device with a patient and to control playing the predetermined visual stimuli on the patient-side portable device for obtaining eye-tracking data of the patient with the eye-tracking device. Once a session is completed, the patient-side portable device can transmit session data, e.g., detected eye-tracking data and information of the played visual stimuli, to a cloud server for data storage, processing, and analysis. The cloud server can be remotely connected with these portable devices, e.g., via a network.

In another example, the technologies implemented herein can provide much more detailed and interactive report outputs that allow users to drill into behavior and metrics for specific scenes or groups of scenes that are related to developmentally relevant skills. The annotations made by the expert clinicians in view of the behaviors of the reference group enable to accurately identify specific skill areas/skills for patient's diagnostics and/or treatment, to effectively adjust data collection playlist for patients on selected skill areas/skills, to monitor patients' improvements or treatment effects on the selected skill areas/skills, and/or to provide automatic, accurate, consistent, speedy, labor-free, and/or cost-effective assessments of development disorders for patients. The technologies enable operators/users to manage and/or explore results of sessions at multiple, customizable levels with details. The skill-specific behavior visualization and metrics can be configured to give the users an objective quantification of how well the patient is generalizing targeted skills outside of treatment context and inform which aspect of treatment are aligning with patient progress. A user (e.g., a treatment provider, a clinician, or a patient guardian) can see whether the patient has any improvement in one or more targeted skill areas, whether a treatment for the patient works or is effective, and/or whether a new or adjusted treatment can be used to replace a current treatment.

The technologies implemented herein can be used to provide earlier identification and assessment of the risk of developmental, cognitive, social, verbal or non-verbal abilities, or mental abilities or disabilities in patients, for example, by measuring visual attention to social information in the environment relative to normative, age-specific benchmarks. The patients can have an age in a range from 5 months to 7 years, e.g., from 16 months to 7 years, from 12 months to 48 months, from 16 to 30 months, or from 18 months to 36 months.

According to certain aspects, changes in visual fixation of a patient over time with respect to certain dynamic stimuli provides a marker of possible developmental, cognitive, social, or mental abilities or disorders (such as ASD) of the patient. A visual fixation is a type of eye movement used to stabilize visual information on the retina, and generally coincides with a person looking at or "fixating" upon a point or region on a display plane. In some embodiments, the visual fixation of the patient is identified, monitored, and tracked over time through repeated eye-tracking sessions and/or through comparison with model data based on a large number of patients in similar ages and/or backgrounds. Data relating to the visual fixation is then compared to relative norms to determine a possible increased risk of such a condition in the patient. A change in visual fixation (in particular, a decline or increase in visual fixation to the image of eyes, body, or other region-of-interest of a person or object displayed on a visual stimulus) as compared to similar visual fixation data of typically-developing patients or to a patient's own, prior visual fixation data provides an indication of a developmental, cognitive, or mental disorder. The technologies can be applied to quantitatively measure and monitor symptomatology of the respective ability or disability and, in certain cases, provide more accurate and relevant prescriptive information to patients, families, and service providers. According to additional aspects, the technologies can be used to predict outcome in patients with autism (thus providing prescriptive power) while also providing similar diagnostic and prescriptive measures for global developmental, cognitive, social, or mental ability or disabilities.

As detailed below, the technologies described herein for the detection of developmental, cognitive, social, or mental disabilities can be applicable to the detection of conditions including, but not limited to, expressive and receptive language developmental delays, non-verbal developmental delays, intellectual disabilities, intellectual disabilities of known or unknown genetic origin, traumatic brain injuries, disorders of infancy not otherwise specified (DOI-NOS), social communication disorder, and autism spectrum disorders (ASD), as well as such conditions as attention deficit hyperactivity disorder (ADHD), attention deficit disorder (ADD), post-traumatic stress disorder (PTSD), concussion, sports injuries, and dementia.

It is appreciated that methods in accordance with the present disclosure may include any combination of the embodiments described herein. That is, methods in accordance with the present disclosure are not limited to the combinations of embodiments specifically described herein, but also include any combination of the embodiments provided.

The details of one or more embodiments of the present disclosure are set forth in the accompanying drawings and the description below. Other embodiments and advantages of the present disclosure will be apparent from the description and drawings, and from the claims.

BRIEF DESCRIPTION OF THE DRAWINGS

FIG. 5 illustrates example session data including (a) movie playlist data; (b) eye-tracking sensor data, according to one or more embodiments of the present disclosure.

FIG. 13B-1 illustrates an example portion of an evaluation report, showing comparisons between annotated video scenes, information of typical looking behavior group, and information of patient's looking behavior for different specific skill areas, according to one or more embodiments of the present disclosure.

FIG. 13B-2 illustrates another example portion of the evaluation report, showing monitoring of treatment-specific skills and information on featured skills, according to one or more embodiments of the present disclosure.

FIG. 14 is a flowchart of an example process for managing specific skills for development disorder assessment, according to one or more embodiments of the present disclosure.

FIG. 15C illustrates an example illustrative user interface presented on a computing device when a cloud server runs a data aggregator application for the operator to manually enter patient information, according to one or more embodiments of the present disclosure.

FIGS. 16A to 16F illustrate example result interfaces of an example evaluation report of an evaluation system, according to one or more embodiments of the present disclosure.

FIG. 17B is a flowchart of an example process for managing evaluation reports, according to one or more embodiments of the present disclosure.

Like reference numbers and designations in the various drawings indicate like elements. It is also to be understood that the various exemplary implementations shown in the figures are merely illustrative representations and are not necessarily drawn to scale.

DETAILED DESCRIPTION

The present disclosure describes portable devices having user-detection equipment, such as eye-tracker devices or other sensors, and computer systems and methods including such portable devices or the data collected from such devices (such as eye-tracking data and/or other multi-modal data such as facial expressions, verbal expression, and/or physical movements). In some examples, the systems, devices, methods, and techniques described herein can use the eye-tracking data and/or multi-modal data (e.g., facial expressions, verbal expressions, and/or physical movements) generated in response to display of specific predetermined visual stimuli (e.g., one or more movies or videos), and to the patients provide an improved, objective assessment of developmental, cognitive, social, or mental abilities or disabilities, including Autism Spectrum Disorder (ASD), in patients. The techniques can provide detailed and interactive report outputs, allowing users to drill into behavior and metrics for specific scenes or groups of scenes that are related to specific skill areas (and/or skills) such as developmentally relevant skill areas/skills (or treatment-specific skills). In the present disclosure, the term "skill area" refers to a group of skills related to one another. The term "skill area" can be interchangeably used with the term "development concept" or "skill category." Example skill areas can include manding, listener responding, turn-taking, joint attention, tact, and/or play. The skill area can be associated with developmental assessment and/or treatment. For illustration purposes, treatment-specific skill area (or skill) is used as an example of a specific skill area (or skill).

Figure 11:
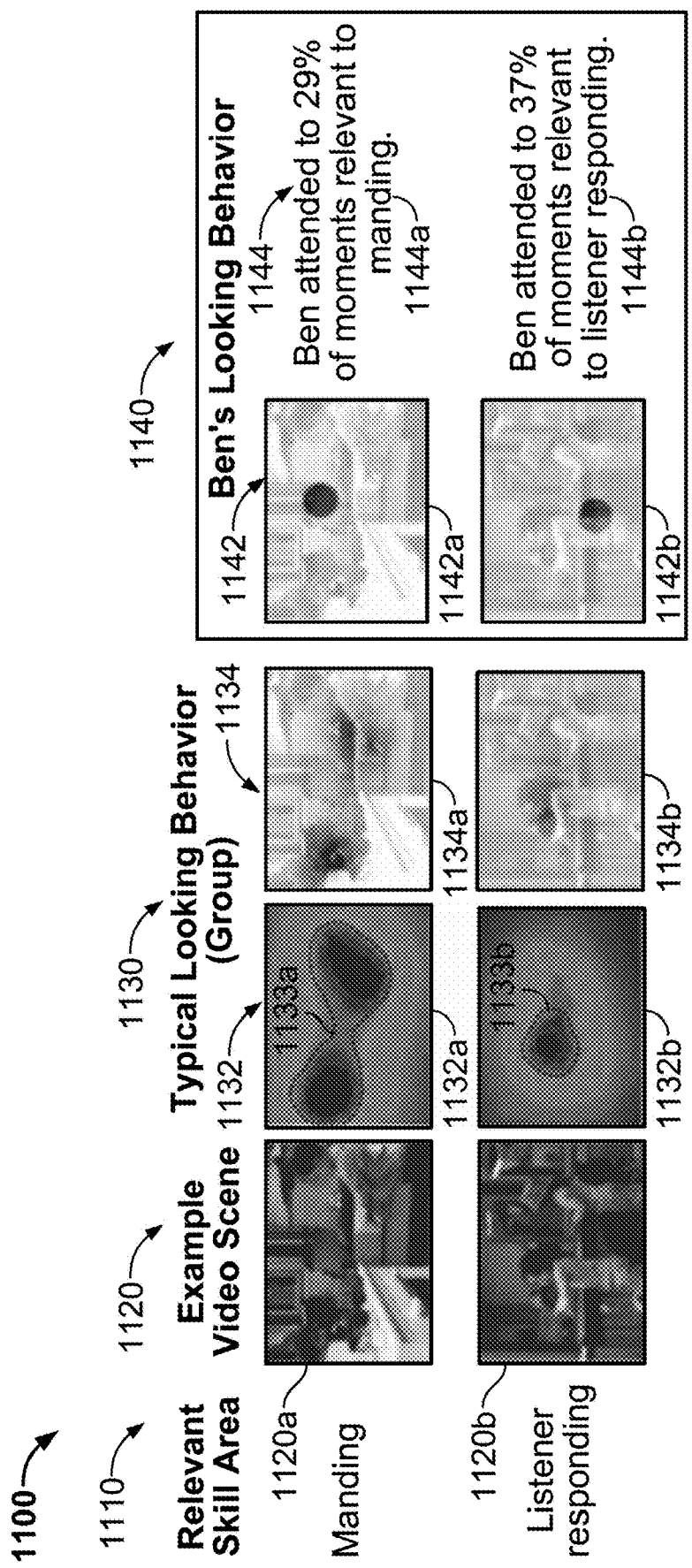
FIG. 11 illustrates an example of comparisons between annotated video scenes, information of typical looking behavior group, and information of patient's looking behavior for different specific skill areas, according to one or more embodiments of the present disclosure.

In some implementations, e.g., as discussed with further details in FIG. 11, the predetermined visual stimuli can be pre-annotated moment-by-moment for skill relevance, e.g., by connecting specific skill areas and/or skills with scenes of the visual stimuli that are relevant to these skill areas and/or skills. These skill areas or skills can be targeted in treatment, e.g., important to the Board Certified Behavior Analyst® (BCBA®). Example specific skill areas can include manding, listener responding, turn-taking, joint attention, tact, and/or play. The annotations can be made by one or more expert clinicians viewing the scenes of the visual stimuli and optionally behaviors (e.g., looking behaviors, facial expressions, verbal expressions, and/or physical movements) of a reference group (e.g., typical children with similar ages) when viewing the same visual stimuli. The annotations of the scenes can be for any developmental skill area (or concept), treatment prompt/measure, severity index, or any other skill that is present in or relevant to the scene content. The visualization of behaviors at example scenes can be considered as a representative of a skill area or a skill. The behavior convergence can be quantified for scenes annotated for a specific skill area or skill, in view of the reference group, which can be used as an additional skill-specific metrics.

The annotations made by the expert clinicians in view of the behaviors of the reference group enable to accurately identify specific skill areas/skills for patient's diagnostics and/or treatment, to effectively adjust data collection playlist for patients on selected skill areas/skills, to monitor patients' improvements or treatment effects on the selected skill areas/skills, and/or to provide automatic, accurate, consistent, speedy, labor-free, and/or cost-effective assessments of development disorders for patients. The techniques enable operators/users to manage and/or explore results of sessions at multiple, customizable levels with details. The skill-specific behavior visualization and metrics can be configured to give the users an objective quantification of how well the patient is generalizing targeted skills outside of treatment context and inform which aspect of treatment are aligning with patient progress.

For example, the techniques enable to customize data collection playlist of the visual stimuli. From a web portal of a network-connected server, when choosing to launch a session for a patient, an operator (e.g., a treatment provider or a clinician) can be prompted on a user interface presented on a screen of an operator-side computing device to select a type of session (e.g., a diagnostic session, a monitoring session, or a targeted monitoring session), e.g., as discussed with further details in FIGS. 12A-12B. If the targeted monitoring session is selected, a window can be prompted for the operator to select a set of skill areas that the operator would like to target. A default selection can be any skill areas selected in a prior targeted monitoring session. The data collection playlist, to be presented on a patient-side computing device in communication with the operator-side computing device and/or the network-connected server, can prioritize data collection in videos that have moments of relevance to the selected skill areas, e.g., by reordering a standard playlist, adding new videos that have been specifically enriched for the selected skill areas, and/or reducing or removing videos that are unrelated to the selected skill areas.

Figure 13A:
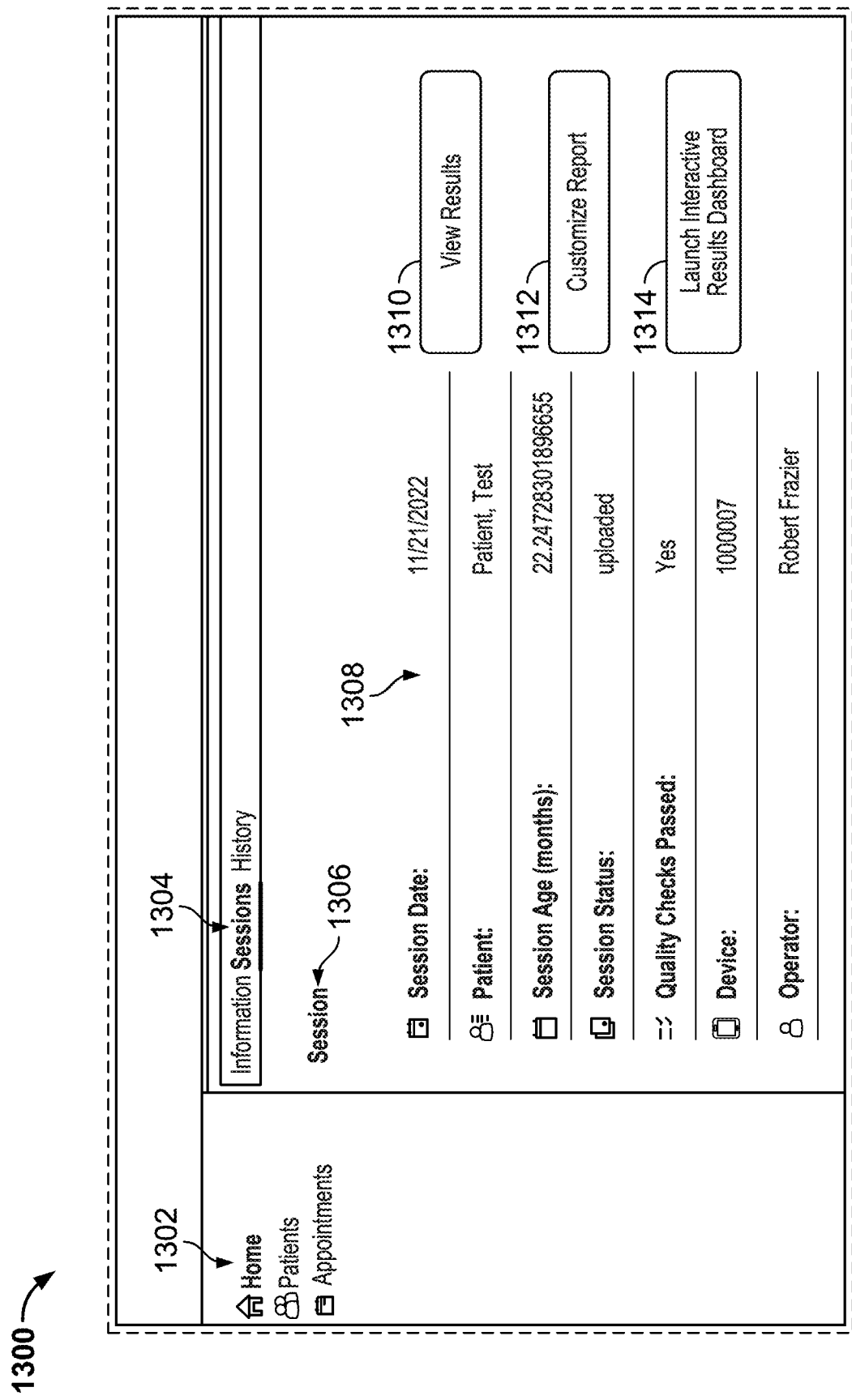
FIG. 13A illustrates an example illustrative user interface for reviewing session information on a user device, according to one or more embodiments of the present disclosure.
Figures 2, 13B:
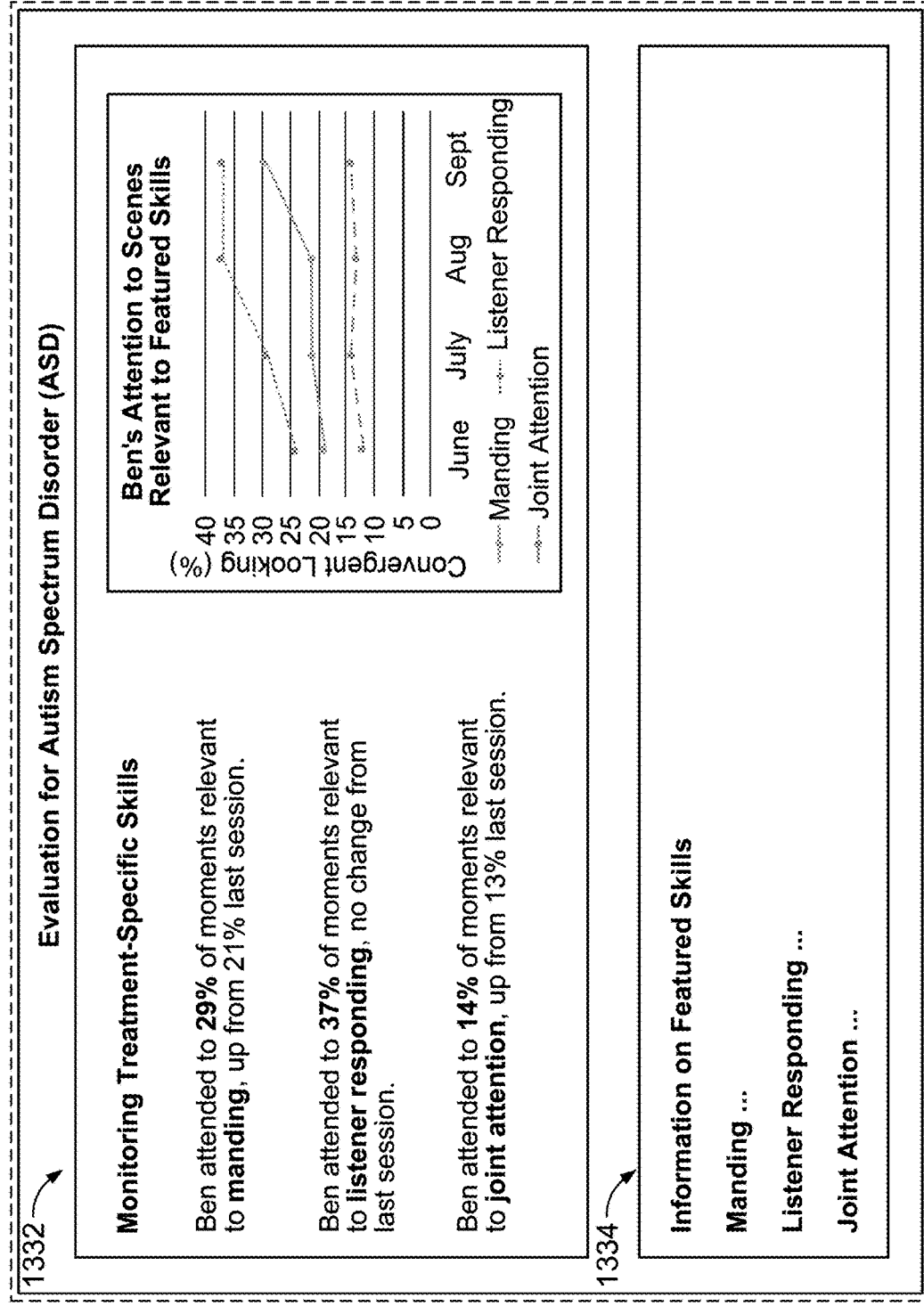
Figure 13C:
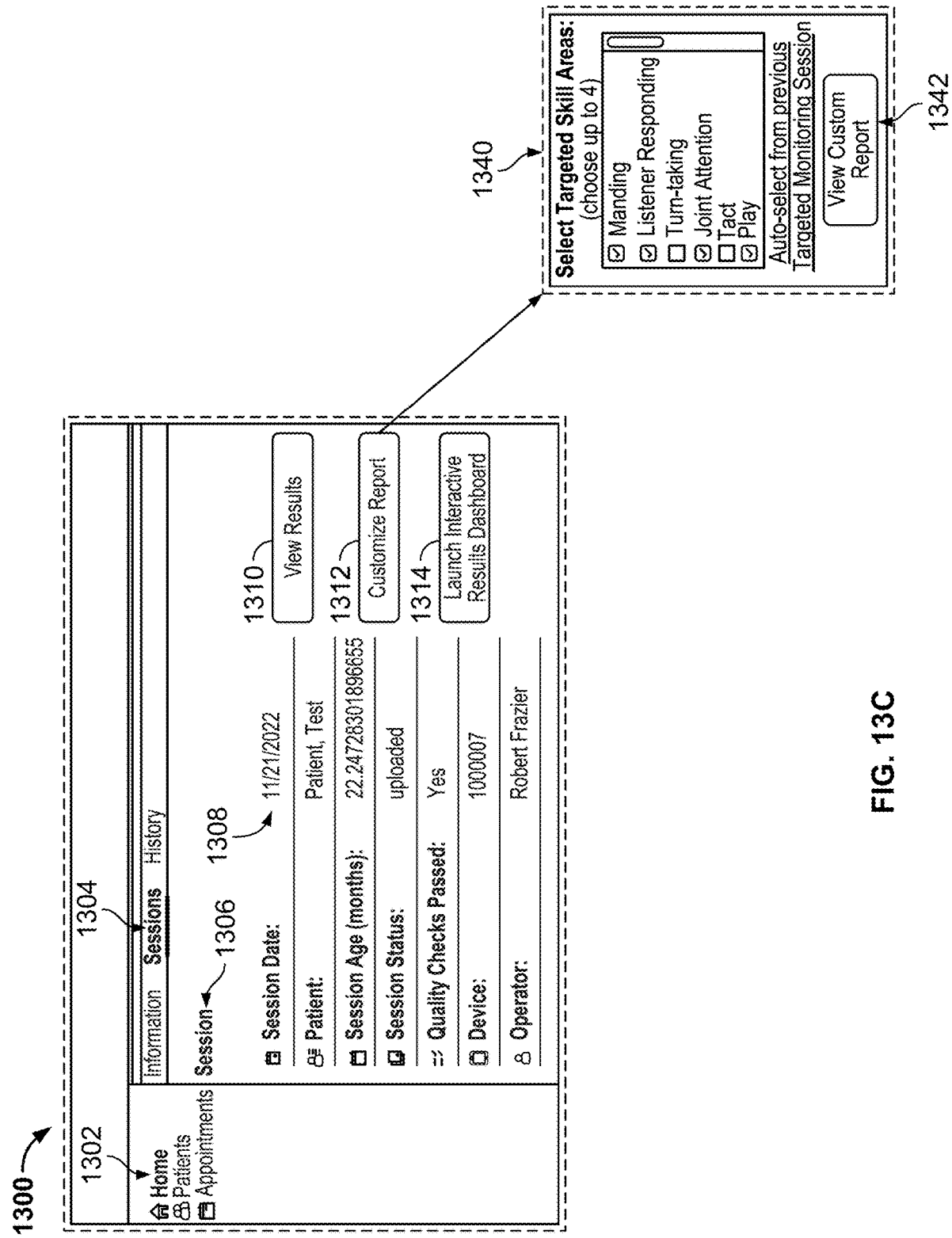
FIG. 13C illustrates an example illustrative window presented on the user device for selecting targeted skill areas to generate a custom report, according to one or more embodiments of the present disclosure.

In some implementations, e.g., as discussed with further details in FIGS. 13A-13C, the techniques enable to show information (e.g., behaviors) of a patient in one or more specific skill areas in a diagnostic report of the patient to a user (e.g., a treatment provider, a clinician, or a patient's guardian). The information of the patient can be shown, e.g., in comparison with information of the reference group such as a distribution map (e.g., a salience map) or frames/moments showing areas of typical looking behaviors). The information of the patient can include the patient's convergent looking percentage (or attendance percentage) of moments relevant to a specific skill area. The one or more specific skill areas for the patient can be automatically selected for, e.g., those with the greatest amount of reliable data, the most popularly requested skills, those with a particularly high, low, or representative score, or a combination thereof. The one or more specific skill areas can be previously selected as targeted skill areas when starting a targeted monitoring session or when customizing diagnostic results for the patient. If a monitoring session is performed and there are one or more previous sessions performed with the patient, the monitoring report can indicate a change of the patient's convergent looking percentages in comparison with previous sessions. In such a way, the user (e.g., a treatment provider, a clinician, or a patient guardian) can see whether the patient has any improvement in one or more targeted skill areas, whether a treatment for the patient works or is effective, and/or whether a new or adjusted treatment can be used to replace a current treatment.

Figure 13D:
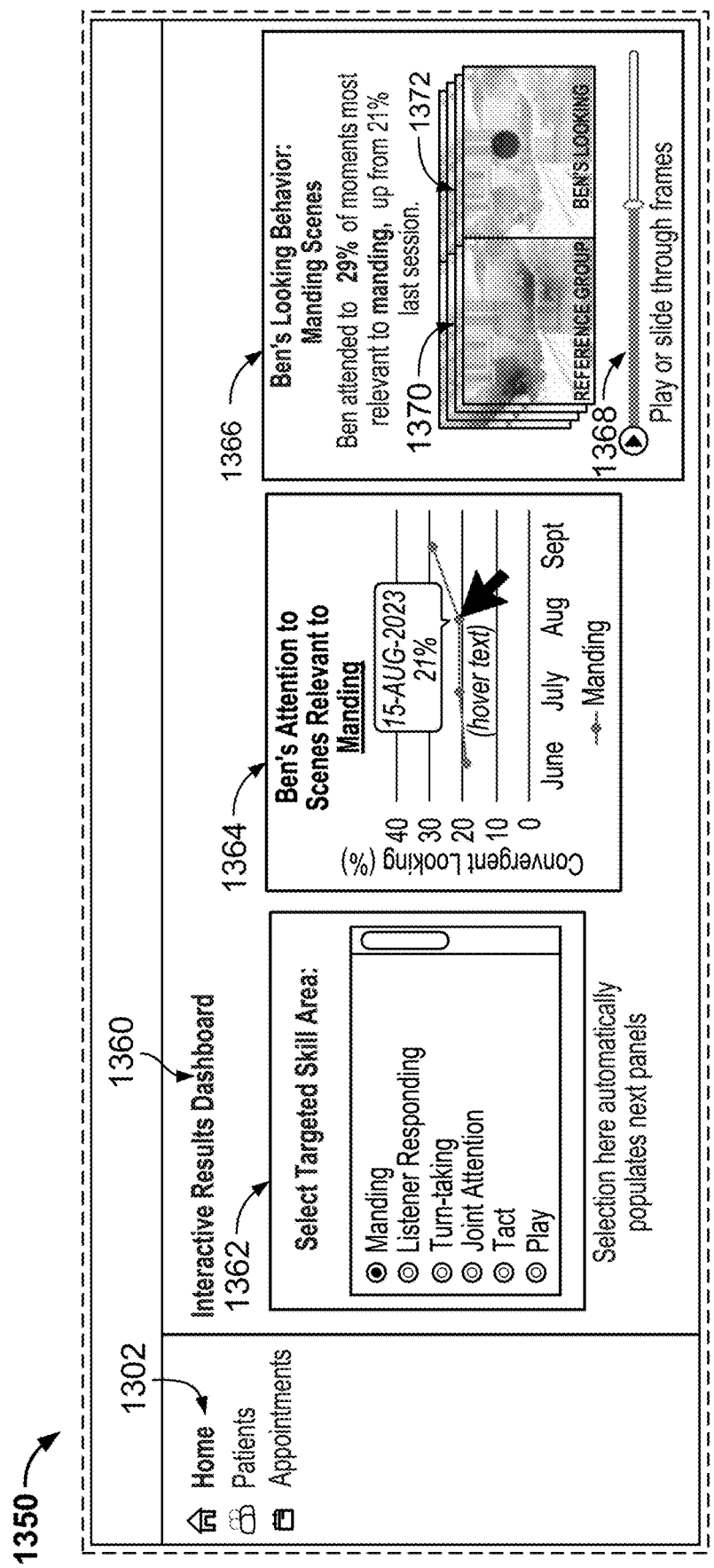
FIG. 13D illustrates an example interactive results dashboard presented on the user device, according to one or more embodiments of the present disclosure.

The techniques can also enable the user to select an interactive result dashboard from a patient session page on the web portal, e.g., as discussed with further details in FIG. 13D. The user can interactively explore results of any skill areas, e.g., patients' scores of a specific skill over a period of time or over a number of sequential sessions, and/or moment-by-moment (or frame-by-frame) comparisons of behaviors (e.g., looking behaviors) of the patient and the reference group. For example, the user can view possible skills grouped by a skill area or a developmental concept, age, or treatment type. The interactive result dashboard enables the user to select a subset of targeted skill areas of interest and view combined metrics for the selected subset. The interactive result dashboard can also enable the user to watch video or look through moments/frames of the patient's behavior at each moment contributing to skill-specific metrics, and/or alongside the behavior of the reference group and/or still images of the scene content.

In some implementations, the patient-side computing device can be assembled with a recording device (e.g., as described with further details in FIGS. 1A-1B), besides an eye-tracking device, or one or more external recording devices can be configured to record videos and/or audios of patients during a watching session, during unstructured social interactions, and/or during a treatment session. Those videos and/or audios can be processed to generate multi-modal data by an artificial intelligence (AI) model, such as a machine learning (ML) model, a single-layer neural network model, a multi-layer neural network model, or another trained AI model that has been trained with videos/audios of a reference group during the same sessions with expert clinicians' guidance/annotations for a list of treatment-specific skills. The multi-modal data can replace, supplement, validate, or provide additional context to the treatment-specific skills monitoring or developmental disorder diagnosis, assessment, and/or severity measures.

In some implementations, the eye-tracking device includes one or more eye-tracking units configured to directly capture/track eye movements of a patient (e.g., by detecting reflected and/or scattered illumination light such as infrared light) by the one or more eye-tracking units. In some implementations, the eye-tracking device includes one or more image acquisition devices (e.g., a camera) configured to determine eye movements of a patient based on captured images of eyes or positions of eyes of the patient and/or captured images of head movements/facial data while the patient is watching visual stimuli. In some implementations, the eye-tracking device includes one or more eye-tracking units and one or more image acquisition devices, and eye movement data can include at least one of the direct eye movements of the patient, the captured images and/or positions of the eyes of the patient, or eye movements derived from the captured images and/or positions.

In some implementations, the eye-tracking device is configured to convert the eye movement data of the patient into eye-tracking data that can contain information such as pupil position, gaze vector of each eye, and/or gaze point. In some implementations, the eye-tracking device is configured to determine first eye-tracking data based on the direct eye movements of the patient, and second eye-tracking data based on derived eye movements of the patient based on the captured images and/or positions of the eyes of the patient. The first eye-tracking data and the second eye-tracking data can replace, supplement, validate, or provide additional context to each other. The eye-tracking device can be configured to generate final eye-tracking data for the patient based on the first eye-tracking data and the second eye-tracking data.

The eye-tracking device can transmit eye-tracking data of a patient to an evaluation system (such as EarliPoint) for processing, e.g., to generate an assessment report or an evaluation report for the patient. The evaluation system can include, e.g., a cloud server as described in the present disclosure such as cloud server 110 of FIG. 1A or a cloud server with respect to FIGS. 2A-2G. In some cases, the eye-tracking device transmits the first eye-tracking data to the evaluation system for processing. In some cases, the eye-tracking device transmits the second eye-tracking data to the evaluation system for processing. In some cases, the eye-tracking device transmits the first eye-tracking data and the second eye-tracking data to the evaluation system for processing, where processed results based on the first eye-tracking data and the second eye-tracking data can replace, supplement, validate, or provide additional context to each other. In some cases, the eye-tracking device transmits the final eye-tracking data to the evaluation system for processing. In some cases, the eye-tracking device transmits the first eye-tracking data, the second eye-tracking data, and the final eye-tracking data to the evaluation system for processing.

Figure 15A:
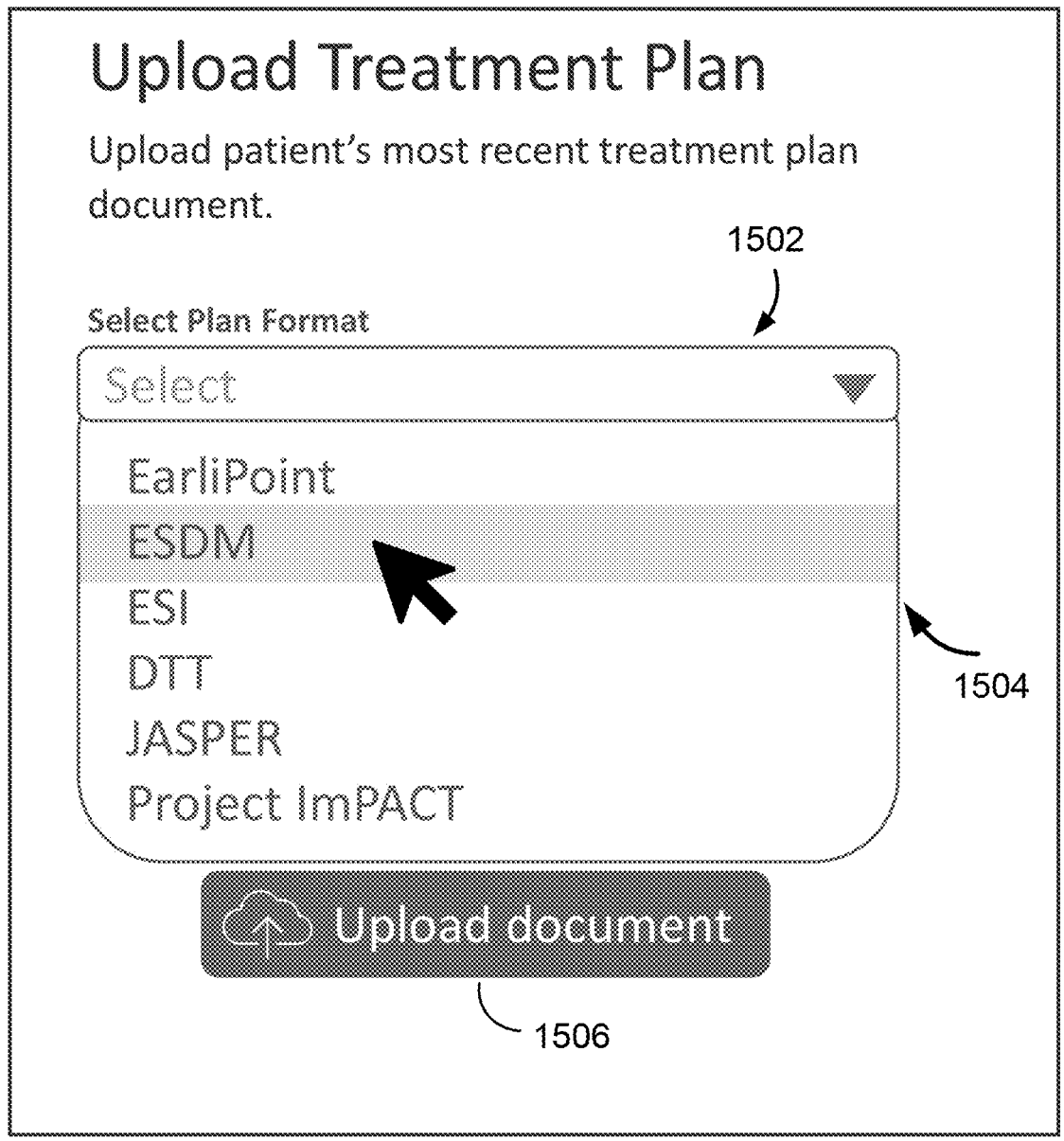
FIG. 15A illustrates an example illustrative user interface presented on a computing device when a cloud server runs a data aggregator application, according to one or more embodiments of the present disclosure.
Figure 15B:
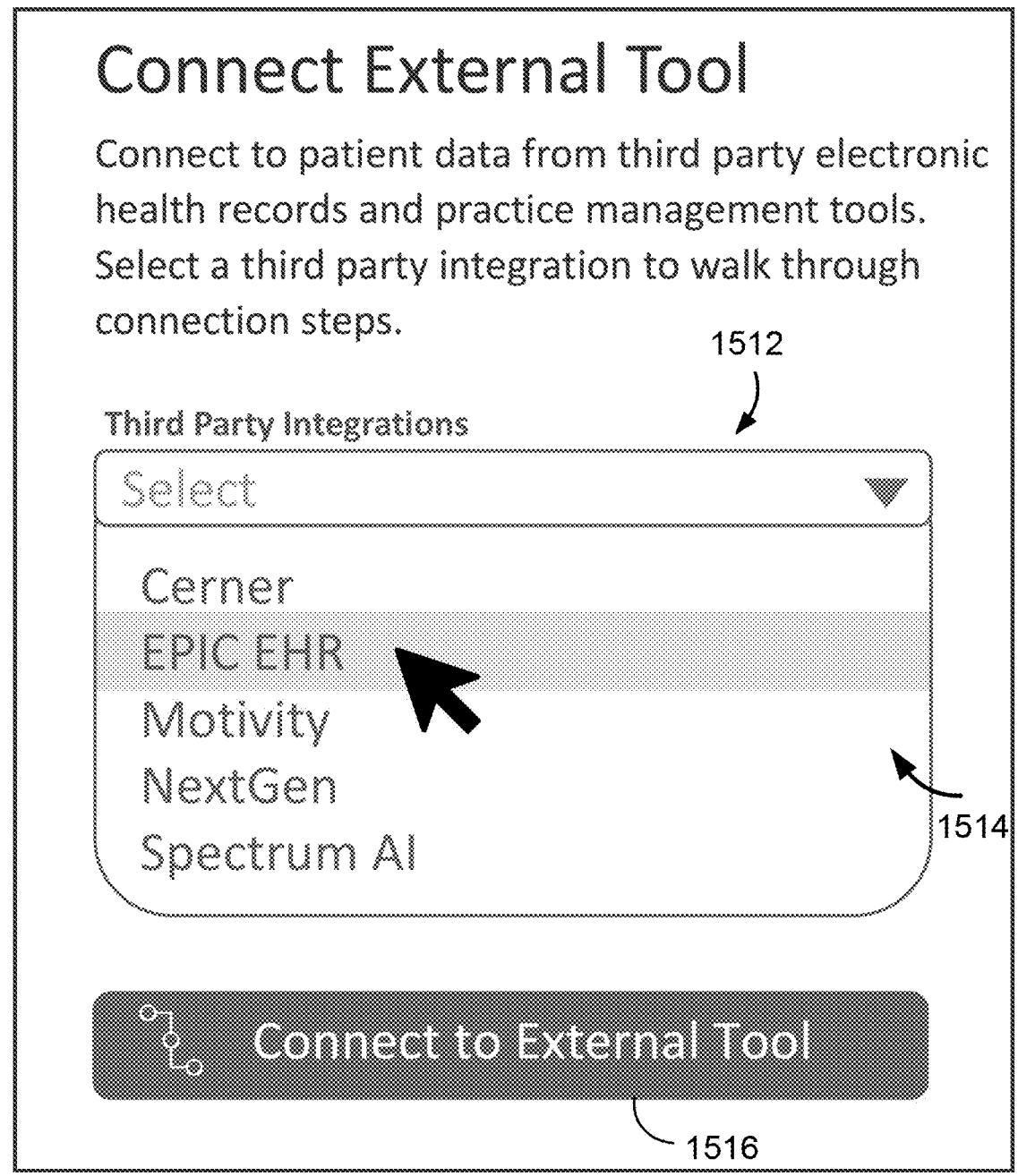
FIG. 15B illustrates an example illustrative user interface presented on a computing device when a cloud server runs a data aggregator application to aggregate data from an external tool, according to one or more embodiments of the present disclosure.

In some implementations, the evaluation system for development disorders provides a data aggregator, e.g., as described with further details in FIGS. 15A-15B. The data aggregator can be configured to connect with one or more third party tools to ingest (e.g., by parsing) a patient's treatment data, including data from EHR (Electronic Health Records)/EMR (Electronic Medical Record) and ABA (Applied Behavior Analysis) practice management tools, and optionally reference patients' data, ingest (e.g., by parsing) the patient's (and/or other patients') treatment plans, goals, behavioral presses, patient responses over time, and other relevant clinical or treatment data. The data aggregator can be configured to, combined with assessment data by the evaluation system, build a massive and unique data repository of clinical treatment and patient trajectories, which can enable a comprehensive understanding on the patient. The techniques enable the data aggregator to retrieve reference data based on patient information (e.g., based on similar group, age, background, developmental stage, demography, or region), so that the evaluation system can generate a specific treatment plan based on all the relevant data including patient's own data and the reference data.

In some implementations, the evaluation system is configured to provide a practice management tool (e.g., as described with further details in FIGS. 15C-15D and 15H) that can offer its own direct entry practice management tool for clinicians, e.g., who haven't use a third party system for tracking treatment plans and data. The practice management tool can be configured such that clinicians can manually enter treatment plan information or upload an existing treatment plan document via a web browser application of the evaluation system. Clinicians can also add notations to treatment goals or enter treatment data live during treatment delivery, which can also be used to track treatment billing. Inputs can be automatically parsed and processed by the evaluation system to pull out and tabulate relevant data including hours spent per skill.

Figures 12A, 12B:
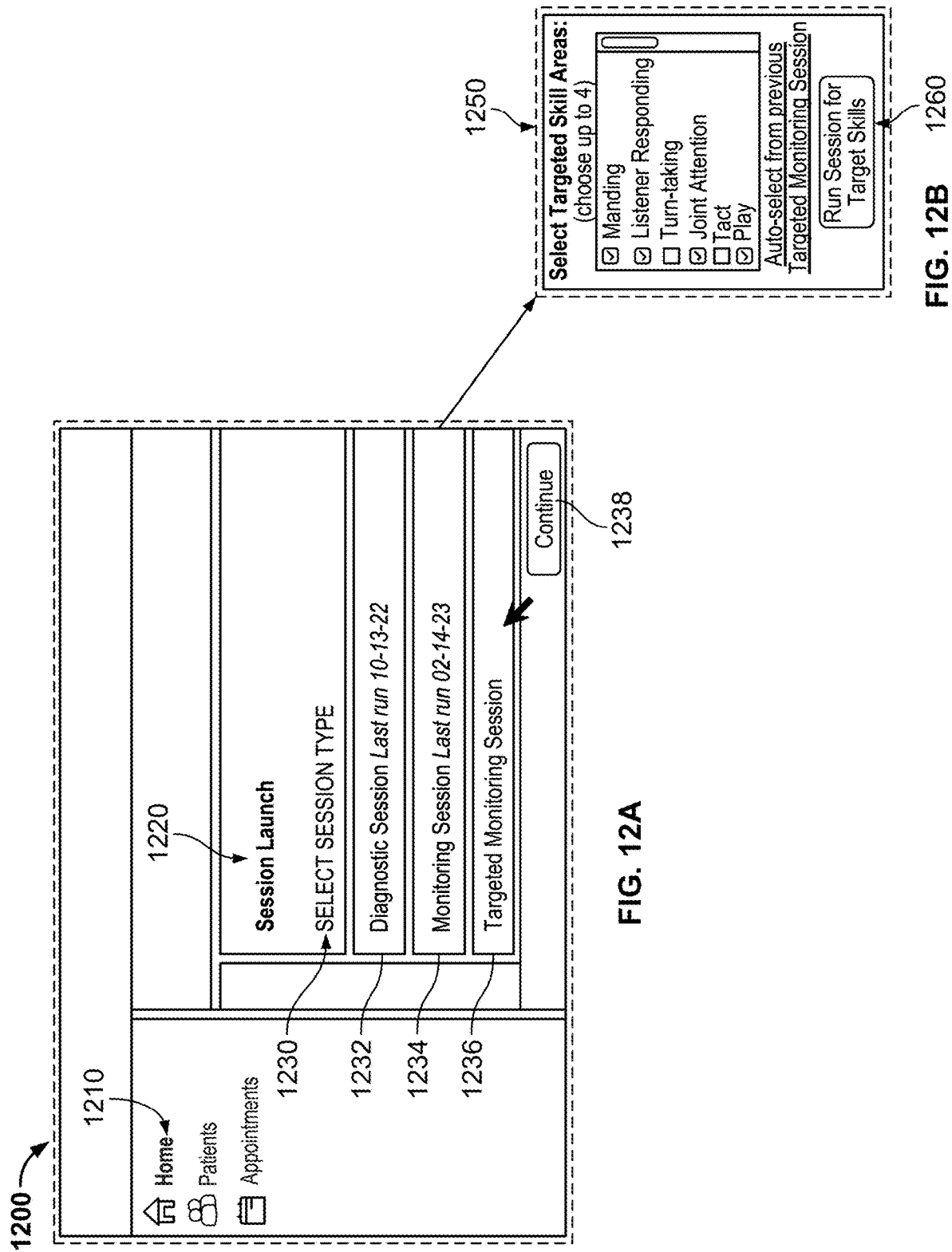
FIG. 12A illustrates an example illustrative user interface presented on an operator device for session launch, according to one or more embodiments of the present disclosure.
FIG. 12B illustrates an example illustrative window presented on the operator device for selecting targeted skill areas for targeted monitoring session, according to one or more embodiments of the present disclosure.
Figure 15C:
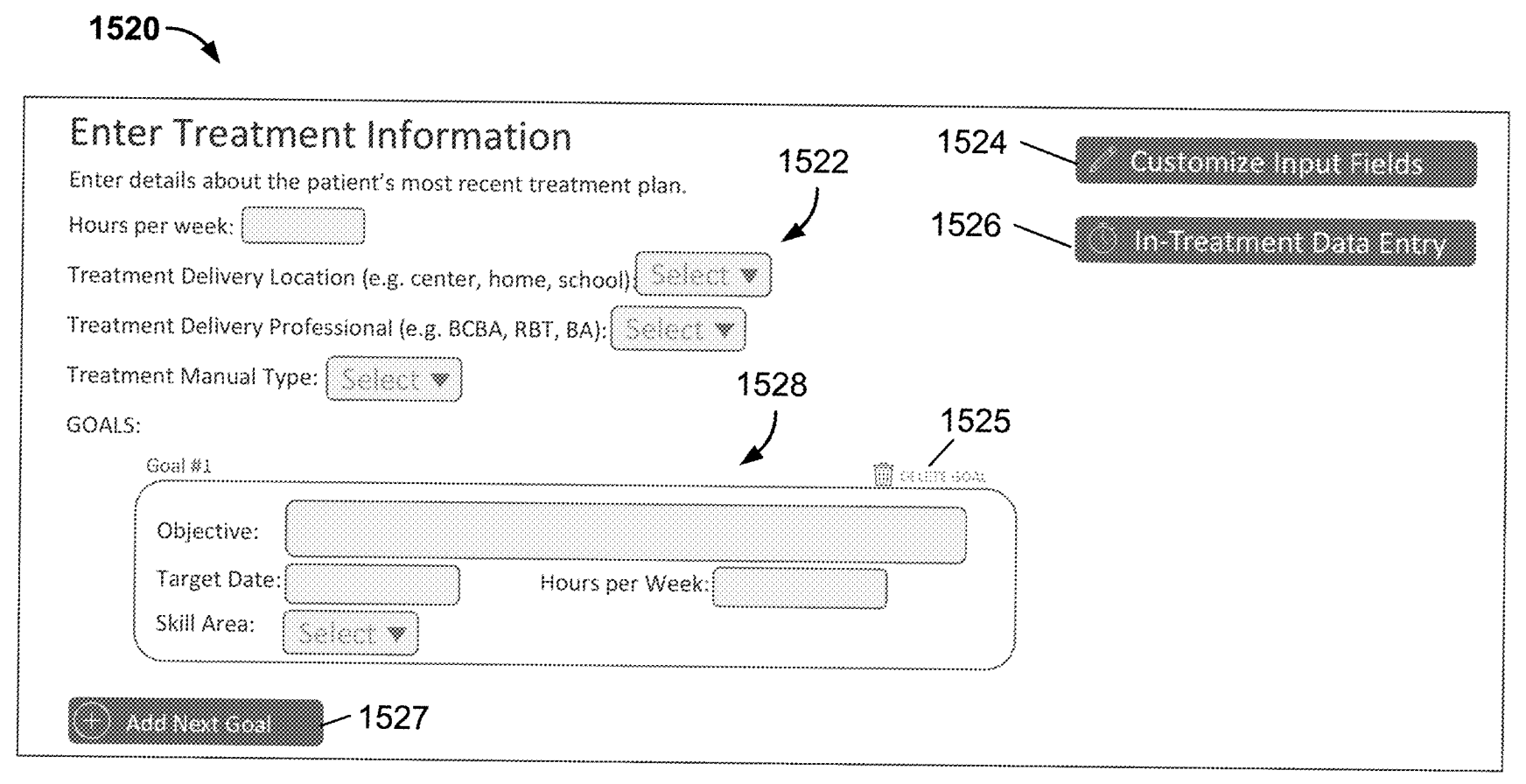
Figure 15D:
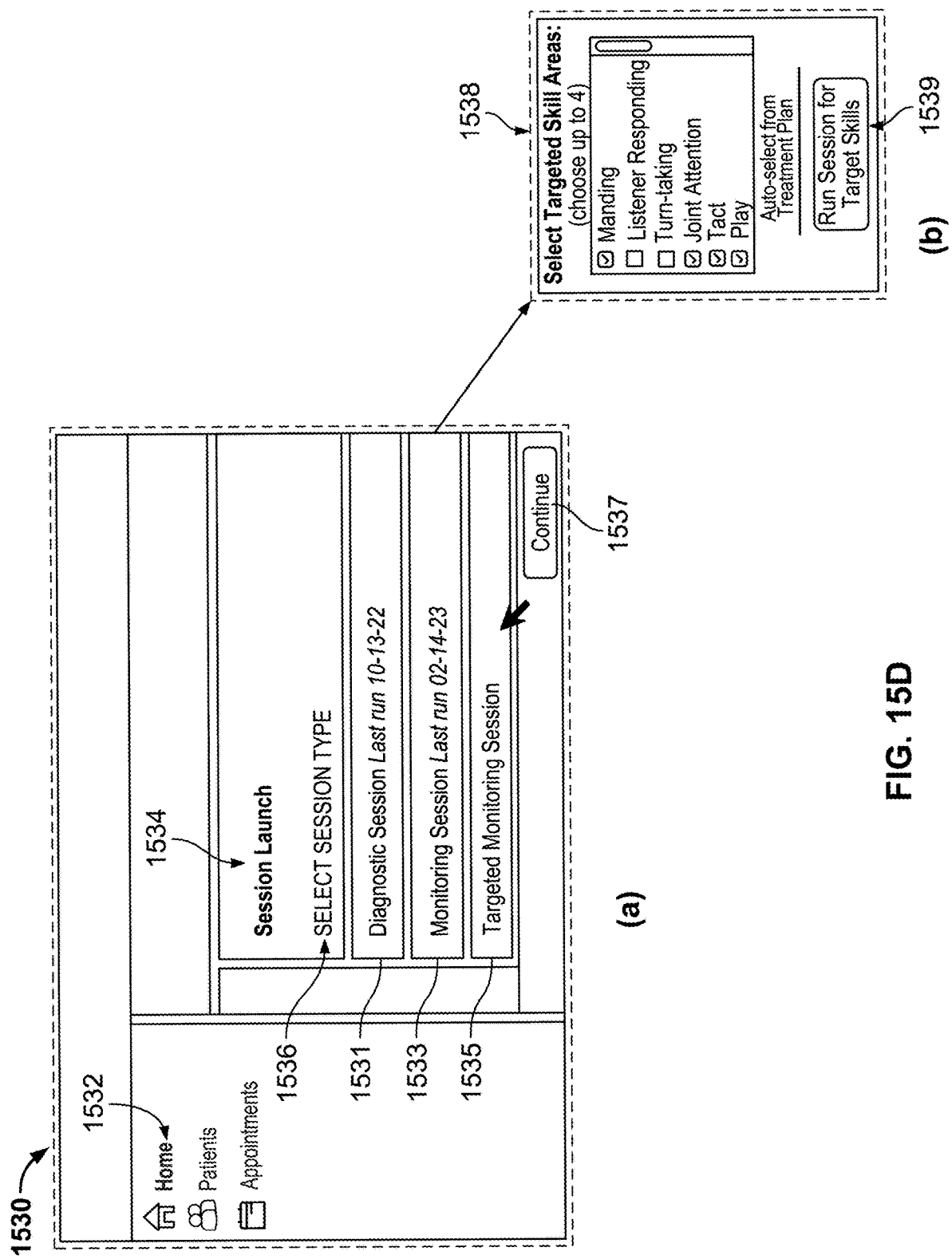
FIG. 15D illustrates an example illustrative user interface presented on a computing device for session launch, according to one or more embodiments of the present disclosure.

The evaluation system can be also configured to execute a targeted monitoring session or a customizable eye-tracking session with a playlist configured to quantify progress in the skill areas most relevant to the patient's treatment plan, strengths, weaknesses, and/or developmental stage (e.g., as described with further details in FIG. 12A-12B or 15D). The evaluation system can be configured for treatment progress monitoring, e.g., automated comparison of the patient's current treatment plan to objective skill-level progress in the eye-tracking session to identify areas of the patient's treatment that correlate with measurable skill improvement. The evaluation system can be configured to generate a prescriptive treatment plan based on models and aggregated treatment data, e.g., by an artificial intelligence (AI) model or algorithm. The evaluation system can recommend an optimal treatment approach (e.g., EarliPoint, ESDM (The Early Start Denver Model), ESI (Early Social Interaction), DTT (Discrete Trial Training), Jasper (Joint Attention Symbolic Play Engagement Regulation), or project ImPACT (Improving Parents As Communication Teachers)) and generate a specific plan based on the patient's unique presentation. The treatment plan can be custom formatted to import easily to and from third-party tools.

In some embodiments, the evaluation system can provide specific tutorials (e.g., videos/audios/texts) associated with a selected treatment plan to treatment providers, such that the treatment providers can understand the selected treatment plan and learn how to implement the selected treatment plan. The specific tutorials are content-based and can be selected from a number of tutorials based on the selected treatment plan, such that the treatment providers can understand the selected treatment plan just based on the selected tutorials (e.g., less than 10 tutorials), without viewing a large number of tutorials (e.g., about 100 tutorials). In such a way, the evaluation system enables unexperienced treatment providers or treatment provides with little experience (e.g., providers in rural areas) to understand, interpret, and/or execute the selected treatment plan. This also enables experienced providers to use the selected tutorials as evidence or references or support to understand, interpret, and/or execute the selected treatment plan.

In some embodiments, the evaluation system generates an evaluation report of developmental disorder for a patient, e.g., as described with further details in FIGS. 8A-8C or FIGS. 16A-16F. The evaluation report can include patient information, session information, a summary of evaluation results (e.g., ASD or non-ASD). The evaluation results can also include assessment results that can include one or more index scores, e.g., social disability index score, verbal ability index score, and nonverbal learning index score, which can be obtained from an artificial intelligence (AI) model, such as a machine learning (ML) model, a single-layer neural network model, a multi-layer neural network model, or another trained AI model, in response to the input of the processed session data and the corresponding model data (described above) for a particular session. The evaluation report can include correlations (e.g., side-by-side graphic correlations) that present one or more of the individual index scores of the evaluation system (as obtained from the AI model described above) correlated to a "reference assessment measure," such as ADOS-2 Measures or Mullen Scales of Early Learning Measures, thereby providing added comprehension for the healthcare provider viewing the evaluation report (even where the healthcare provider has less experience). As used herein, the term "reference assessment measure" represents a measurement value from an assessment scale, tool, or system, which has been professionally adopted, implemented, and/or peer-reviewed by those medically trained in diagnosing one or more development disorders (such as ASD). The assessment scale, tool, or system can include at least one of ADOS-2 (Autism Diagnostic Observation Schedule-Second Edition), MSEL (Mullen Scales of Early Learning), ADI-R (Autism Diagnostic Interview, Revised), CARS (Childhood Autism Rating Scale), VABS (Vineland Adaptive Behavior Scales), DAS-II (Differential Ability Scales II), WISC (Wechsler Intelligence Scale for Children), WASI (Wechsler Abbreviated Scale of Intelligence), or VB-MAPP (Verbal Behavior Milestones Assessment and Placement Program). The term "reference assessment measure" can be also referred to as "clinical reference assessment measure," "developmental assessment measure," "developmental reference measure," "standard clinical assessment," "standard developmental reference measure," or any other suitable term. In some examples, the reference assessment measure is used for assessment of one or more developmental disorders or one or more developmental skills. In some examples, the reference assessment measure is used for treatment. The evaluation report can also include visualized individual test results (e.g., including a patient's looking behavior while watching a visual stimuli), and/or attention funnel (e.g., moment-by-moment looking behavior over a number of visual scenes).

To provide an overall understanding of the systems, devices, and methods described herein, certain illustrative embodiments will be described. It will be understood that such data, if not indicating measures for a disorder, may provide a measure of the degree of typicality of normative development, providing an indication of variability in typical development. Further, all of the components and other features outlined below may be combined with one another in any suitable manner and may be adapted and applied to systems outside of medical diagnosis. For example, the interactive visual stimuli of the present disclosure may be used as a therapeutic tool. Further, the collected data may yield measures of certain types of visual stimuli that patients attend to preferentially. Such measures of preference have applications both in and without the fields of medical diagnosis and therapy, including, for example advertising or other industries where data related to visual stimuli preference is of interest.

Example Environments and Systems

Figure 1A:
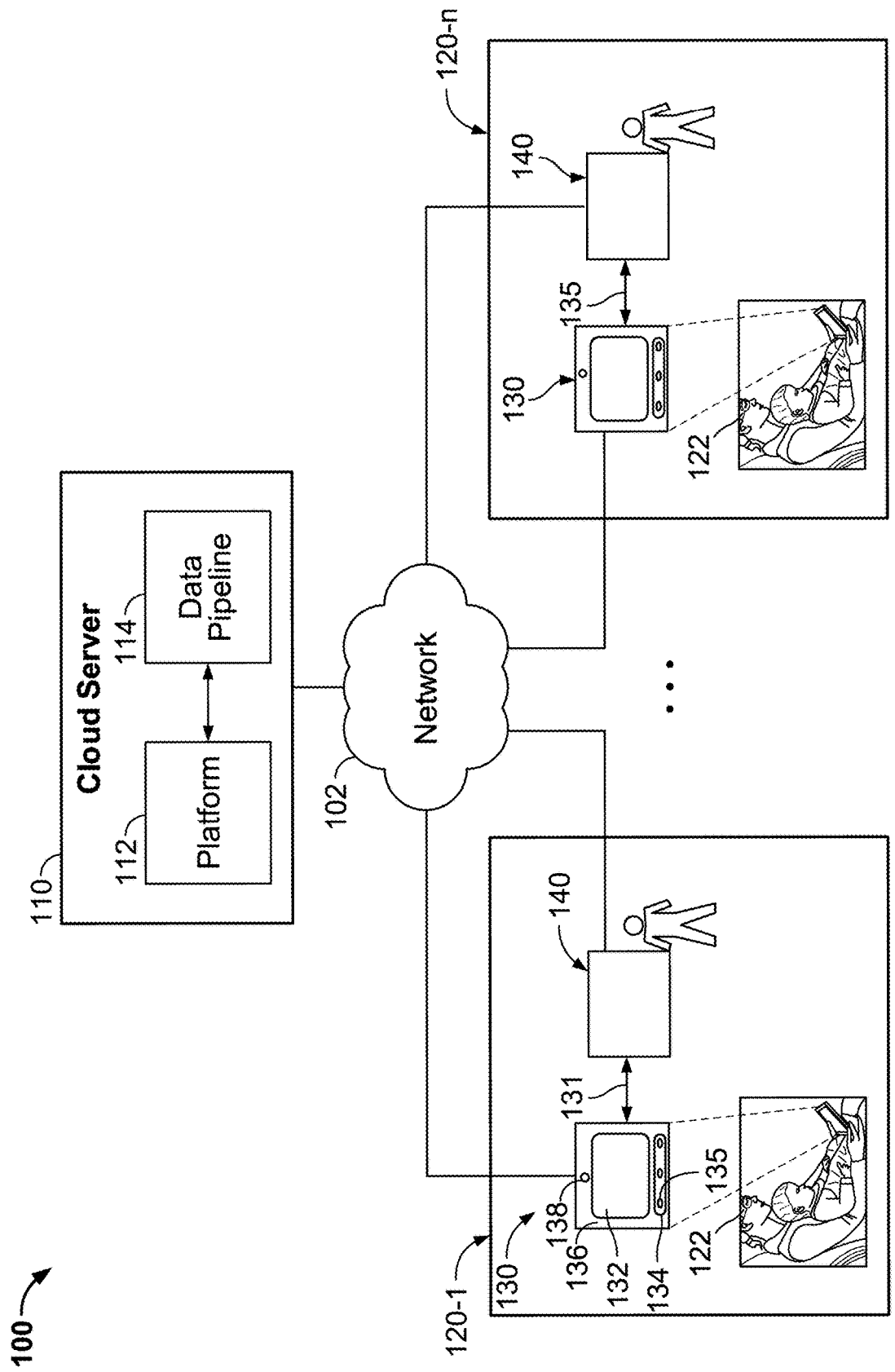
FIG. 1A is a block diagram of an example environment for assessing developmental disorders, according to one or more embodiments of the present disclosure.

FIG. 1A is a block diagram of an example environment 100 for assessing developmental disorders via eye tracking, according to one or more embodiments of the present disclosure. The environment 100 involves a cloud server 110 and a plurality of computing systems 120-1, . . . , 120-n (referred to generally as computing systems 120 or individually as computing system 120) that communicate via a network 102. The cloud server 110 can provide developmental disorder assessment or diagnostic services to a number of users (e.g., treatment providers). A treatment provider can use a corresponding computing system 120 to conveniently and reliably collect data for patients in sessions (e.g., procedures associated with collecting data) of any age, from newborns to the elderly, with example embodiments described below that are particularly suited for toddlers or other young patients. The data collected in a session (or session data) can include eye-tracking data generated in response to display of specific predetermined visual stimuli (e.g., one or more videos) to the patients. The computing system 120 can securely transmit the session data to the cloud server 110, and the cloud server 110 can store, process, and analyze the session data for the diagnosis of ASD or other cognitive, developmental, social or mental abilities or disabilities for the patients, and provide diagnostic results or reports to the treatment providers in a highly secure, robust, speedy, and accurate manner, as discussed with further details below, A treatment provider can be a single healthcare organization that includes, but is not limited to, an autism center, a healthcare facility, a specialist, a physician, or a clinical study. The healthcare organization can provide developmental assessment and diagnosis, clinical care, and/or therapy services to patients. As illustrated in FIG. 1A, a patient (e.g., an infant or a child) can be brought by a caregiver (e.g., a parent) to the healthcare facility. An operator (e.g., a specialist, a physician, a medical assistant, a technician, or other medical professional in the healthcare facility) can use the computing system 120 to collect, e.g., non-invasive, eye-tracking data from the patient while he or she watches visual stimuli (e.g., dynamic visual stimuli, such as movies) depicting common social interactions (e.g., dyadic or triadic interactions). The stimuli displayed to the patient for purposes of data collection can be specific for the patient, e.g., based on age and condition of the patient. The stimuli can be any suitable visual image (whether static or dynamic), including movies or videos, as well as still images or any other visual stimuli. It will be understood that movies or videos are referenced solely by way of example and that any such discussion also applies to other forms of visual stimuli.

In some embodiments, as illustrated in FIG. 1A, the computing system 120 includes at least two separate computing devices 130 and 140, e.g., an operator-side computing device 140 and at least one patient-side computing device 130. Optionally, the two computing devices 130 and 140 can be wirelessly connected, e.g., via a wireless connection 131, without physical connection. The wireless connection 131 can be through a cellular network, a wireless network, Bluetooth, a near-field communication (NFC) or other standard wireless network protocol. In some embodiments, the patient-side computing device 130 is configured to connect to the operator-side computing device 140 through a wired connection such as universal serial bus (USB), e.g., when the wireless connection 131 fails.

In some cases, the two computing devices 130 and 140 communicate with each other by separately communicating with the cloud server 110 via the network 102, and the cloud server 110, in turn, provides communication between the operator-side computing device 140 and the patient-side computing device 130. For example, as discussed with further details in FIGS. 4A-4B, an operator can log in a web portal running on the cloud server 110 for device management, patient management, and data management, e.g., through a web-based operator application. The operator can use the operator-side computing device 140 (e.g., a tablet) to communicate with multiple patient-side portable devices 130, e.g., in a same medical facility, for eye-tracking data acquisitions of multiple patients in multiple sessions, which can greatly simplify the computing system 120, reduce the system cost, improve work efficiency, and reduce the operator's workload.

Figure 19:
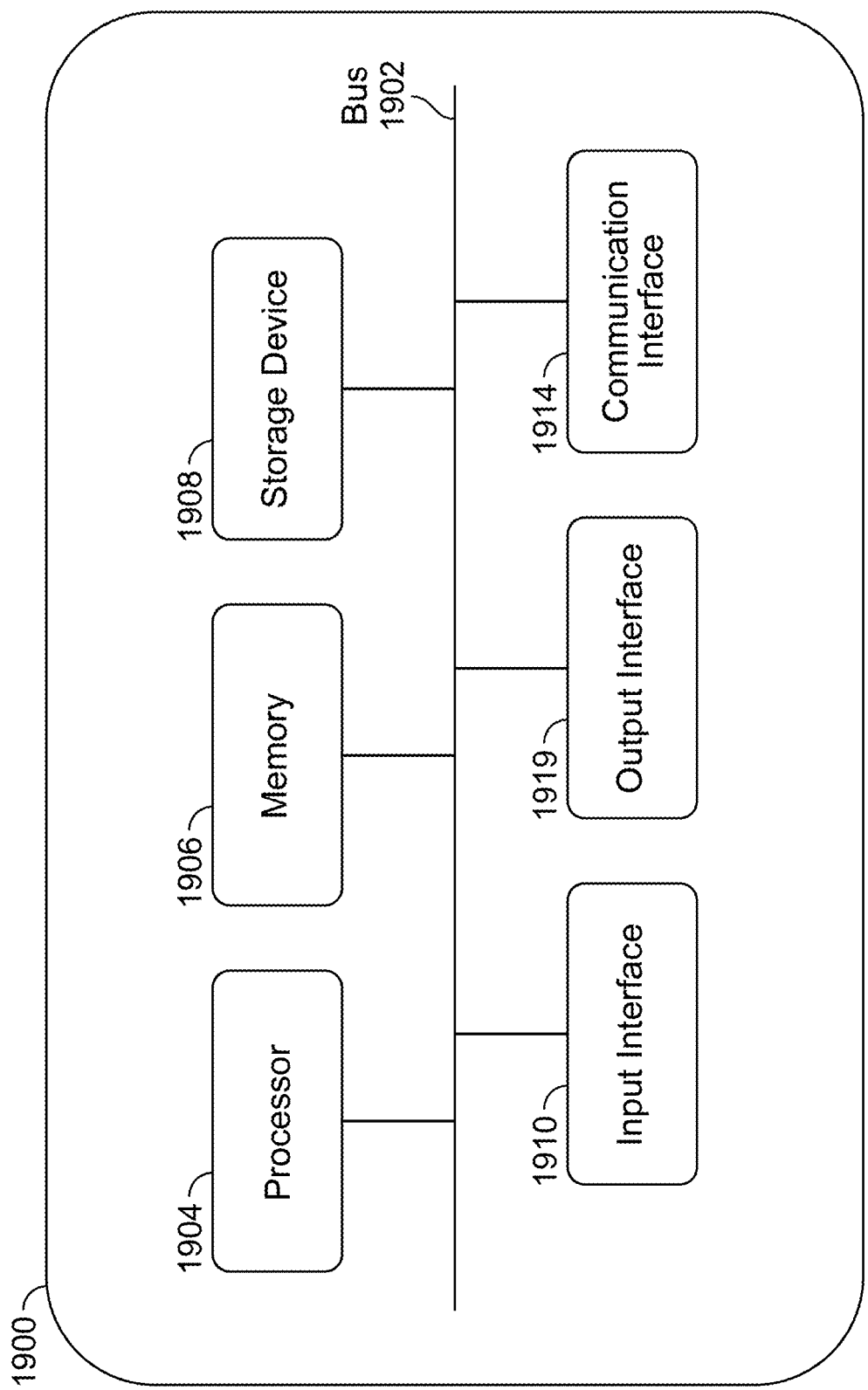
FIG. 19 illustrates an architecture for a computing device, according to one or more embodiments of the present disclosure.

The computing device 130, 140 can include any appropriate type of device such as a tablet computing device, a camera, a handheld computer, a portable device, a mobile device, a personal digital assistant (PDA), a cellular telephone, a network appliance, a smart mobile phone, an enhanced general packet radio service (EGPRS) mobile phone, or any appropriate combination of any two or more of these data processing devices or other data processing devices. As an example, FIG. 19 illustrates an architecture for a computing device, which can be implemented as the computing device 130 or 140.

At least one of the computing device 130 or the computing device 140 can be a portable device, e.g., a tablet device. In some cases, both computing devices 130, 140 are portable and wirelessly connected with each other. In such a way, the computing system 120 can be more easily moved and relocated, and allows more flexibility for the operator to select his or her position relative to the patient. For example, the operator (carrying the operator-side computing device 140) is not physically tethered to the patient-side computing device 130 and can easily position himself or herself in an optimal location (e.g., away from the patient's immediate field of view) during setup and data collection. Further, the patient (e.g., a toddler or other child) can be carried by a caregiver (e.g., a parent) in a more suitable location and in a more comfortable way, which may enable the patient to be more engaged in the played visual stimuli for effective and accurate eye-tracking data acquisition. The patient-side computing device 130 can be carried by the caregiver or arranged (e.g., adjustably) in front of the patient and the caregiver.

As illustrated in FIG. 1A, the patient-side computing device 130 includes a screen 132 (e.g., a display screen) for displaying or presenting visual stimuli to the patient. The patient-side computing device 130 can also include an eye-tracking device 134 or be integrated with an eye-tracking device 134 in a same housing 136. In some embodiments, the patient-side computing device 130 integrated with the eye-tracking device 134 together can be referred to as an eye-tracking console or an eye-tracking system.

The eye-tracking device 134 can be connected to the patient-side computing device 130 via a wired connection, e.g., using an USB cable or an electrical wire or using electrical pins. In some cases, the eye-tracking device 134 is configured to be connected to the patient-side computing device 130 via a wireless connection, e.g., Bluetooth or NFC. The eye-tracking device 134 can be arranged in a suitable position with respect to the screen 132 and/or the patient, where the eye-tracking device 134 can capture eye movement of the patient while watching the visual stimuli, while also minimizing visual distractions from the patient's field-of-view.

As illustrated in FIG. 1A, the eye-tracking device 134 can include one or more eye-tracking units (or sensors) 135 arranged under the bottom of the screen 132. The one or more eye-tracking units 135 can be arranged on one or more sides of the screen 132, on top of the screen 132, and/or around the screen 132. The one or more eye-tracking units 135 can be mechanically mounted to the patient-side computing device 130 at a location adjacent to a periphery of the screen 132. For example, the patient-side computing device 130 can include the screen 132 and a screen holder structure that retains the eye-tracking device 134 in a fixed, predetermined location relative to the screen 132. In some embodiments, the eye-tracking device 134 includes a first eye-tracking unit configured to capture or collect eye movement of a left eye of a patient and a second eye-tracking unit configured to capture or collect eye movement of a right eye of the patient. The eye-tracking device 134 can further include a third eye-tracking unit configured to capture positions of the eyes of the patient or an image acquisition unit (e.g., a camera) configured to capture an image of the eyes of the patient. In some implementations, the eye-tracking device 134 is configured to determine eye movements based on captured positions and/or images of the eyes of the patient by the third eye-tracking unit. In some implementations, eye-movement data of the patient includes at least one of collected eye movements of the eyes of the patient (e.g., by the first and second eye-tracking units), eye movements derived from the captured positions and/or images (e.g., by the third eye-tracking unit), the captured positions, or the captured images. As described below, the eye-movement data can be converted into eye-tracking data to be processed in the cloud server 110.

An eye-tracking unit includes a sensor that can detect a person's presence and follow what he/she is looking at in real-time or measure where the person is looking or how the eyes react to stimuli. The sensor can convert eye movements of the person into a data stream that contains information such as pupil position, the gaze vector for each eye, and/or gaze point. In some embodiments, an eye-tracking unit includes a camera (e.g., an infrared-sensitive camera), an illumination source (e.g., infrared light (IR) illumination), and an algorithm for data collection and/or processing. The eye-tracking unit can be configured to track pupil or corneal reflection or reflex (CR). The algorithm can be configured for pupil center and/or cornea detection and/or artifact rejection. In some embodiments, the eye-tracking unit includes an image acquisition unit (e.g., a camera) configured to capture images of eyes of a patient while the patient is watching visual stimuli. The eye-tracking unit can be configured to process the captured images of the eyes of the patient to determine eye movements of the eyes while the patient is watching the visual stimuli. The eye-tracking device 134 (e.g., the eye-tracking unit) can be configured to convert the eye movement data to eye-tracking data that can also include information such as pupil position, the gaze vector for each eye, and/or gaze point. In some implementations, the eye-tracking device 134 can transmit the eye-tracking data based on the captured images of the eyes to the cloud server 110 for further processing.

In some implementations, the eye-tracking device 134 determines first eye-tracking data based on tracked pupil or corneal reflection or CR, and determines second eye-tracking data based on the captured images of the eyes. The first eye-tracking data and the second eye-tracking data can be processed by the eye-tracking device 134 to replace, supplement, validate, or provide additional context to each other. The eye-tracking device 134 can be configured to generate final eye-tracking data for the patient based on the first eye-tracking data and the second eye-tracking data. The eye-tracking device 134 can transmit the final eye-tracking data based on the captured images of the eyes to the cloud server 110 for further processing. In some implementations, the eye-tracking device 134 transmits the first eye-tracking data and the second eye-tracking data to the cloud server 110 for further processing, where a first processed result based on the first eye-tracking data and a second processed result based on the second eye-tracking data can replace, supplement, validate, or provide additional context to each other. An assessment result can be determined based on the first processed result and the second processed result.

As there may be variations in eye size, fovea position and general physiology that can be accommodated for each individual, before using an eye-tracking unit to collect eye-tracking data for a participant (e.g., a patient), an eye-tracking unit can be first calibrated. In the calibration, a physical position of an eye is algorithmically associated with a point in space that the participant is looking at (e.g., gaze). Gaze position can be a function of the perception of the participant. In some embodiments, a calibration involves a participant looking at fixed, known calibration targets (e.g., points) in a visual field. Calibrations can include a single, centered target, or 2, 5, 9, or even 13 targets. The algorithm can create a mathematical translation between eye position (minus CR) and gaze position for each target, then create a matrix to cover the entire calibration area, e.g., with interpolation in between each target. The more targets used, the higher and more uniform the accuracy can be across the entire visual field. The calibration area defines the highest accuracy part of the eye-tracking unit's range, with accuracy falling if the eye moves at an angle larger than the targets used.

In some embodiments, an eye-tracking unit is capable of performing self-calibration, e.g., by creating models of the eye and passively measuring the characteristics of each individual. Calibration can also be done without the participant's active cooperation by making assumptions about gaze position based on content, effectively "hiding" calibration targets in other visual information. In some embodiments, no calibration is performed for an eye-tracking unit if useful data can be taken from raw pupil position, e.g., using a medical vestibulo-ocular reflex (VOR) system or a fatigue monitoring system.

In some cases, a validation can be performed to measure the success of the calibration, e.g., by showing new targets and measuring the accuracy of the calculated gaze. Tolerance for a calibration accuracy can depend on an application of the eye-tracking unit. For example, an error of between 0.25 and 0.5 degrees of visual angle may be considered acceptable. For some applications, more than 1 degree is considered a failed calibration and requires another attempt. Participants can improve on the second or third try. Participants who consistently have a high validation error may have a vision or physiological problem that precludes their participation in an experiment. The validation results can be expressed in degrees of visual angle and displayed graphically.

Figure 2A:
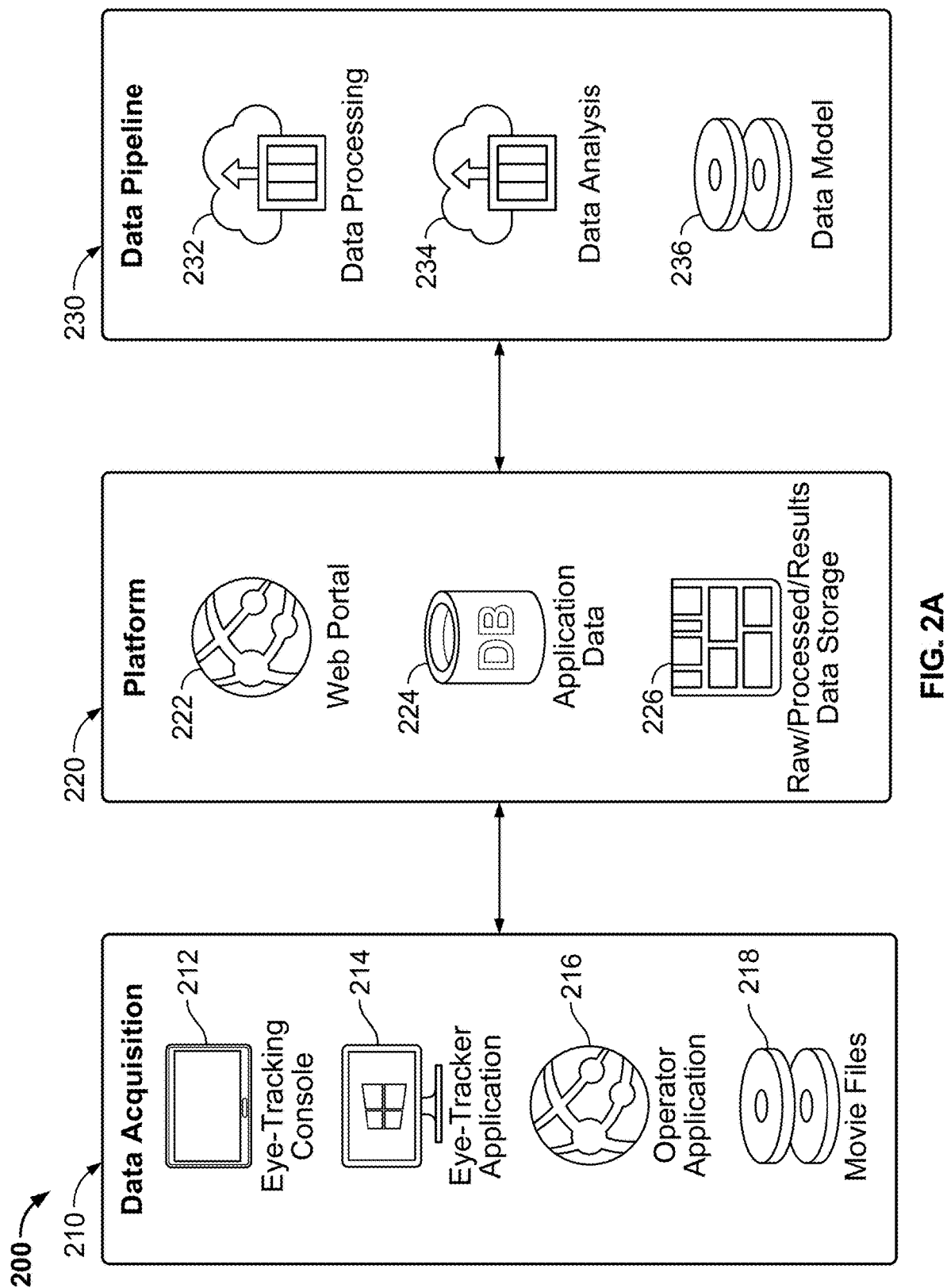
FIG. 2A is a block diagram of an example system for assessing developmental disorders via eye tracking, according to one or more embodiments of the present disclosure.

The patient-side computing device 130 can include, as illustrated in FIG. 2A, an eye-tracking application (or software) configured to retrieve or receive raw eye-tracking data collected by the eye-tracking device 134. The patient-side computing device 130 can generate session data based on the raw eye-tracking data, e.g., storing the raw eye-tracking data with associated information (timestamp information) in a data file (e.g., in .tsv format, .idf format, or any suitable format), as illustrated in FIG. 5(b). The session data can also include information of played or presented visual stimuli in another data file (e.g., in .tsv format or any suitable format), as illustrated in FIG. 5(a). The information can include timestamp information for each visual stimulus played.

In some embodiments, the patient-side computing device 130 stores a number of predetermined visual stimuli (e.g., movie or video files) that are grouped to correspond to patients of particular age groups and/or condition groups. For example, a first list of predetermined visual stimuli can be configured for ASD assessment for patients in a first age range (e.g., 5 to 16 months old), and a second list of predetermined visual stimuli can be configured for ASD assessment for patients in a second age range (e.g., 16 to 30 months old) different from the first age range. In some embodiments, an operator can use the operator-side computing device 140 to control which list of predetermined visual stimuli to play to a specific patient based on information of the specific patient. In some embodiments, the operator application sends age information upon patient selection to the eye-tracking application which then dynamically selects the appropriate preset playlist based on the age information, without operator intervention or selection. In some embodiments, the number of predetermined visual stimuli can be also stored in the operator-side computing device 140.

The testing methodology depends on the patient being awake and looking at the screen 132 of the patient-side computing device 130. During both the calibration as well as the data collection procedures, predetermined movies and/or other visual stimuli are presented to the patient via the patient-side computing device 130. These movies and/or other visual stimuli may include human or animated actors who make hand/face/body movements. As discussed with further details in FIG. 5, during the data collection period, the computing system 120 can periodically show calibration or fixation targets (that may be animated) to the patient. These data can be used later to verify accuracy.

Figure 1B:
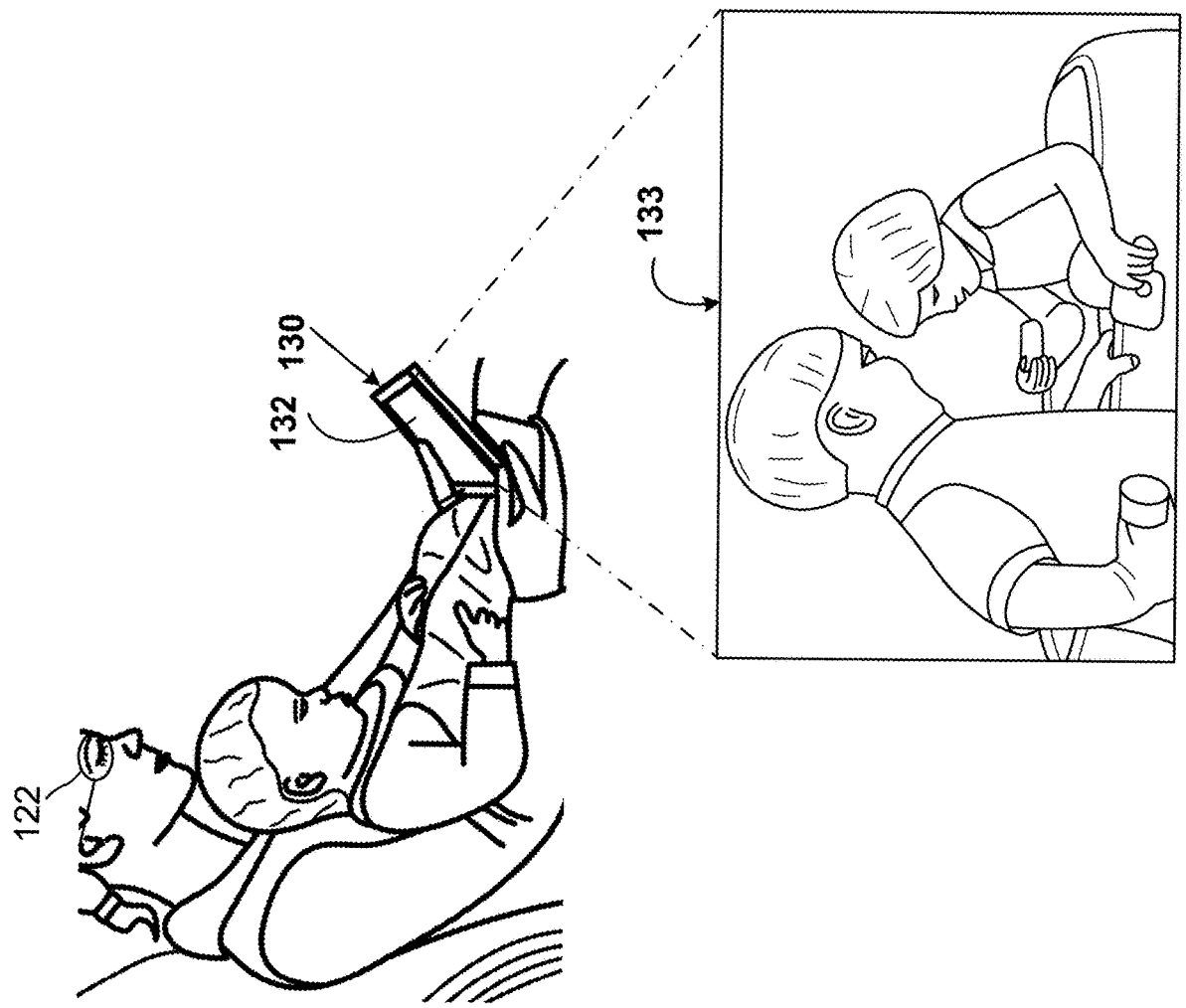
FIG. 1B shows an example of illustrative visual stimuli presented on a screen of a patient device, according to one or more embodiments of the present disclosure.

The visual stimuli (e.g., movies or video scenes) that are displayed to a patient may be dependent on the patient's age. That is, the visual stimuli can be age-specific. In some embodiments, processing session data includes measuring the amount of fixation time a patient spends looking at an actor's eyes, mouth, or body, or other predetermined region-of-interest, and the amount of time that patient spends looking at background areas in the video. As illustrated in FIG. 1B, video scenes, shown to the patient via the screen 132 of the patient-side computing device 130, may depict scenes of social interaction 133 (e.g., an actor looking directly into the camera, trying to engage the viewing patient, for instance, or scenes of children at play). In some embodiments, the video scenes can include other suitable stimuli including, for example, animations and preferential viewing tasks, e.g., as illustrated with further details in FIGS. 4C-4F. Measures of fixation time with respect to particular spatial locations in the video may relate to a patient's level of social and/or cognitive development. For example, children between ages 12-15 months show increasing mouth fixation, and alternate between eye and mouth fixation, as a result of their developmental stage of language development. As another example, a decline in visual fixation over time by a patient with respect to the eyes of actors in videos may be an indicator of ASD or another developmental condition in the patient. Analysis of the patient's viewing patterns (during the displayed movies and across a plurality of viewing sessions or compared to historical data of patients having substantially same age and/or conditions) can be performed for the diagnosis and monitoring of a developmental, cognitive, social or mental ability or disability including ASD.

As both the patient and the caregiver face the eye-tracking device 134 on the patient-side computing device, detection light (e.g., infrared light) emitted from the eye-tracking device 134 can propagate toward eyes of the patient and eyes of the caregiver. In some implementations, a caregiver of a patient (e.g., a parent) is given a pair of glasses 122 to wear while holding the patient to watch visual stimuli displayed on the patient-side computing device 130, e.g., as illustrated in FIGS. 1A-1B. The pair of glasses 122 can be configured to filter or block the detection light from from the eye-tracking device 134, such that the eye-tracking device 134 can only collect reflected or scattered light from eyes of the patient for tracking/capturing eye movements of the patient while the patient (and the caregiver) is watching the visual stimuli. In such a way, a detection accuracy of the eye-tracking device 134 can be improved, without interference from the caregiver's eye movement data.

In some implementations, the patient-side computing device 130 includes a recording device 138 configured to record images, audios, and/or videos of a patient while the patient is looking at visual stimuli presented on the screen 132 of the patient-side computing device 130 during a watching session, during unstructured social interactions, and/or during a treatment session (e.g., with a treatment provider). The recording device 138 can be a camera, an audio recorder, or a video recorder. In some implementations, as illustrated in FIG. 1A, the recording device 138 can be arranged in the housing 136, e.g., positioned on a top of the screen 132, compared to the eye-tracking device 134 arranged under the bottom of the screen 132.

Figure 1C:
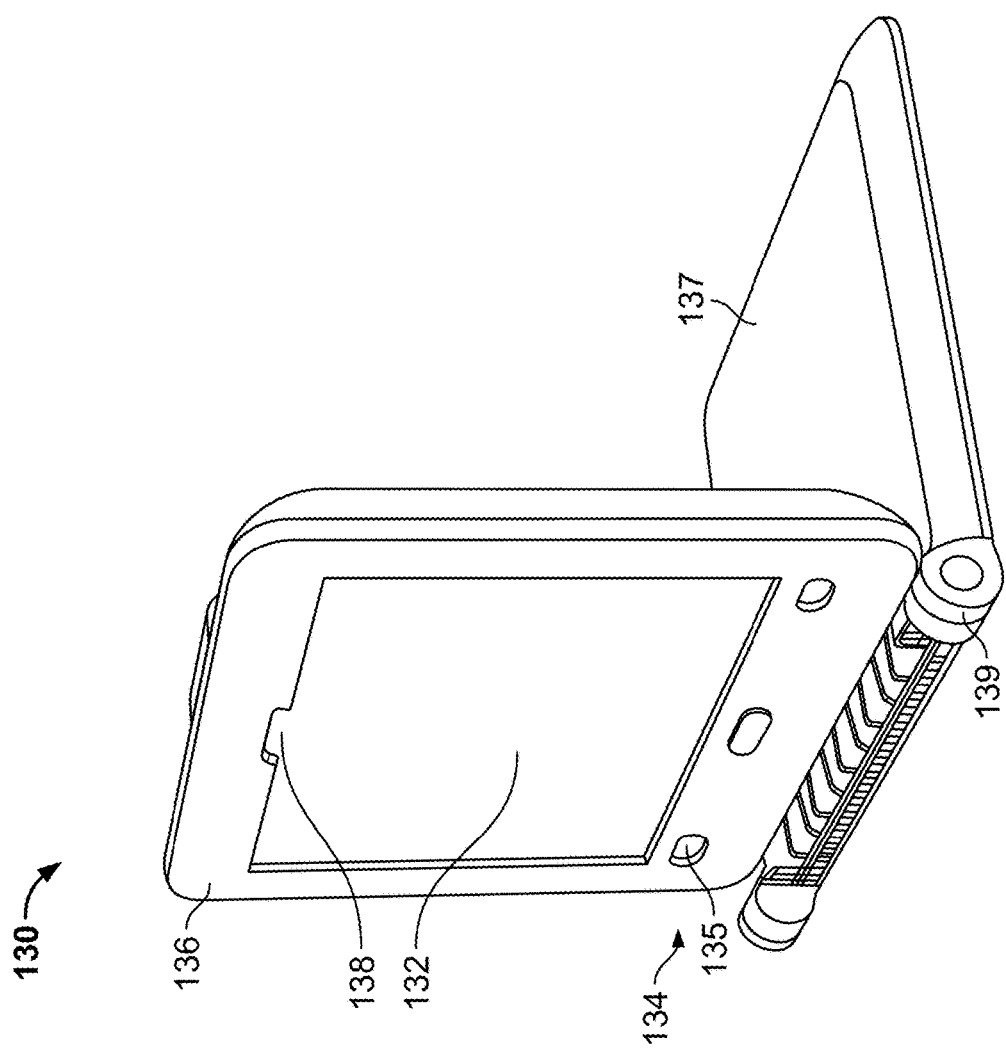
FIG. 1C shows an example of a patient device, according to one or more embodiments of the present disclosure.

FIG. 1C shows an example of the patient-side computing device 130 including the eye-tracking device 134 and the recording device 138. The housing 136 can have a recess at a middle on top of the screen 132, and the recording device 138 can be configured to be arranged in the recess. As illustrated in FIG. 1C, the patient-side computing device 130 can include a foldable base (or support) 137 through one or more joints 139 between the housing 136 and the base 137. The base 137 can be rotated to be close to function as a cover to cover the screen 132, or to be opened to function as a support. The patient-side computing device 130 can be adjustable to accommodate the operation of the recording device 138, e.g., based on a height of the patient and/or a looking angle of the patient. The patient-side computing device 130 can be carried (e.g., as illustrated in FIG. 1A) by a guardian of the patient (such as a parent), or be put on a table, e.g., playing videos during a session.

In some implementations, the patient-side computing device 130 includes one or more recording devices 138, for example, positioned on the top of the screen 132. In some examples, one recording device is at the middle of the top and two other recording devices at two sides of the top. In some examples, two recording devices are distributed at the top. In some implementations, alternatively or additionally, one or more external recording devices are arranged (e.g., on a ceiling, and/or a corner and/or a wall) in the healthcare facility where the patient is and configured to record images, audios, and/or videos about information of the patient.

Compared to the eye-tracking device 134 configured to capture eye-tracking data of the patient, the recording device 138 and/or the one or more external recording devices can be configured to capture other information of the patient, e.g., facial information (such as facial expressions), verbal information, and/or physical behaviors. For example, while the patient is watching the visual stimuli, the patient can repeat what a character in the visual stimuli said, talk to others, smile, raise hands, point fingers, stand up and down, or be quiet, which can be captured by the recording device 138 and/or the one or more external recording devices. The other information can be referred to as multi-modal data to expand data input, together with the eye-tracking data, to a system for assessing developmental disorders, e.g., the cloud server 110. The multi-modal data can replace, supplement, validate, and/or provide additional context to development disorder assessment, besides or in conjunction with the eye-tracking data.

In some implementations, as discussed with further details below, similar to the eye-tracking data, the multi-modal data can be used to monitor one or more specific (such as treatment-specific) skill areas, e.g., manding, listener responding, joint-attention, tact, play, turn-taking, and/or any other skill areas. In some cases, clinicians or treatment providers review one or more videos of an individual patient to assess the individual patient's developmental disorders in these skill areas, which may be subjective, time-consuming, not reliable, and/or lack of consistence. In contrast, the techniques implemented in the present disclosure can use one or more artificial intelligence (AI) models (e.g., machine learning (ML) models) to automatically analyze multi-modal data for individual patients to identify one or more specific skill areas for assessing the patient's developmental disorders, which can greatly improve the processing speed, consistency, accuracy, and/or reduce the time/cost for clinicians or treatment providers.

In some implementations, multi-modal data (e.g., in the form of image data, audio data, and/or video data) for a reference group (e.g., typical children with similar ages, genders, and/or situations) are obtained, e.g., during a session of watching visual stimuli, before the session, and/or after the session. One or more expert clinicians can analyze the multi-modal data for the reference group and annotate the multi-modal data with one or more specific skill areas (and skills). The annotated multi-modal data for the reference group can be provided to the one or more AI or ML models for training, e.g., in conjunction with eye-tracking data taken for the reference group. When multi-modal data of an individual patient is input to the trained one or more AI or ML models, the one or more AI or ML models can automatically analyze the multi-modal data of the individual patient, optionally in conjunction with eye-tracking data, to identify one or more specific skills for assessing the individual patient's developmental disorders.

Figure 1D:
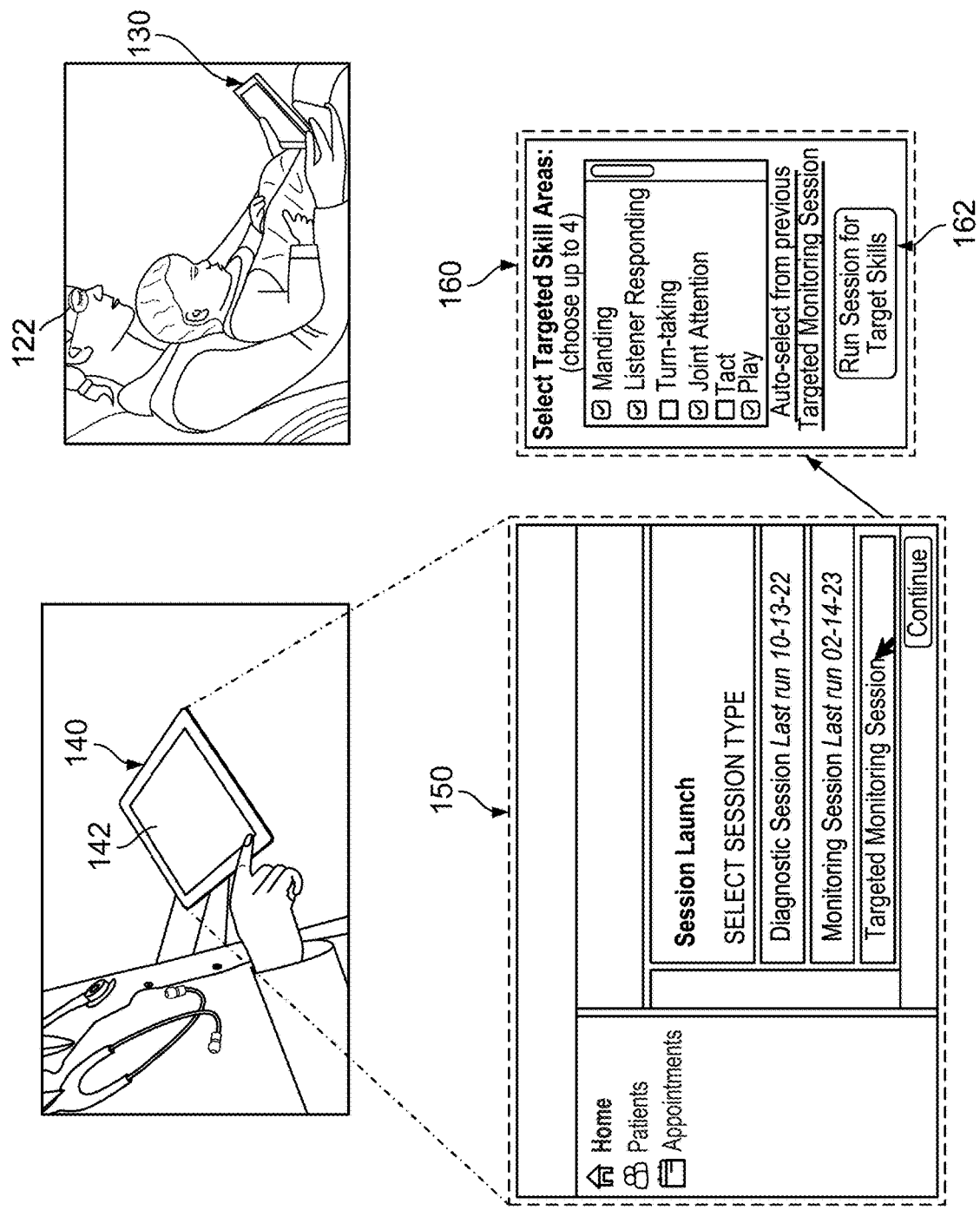
FIG. 1D shows an example of illustrative user interfaces presented on an operator device, according to one or more embodiments of the present disclosure.

The operator-side computing device 140 is configured to run an operator application (or software). In some embodiments, the operator application is installed and run in the operator-side computing device 140. In some embodiments, the operator application runs on the cloud server 110, and an operator can log in a web portal to interact with the operator application through a user interface presented on a screen 142 of the operator-side computing device 140, e.g., as illustrated in FIG. 1D. In some implementations, as discussed with further details in FIGS. 4A-4J, 12A-12B, and 13A-13D, the operator application can be configured to supervise or control the steps of the eye-tracking application or software in the patient-side computing device 130, e.g., to select and play specific visual stimuli for a patient and to collect raw eye tracking data, and/or to review results or reports.

In some examples, e.g., as shown in FIG. 1D and as discussed with further details in FIGS. 12A-12B, the operator application can present different sessions (e.g., diagnostic session, monitoring session, targeted monitoring session) in a user interface 150 for the operator to choose. For example, in a same healthcare facility with the patient, when the operator selects launching targeted monitoring session, the operator application can pop up a new window 160 for the operator to select targeted skill areas (e.g., Manding, Listener Responding, Joint Attention, and Play) for monitoring the patient's behaviors in these targeted skill areas in the session. As discussed with further details below (e.g., in FIG. 11), individual moments or frames in a playlist of visual stimuli can be annotated to specify one or more specific skill areas (and/or skills) by expert clinicians, e.g., in view of looking behaviors of a reference group. If the operator selects targeted skill areas in a session, the operator application can adjust visual stimuli to be presented to a patient on the patient-side computing device 130 based on the selected targeted skill areas, e.g., prioritizing videos annotated/known to monitor the selected targeted skill areas, and/or enriching additional videos related to the selected targeted skill areas, and/or removing frames unrelated to the selected targeted skill areas, and/or optimizing the playlist to maximize targeted skill areas. When the operator selects a user interface element 162 to run the session in the new window 160 the adjusted visual stimuli can be presented on the patient-side computing device 130 to the patient.

In some examples, as discussed with further details in FIGS. 13A and 13C, the operator can review diagnostic results/reports using the operator-side computing device 140 (or any other computing device associated with the operator). The operator application can present a user interface on the screen 142 of the operator-side computing device 140. The user interface can include options for the operator to select, for example, different patients or a patient's different sessions or history. Through the user interface, the operator can also view default results (e.g., as illustrated in FIG. 8A-8C and FIGS. 13B-1 and 13B-2), customized report (e.g., as illustrated in FIG. 13C), and/or launch interactive results dashboard (e.g., as illustrated in FIG. 13D). For example, when the operator selects viewing customized report, the operator application can pop up a new window for the operator to select targeted skill areas (e.g., Manding, Listener Responding, Joint Attention, and Play) to customize the diagnostic or monitoring report. In some examples, if the operator selects the target monitoring session, the operator application can automatically customize the report of the targeted monitoring session to select the same targeted skill areas as chosen for the playlist for the targeted monitoring session. The new window 160 can be overlaid on the user interface 150, side by side with the user interface 150, or have an overlap with the user interface 150. The user interface 150 can be changed to the new window 160.

In some embodiments, the operator application interfaces with the eye-tracking software via a software development kit (SDK). In some embodiments, communication between the patient-side computing device 130 and the operator-side computing device 140 or communication between the operator application and the eye-tracking application can be done using WebSocket communication. WebSocket communication allows bi-directional communication between two devices. This bi-directional communication allows an operator to control the patient-side computing device 130 while receiving information from the patient-side computing device 130 at the same time. WebSocket communication can be done using the secure implementation of WebSocket known as WebSocket Secure (WSS). As noted above, communication between the patient-side computing device 130 and the operator-side computing device 140 (e.g., communication between the operator application and the eye-tracking application) can be through the cloud server 110. For example, an operator can use the operator-side computing device 140 to log in a web portal running on the cloud server 110 and establish a wireless connection with the patient-side computing device 130 for eye-tracking data acquisitions of the patient.

The operator application can be additionally used to perform other functions, e.g., presenting an interface to the operator showing the patient's name, date of birth, etc., information relating to the stimuli (e.g., movies) that are shown to the patient, and the like. The operator can also use the operator-side computing device 140 to log in the web portal of the cloud server 110 for device management, patient management, and data management. In some embodiments, the operator application runs on the cloud server 110 and is controlled by the operator using the operator-side computing device through the web portal. The operator can operate the computing system 120 with only minimal training.

As discussed with further details in FIGS. 3, 4A-4J, and 5, the computing system 120 can be configured for session data acquisition. In some embodiments, a session is initialized by establishing a connection between the operator-side computing device 140 and the patient-side computing device 130. After entering the patient's information into the operator application (e.g., a custom software) running on the operator-side computing device 140, the operator application can control the eye-tracking application running on the patient-side computing device 130 to select age-specific stimuli and instruct the operator or the caregiver of the patient to position the patient-side computing device 130 in front of the patient at a proper orientation and/or location. The operator can use the operator-side computing device 140 to control the operator application and/or the eye-tracking application or software to (a) calibrate the eye-tracking device 134 to the patient, (b) validate that the calibration is accurate, and (c) collect eye-tracking data from the patient as he or she watches the dynamic videos or other visual stimuli in the session, e.g., from the patient moving his or her eyes in response to predetermined movies or other visual stimuli. After the session ends, both the eye tracking data and information relating to the stimuli (e.g., a list of the stimuli viewed by the patient) can be stored in two separate data files as session data. Then the session data can be transferred, e.g., automatically by the patient-side computing device 130, to a secure database in the cloud server 110, e.g., via the network 102. The database can be remote from the computing system 120 and configured to accommodate and aggregate collected data from a number of computing systems 120.

The network 102 can include a large computer network, such as a local area network (LAN), a wide area network (WAN), the Internet, a cellular network, or a combination thereof connecting any number of mobile computing devices, fixed computing devices and server systems. Each of the computing devices 130, 140 in the computing system 120 can communicate with the cloud server 110 through the network 102.

In some embodiments, communication between on-premises computing devices 130, 140 and the cloud server 110 can be done using Hypertext Transfer Protocol (HTTP). HTTP follows a request and response model where a client (e.g., through a browser or desktop application) sends a request to the server and the server sends a response. The response sent from the server can contain various types of information such as documents, structured data, or authentication information. HTTP communication can be done using the secure implementation of HTTP known as Hypertext Transfer Protocol Secure (HTTPS). Information passed over HTTPS is encrypted to protect both the privacy and integrity of the information.

Figure 18:
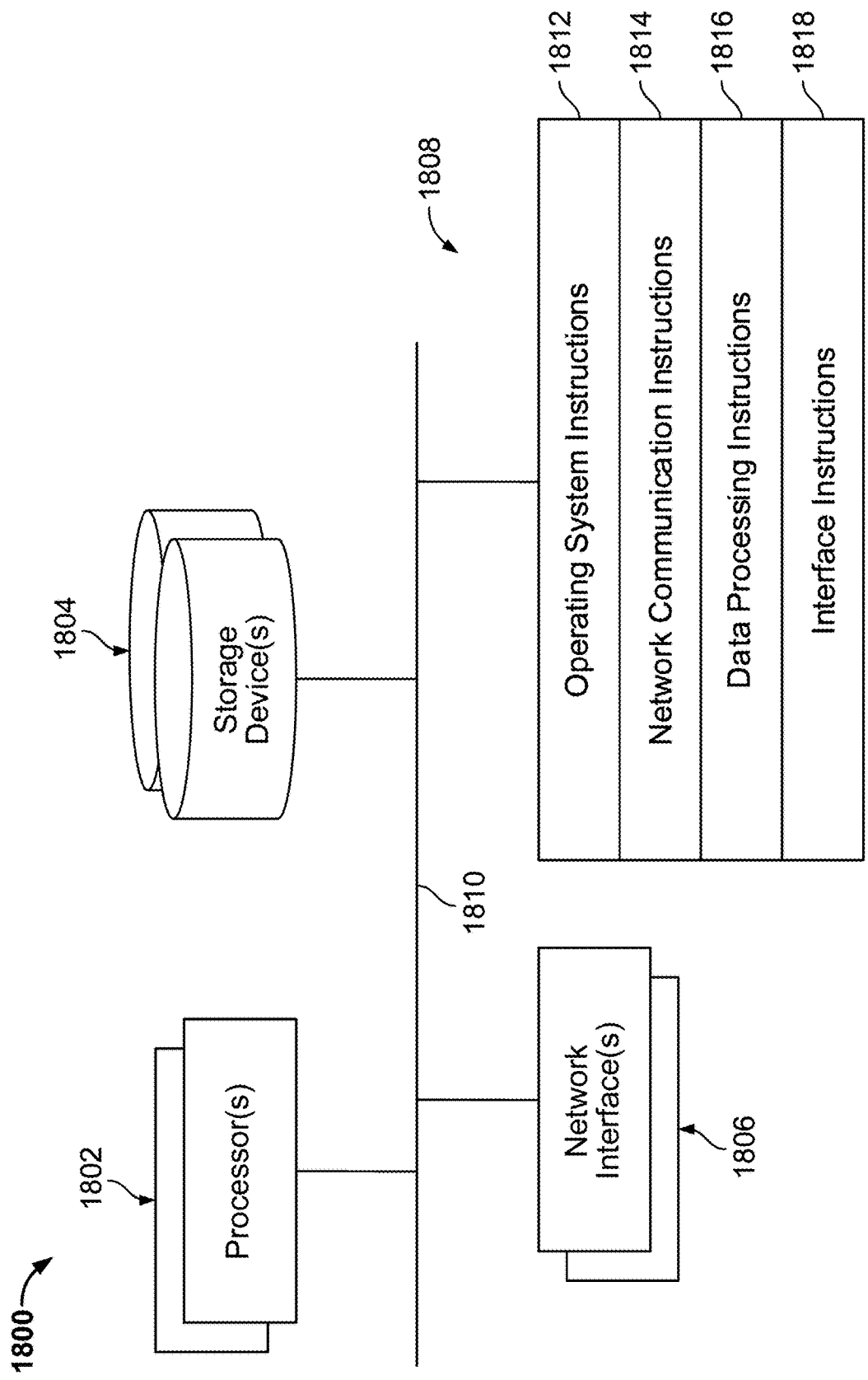
FIG. 18 illustrates an architecture for a cloud computing system, according to one or more embodiments of the present disclosure.

The cloud server 110 can be a computing system hosted in a cloud environment. The cloud server 110 can include one or more computing devices and one or more machine-readable repositories, or databases. In some embodiments, the cloud server 110 can be a cloud computing system that includes one or more server computers in a local or distributed network each having one or more processing cores. The cloud server 110 can be implemented in a parallel processing or peer-to-peer infrastructure or on a single device with one or more processors. As an example, FIG. 18 is an architecture for a cloud computing system which can be implemented as the cloud server 110.

As illustrated in FIG. 1A, the cloud server 110 includes a cloud platform 112 and a data pipeline system 114. As discussed with further details in FIGS. 2A-2G, the cloud platform 112 can be configured to provide a web portal, store application data associated with treatment providers or tenants, and store data, e.g., raw eye-tracking data, processed data, analytical and/or diagnostic results. The data pipeline system 114 is configured to perform data processing and data analysis.

Figure 6:
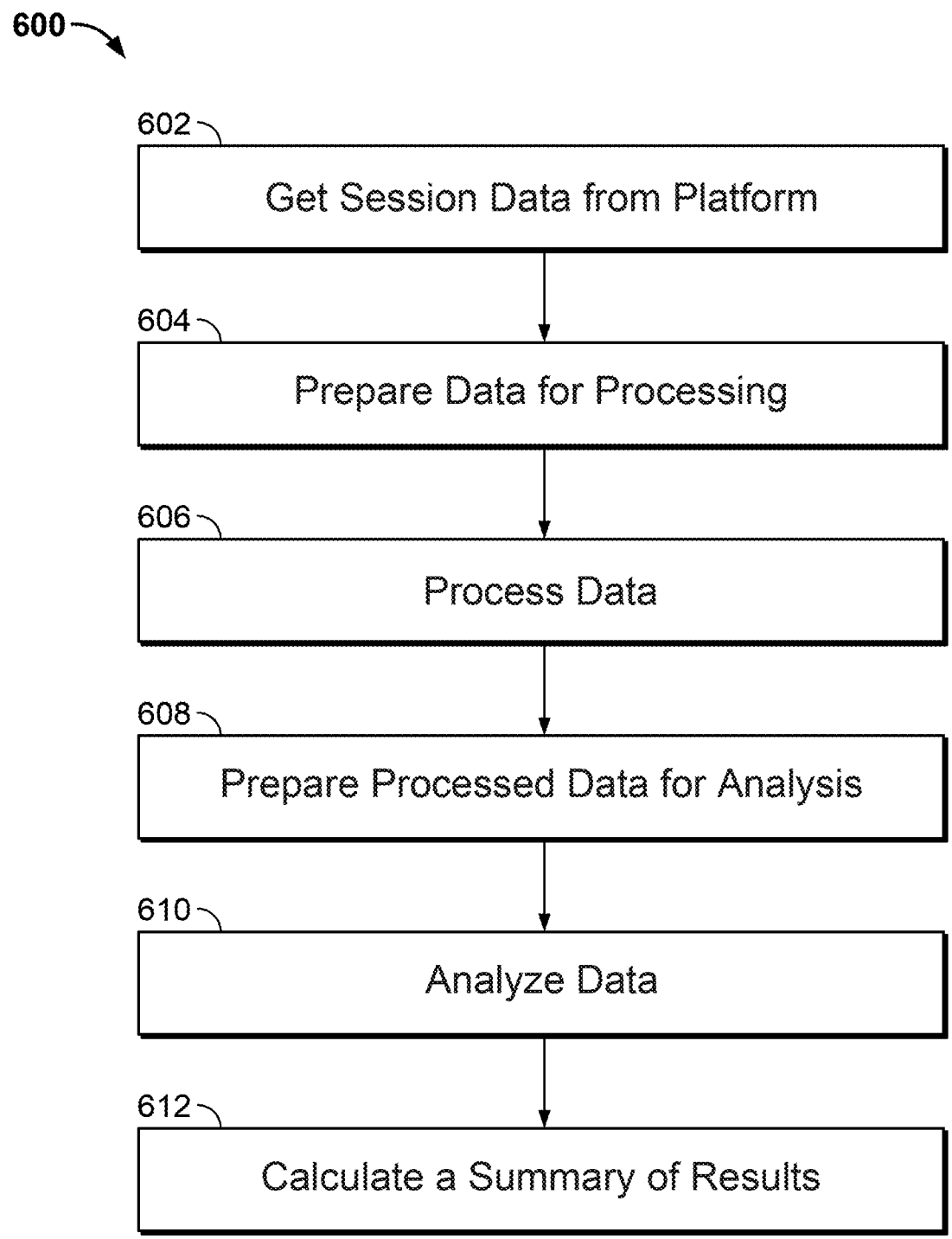
FIG. 6 is a flowchart of an example process for managing session data, according to one or more embodiments of the present disclosure.
Figure 7A:
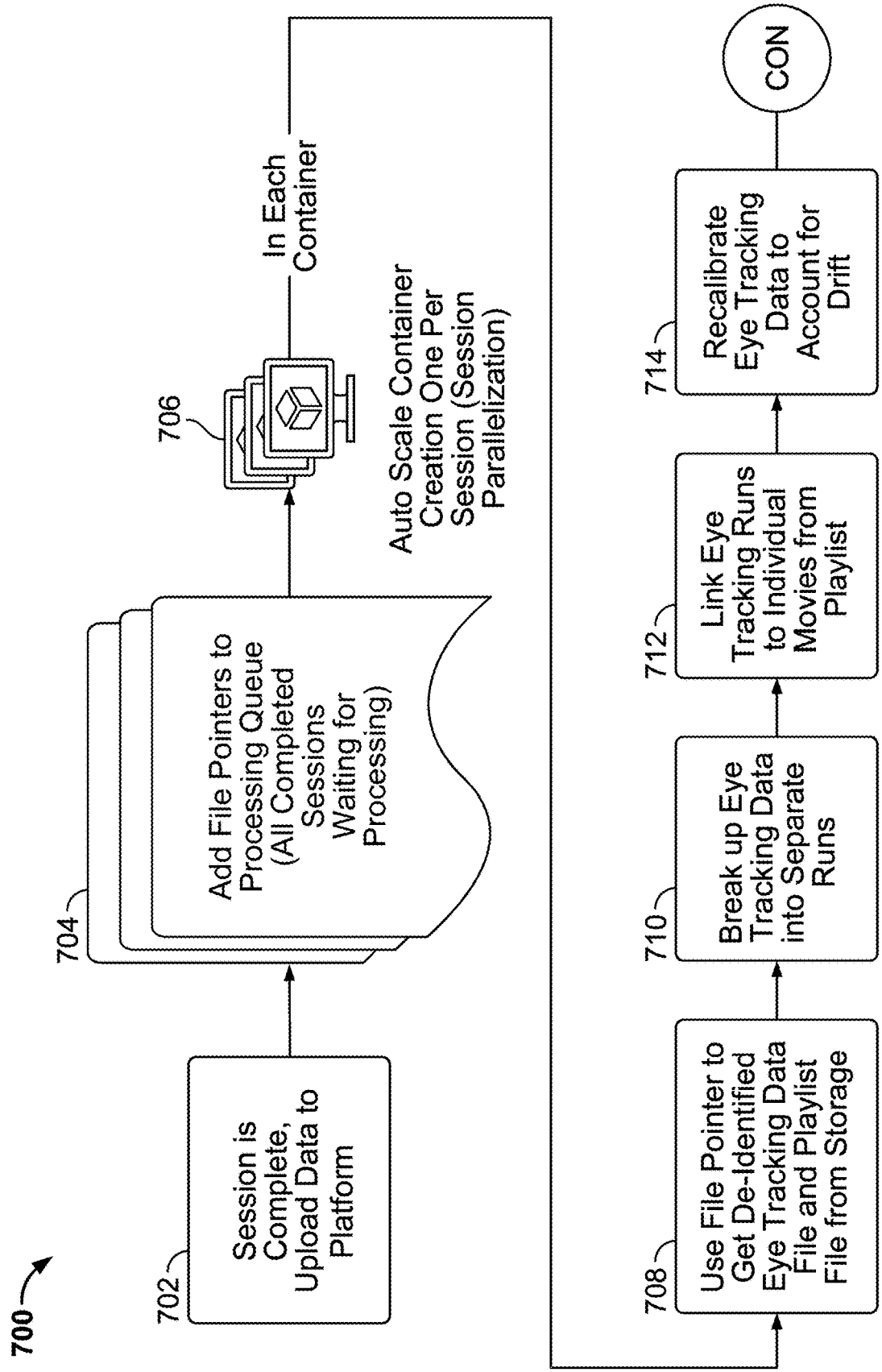
FIGS. 7A-7B show a flowchart of another example process for managing session data, according to one or more embodiments of the present disclosure.
Figure 7B:
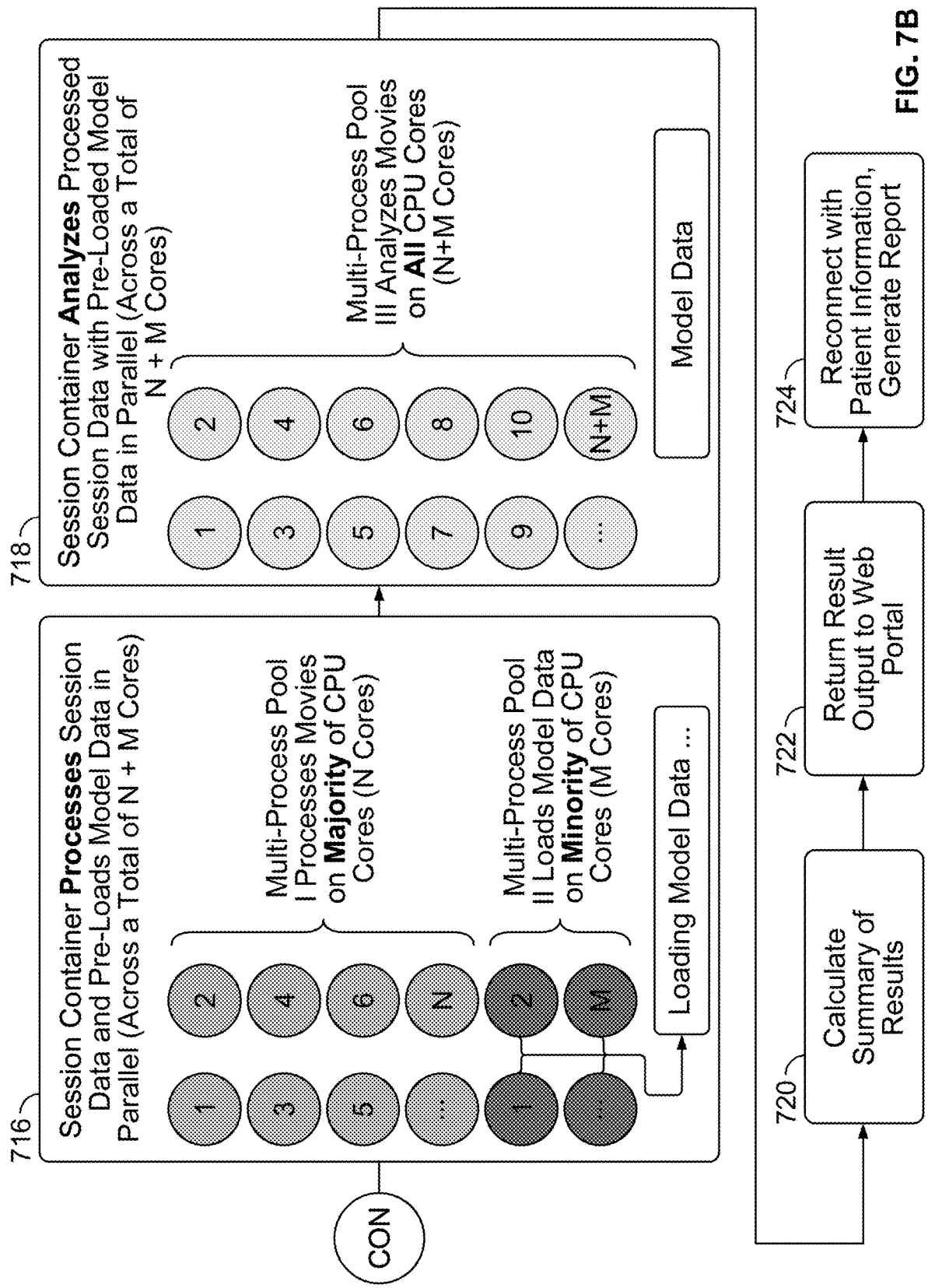

In some embodiments, as discussed with further details in FIGS. 6 and 7A-7B, the cloud server 110 is configured to automatically receive, process, and analyze session data from multiple computing systems. Moreover, the cloud server can process and analyze session data of a number of sessions from a large number of computing systems in parallel, which can greatly improve session processing speed and provide diagnosis results in a short period of time, e.g., within a 24-hour window. For example, receipt of session data by the cloud server 110 (e.g., by the cloud platform 112) can initiate an automatic software-implemented processing and analysis process (e.g., by the data pipeline system 114). In the process, the patient's individual data can be compared to models of eye-tracking data which were previously generated from historical eye-tracking data of patients having substantially same ages, backgrounds, and/or conditions. The result of the comparison can be a diagnosis of a neurodevelopmental disorder including but not limited to ASD, a measure of the patient's developmental/cognitive functioning and/or prescriptive recommendation for a treatment plan. Alternatively or additionally, the collected data is compared and/or reviewed for a given patient over multiple sessions (and over a predetermined time period) to identify a potential change in visual fixation (e.g., a decline in visual fixation). Those results may be condensed into a diagnostic report, for use by the patient's physician. In some embodiments, once a diagnostic result is ready, the cloud server 110 can transfer the diagnostic result to the operator-side computing device 140, and the diagnostic result can be presented on a user interface of the operator-side computing device 140, e.g., as discussed with further details in FIGS. 8A-8C or FIGS. 16A-16F.

In some embodiments, a large amount of model data, including data related to patients at similar ages, similar backgrounds, and/or similar situations, can be used with processed session data for a patient to generate a diagnosis result for the patient, e.g., using comparison or inference via statistical models, algorithms, artificial intelligence (AI) models such as machine learning or artificial neural network models, which can greatly increase accuracy of the diagnosis results.

The environment 100 involves three major steps corresponding to the three parts of the environment 100 shown in FIG. 1A (e.g., the computing system 120 for data acquisition, the cloud platform 112, and the data pipeline system 114). As discussed with further details in FIGS. 2A-2G, the three parts can be configured together to reliably collect data for patients, and efficiently process and analyze the collected data for the diagnosis of ASD or other cognitive, developmental, social or mental abilities or disabilities.

FIG. 2A is a block diagram of an example system 200 for assessing developmental disorders via eye tracking, according to one or more embodiments of the present disclosure. The system 200 can be implemented in the environment 100 of FIG. 1. The system 200 can be considered as an evaluation system for development disorders. In some examples, the evaluation system is represented as EarliPoint. According to three steps of a data process, the system 200 includes three subsystems: data acquisition subsystem 210, a platform subsystem 220, and a data pipeline subsystem 230. Each subsystem can be composed of corresponding hardware and software items. The platform subsystem 220 and the data pipeline subsystem 230 can form a cloud server, e.g., the cloud server 110 of FIG. 1A.

The data acquisition subsystem 210 is configured to collect eye-tracking data of patients. The data acquisition subsystem 210 can be the computing system 120 of FIG. 1. As shown in FIG. 2A, the data acquisition subsystem 210 includes an eye-tracking console 212 running an eye-tracker application 214 and an operator-side computing device (e.g., 140 of FIG. 1) running an operator application 216. In some embodiments, the operator application 216 is deployed in the operator-side computing device. In some embodiments, the operator application 216 is deployed in the platform subsystem 220, and the operator can use the operator-side computing device to log in the platform subsystem 220 through a web portal 222 to run the operator application 216 on the platform subsystem 220. Deploying the operator application 216 in the platform subsystem 220 can avoid deploying the operator application 216 in one or more operator-side computing devices, which can reduce software and hardware requirements for the operator-side computing devices, and enable to conveniently maintain or update the operator application 216, e.g., without maintaining or updating the operator information on each of the one or more operator-side computing devices.

The eye-tracking console 212 can be an integrated device including the patient-side computing device 130 (e.g., a tablet) and the eye-tracking device 134 of FIG. 1. As noted above, the data acquisition subsystem 210 can include a number of movie files 218 that are stored in the eye-tracking console 212 and optionally in the operator-side computing device. The movie files 218 can be predetermined age-specific visual stimuli for patients at different ages and/or different conditions.

As described in FIG. 1A, the platform subsystem 220 and the data pipeline subsystem 230 can be included in a network-connected server such as a cloud server (e.g., the cloud server 110 of FIG. 1) and implemented in a centralized cloud-hosted environment that is provided by a cloud provider, e.g., Microsoft Azure. In some embodiments, the platform subsystem 220 is configured for management and orchestration of resources of the cloud-hosted environment. The platform subsystem 220 can be the cloud platform 112 of FIG. 1. As illustrated in FIG. 2A, the platform subsystem 220 includes a web portal 222, database 224 storing application data, and database 226.

The web portal 222 can be a web-based interface. Through the web portal 222, an operator (e.g., a medical professional) can login into, e.g., using the operator-side computing device, the platform subsystem 220 to manage (view and/or query) application data stored in the database 224 and/or data in the database 226. For example, the web portal 222 allows for an operator to view diagnostic results. A prewritten course of action may be provided based on the diagnostic results (e.g., seek further evaluation).

Figure 2B:
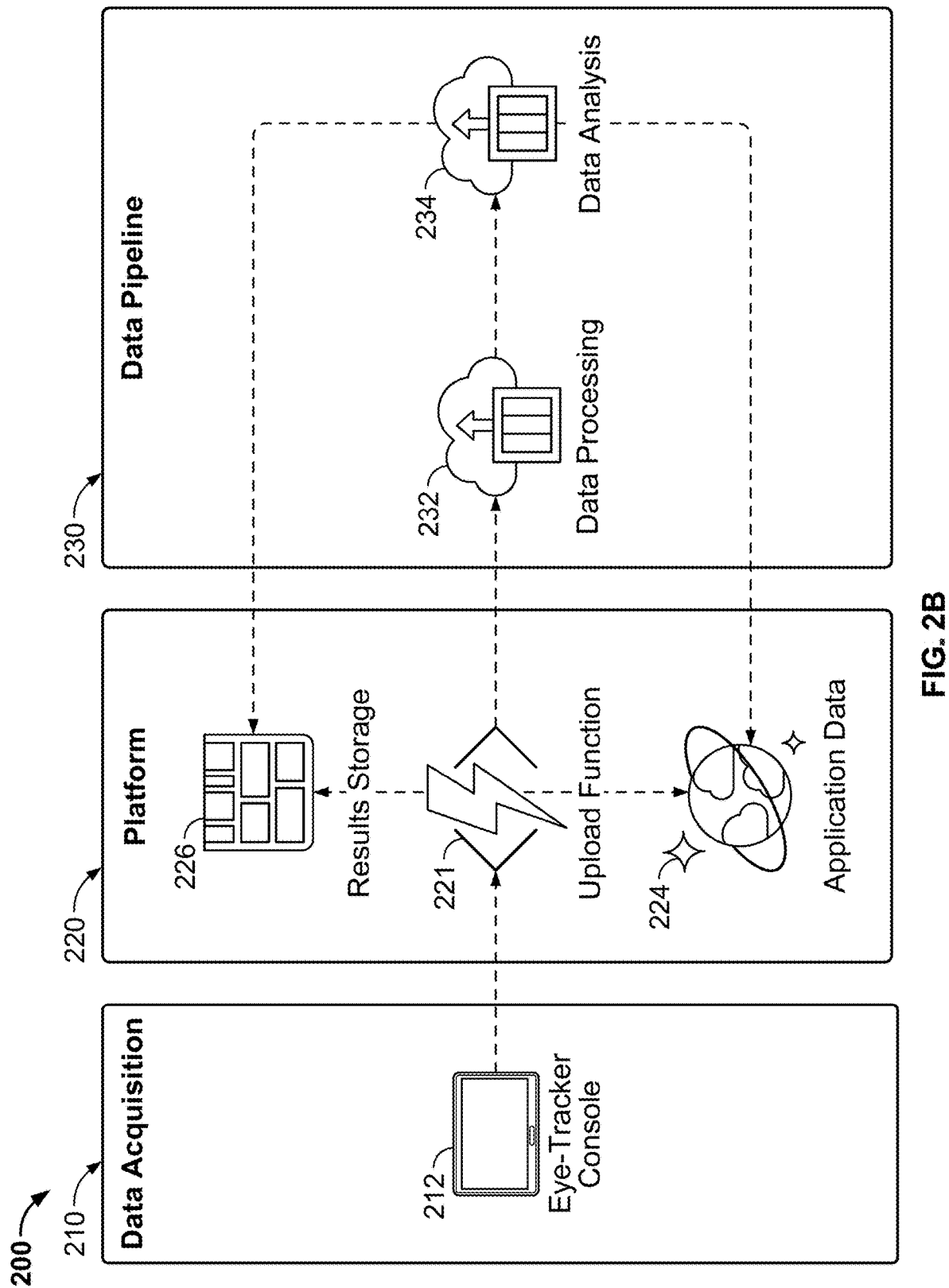
FIG. 2B shows an example of managing session data in the system of FIG. 2A, according to one or more embodiments of the present disclosure.
Figure 2C:
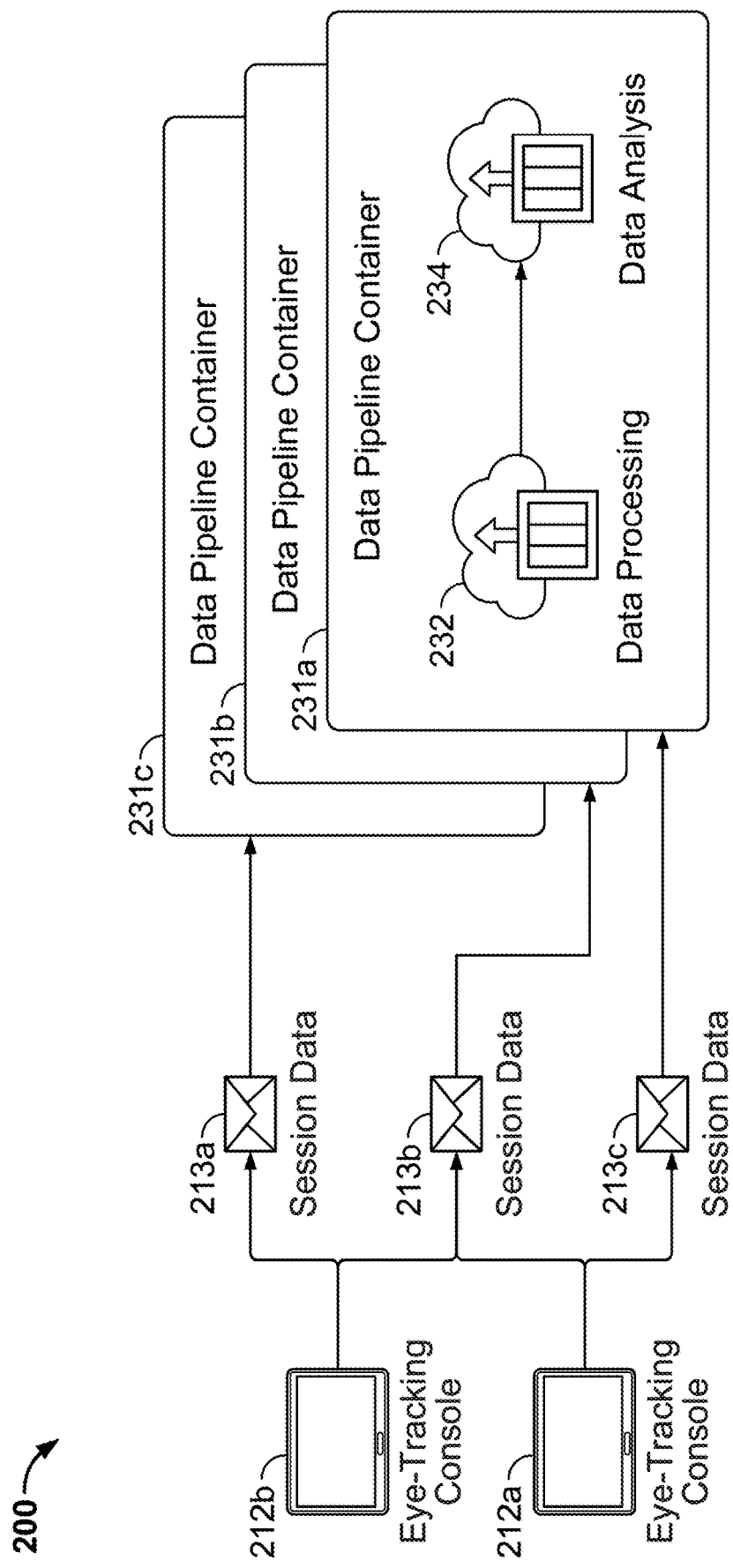
FIG. 2C shows an example of managing multiple session data in parallel in the system of FIG. 2A, according to one or more embodiments of the present disclosure.
Figure 2D:
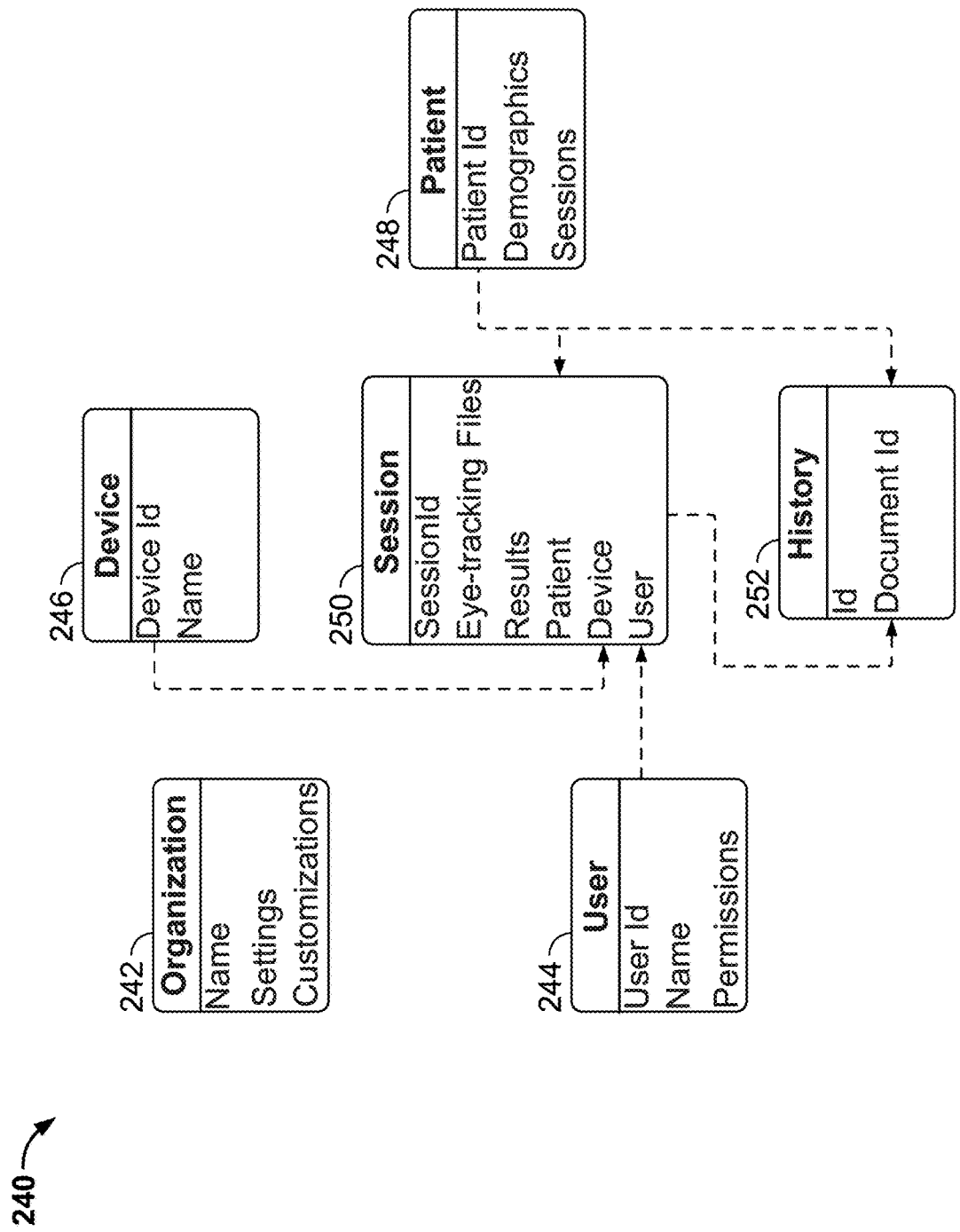
FIG. 2D shows an example database storing different types of documents as application data in the system of FIG. 2A, according to one or more embodiments of the present disclosure.

As an example of the database 224, FIG. 2D shows a database 240 storing different types of documents. The database 240 can be a NoSQL database such as Azure Cosmos DB. The different types of documents can be stored as application data in the database 240. Unlike relational databases, NoSQL databases do not have strong relationships between documents. Dotted lines in FIG. 2D indicate references and information embedding between the documents.

In some embodiments, the database 240 stores corresponding application data for a treatment provider (or a tenant). The treatment provider can be a healthcare organization that includes, but is not limited to, an autism center, a healthcare facility, a specialist, a physician, or a clinical study. An organization can vary in structure, patient volume, and lifespan. As illustrated in FIG. 2D, the corresponding application data can include organization document 242, user document 244, device document 246, patient document 248, session document 250, and history document 252. A user can be an operator associated with the healthcare organization, e.g., a medical assistant, a specialist, a physician, or any other medical professional.

The organization document 242 contains settings and customizations for the organization. The user document 244 contains the identifier information along with a user's roles and permissions. The user role indicates whether the user is either an administrator or operator that is associated with a different security level or permission. The device document 246 contains identifier information for each eye-tracking console, e.g., 212 of FIG. 2A, associated with the organization. The patient document 248 contains information about the patient, e.g., an infant or a child treated as a patient for development assessment. The session document 250 contains information related to a session that can be composed of a session identifier (session ID), a reference to the patient, a reference to the user performing the session, a pointer to the eye-tracking data, and the results of data processing and analysis. The history document 252 can be used to maintain a version history of changes to a document. The document mirrors the structure of its parent document and include additional audit information. In some embodiments, the database 224 allows for URL-based querying (e.g., for those with administrative roles) to query across multiple variables. For example, variable may include patients/devices/sessions, adverse events, etc.

In some embodiments, the cloud server including the platform subsystem 220 and the data pipeline subsystem 230 can be implemented in a centralized cloud environment, which can provide more flexibility to expand a capability of the cloud server. For example, the cloud server can utilize a multi-tenant architecture for providing Software as a Service (SaaS) subscription-based diagnostic services to treatment providers. In the multi-tenant architecture, treatment providers share a single version of the software across a variety of geographic locations. The term "tenant" in a multi-tenant architecture describes a single treatment provider of the system. Resources of the cloud server can be dynamically managed based on a total number of tenants and expected average workload, e.g., how many tenants are accessing the cloud server at a given time point. The cloud server can adopt horizontal scaling techniques such as auto-scaling to handle spikes in the resource workload.

In a multi-tenant architecture where the application is shared, it is important to isolate their tenant data and prevent other tenants from accessing their tenant data. This is known as isolation. There are 3 different isolation strategies that can be implemented: shared database, database per tenant, and application per tenant. In Shared Database strategy, tenants share a single instance of the application, and all data is stored in a single database. In Database Per Tenant strategy, e.g., strategy 260 illustrated in diagram (a) of FIG. 2E, tenants share a single instance of an application in an application layer 262 but have their own databases 264 (e.g., database 224 of FIG. 2A or 240 of FIG. 2D). In Application Per Tenant strategy, e.g., strategy 270 illustrated in diagram (b) of FIG. 2E, each tenant gets its own instance of an application in a respective application layer 272 and its own database 274 (e.g., database 224 of FIG. 2A or 240 of FIG. 2D). The cloud server can deploy the Database per Tenant strategy 260 or the Application per Tenant strategy 270 to treatment providers.

With continued reference to FIG. 2A, the database 226 is configured to store raw eye-tracking data or session data, processed session data, analytical results, and/or diagnostic results or reports. The database 226 can be a storage platform (e.g., Azure Blob), and can be paired with tools written in any suitable programming language (e.g., Python, Matlab), allowing for URL based interface and query to the database 226. Additionally, the database 226 may be compatible with programming languages (e.g., Python, Matlab) used for transferring data from the data acquisition subsystem 210 to the database 226, and from the database 226 to the data pipeline subsystem 230. For example, where the patient-side computing device (e.g., 130 of FIG. 1) is located at a medical facility, data collection occurs at that facility and the data are transferred between the database 226 and the patient-side computing device. The database 226 can be secure, HIPAA-compliant, and protected by a redundant backup system.

In some embodiments, the platform subsystem 220 is configured to enable one or more operations including (a) intake of new patient information, (b) storage of raw data files (e.g., including eye tracking data), (c) automated and secure transfer of files between a data collection device (e.g., the eye-tracking console 212 of FIG. 2A), data processing computer, and database, (d) tabulation and querying of data for the purposes of assessing device utilization and other data quality metrics, and e) access to results of processing by physicians. One or more of the operations (a) to (c) can be performed by an upload function module 221 in the platform subsystem 220.

With continued reference to FIG. 2A, the data pipeline subsystem 230 is configured to process and analyze patient eye-tracking data along with producing a diagnostic result. In some embodiments, the data pipeline subsystem 230 includes data processing module 232, data analysis module 234, and model data 236. As discussed with further details in FIGS. 7A-7B below, the data processing module 232 is configured to process session data including eye-tracking data to obtain processed session data, and the data analysis module 234 is configured to analyze the processed session data using the model data 236 to generate a diagnostic result.

In some embodiments, the system 200 includes interfaces for devices and subsystems. An interface can be inter-subsystem. For example, the system 200 can also include an interface between the data acquisition subsystem 210 to the cloud platform subsystem 220, and an interface from the cloud platform subsystem 220 to the data pipeline subsystem 230. An interface can be intra-subsystem. For example, the system 200 can include an interface between eye-tracking console hardware (e.g., a tablet and an eye-tracking device) and eye-tracking application software.

FIG. 2B shows an example of processing single session data in the system 200 of FIG. 2A, according to one or more embodiments of the present disclosure. As discussed above, after a data collection session is completed, the eye-tracking console 212 can automatically transfer session data of the session to the platform subsystem 220. The session data can include two files: one containing raw eye-tracking data (e.g., gaze position coordinates, blink data, pupil size data, or a combination thereof) and the other containing information relating to the stimuli (e.g., a list or playlist of those movies viewed by the patient). Through the upload function module 221 implemented in the platform subsystem 220, the session data can be stored in the database 226 and stored into application data in the database 224. Then, the stored session data can be automatically transferred from the platform subsystem 220 to the data pipeline subsystem 230 for data processing and analysis, without human intervention. For example, a software script written in any suitable programming language (e.g., Python, Matlab) may be used to transfer raw, unprocessed data files from the database 226 to the data pipeline subsystem 230 for processing. The session data is first processed by the data processing module 232 and then analyzed by the data analysis module 234, which yields diagnostic information about the patient.

In some embodiments, three files are generated, one containing processed eye-tracking data, one containing a summary of eye tracking statistics, and one containing the diagnostic information. The file containing diagnostic information can be uploaded to the database 224 to be associated with the patient in the application data, as illustrated in FIG. 2D. The three files can then be uploaded to the database 226 for storage. In some cases, the processed eye-tracking data are tabulated into a session table. Summary of eye tracking information (e.g., fixation samples/movie, etc.) can be read from the processed summary file and tabulated in the database 226 for subsequent query. Summary values (e.g., percentage fixation/movie, etc.) can be then calculated within the database 226.

FIG. 2C shows an example of processing multiple session data in parallel in the system 200 of FIG. 2A, according to one or more embodiments of the present disclosure. As illustrated in FIG. 2C, multiple eye-tracking consoles 212*a*, 212b can transmit a plurality of session data 213a, 213b, 213c of sessions (referred to generally as session data 213 or individually as session data 213) to the platform subsystem 220. In the data pipeline subsystem 230, the data processing module 232 and the data analysis module 234 can be written in a suitable programming language (e.g., Python), which enable to deploy the data processing module 232 and data analysis module 234 in containers 231a, 231b, 231c (referred to generally as containers 231 or individually as container 231). Each session can be processed using its own instance of data processing and analysis. The use of containers allows data processing and analysis to be done as session data are uploaded from the data acquisition subsystem 210, which can result in sessions being returned within a short period of time, e.g., within a 24-hour window.

As discussed with further details in FIGS. 7A-7B, the cloud server can process and analyze session data of a number of sessions from a large number of computing systems in parallel. First, the cloud server can deploy a respective container (e.g., 231) for each session, and the respective container can include a corresponding data processing module 232 and a corresponding data analysis module 234. In this way, once session data (e.g., 213) of a session is uploaded by a corresponding eye tracking console 212, the session data of the session can be processed and analyzed using its own container (e.g., 231 having its own instance of data processing and data analysis). Second, while session data of multiple sessions are being processed in corresponding containers, e.g., using a majority of processing units (or cores) in the cloud server, model data for analyzing the processed session data can be pre-loaded into the corresponding containers in parallel, e.g., using the remaining or a minority of the processing units in the cloud server. Third, all of the processed session data and the loaded model data can be analyzed in the corresponding containers in parallel, e.g., using the total number of processing units in the cloud server. The use of parallelization in multiple ways can greatly improve the speed of session data processing and analysis and provide speedy diagnostic results in the short period of time, e.g., within a 24-hour window. For example, once a diagnostic result is available, the cloud server can transmit the diagnostic result to a corresponding operator-side computing device (e.g., 140 of FIG. 1), and the diagnostic result can then be displayed in a result interface of the operator application 216. The parallelization can also make the cloud server be more efficient in resource utilization, which can further improve the system performance.

Figure 2E:
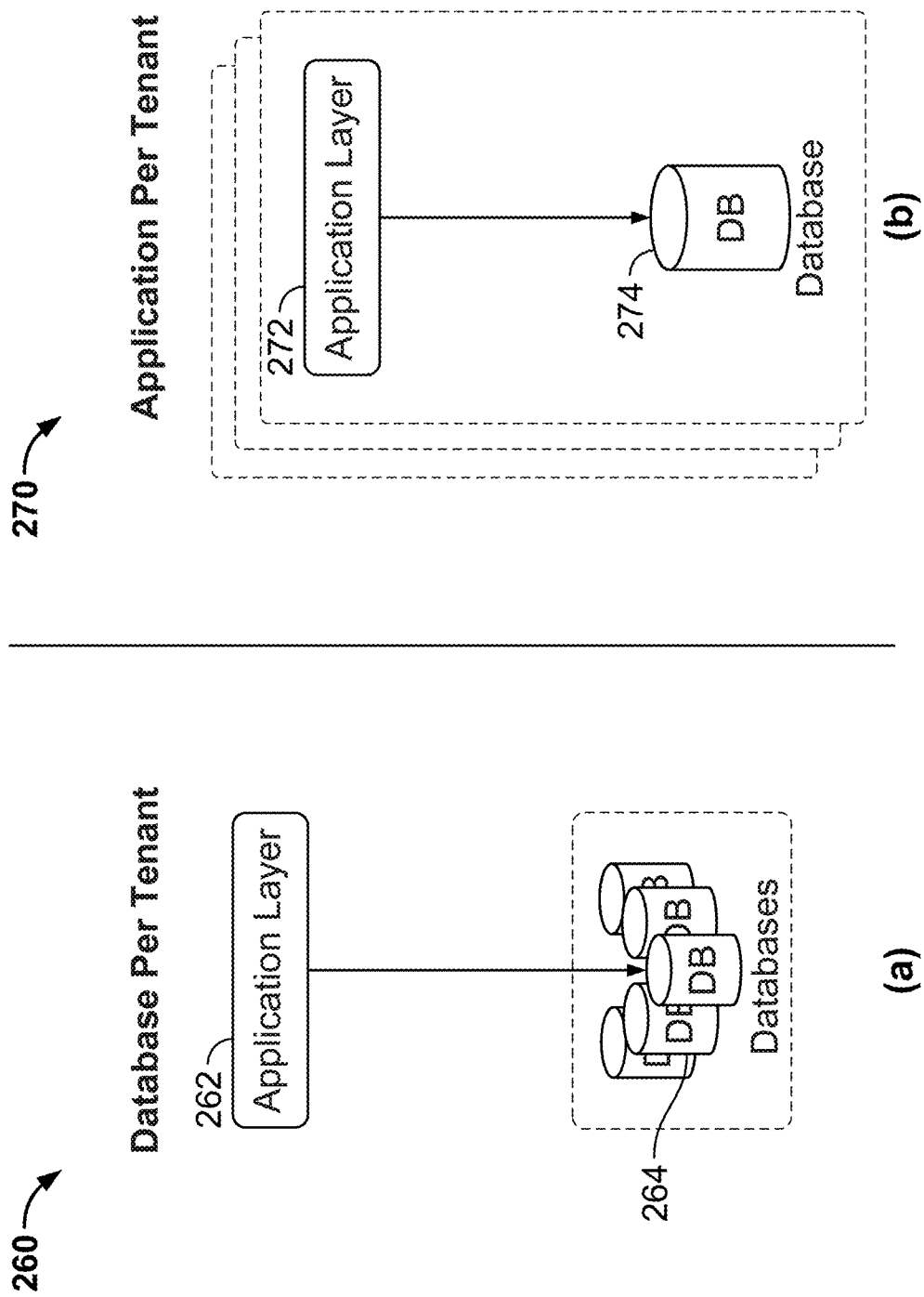
FIG. 2E shows examples of multi-tenant architectures in the system of FIG. 2A, according to one or more embodiments of the present disclosure.
Figure 2F:
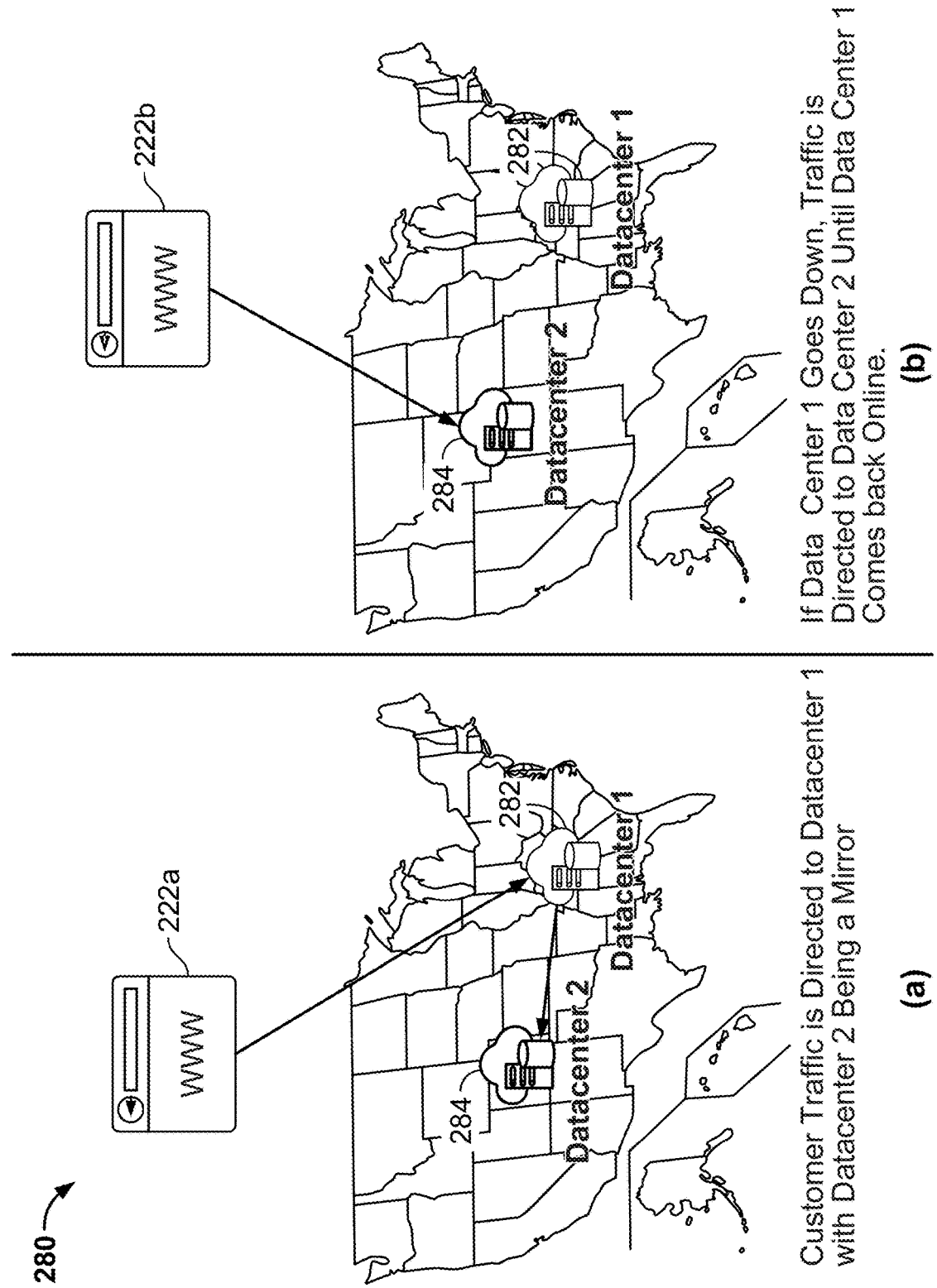
FIGS. 2F-2G show an example for data backup for the system of FIG. 2A, according to one or more embodiments of the present disclosure.

FIG. 2F show an example configuration 280 for data backup for the system 200 of FIG. 2A, according to one or more embodiments of the present disclosure. The configuration 280 can enable high availability of services to treatment providers, such that the treatment providers can access their services regardless of any outages in one or more particular regions of the cloud server (e.g., the platform subsystem 220 and the data pipeline subsystem 230).

High availability refers to treatment providers' abilities to access their services regardless of whether a cloud service provider suffers an outage. Availability can be achieved by replicating a resource in a different physical location. The cloud server implemented herein can be provided by a cloud service provider that can provide Platform as a Service (PaaS) resources with either high availability built-in or configurable high availability. The resources that are hosted in the cloud environment can have high availability using high-availability service level agreements or through the use of geo-redundancy.

FIG. 2F shows an example of high-availability through geo-redundancy. As shown in FIG. 2F(a), resources of the cloud server can be hosted in a first data center 282 having a web portal 222a. The resources are replicated in a second data center 284. When the first data center 282 works properly, treatment provider traffic is directed to the first data center 282, with the second data center 282b being a mirror. However, as shown in FIG. 2F(b), when the first data center 282 goes down, the treatment provider traffic is redirected to the replicated resources in the second data center 284 running a replicated web portal 222b. The switching process can be seamless, and treatment providers may be unaware of the switch to different resources in a replicated data center.

Figure 2G:
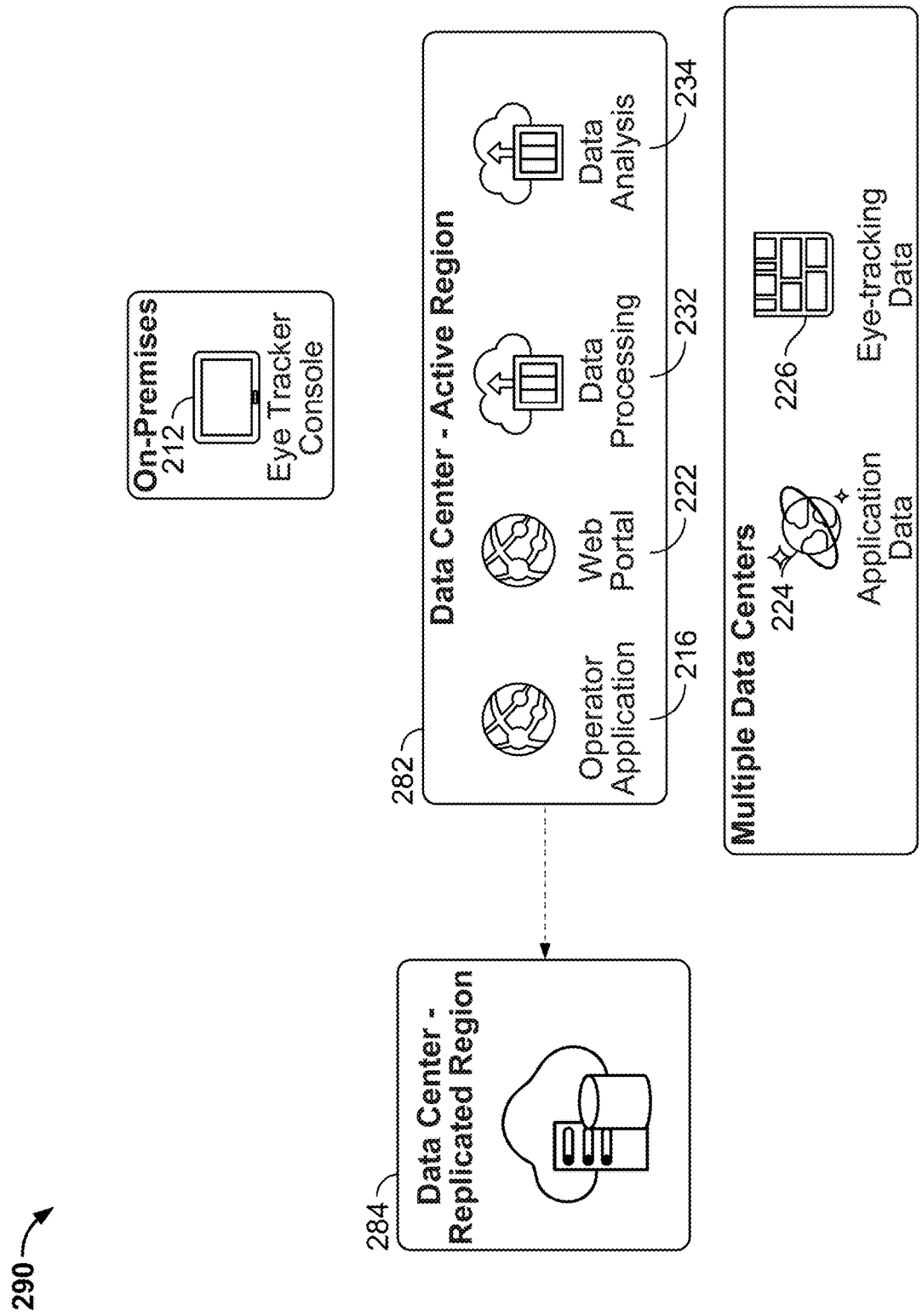

FIG. 2G shows an example data backup for the system 200, e.g., the platform subsystem 220 and the data pipeline subsystem 230. The database 224 storing application data and the database 226 storing raw and processed eye-tracking data and analyzed or diagnostic results can be stored in multiple data centers. The web portal 222 in the platform subsystem 220, and the data processing module 232 and the data analysis module 234 in the data pipeline subsystem 230, and optionally operator application 216 (running on the platform subsystem 220) can be included in an active data center 282, and can be replicated in a backup data center 284.

Example Processes for Session Data Acquisition

Figure 3:
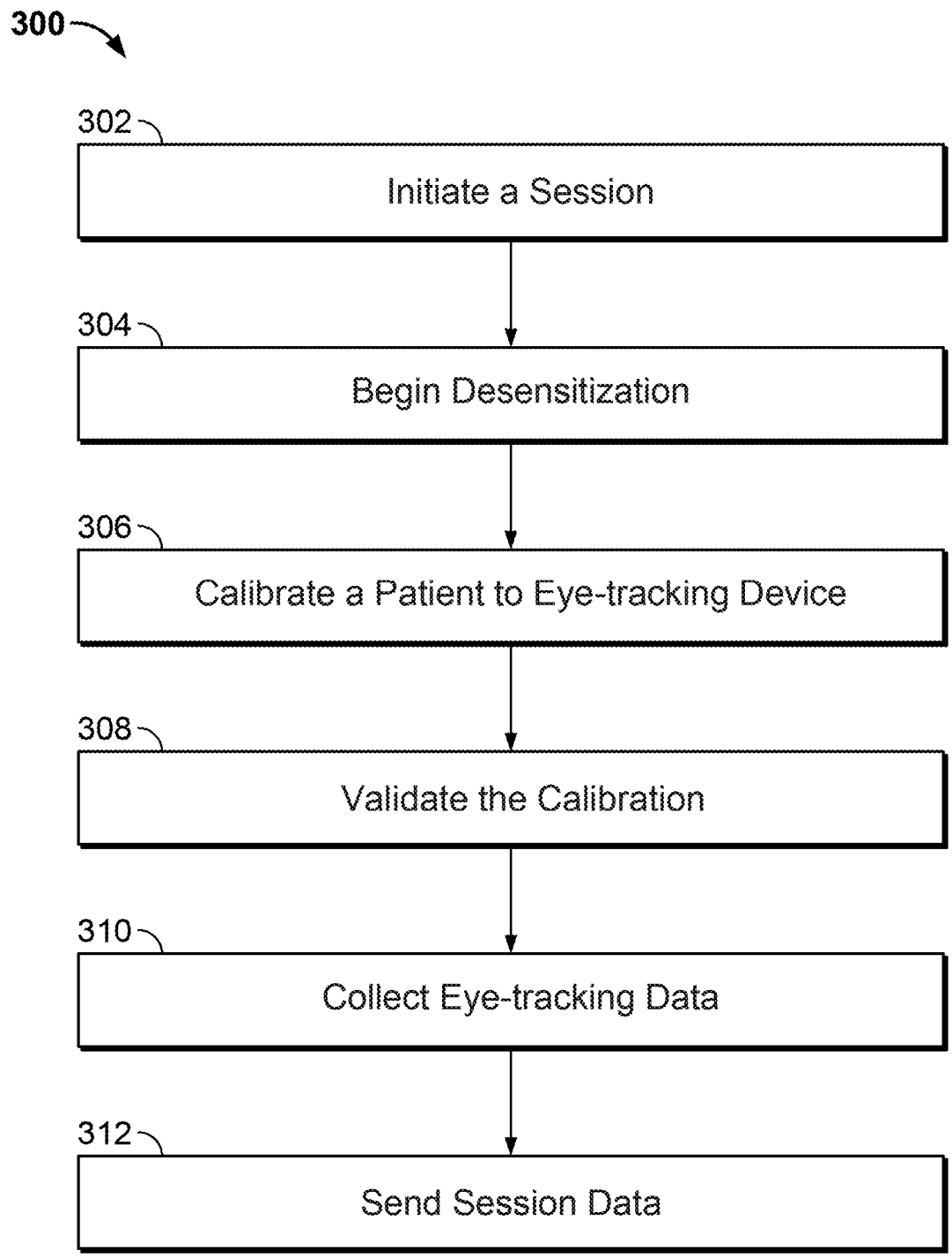
FIG. 3 is a flowchart of an example process for session data acquisition, according to one or more embodiments of the present disclosure.

FIG. 3 is a flowchart of an example process 300 for session data acquisition, according to one or more embodiments of the present disclosure. The process 300 can be performed by a system, e.g., the computing system of 120 of FIG. 1A or the data acquisition subsystem 210 of FIG. 2A. The system includes an operator-side computing device (e.g., 140 of FIG. 1) and one or more patient-side computing devices (e.g., 130 of FIG. 1) integrated with associated eye-tracking devices (e.g., 134 of FIG. 1). Each of the operator-side computing device and the one or more patient-side computing devices can communicate with a network-based server or a cloud server (e.g., the cloud server 110 of FIG. 1A or the cloud server as described in FIGS. 2A-2G) via a network (e.g., the network 102 of FIG. 1). The system can be associated with a treatment provider, e.g., providing developmental disorder assessment and/or treatment services to patients. The cloud server can be associated with a service provider for providing services, e.g., data processing, analysis, and diagnostic results, to treatment providers. For illustration, FIGS. 4A-4J show a series of illustrative display screens (or user interfaces) presented on an operator-side computing device (a) and on a patient-side computing device (b) during session data acquisition (e.g., in the process 300 of FIG. 3), according to one or more embodiments of the present disclosure.

At step 302, a session is initiated, e.g., by establishing a connection or communication between the operator-side computing device and a patient-side computing device. In some embodiments, the two computing devices 130 and 140 can be wirelessly connected, e.g., via a wireless connection, without physical connection. The wireless connection can be through a cellular network, a wireless network, Bluetooth, a near-field communication (NFC) or other standard wireless network protocol. In some cases, the patient-side computing device can be also configured to connect to the operator-side computing device through a wired connection such as universal serial bus (USB), e.g., when the wireless connection fails.

Figure 4A:
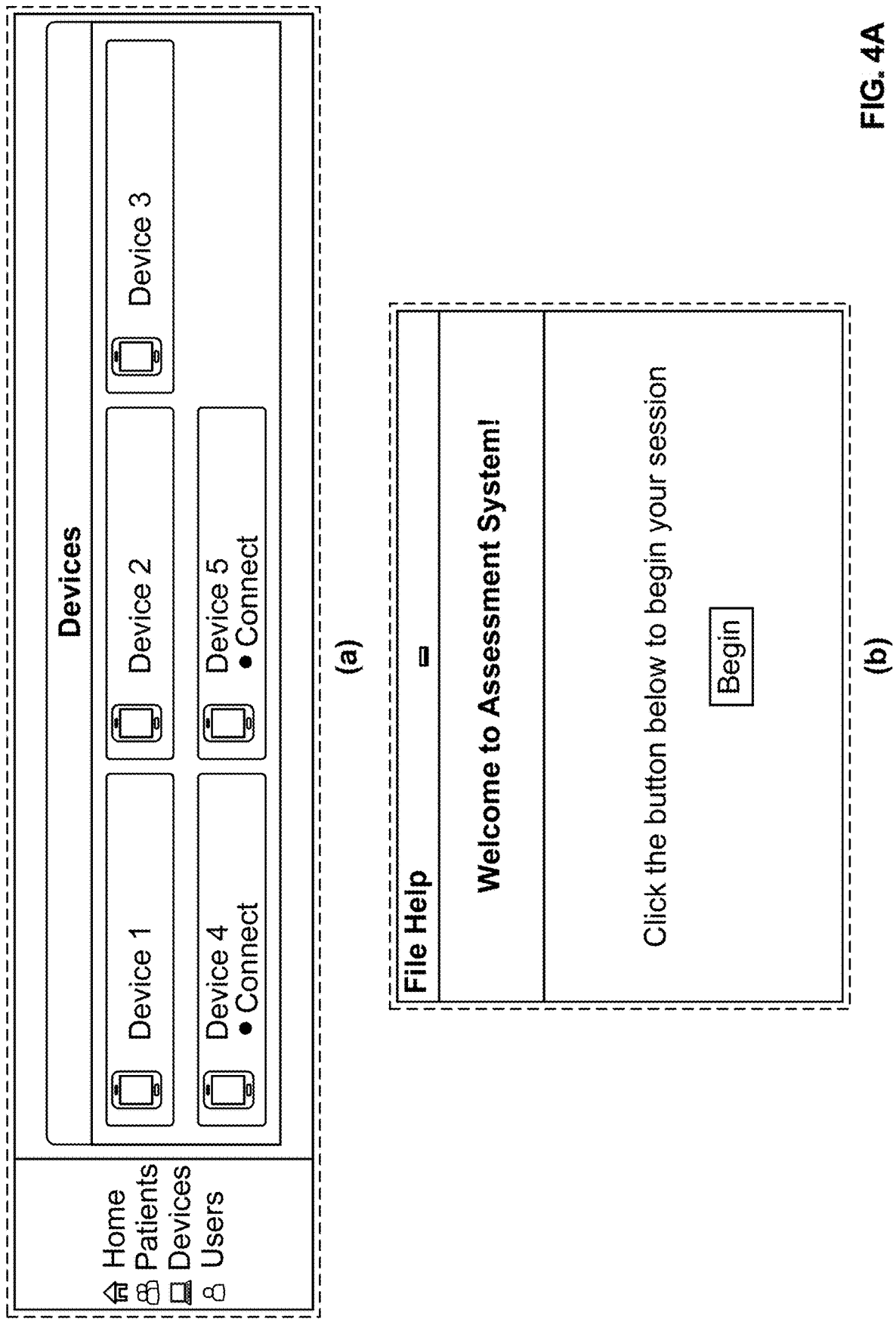
FIGS. 4A-4J show a series of illustrative user interfaces presented on an operator device (diagram a) and on a participant device (diagram b) during session data acquisition, according to one or more embodiments of the present disclosure.

In some embodiments, the connection between the operator-side computing device and the patient-side computing device is established by the two computing device communicating with the cloud server that, in turn, provides communication between the operator-side computing device and the patient-side computing device. For example, as illustrated in FIG. 4A, an operator (e.g., a medical assistant, a medical professional, or any other representative of the treatment provider) can log in a web portal (e.g., 222 of FIG. 2A) running on the cloud server for device management, patient management, and data management. The operator can have a corresponding user role and permission, e.g., as discussed in FIG. 2D. Diagram (a) of FIG. 4A shows a user interface (UI) presented on a display screen of the operator-side computing device after the operator logs in the web portal using the operator-side computing device. The UI can be a user interface of an operator application (e.g., 216 of FIG. 2A) running on the cloud server or on the operator-side computing device.

As shown in diagram (a) of FIG. 4A, the UI includes a menu showing buttons "Home", "Patients", "Devices", and "Users". By clicking a button, corresponding information (e.g., patient information, device information, or user information) can be presented in the UI. For example, when the button "Devices" is clicked, the UI shows a list of names of patient-side computing devices, e.g., Device 1, Device 2, Device 3, Device 4, Device 5, that are controllable by the operator. If a patient-side computing device is connected to the cloud server, e.g., Device 4, Device 5, an indication, e.g., a string showing "connect", can be presented adjacent to the name of the patient-side computing device. The operator can select one of the names, e.g., Device 4, to connect a corresponding patient-side computing device with the operator-side computing device. Once the name is selected, the UI shows a request for an access code to be input for connecting the corresponding patient-side computing device, as shown in diagram (a) of FIG. 4B.

Diagram (b) of FIG. 4A shows a user interface presented on a screen (e.g., 132 of FIG. 1) of a patient-side computing device, e.g., Device 4. For example, the UI can be presented after the patient-side computing device is turned on and logged in by the operator. The UI can show a button "Begin" that can be clicked, e.g., by the operator, to start a session. After the button "Begin" is clicked, the patient-side computing device is connected to the cloud server, e.g., to the web portal. The cloud server can associate the patient-side computing device with the operator based on an identifier of the patient-side computing device, e.g., as shown in FIG. 2D. Once the patient-side computing device is successfully connected to the cloud server, the UI presented on the patient-side computing device can show information of an access code, e.g., "5678", generated by the web portal for connection with the operator-side computing device, as shown in diagram (b) of FIG. 4B. The operator can get the access code from the UI presented on the patient-side computing device and input it on the UI presented on the operator-side computing device, then submit the access code to the web portal. After the web portal confirms the access code input in the operator-side computing device matches with the access code generator for the patient-side computing device, the web portal can establish a wireless connection between the operator-side computing device and the patient-side computing device.

Figure 4B:
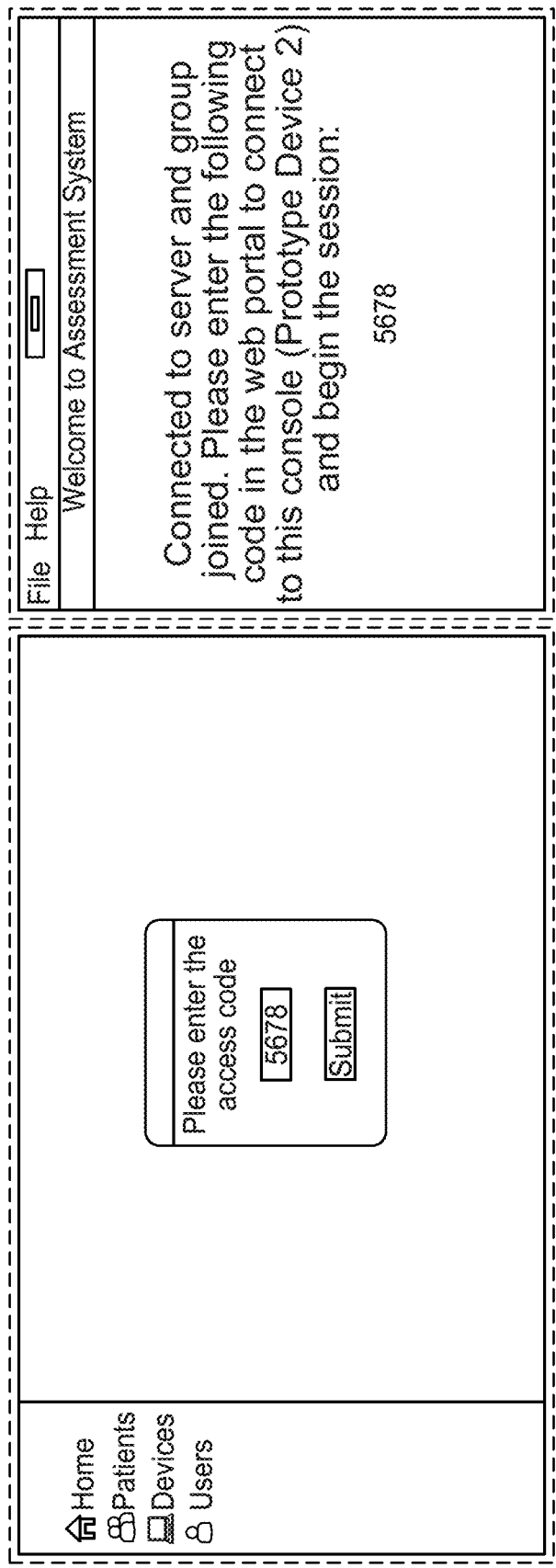
Figure 4C:
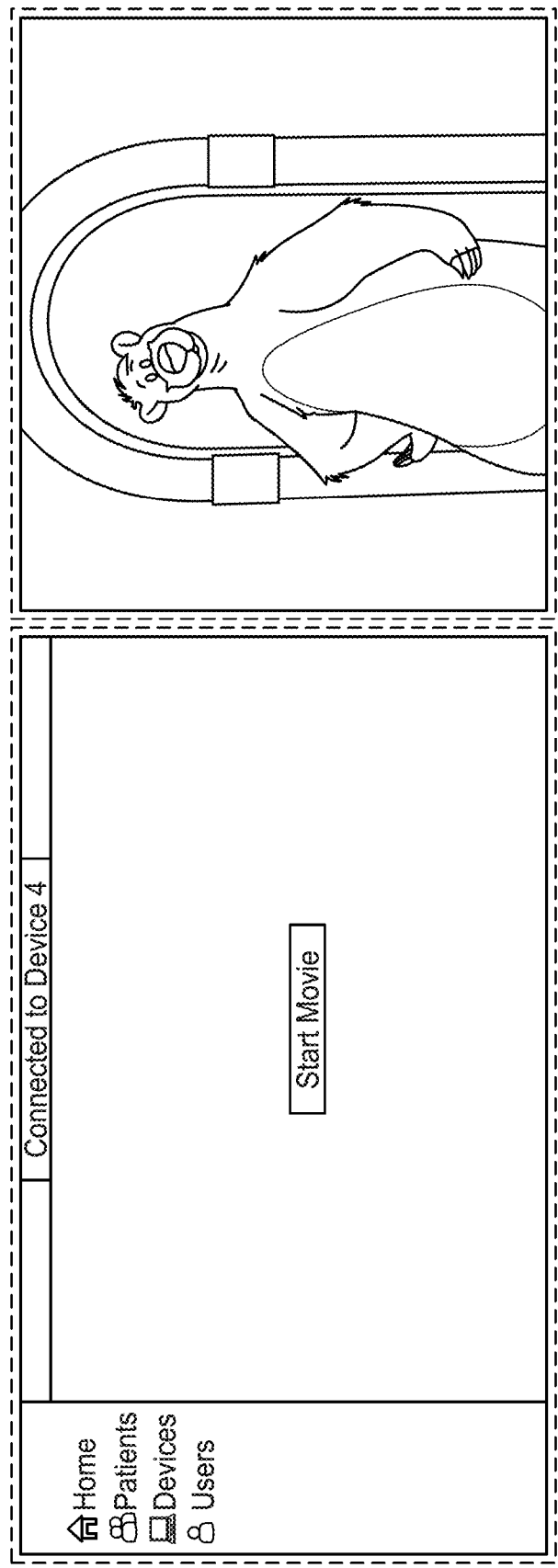

Once the connection between the operator-side computing device and the patient-side computing device (e.g., Device 4) is established, connection information, e.g., "Connected to Device 4", can be displayed on the UI of the operator-side computing device, e.g., as illustrated in diagram (a) of FIG. 4C. Meanwhile, the UI can show a button for starting displaying visual information, e.g., movies, on the screen of the patient-side computing device to a patient. A human caregiver of the patient, e.g., a parent, can bring (or carry) the patient to watch the movies presented on the screen of the patient-side computing device. In some embodiments, the human caregiver of the patient can wear eyeglasses configured to filter or block light (e.g., IR light) from the eye-tracking device, such that the eye-tracking device can only collect reflected or scattered light from eyes of the patient, not eyes of the human caregiver, for tracking/capturing eye movements of the patient while the patient (and the human caregiver) is watching visual stimuli on the patient-side computing device.

At step 304, desensitization begins, e.g., by the operator clicking the button "start movie" on the UI of the operator-side computing device, which can cause displaying visual desensitization information (e.g., movie) on the screen of the patient-side computing device to the patient, as illustrated in diagram (b) of FIG. 4C.

During the display of the desensitization movie, data are generally not recorded. Instead, the movie is displayed to gain the attention of the patient. The movie may reflexively cause exogenous cueing by the patient without the need for verbal mediation or instruction by the operator. For example, the operator need not give instructions to look at the screen of the patient-side computing device because the movie itself captures the patient's attention.

Figure 4D:
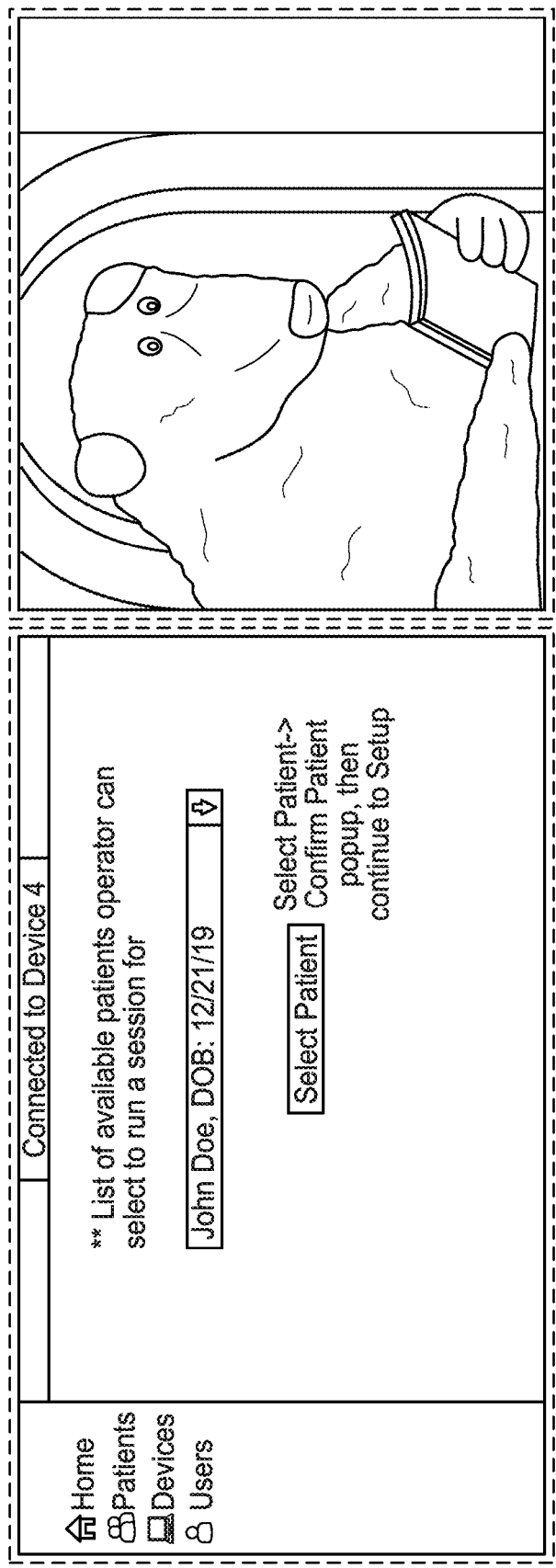

While the desensitization movie is displayed on the screen of the patient-side computing device, as shown in diagram (b) of FIG. 4D, the operator can select patient information of the patient through the UI of the operator-side computing device, as shown in diagram (a) of FIG. 4D. The operator can select a patient from a list of existing patients associated with the operator in the cloud server, e.g., as shown in FIG. 2D, or create a patient profile for a new patient. After the patient is confirmed, the process starts to setup the eye-tracking device (or the patient-side computing device) with respect to the patient, by showing setup information on the UI of the operator-side computing device, as illustrated in diagram (a) of FIG. 4E. The operator can also select "Pause Movie" or "Skip Movie" on the UI of the operator-side computing device.

Figure 4E:
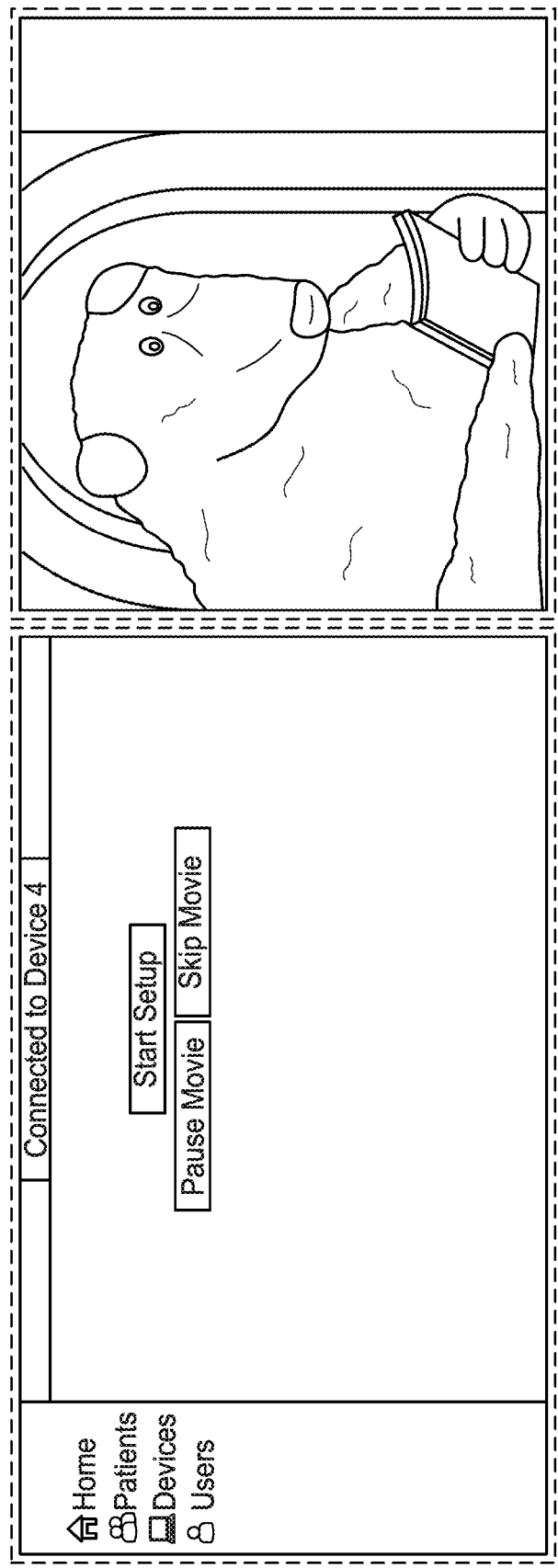
Figure 4F:
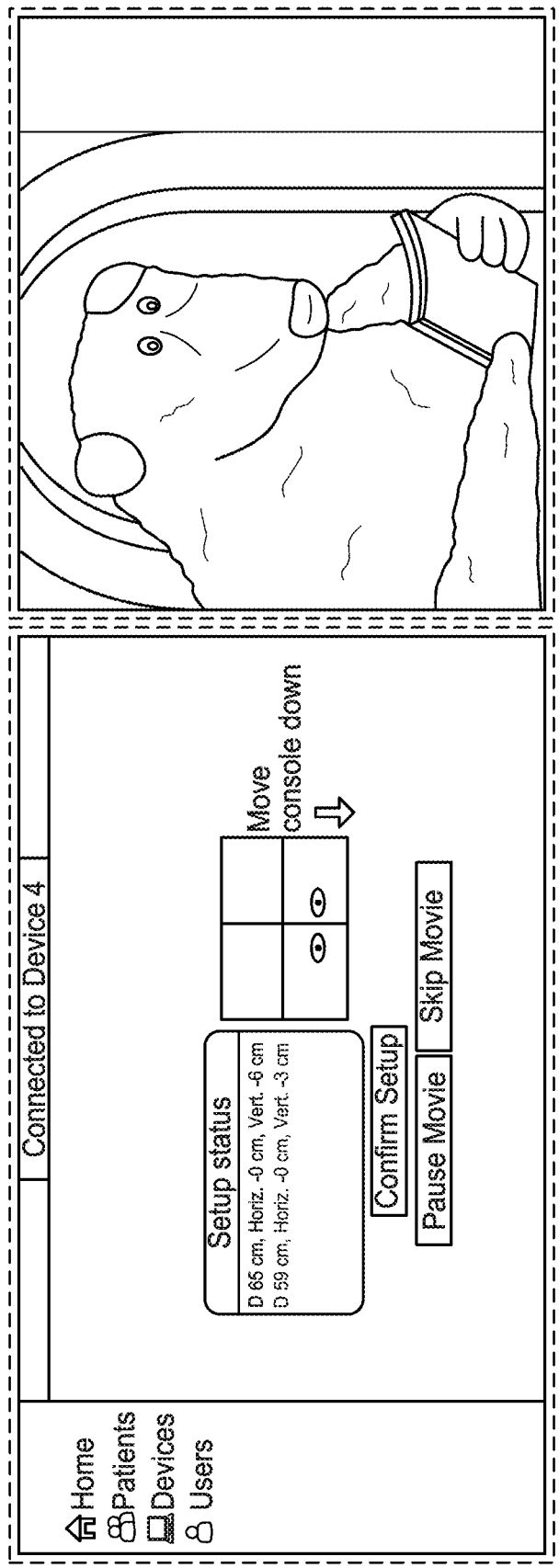

During the setup, the desensitization movie can be kept playing on the screen of the patient-side computing device, as illustrated in diagram (b) of FIG. 4E and diagram (b) of FIG. 4F. As shown in diagram (a) of FIG. 4F, on the UI of the operator-side computing device, a relative position between the eye-tracking device and eyes of the patient is shown, e.g., by text or graphically. The relative position can be determined by capturing image data of the eyes of the patient using an image acquisition device (e.g., a camera) included in or adjacent to the eye-tracking device. In some embodiments, after the operator clicked the button "Start Setup" in the UI of the operator-side computing device, as shown in diagram (a) of FIG. 4E, the operator application running on the cloud server can send a command to the patient-side computing device to capture an image of the eyes of the patient using the image acquisition device. The patient-side computing device can then transmit the captured image to the cloud server, and the operator application can process the image to determine a relative position between the eye-tracking device and the eyes of the patient. The relative position can include a distance between the eye-tracking device and the eyes of the patient, a horizontal and/or vertical deviation between a center of the eyes and a center of a field of view (or a detection area) of the eye-tracking device. Based on the relative position, the operator application can show an instruction for adjusting a position of the eye-tracking device, e.g., "Move console down", on the UI of the operator-side computing device, as shown in diagram (a) of FIG. 4F. Once the relative position of the eyes of the patient and the eye-tracking device is acceptable, the operator can confirm the setup, e.g., by clicking the button for "Confirm Setup" in the UI. In some embodiments, in response to determining that the relative location of the eyes of the patient and the eye-tracking device is smaller than a predetermined threshold (e.g., the horizontal/vertical deviation is smaller than 0.1 cm), the operator application can determine that the setup is completed and show an indication to the operator.

At step 306, the patient is calibrated with the eye-tracking device. After the setup is completed, the operator application can present a button for "Start Calibration" on the UI of the operator-side computing device, as shown in diagram (a) of FIG. 4G. In some embodiments, a calibration involves a patient looking at one or more fixed, known calibration targets (e.g., points or icons) in a visual field. The calibration or fixation target reflexively captures the patient's attention and results in a saccade towards, and fixation upon, a known target location. The target reliably elicits fixations to a finite location; for example, a radially symmetric target spanning less than 0.5 degrees of visual angle. Other examples include concentric patterns, shapes, or shrinking stimuli that, even if initially larger in size, reliably elicit fixations to fixed target locations.

Figure 4G:
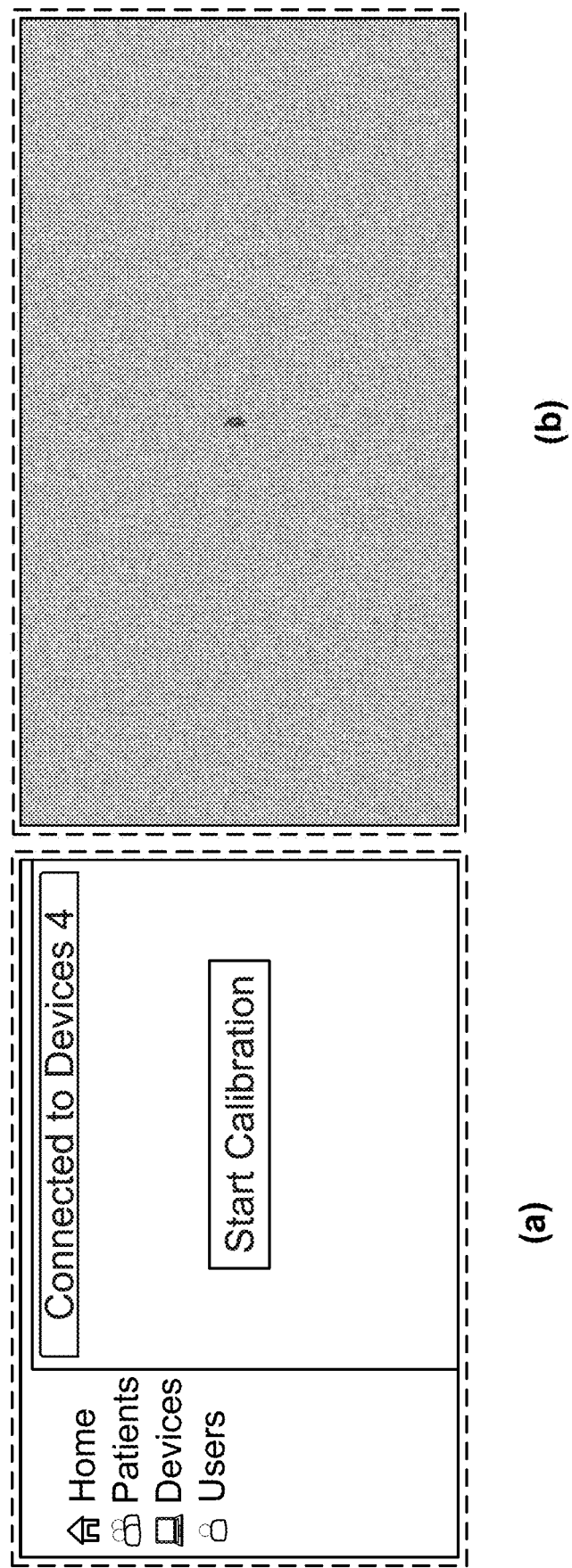

For example, once the operator clicks the button to start the calibration, a plurality of calibration targets can be sequentially presented at predetermined locations (or target locations) (e.g., a center, a left top corner, or a right bottom corner) on the screen of the patient-side computing device, e.g., as shown in diagram (b) of FIG. 4G. While presenting the plurality of calibration targets on the screen of the patient-side computing device, the eye-tracking device can be activated to capture eye-tracking calibration data of the patient, e.g., in response to receiving a command from the operator application. An eye-tracking application (e.g., 214 of FIG. 2A) can run on the patient-side computing device to collect the eye-tracking calibration data of the patient.

In some embodiments, the patient-side computing device (e.g., the eye-tracking application) is configured to determine a position of a corresponding visual fixation of a calibration target and then compare the determined position of the corresponding visual fixation of the patient with a predetermined location where the calibration target was presented. Based on a result of the comparison, the eye-tracking application can determine whether the calibration target is calibrated. If a distance between a position of the corresponding visual fixation of the patient and the predetermined location for a calibration target is within a predetermined threshold, the eye-tracking application can determine that the corresponding visual fixation of the patient matches with the predetermined location for the calibration target, or the calibration target is calibrated. If the distance is greater than or identical to the predetermined threshold, the eye-tracking application can determine that the corresponding visual fixation of the patient does not match the predetermined location, or the calibration target fails the calibration.

In some embodiments, the patient-side computing device transmits information about the captured eye-tracking calibration data of the patient and/or the predetermined locations to the operator-side computing device or the cloud server, the operator application can determine the positions of the corresponding visual fixations of the patient and compare the determined positions with the plurality of predetermined locations, and/or determine whether a calibration target is calibrated based on a result of the comparison.

In some embodiments, a first calibration target can be first presented at a center of the screen, and the calibration can continue with four more calibration targets presented at each corner of the screen along a rotating direction. The operator application can alert the operator the active status of calibration, e.g., calibrating point 1, calibrating point 2, calibrating point 3, or calibration complete 4/5 targets). Between each calibration target, a desensitization movie plays for a set period of time before a new calibration target is shown. Each calibration target can loop a set number of times before determining that the calibration target fails to be calibrated and moving on to the next calibration target. If a calibration target fails the calibration, it can be reattempted after all remaining calibration targets are shown and gaze collection attempted.

At step 308, the calibration is validated. The validation can be performed to measure the success of the calibration, e.g., by showing new targets and measuring the accuracy of the calculated gaze. The validation can show a smaller number of calibration targets, e.g., 3, than that for the calibration step 306, e.g., 5. A desensitization movie can be played between showing two adjacent calibration targets.

In some embodiments, based on the result of the comparison between determined positions of the corresponding visual fixations of the patient with predetermined locations where the calibration targets were presented, initial validations with varying levels of success (e.g., number of calibration targets calibrated or validated) can automatically instruct the operator to (1) recalibrate the eye-tracking device with the patient, (2) revalidate those calibration targets which could not be validated, or (3) accept the calibration and continue to data collection at step 310.

Figure 4H:
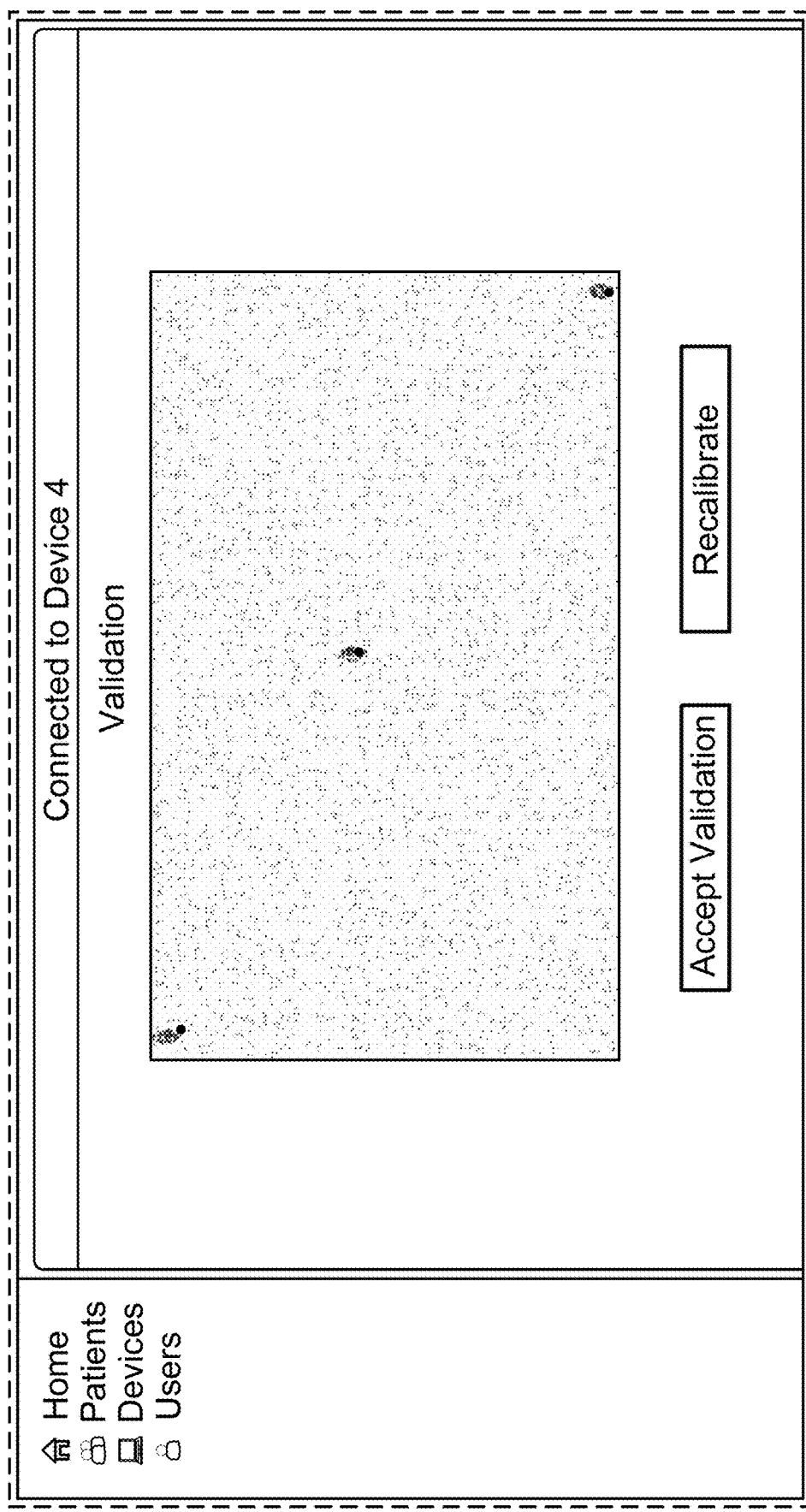

In some embodiments, the operator may have a discretion to decide whether to accept the calibration. As shown in FIG. 4H, on the display screen of the operator-side computing device, the calibration targets are simultaneously presented at the plurality of predetermined locations with representations (e.g., points) of the corresponding visual fixations of the patient at the determined positions of the corresponding visual fixations of the patient. The UI can also show a first button for "Accept Validation" and a second button for "Recalibrate". The operator can view the matching between the plurality of calibration targets and the representations of the corresponding visual fixations of the patient and determine whether to accept validation (by clicking the first button) or recalibrate the patient to the eye-tracking device (by clicking the second button).

At step 310, eye-tracking data of the patient is collected, e.g., after the calibration is validated or the operator accepts the validation, by presenting a playlist of predetermined visual stimuli (e.g., stimuli movies) to the patient on the screen of the patient-side computing device. As shown in FIG. 5(a), the list of predetermined visual stimuli can include a number of social stimuli videos (e.g., 0075PEER, 0076PEER, 0079PEER) specific to the patient, e.g., based on the patient's age and/or condition. Between each social stimuli videos or before presenting each social stimulus video, a centering video (e.g., a centerstim video) can be shown for briefly centering gaze of the patient. In some embodiments, as shown in FIG. 5(a), a calibration check (e.g., similar to that at step 306) is performed in the data collection step, e.g., between showing centering videos. For example, the calibration check can include showing five calibration targets, CCTL for calibration check top left, CCTR for calibration check top right, CCBL for calibration check bottom left, CCCC for calibration check center-center, CCBR for calibration check bottom right. Data related to the calibration check can be used in post hoc processing, e.g., for recalibrating eye-tracking data and/or for determining a calibration accuracy.

Figure 4I:
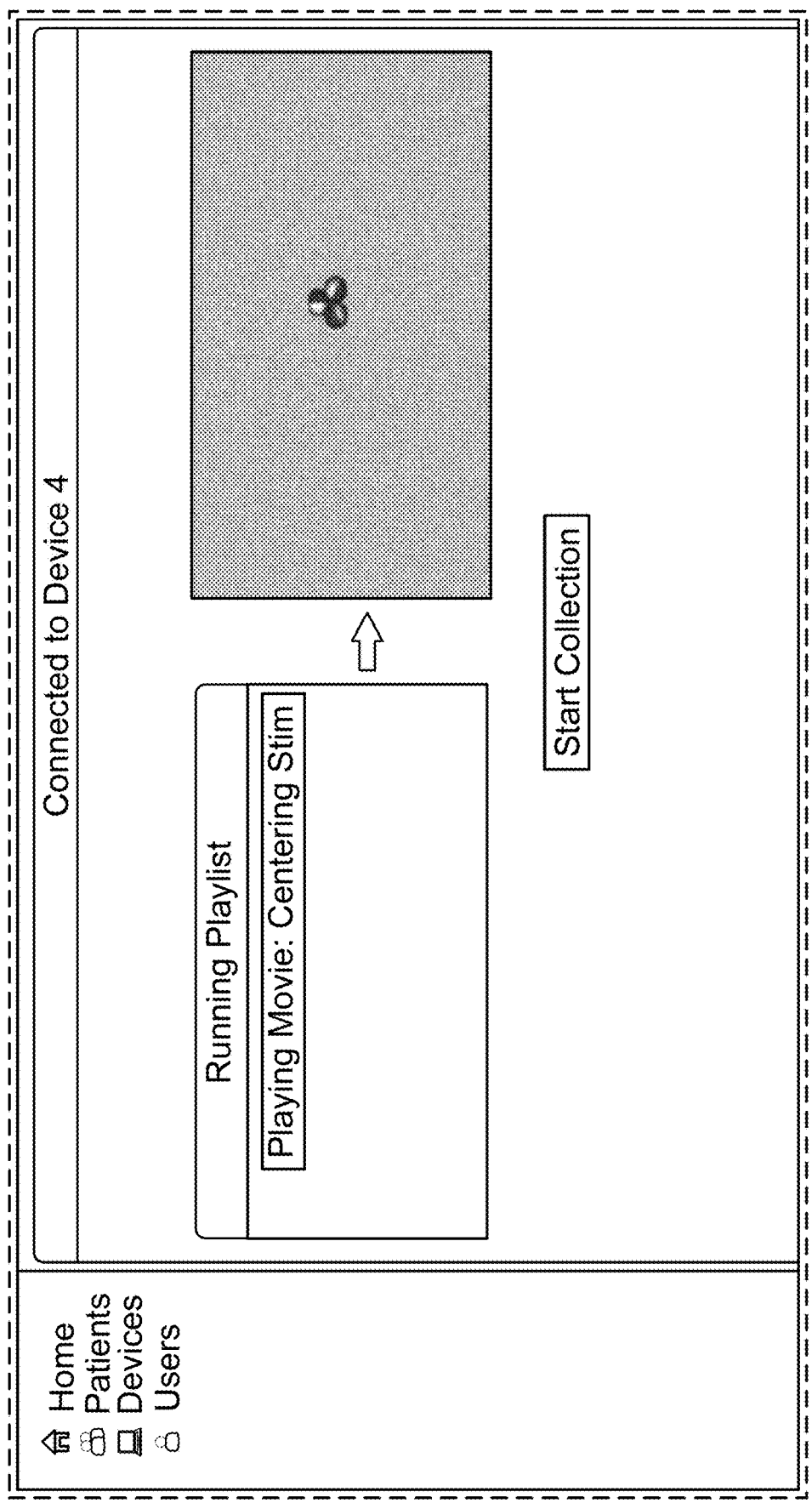

In a particular example, a sequence of data collection at step 310 can be as follows:
1. Centering stim
2. Stimuli movie
3. Centering Stim
4. Stimuli Movie or calibration check (e.g., displaying 5 calibration targets such as randomly played between 2 to 4 stimuli movies)
5. Repeat steps 1-4 until the playlist of predetermined stimuli movies completes In some embodiments, as shown in FIG. 4I, the UI on the operator-side computing device shows a button for "Start Collection". After the operator clicks the button for "start collection", the playlist of predetermined visual stimuli can be sequentially presented on the screen of the patient-side computing device according to a predetermined sequence. On the screen of the operator-side computing device, as shown in FIG. 4I, the UI can show a status of running the playlist in text (e.g., playing movie: centering stim) or showing a same content (e.g., showing a centering stim video) as that presented on the screen of the patient-side computing device.

Figure 4J:
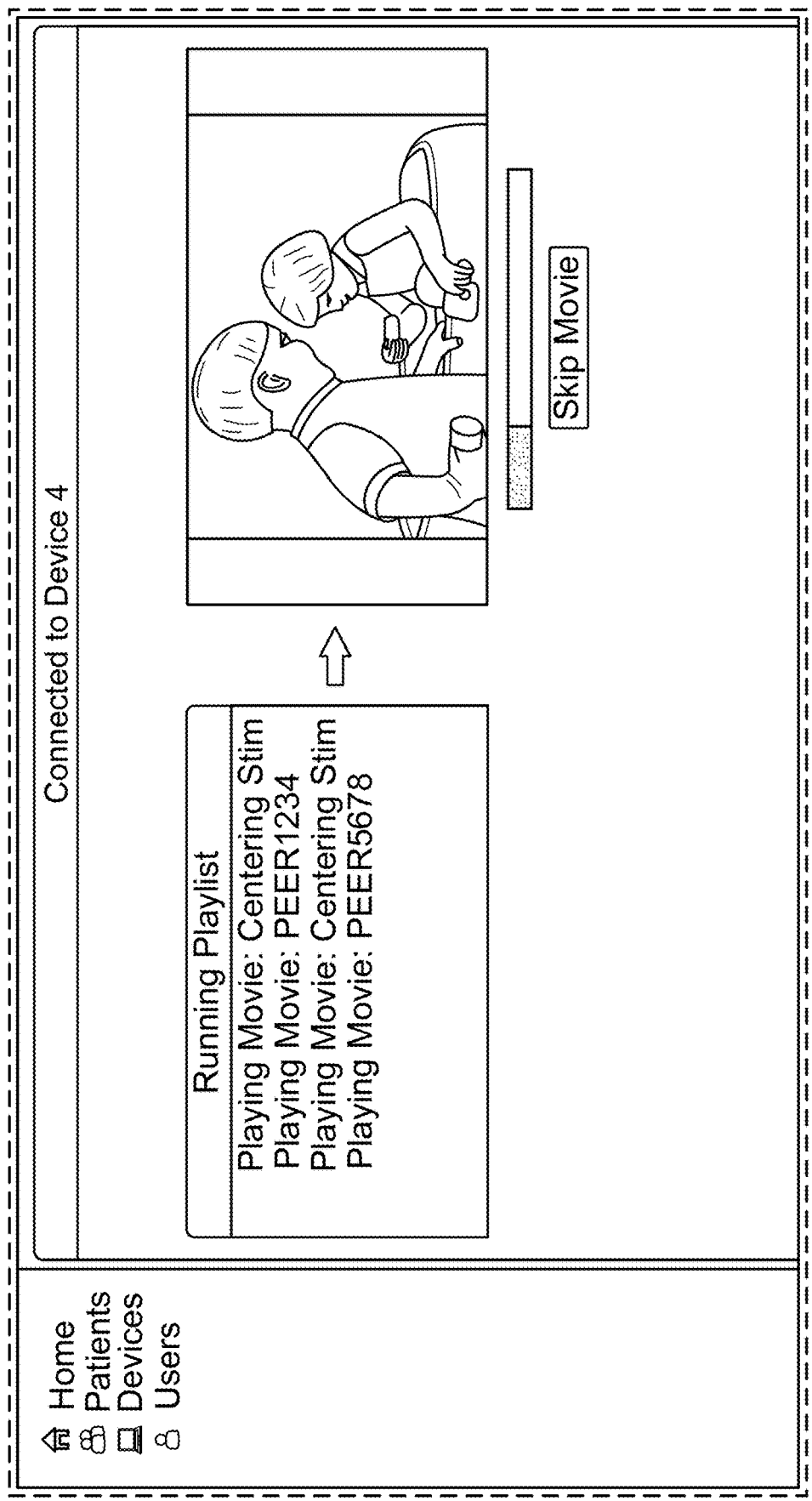

In some embodiments, as shown in FIG. 4J, the UI can show a running playlist of videos that have been played or being played, e.g., Centering Stim, PEER1234, Centering Stim, PEER5678. The UI can also show the video that is being presented on the screen of the patient-side computing device. The UI can also show a progress bar indicating a percentage of stimuli movies that have been played among the playlist of predetermined stimuli movies. The UI can also show a button for the operator to skip movie.

In some embodiments, calibration accuracy of collected eye-tracking data (e.g., 812 of FIG. 8A) can be assessed, e.g., via the presentation of visual stimuli that reflexively capture attention and result in a saccade towards, and fixation upon, a known target location. The target reliably elicits fixations to a finite location; for example, a radially symmetric target spans less than 0.5 degrees of visual angle. Other examples include concentric patterns, shapes, or shrinking stimuli that, even if initially larger in size, reliably elicit fixations to fixed target locations. Such stimuli may be tested under data collection with head restraint to ensure that they reliably elicit fixations under ideal testing circumstances; then their use can be expanded to include non-head-restrained data collection.

In some embodiments, numerical assessment of the accuracy of collected eye-tracking data may include the following steps: (1) presenting a fixation target that reliably elicits fixation to a small area of the visual display unit; (2) recording eye-tracking data throughout target presentation; (3) identifying fixations in collected eye-tracking data; (4) calculating a difference between fixation location coordinates and target location coordinates; and (5) storing the calculated difference between fixation location coordinates and target location coordinates as vector data (direction and magnitude) for as few as one target or for as many targets as possible (e.g., five or nine but can be more). In some embodiments, recalibrating or post-processing step can be executed, e.g., by applying spatial transform to align fixation location coordinates with actual target location coordinates, by approaches including but not limited to (a) Trilinear interpolation, (b) linear interpolation in barycentric coordinates, (c) affine transformation, and (d) piecewise polynomial transformation.

Once the playlist of predetermined visual stimuli is completely played, the session ends. The patient-side computing device can generate session data based on raw eye-tracking data collected by the eye-tracking device, e.g., storing the raw eye-tracking data with associated information (timestamp information) in a data file (e.g., in .tsv format, .idf format, or any suitable format), as illustrated in FIG. 5(b). The raw eye-tracking data can include values for a number of eye-tracking parameters at different timestamps. The eye-tracking parameters can include gaze coordinate information of left eye, right eye, left pupil, and/or right pupil.

The session data can also include information of played or presented visual stimuli in another data file (e.g., in .tsv format or any suitable format), as illustrated in FIG. 5(a). The information can include timestamp information and name of each visual stimulus played. The timestamp information of visual stimuli can be associated with the timestamp information of the eye-tracking data, so that eye-tracking data for each visual stimulus (and/or calibration check) can be individually determined based on the timestamp information in these two data files.

At step 312, session data is sent to the cloud server. Once the session data is generated by the patient-side computing device, the patient-side computing device can transmit the session data to the cloud server. As discussed in FIGS. 2A-2G and with further details in FIGS. 6, 7A-7B, and 8, the cloud server can first store the session data in a centralized database, e.g., the database 226 of FIGS. 2A-2B, then process the session data, analyze the processed data, and generate a diagnostic result of the patient, which can be accessible or viewable by the operator or a medical professional.

Example Data Processing and Analysis

FIG. 6 is a flowchart of an example process 600 for managing session data, e.g., data processing and analysis, by a cloud server (e.g., the cloud server 110 of FIG. 1A or the cloud server as described in FIGS. 2A-2G), according to one or more embodiments of the present disclosure. FIGS. 7A-7B show a flowchart of an example process 700 for managing session data by the cloud server with more details than FIG. 6, according to one or more embodiments of the present disclosure.

At step 702, once a session is complete, a corresponding patient-side computing device (e.g., 130 of FIG. 1) or eye tracking console (e.g., 212 of FIGS. 2A-2G) transmits session data of the session to a cloud platform of the cloud server, e.g., through a web portal. The cloud platform can be the platform 112 of FIG. 1A or the platform subsystem 220 of FIGS. 2A-2G. In response to receiving the session data, the cloud platform of the cloud server stores the session data in a database (e.g., the database 226 of FIGS. 2A-2G) in the cloud platform. Then, the cloud platform automatically transfers the session data to a data pipeline system (e.g., 114 of FIG. 1A or 230 of FIGS. 2A-2G) for data processing and analysis.

At step 704, file pointers for session data of sessions are added to a processing queue (step 704). Session data of all completed sessions wait for processing according to the processing queue. As soon as session data of a session is uploaded and stored in the cloud server, a corresponding file pointer can be assigned to the session data of the session and added in the processing queue. A file pointer can be an identifier for session data of a respective session. The session data of the respective session can be retrieved from the database in the cloud platform based on the file pointer.

At step 706, a respective container is created for session data of each session, e.g., based on auto scaling technology, which can implement session parallelization. For example, in response to adding a file pointer for a new session into the processing queue, a new container can be created for the new session. Each container (e.g., 231 of FIG. 2C) can have its own instance of data processing module and data analysis module, e.g., as illustrated in FIG. 2C.

In each container, steps 708 to 714 are performed for session data of a corresponding session, e.g., by data processing module 232 of FIGS. 2A-2G. Note that steps 708 to 714 can be performed for session data of multiple sessions in multiple containers in parallel.

At step 708 (corresponding to step 602 of FIG. 6), the session data is obtained from the database in the cloud platform using a corresponding file pointer. As noted above, the session data can include two files: eye-tracking data file (e.g., as illustrated in FIG. 5(b)) and a playlist file (e.g., as illustrated in FIG. 5(a)).

Referring to FIG. 6, step 602 can correspond to step 708. At step 604, the session data is prepared for processing. Step 604 can include one or more steps as described in steps 710 to 714 of FIG. 7.

Step 604 can include linking eye-tracking data in the eye-tracking data file to movies played in the playlist file. In some embodiments, as illustrated in FIG. 7A, at step 710, the eye-tracking data is broken up into separate runs, e.g., based on timestamp information in these two files. Each run can correspond to playing a corresponding movie (e.g., the centering target, a predetermined visual stimuli, or one or more calibration targets). For example, eye-tracking data corresponding to timestamps within a range defined by timestamps of two adjacent movies is included in a run. At step 712, eye-tracking data in each run is linked to the corresponding movie from the playlist, based on timestamp information in these two files. In some embodiments, the eye-tracking data are not broken up into separate runs, instead, are processed as a continuous stream with data samples linked to corresponding movies in the playlist.

At step 714, eye-tracking data is recalibrated to account for drift or deviation. In some embodiments, eye-tracking data collected in the calibration step during presenting the playlist, e.g., as illustrated in diagram (a) of FIG. 5, can be used to calibrate or align the eye-tracking data collected during playing individual movies in the different runs. For example, with data from times adjacent to when additional calibration targets were shown, any discrepancies in gaze position are corrected. Some larger discrepancies may exclude certain data from subsequent analysis.

At step 606, the prepared session data is processed. In some embodiments, the data processing module extracts relevant information, e.g., visual fixation of the patient and/or visual fixations to objects or regions of interest in the movie, from the prepared session data. In some embodiments, data are resampled to account for any variance in time between samples. The data can be resampled using any suitable interpolation and/or smoothing technique. The data can be converted from a specified original resolution and/or coordinate system of the collected eye-tracking data to an appropriate resolution and/or coordinate system for analysis. For example, raw data can be collected at a higher resolution (e.g., 1024×768 pixels) than that of the presented stimuli (e.g., rescaled to 640×480 pixels). In some embodiments, the data processing module can automatically identify basic oculomotor events (unwanted fixations, saccades, blinks, off-screen or missing data, etc.), and can automatically identify times at which the subject was fixating (in an undesirable way), saccading, blinking, or times when the subject was not looking at the screen. The data processing module can adjust for aberrations in gaze position estimations as output by the eye-tracking device.

In some embodiments, as illustrated in step 716 of FIG. 7B, session data for multiple sessions of patients are processed in multiple session containers in parallel with pre-loading corresponding model data for the patients into the multiple session containers. In some examples, the session data of the multiple sessions are being processed in the multiple session containers using a majority of processing units (e.g., N processing cores) in the cloud server, while the corresponding model data are pre-loaded into the multiple session containers in parallel, using a minority of the processing units (e.g., M processing cores) in the cloud server. A processing unit or core can be a central processing unit (CPU). The parallelization can avoid additional time for waiting for uploading the model data.

The cloud server can pre-store model data in the database, e.g., 226 of FIGS. 2A-2G. The model data can include data of a large number of instances of significant difference in gaze position for patients (e.g., infants, toddlers or children) across varying levels of social, cognitive, or developmental functioning. Corresponding model data for a patient can include data related to the patient at a similar age, a similar background, and/or a similar condition, which can be used with processed session data for the patient to generate a diagnostic result for the patient. The corresponding model data for the patient can be identified and retrieved from the database, e.g., based on the age of the patient, the background of the patient, and/or the condition of the patient. Step 608 of the process 600, at which processed data is prepared for analysis, can include obtaining the processed data in the multiple session containers and pre-loading the corresponding model data in the multiple session containers.

At step 610, processed data is analyzed to generate an analyzed result. In some embodiments, for a session, the processed data is compared with corresponding model data in a corresponding session container to get a comparison result. In some embodiments, the data analysis module generate a result using the processed data and the corresponding model data, e.g., using comparison or inference via statistical models, algorithms, artificial intelligence (AI) models such as machine learning or artificial neural network models. In some embodiments, as illustrated in step 718 of FIG. 7B, in the multiple session containers, processed session data and pre-loaded model data are analyzed in parallel using a total number of processing units, e.g., N+M cores.

In some embodiments, processed session data are compared with corresponding data models to determine a level of a developmental, cognitive, social, or mental condition. A generated score is then compared to predetermined cutoff or other values to determine the patient's diagnosis of ASD, as well as a level of severity of the condition. In certain other embodiments, a patient's point-of-gaze data (e.g., visual fixation data) is analyzed over a predetermined time period (e.g., over multiple sessions spanning several months) to identify a decline, increase, or other salient change in visual fixation (e.g., point-of-gaze data that initially corresponds to that of typically-developing children changing to more erratic point-of-gaze data corresponding to that of children exhibiting ASD, or point-of-gaze data that becomes more similar to typically-developing children in response to targeted therapy).

Figure 8A:
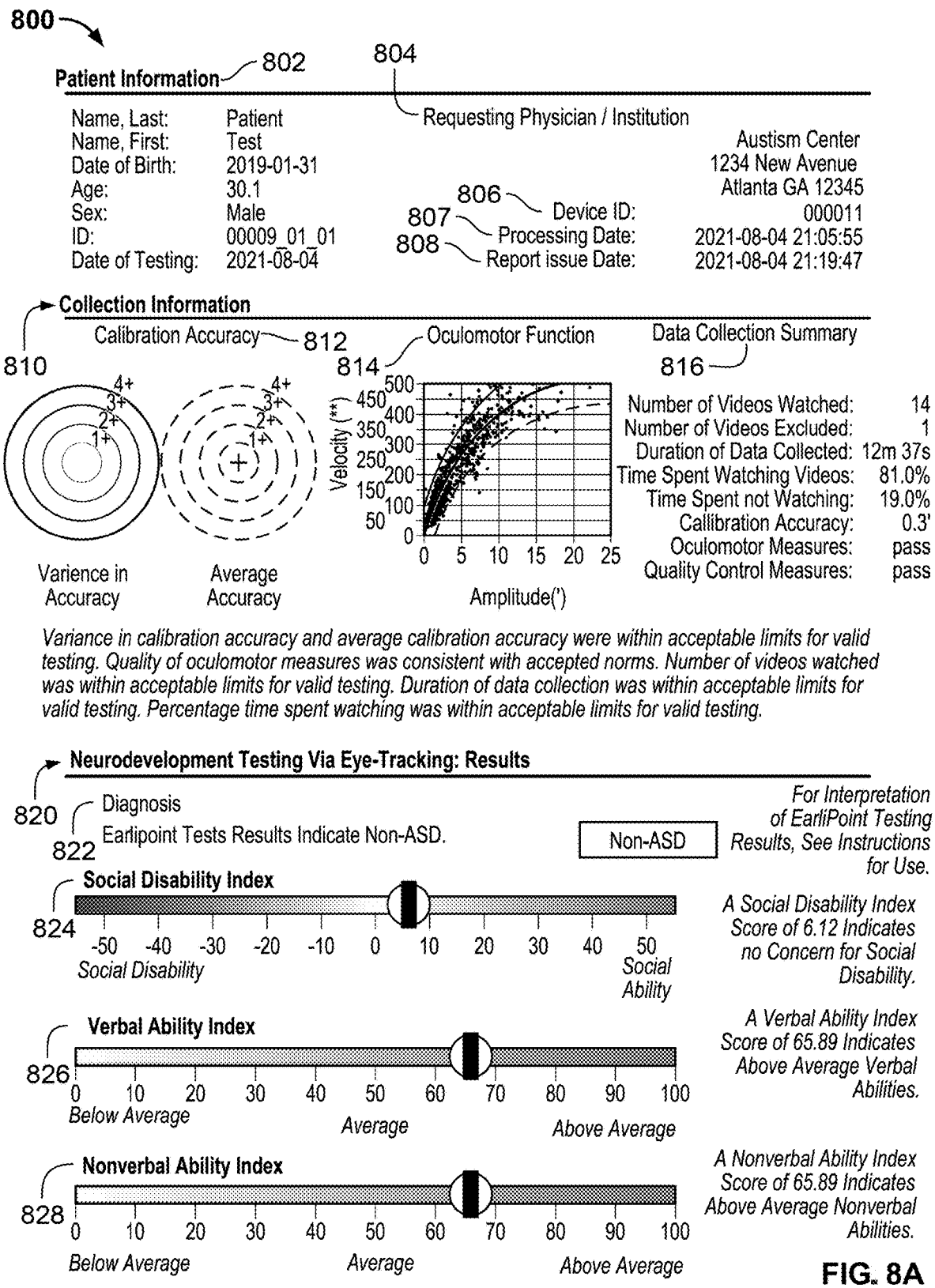
FIG. 8A illustrates an example result interface displaying at least one index value based on eye-tracking data, according to one or more embodiments of the present disclosure.

At step 720 (corresponding to step 612), a summary of results is calculated. As noted above, the analyzed result can be used to determine a score for at least one index, e.g., social disability index, verbal ability index, nonverbal ability index, social adaptiveness index, and/or social communication index. Based on a comparison of the score with at least one predetermined cutoff value, the patient's diagnosis of ASD, as well as a level of severity of the condition can be calculated. For example, as illustrated in FIG. 8A, based on the analyzed result and/or any other suitable information (e.g., from other related analysis on the patient), a social disability index score of 6.12 is shown in a range from −50 (social disability) to 50 (social ability) and indicates no concern for social disability; a verbal ability index score of 85.89 is shown in a range from 0 to 100 and indicates above average verbal abilities; a nonverbal ability index score of 85.89 is shown in a range from 0 to 100 and indicates above average nonverbal abilities. Moreover, a diagnosis of Non-ASD can be also calculated based on the analyzed data.

In some embodiments, a summary of results includes a visualization of the individual's eye-tracking data (e.g., point-of-gaze data) overlaid on movie stills from socially relevant moments, allowing clinicians and parents to better understand how the patient visually attends to social information. For example, at step 610, the movie stills for which the patient has usable data can be cross-referenced against the list of movie stills that have been pre-determined to elicit eye-gaze behavior with information about diagnostic status, including symptom severity. The visualization can also include a visualization of aggregated reference data from typically developing children, for example, matched on patient attributes such as age, sex, etc. These visualizations can be side-by-side so that the clinician and/or parent can compare the individual patient data to the reference data, and see how gaze pattern align or diverge. These visualizations may include annotations explaining movie content, eye-gaze patterns, and more.

In some embodiments, a summary of the results includes an animation visualizing the patient's eye-tracking data overlaid on movie stills from socially relevant moments. For example, the web portal may contain a dashboard that allows the clinician to view the stimulus movie shown the patient, with their eye-gaze data overlaid. The dashboard may be configurable to allow the user to select which movies to visualize, and whether to visualize frames that capture information about the social disability index, verbal ability index, non-verbal index, or any other index calculated in the report.

With continued reference to FIG. 7B, at step 722, a result output is returned to the web portal, e.g., as illustrated in FIG. 2B, by the data pipeline subsystem. In some embodiments, the result output includes three files: one containing processed eye-tracking data, one containing a summary of eye tracking statistics, and one containing the diagnostic information (e.g., the summary of results). The three files can then be uploaded to the database (e.g., 226 of FIGS. 2A-2G) for storage. In some cases, the processed eye-tracking data are tabulated into a session table. Summary of eye tracking information (e.g., fixation samples/movie, etc.) can be read from the processed summary file and tabulated in the database for subsequent query. Summary values (e.g., percentage fixation/movie, etc.) can be then calculated within the database.

At step 724, the result output is reconnected with patient information to generate a diagnostic report or result for the patient. For example, the file containing diagnostic information can be uploaded to an application data database (e.g., 224 of FIGS. 2A-2G) to be associated with the patient in the application data, e.g., as illustrated in FIG. 2D. The diagnostic report or result can be presented to a user associated with the patient in the application data database (an operator or a medical professional such as a physician) or a caregiver associated with the patient in any suitable manner.

In some embodiments, once the diagnostic report or result for the patient is generated, the user can be notified (e.g., by email or message) to log in to view the diagnostic report or result through the web portal. The diagnostic report or result can be presented on a user interface, e.g., as shown in FIG. 8A, or FIGS. 8B-8C, or FIGS. 16A-16F. In some embodiments, once the diagnostic report or result for the patient is generated, the diagnostic report or result can be sent to an operator-side computing device for presenting to the user. The diagnostic report or result can be also sent in a secure email or message to the operator. The diagnostic report or result can be stored in the application data database (e.g., 224 of FIGS. 2A-2G) and/or the database (e.g., 226 of FIGS. 2A-2G).

FIG. 8A illustrates an example result interface 800 displaying an evaluation report (or diagnostic report or result) including at least one index value based on eye-tracking data, according to one or more embodiments of the present disclosure. The result interface 800 shows patient information 802, requesting physician/institution information 804, device ID of a patient-side computing device 806, processing date 807 (indicating time for obtaining session data for processing), report issue date 808.

The result interface 800 also shows collection information 810 that includes calibration accuracy 812, oculomotor function 814, and data collection summary 816. The calibration accuracy 812 and the oculomotor function 814 can be presented graphically. The data collection summary 816 can include at least one of a number of videos watched, a number of videos excluded, a duration of data collected, time spent watching videos, time spent not watching, a calibration accuracy, oculomotor measures, or quality control measures.

The result interface 800 also shows neurodevelopmental testing result 820, which can include a diagnostic result 822 (e.g., ASD or Non-ASD), social disability index information 824, verbal ability index information 826, and nonverbal ability index information 828. The result interface 800 can graphically show these index information 824, 826, 828, with corresponding descriptions.

Figure 8B:
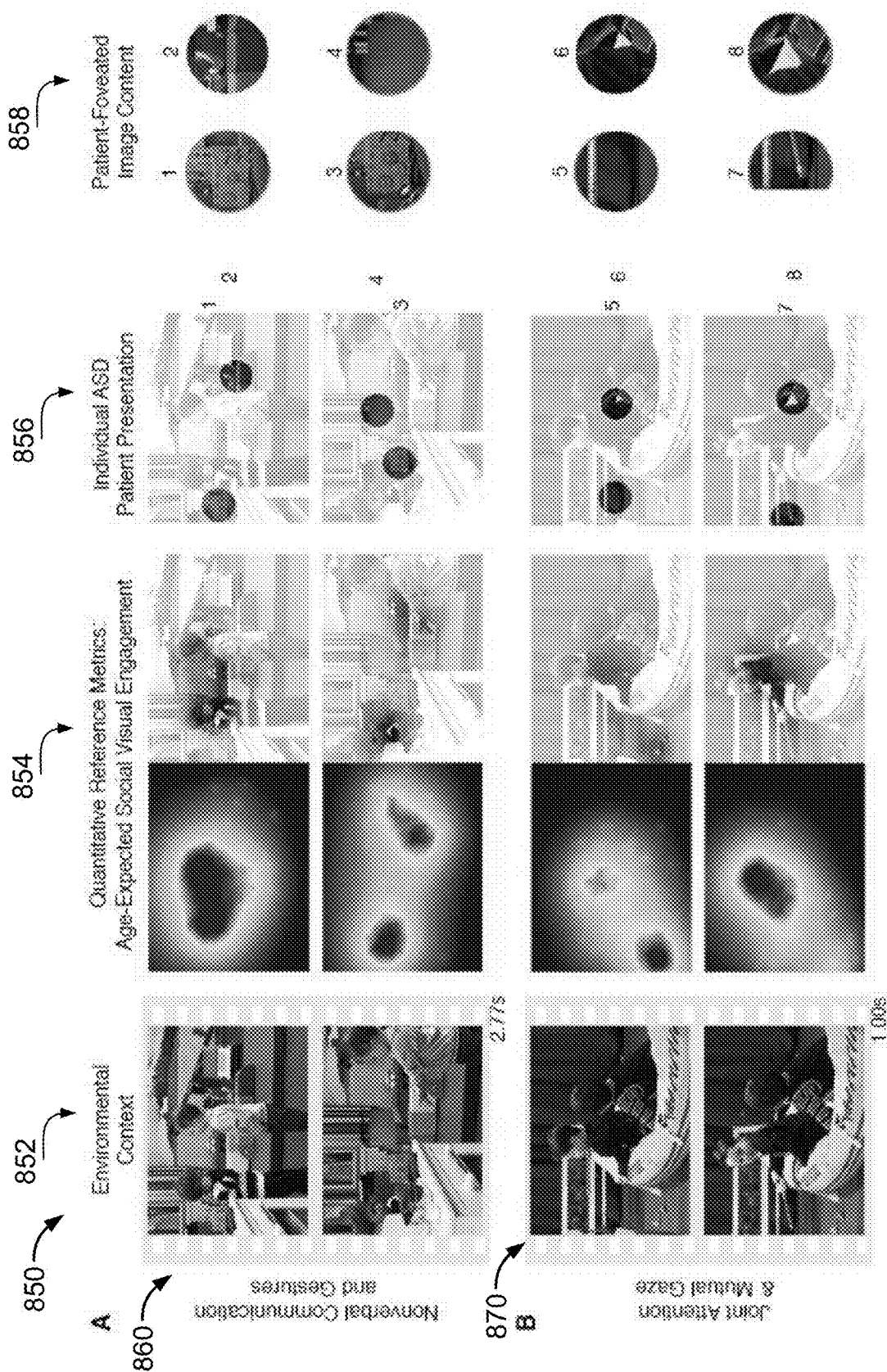
FIGS. 8B-8C illustrate another example result interface displaying performance-based measures of developmental assessment based on eye-tracking data, on instances of: Nonverbal Communication and Gestures (A) and Joint Attention & Mutual Gaze (B) in FIG. 8B, Facial Affect (C) and Pointing and Social Monitoring (D) in FIG. 8C, according to one or more embodiments of the present disclosure.
Figure 8C:
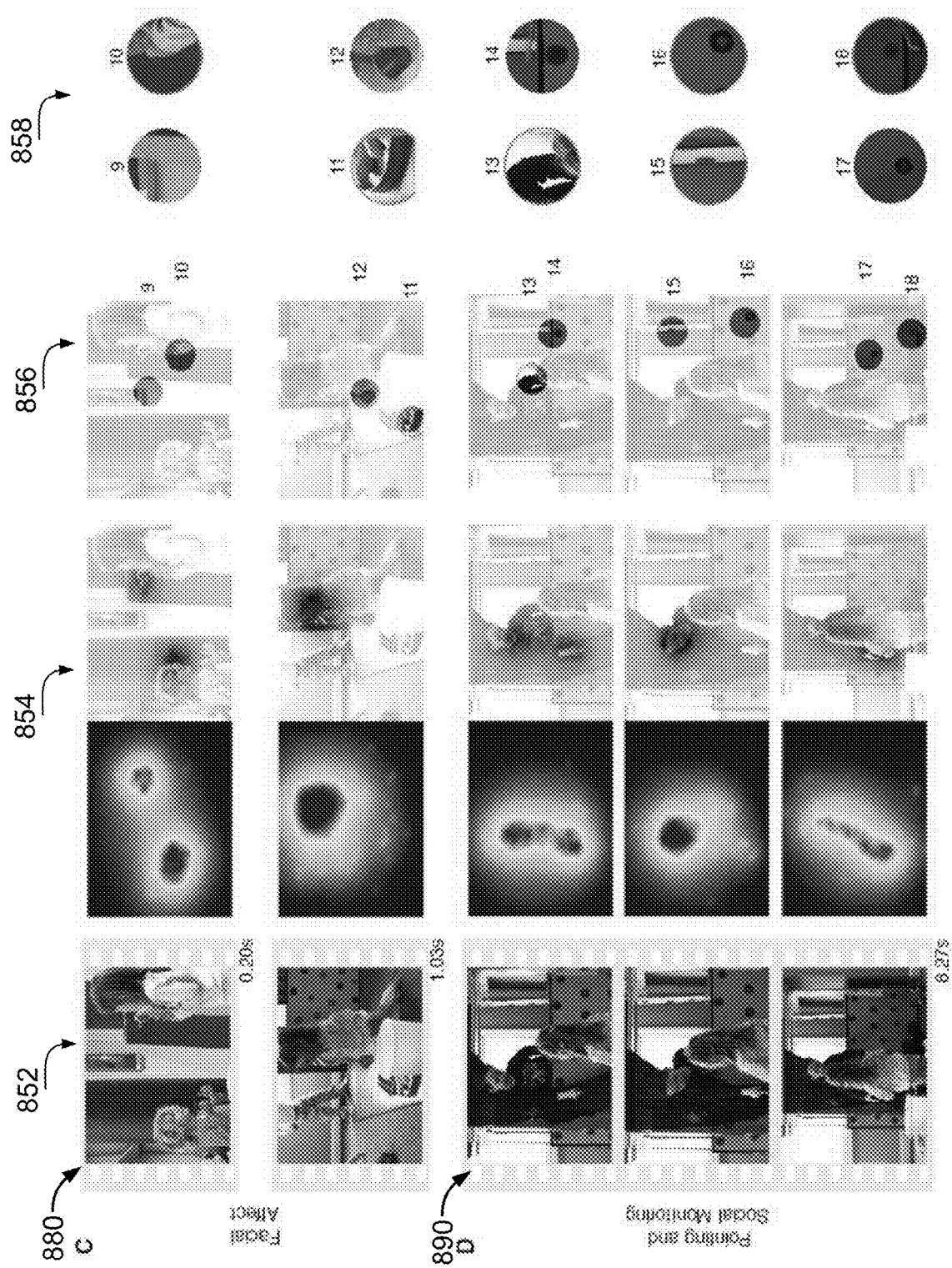

FIGS. 8B-8C illustrate another example result interface 850 displaying performance-based measures of developmental assessment on instances of: Nonverbal Communication and Gestures (A) and Joint Attention & Mutual Gaze (B) in FIG. 8B, Facial Affect (C) and Pointing and Social Monitoring (D) in FIG. 8C, according to one or more embodiments of the present disclosure.

The result interface 850 shows the performance-based measures of children's individual vulnerabilities and opportunities for skills development. Neurodevelopmental assessment via eye-tracking measures how a child engages with social and nonsocial cues occurring continuously within naturalistic environmental contexts (left column 852, shown as still frames from testing videos). In relation to those contexts, normative reference metrics provide objective quantification of non-ASD, age-expected visual engagement (middle column 854 shown as density distributions in both pseudocolor format and middle column 856 shown as color-to-grayscale fades overlaid on corresponding still frames). The age-expected reference metrics can be used to measure and visualize patient comparisons, revealing individual strengths, vulnerabilities, and opportunities for skills-building (right column 858, example patient data shown as overlaid circular apertures which encompass the portion of video foveated by each patient, for example, each aperture spans the central ~5.2 degrees of a patient's visual field). Individual patients with ASD present as not fixating on instances of (A) verbal and nonverbal interaction and gesture (860); (B) joint attention and mutual gaze cueing (870); (C) dynamic facial affect (880); and (D) joint attention and social monitoring (890). As shown in FIGS. 8B-8C, children with ASD present as engaging with toys of interest (1, 3, 5, 7); color and contrast cues (2, 6, 8); objects (10, 11, 12); background elements not directly relevant to social context (4, 9, 13); and recurrent visual features (14, 15, 16, 17, 18). Elapsed times at bottom right of still frames highlight the rapidly changing nature of social interaction: in approximately 12 minutes of viewing time, hundreds of verbal and nonverbal communicative cues are presented, each eliciting age-expected patterns of engagement and offering corresponding opportunities for objective, quantitative comparisons of patient behavior.

Example Processes

Figure 9:
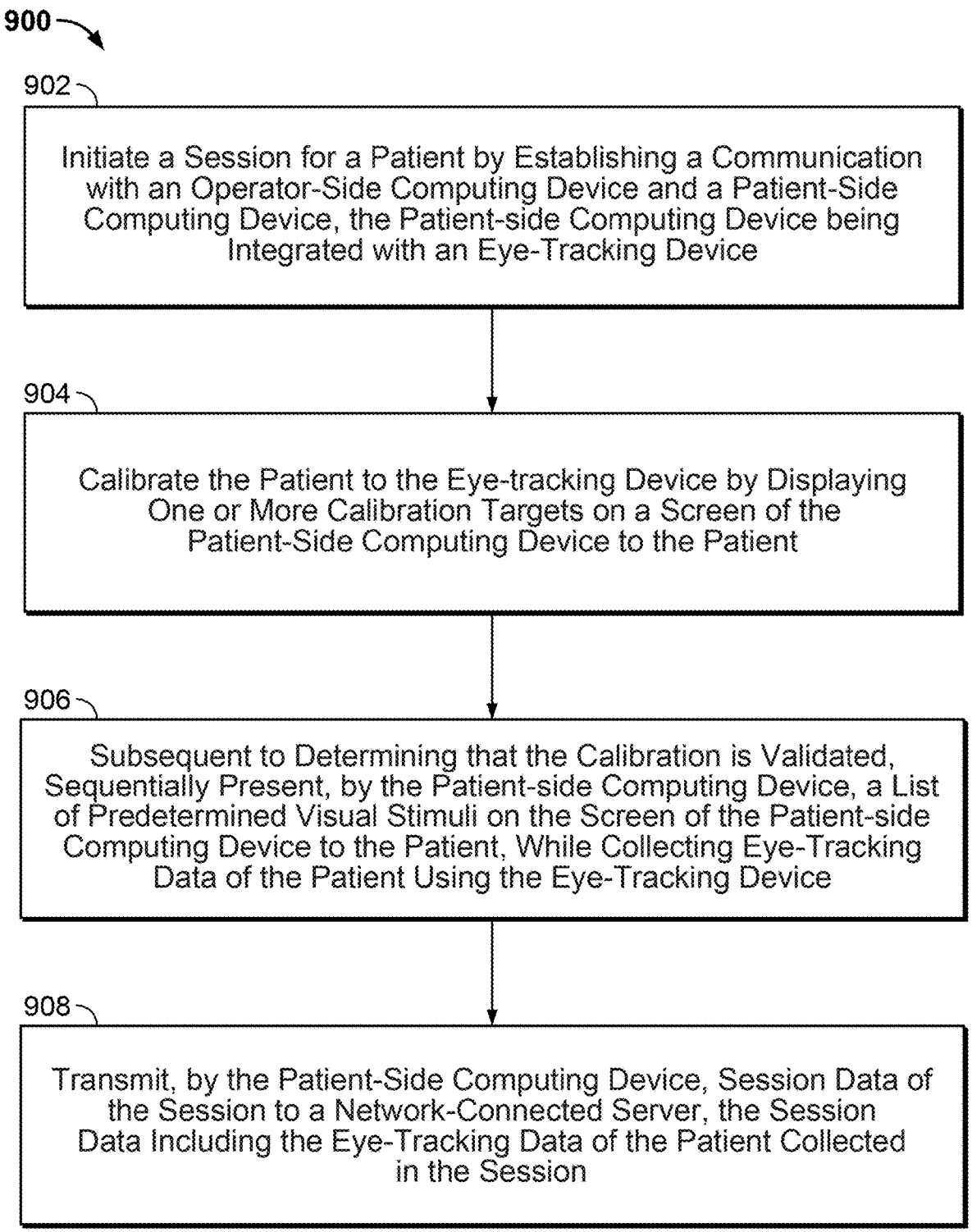
FIG. 9 is a flowchart of an example process for session data acquisition, according to one or more embodiments of the present disclosure.

FIG. 9 is a flowchart of an example process 900 for session data acquisition, according to one or more embodiments of the present disclosure. The process 900 can be performed by a system, e.g., the computing system 120 of FIG. 1A or the data acquisition subsystem 210 of FIGS. 2A-2G. The process 900 can be similar to the process 300 of FIG. 3 and can be described with reference to FIGS. 4A to 4J.

The system includes an operator-side computing device (e.g., 140 of FIG. 1) and one or more patient-side computing devices (e.g., 130 of FIG. 1) integrated with associated eye-tracking devices (e.g., 134 of FIG. 1). At least one of the operator-side computing device or the patient-side computing device can be a portable device. Each of the operator-side computing device and the one or more patient-side computing devices can communicate with a network-based server or a cloud server (e.g., the cloud server 110 of FIG. 1A or the cloud server as described in FIGS. 2A-2G) via a network (e.g., the network 102 of FIG. 1). The system can be associated with a treatment provider, e.g., providing developmental disorder assessment and/or treatment services to patients. The cloud server can be associated with a service provider for providing services, e.g., data processing, analysis, and diagnostic results, to treatment providers. The process 900 can include a number of steps, some of which is performed by the operator-side computing device, some of which is performed by the patient-side computing device and/or the eye-tracking device, and some of which are performed by a combination of the operator-side computing device and the patient-side computing device.

At step 902, a session for a patient is initiated by establishing a communication with the operator-side computing device and the patient-side computing device. In some embodiments, establishing the communication includes establishing a wireless connection between the operator-side computing device and the patient-side computing device, e.g., the wireless connection 131 of FIG. 1.

In some embodiments, establishing the wireless connection between the operator-side computing device and the patient-side computing device includes: accessing, by the operator-side computing device, a web portal (e.g., 222 of FIGS. 2A-2G) at the network-connected server, and in response to receiving a selection of the patient-side computing device in the web portal, wirelessly connecting the operator-side computing device to the patient-side computing device.

In some embodiments, establishing the wireless connection between the operator-side computing device and the patient-side computing device includes, e.g., as illustrated in FIG. 4B, displaying, by the patient-side computing device, connection information on the screen of the patient-side computing device, and in response to receiving an input of the connection information by the operator-side computing device, establishing the wireless connection between the operator-side computing device and the patient-side computing device.

In some embodiments, the process 900 further includes: after establishing the communication, displaying visual desensitization information on the screen of the patient-side computing device to the patient, e.g., as illustrated in FIG. 4C. The eye-tracking device can be configured not to collect eye-tracking data of the patient while displaying the visual desensitization information.

In some embodiments, the process 900 further includes: while displaying the visual desensitization information, accessing, by the operator-side computing device, a web portal at the network-connected server to set up the session for the patient, e.g., as illustrated in FIGS. 4D and 4E. In some cases, setting up the session includes one of selecting the patient among a list of patients or creating a profile for the patient at the network-connected server.

In some embodiments, the process 900 further includes: determining a relative position between the eye-tracking device and at least one eye of the patient, and displaying an instruction to adjust a position of the eye-tracking device or a position of the patient on a user interface of the operator-side computing device, e.g., as illustrated in FIG. 4F. In some cases, the process 900 further includes: in response to determining that the relative location at least one eye of the patient is at a predetermined location in a detection area of the eye-tracking device, determining that the patient is aligned with the eye-tracking device.

At step 904, the patient is calibrated to the eye-tracking device by displaying one or more calibration targets on a screen of the patient-side computing device to the patient, e.g., as illustrated in FIG. 4G. Each of the one or more calibration targets can be sequentially presented at a corresponding predetermined location of the screen of the patient-side computing device, while capturing eye-tracking calibration data of the patient using the eye-tracking device. The process 900 can include: for each of the one or more calibration targets, processing the captured eye-tracking calibration data of the patient to determine a position of a corresponding visual fixation of the patient for the calibration target; comparing the position of the corresponding visual fixation of the patient with the corresponding predetermined location where the calibration target is presented; and determining whether the calibration target is calibrated to the eye-tracking device based on a result of the comparing.

In some embodiments, calibrating the patient to the eye-tracking device further includes: in response to determining that a deviation between the position of the corresponding visual fixation of the patient with the corresponding predetermined location is smaller than or equal to a predetermined threshold, determining that the calibration target is calibrated and displaying a next calibration target, or in response to determining that the deviation is greater than the predetermined threshold, determining that the calibration target fails to be calibrated and re-displaying the calibration target for calibration.

In some embodiments, the process 900 further includes: after calibrating the patient to the eye-tracking device, validating the calibration with one or more new calibration targets. Similar to the calibration described in step 904, validating the calibration includes: sequentially presenting each of the one or more new calibration targets at a corresponding predetermined location of the screen of the patient-side computing device, while capturing eye-tracking calibration data of the patient using the eye-tracking device, and processing the captured eye-tracking calibration data of the patient to determine a position of a corresponding visual fixation of the patient for each of the one or more new calibration targets.

In some embodiments, e.g., as illustrated in FIG. 4H, validating the calibration includes: simultaneously presenting, on a user interface of the operator-side computing device, the one or more new calibration targets at one or more corresponding predetermined locations and representations of the one or more corresponding visual fixations of the patient at the determined one or more positions; and in response to receiving an indication to validate a result of the calibrating, determining that the calibration is validated, or in response to receiving an indication to invalidate the result of the calibrating, starting to re-calibrate the patient to the eye-tracking device.

In some embodiments, validating the calibration includes: determining a number of new calibration targets that each passes a calibration based on the position of the corresponding visual fixation of the patient and the corresponding predetermined position; and if the number or an associated percentage is greater than or equal to a predetermined threshold, determining that the calibration is validated, or if the number or the associated percentage is smaller than the predetermined threshold, determining that the calibration is invalidated and starting to re-calibrate the patient to the eye-tracking device.

At step 906, subsequent to determining that the calibration is validated, a list of predetermined visual stimuli is sequentially presented on the screen of the patient-side computing device to the patient, while collecting eye-tracking data of the patient using the eye-tracking device.

In some embodiments, e.g., as illustrated in FIG. 4I, 4J, or 5, before presenting each of the list of predetermined visual stimuli, a centering target can be presented on the screen of the patient-side computing device to the patient for centering gaze of the patient.

In some embodiments, e.g., as illustrated in FIG. 5, a calibration of the patient to the eye-tracking device is performed between presenting two adjacent visual stimuli among the playlist of predetermined visual stimuli. The eye-tracking data collected in performing the calibration can be used for at least one of calibrating the eye-tracking data of the patient or for determining a calibration accuracy by the network-connected server.

In some embodiments, e.g., as illustrated in FIG. 4J, the process 900 further include: presenting, on a user interface of the operator-side computing device, at least one of: a progress indicator that keeps updating throughout presenting the playlist of predetermined visual stimuli, information of visual stimuli already presented or being presented, information of visual stimuli to be presented a user interface element for skipping a visual stimulus among the playlist of predetermined visual stimuli.

At step 908, session data of the session is transmitted by the patient-side computing device to the network-connected server, the session data including the eye-tracking data of the patient collected in the session. The patient-side computing device can automatically transmit the session data of the session to the network-connected server, in response to one of: determining a completion of presenting the playlist of predetermined visual stimuli on the screen, or receiving a completion indication of the session from the operator-side computing device, e.g., through the web portal on the network-connected server.

In some embodiments, the session data includes information related to the presented playlist of predetermined visual stimuli that can include names of presented predetermined visual stimuli and associated timestamps when the predetermined visual stimuli are presented, e.g., as illustrated in diagram (a) of FIG. 5. The session data can include the eye-tracking data and associated timestamps when the eye-tracking data are generated or collected, e.g., as illustrated in diagram (b) of FIG. 5. In some embodiments, transmitting the session data includes transmitting a first file storing the eye-tracking data of the patient and a second file storing the information related to the presented list of predetermined visual stimuli.

Figure 10:
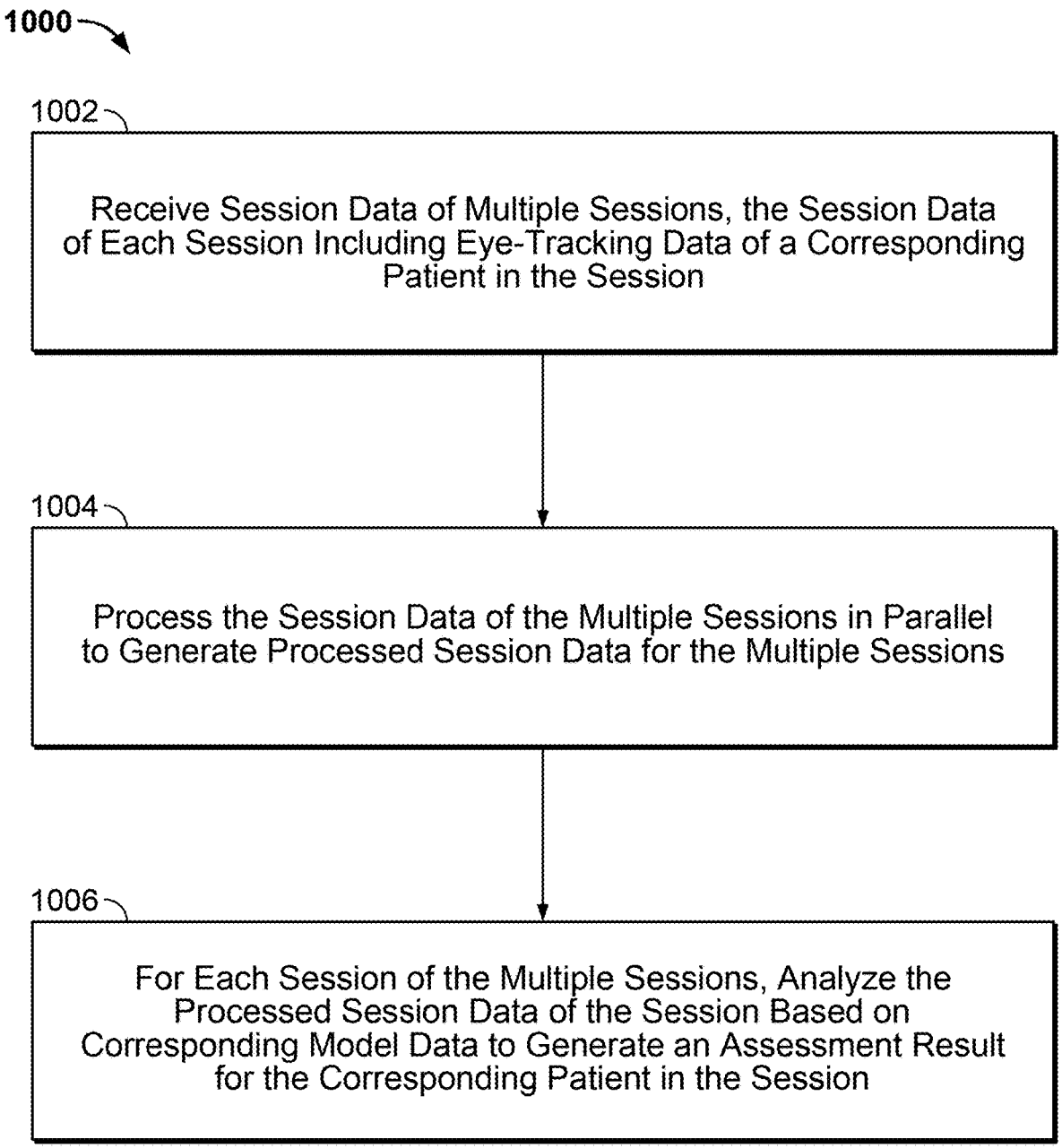
FIG. 10 is a flowchart of an example process for managing session data, according to one or more embodiments of the present disclosure.

FIG. 10 is a flowchart of an example process 1000 for data processing and analysis, according to one or more embodiments of the present disclosure. The process 1000 can be performed by a network-connected server that can be a cloud server in a cloud environment, e.g., the cloud server 110 of FIG. 1A or the cloud server as described in FIGS. 2A-2G. For example, the network-connected server can include a platform, e.g., 112 of FIG. 1A or 220 of FIGS. 2A-2G, and a data pipeline system, e.g., 114 of FIG. 1A or 230 of FIGS. 2A-2G. The platform can include a web portal (e.g., 222 of FIGS. 2A-2G), an application data database (e.g., 224 of FIGS. 2A-2G), and a database (e.g., 226 of FIGS. 2A-2G). The data pipeline system can include one or more data processing modules (e.g., 232 of FIGS. 2A-2G) and one or more data analysis modules (e.g., 234 of FIGS. 2A-2G). The process 1000 can be similar to the process 600 of FIG. 6 or the process 700 of FIGS. 7A-7B.

At step 1002, session data of multiple sessions are received, e.g., as illustrated in FIG. 2B, and the session data of each session includes eye-tracking data of a corresponding patient in the session. At step 1004, the session data of the multiple sessions are processed in parallel to generate processed session data for the multiple sessions. At step 1006, for each session of the multiple sessions, the processed session data of the session is analyzed based on corresponding reference data to generate an assessment result for the corresponding patient in the session.

In some embodiments, the process 1000 further includes: loading the corresponding reference data for the multiple sessions in parallel with processing the session data of the multiple sessions.

In some embodiments, the network-connected server includes a plurality of processing cores. Processing the session data of the multiple sessions in parallel can include, e.g., as illustrated in step 716 of FIG. 7B, using a first plurality of processing cores to process the session data of the multiple sessions in parallel and using a second, different plurality of processing cores to load the corresponding reference data for the multiple sessions. A number of the first plurality of processing cores can be larger than a number of the second plurality of processing cores. In some embodiments, analyzing the processed session data of the multiple sessions based on the loaded corresponding reference data for the multiple sessions can include, e.g., as illustrated in step 718 of FIG. 7B, using the plurality of processing cores including the first plurality of processing cores and the second plurality of processing cores.

In some embodiments, analyzing the processed session data of the multiple sessions based on the loaded corresponding reference data for the multiple sessions includes at least one of: comparing the processed session data of the session to the corresponding reference data, inferring the assessment result for the corresponding patient from the processed session data using the corresponding reference data, or using at least one of a statistical model, a machine learning model, or an artificial intelligence (AI) model.

In some embodiments, the corresponding reference data includes historical eye-tracking data or results for patients having substantially same age or condition as the corresponding patient. In some embodiments, the process 1000 includes: generating the assessment result based on previous session data of the corresponding patient.

In some embodiments, for each session of the multiple session, a respective container is assigned for the session, e.g., as illustrated in FIG. 2C or 7A. The process 1000 can includes: in the respective container, processing the session data of the session and analyzing the processed session data of the session based on the corresponding model data to generate an assessment result for the corresponding patient in the session.

In some embodiments, the eye-tracking data is associated with a list of predetermined visual stimuli presented to the patient while the eye-tracking data is collected in the session, and the session data includes information associated with the list of predetermined visual stimuli in the session.

In some embodiments, the process 1000 further includes, e.g., as illustrated in FIG. 7A, in the respective container, breaking up the eye-tracking data into multiple portions based on the information associated with the list of predetermined visual stimuli, each portion of the eye-tracking data being associated with one of a respective predetermined visual stimulus or a corresponding calibration.

In some embodiments, processing the session data of the session includes processing portions of the eye-tracking data associated with respective predetermined visual stimulus based on information of the respective predetermined visual stimulus. In some embodiments, the process 1000 further includes: in the respective container, recalibrating portions of eye-tracking data associated with respective predetermined visual stimulus based on at least one portion of eye-tracking data associated with the corresponding calibration.

In some embodiments, the process 1000 further includes: in the respective container, determining a calibration accuracy using at least one portion of eye-tracking data associated with the corresponding calibration and a plurality of predetermined locations where a plurality of calibration targets are presented in the corresponding calibration.

In some embodiments, receiving the session data of the multiple sessions includes: receiving, through a web portal, the session data of the multiple sessions from a plurality of computing devices associated with corresponding entities, e.g., as illustrated in FIG. 2C.

In some embodiments, the process 1000 further includes, e.g., as illustrated in FIG. 7A, in response to receiving session data of a session, adding a file pointer for the session data of the session in a processing queue to be processed.

The process 1000 can further include: storing the session data of the session using the file pointer for the session in a database; and retrieving the session data of the session from the database using the file pointer for the session.

In some embodiments, the process 1000 further includes: for each entity, storing session data from one or more computing devices associated with the entity in a respective repository in the application data database, e.g., as illustrated in FIG. 2E. The respective repository can be isolated from one or more other repositories and inaccessible by one or more other entities. The application data database can be a NoSQL database.

In some examples, the respective repository for the entity includes, e.g., as illustrated in FIG. 2D, at least one of: information of the entity, information of one or more operators or operator-side computing devices associated with the entity, information of one or more patient-side computing devices associated with the entity, information of one or more sessions conducted in the entity, information of one or more patients associated with the entity, or history information of the respective repository.

In some embodiments, the process 1000 further includes: dynamically adjusting resources of the network-connected server based on a number of computing devices that access the network-connected server, e.g., as illustrated in FIG. 2F. The process 1000 can further include: replicating data of a first data center to a second data center, and in response to determining that the first data center is inaccessible, automatically directing traffic to the second data center.

In some embodiments, each of the first data center and the second data center includes at least one instance of a web portal accessible for the operator-side computing device, an operator application, or an application layer for data processing and data analysis, e.g., as illustrated in FIG. 2G. The process can further include: storing same data in multiple data centers. The data can include: application data for entities and information associated with the eye-tracking data.

In some embodiments, the process 1000 further includes: associating the generated assessment result with the corresponding patient in the session, and generating an assessment report for the corresponding patient, e.g., as illustrated in step 724 of FIG. 7B.

In some embodiments, the process 1000 further includes: outputting assessment results or assessment reports to be presented at a user interface of the operator-side computing device, e.g., through the web portal.

In some embodiments, e.g., as illustrated in FIG. 8A. the assessment report includes at least one of: information of the corresponding patient, information of an entity performing the session for the corresponding patient, information of a calibration accuracy in the session, information of session data collection, or the assessment result for the corresponding patient. In some embodiments, the assessment result indicates a likelihood that the corresponding patient has a developmental, cognitive, social, or mental disability or ability. For example, the assessment result indicates a likelihood that the corresponding patient has an Austin Spectrum Disorder (ASD) or a non-ASD. In some embodiments, the assessment result includes a respective score for each of one or more of social disability index, verbal ability index, and nonverbal ability, e.g., as illustrated in FIG. 8A.

In some embodiments, the corresponding patient has an age in a range from 5 months to 7 years, comprising an age in a range from 5 months to 43 months or 48 months, an age in a range from 16 to 30 months, an age in a range from 18 months to 36 months, an age in a range from 16 months to 48 months, or an age in a range from 16 months to 7 years.

Example Specific Skills Monitoring

As discussed above, e.g., with respect to FIG. 8A, a diagnostic report can give an overall diagnostic outcome (e.g., ASD or non-ASD), as well as scores and information on three severity indices (e.g., social disability, verbal ability, and nonverbal learning). Implementations of the present disclosure can provide much more detailed and interactive report outputs that allow users to drill into behavior and metrics for specific scenes or groups of scenes that are related to developmentally relevant skills such as treatment-specific skill areas/skills, e.g., as discussed with further details in FIGS. 11 to 14.

FIG. 11 illustrates an example 1100 of comparisons between annotated video scenes 1120, information of typical looking behavior group 1130, and information of patient's looking behavior 1140 for different specific skill areas 1110, according to one or more embodiments of the present disclosure. The information of typical looking behavior group 1130 can include a distribution map 1132 and an example highlighted video scene 1134. The distribution map 1132 can be a salience map. The information of patient's looking behavior 1140 can include a representative video scene 1142 (that can be a highlighted video scene) and a specific-skill metric (e.g., convergent looking percentage or attendance percentage) 1144.

A patient's development assessment can be related to one or more specific skill areas (or a development concept or skill category). A skill area can include one or more skills that can be related to one another. A skill can be associated with one or more skill areas. A specific skill area can be manding, listener responding, turn-taking, joint attention, tact, or play. A specific skill area can correspond to one or more treatments, and a treatment can be associated with one or more specific skill areas.

As an example, the skill area "joint attention" can include a plurality of skills, e.g., pointing to something, following someone else's point, and/or looking at someone's pointing. As another example, the skill area "manding" indicates a request for something, which can include, e.g., pointing to something (with pose), and/or verbally requesting something. As another example, pointing to something can be associated with the skill areas "joint attention" and "manding."

For a session (e.g., a diagnostics session, a monitoring session, or a targeted monitoring session), a data collection playlist of visual stimuli can include a plurality of videos (or movies), e.g., as described with respect to FIGS. 4A-4J. A video can include multiple video scenes (moments or frames), e.g., the example video scenes 1120 as shown in FIG. 11. A video scene can be related to one or more skill areas or skills.

As an example, in the example video scene 1120a, boy A (on the right) puts out his hand towards boy B (on the left) and asks for a toy. Boy B holding the toy says no. While watching the video scene 1120a, a typical (normal) child may look at boy A's hand and/or boy B's toy, in contrast, a child with developmental disorder may look around, e.g., at a picture on a wall, or foot of boy A or boy B. As another example, in the example video scene 1120b, girl C turns her head towards and listen to someone who is speaking. While watching the video scene 1120b, a typical (normal) child may look at girl C's head or eyes, in contrast, a child with developmental disorder may look at somewhere else, e.g., a nearby table.

The information of a typical looking behavior group 1130 can include a distribution map 1132 and a highlighted video scene 1134. The highlighted video scene 1134 can be a representative video scene among a number of video scenes for the reference group. The distribution map 1132 (e.g., the map 1132a for the video scene 1120a or the map 1132b for the video scene 1120b) shows a distribution of looking areas (or looking behavior) of a number of persons (e.g., children) in a reference group, e.g., obtained based on analysis of eye-tracking data as discussed above. The distribution map 1132 can be a salience map. The distribution map 1132 can be shown in color or grey. The higher a map value is, the higher a normal level of a child is. The reference group can include children with normal development and children with abnormal development (or development disorders). The children in the reference group can have a similar age, gender, and/or other similar situations. The highlighted video scene 1134 (e.g., the highlighted video scene 1134a for the video scene 1120a or the highlighted video scene 1134b for the video scene 1120b), compared to the original video scene 1120a, highlights two areas corresponding to two areas looked by most of the children in the reference group.

One or more expert clinicians can review each video scene in a video (e.g., frame by frame or moment by moment) and annotate which skill area and/or specific skill the video scene is related to. For example, the expert clinicians can annotate the video scene 1120a to be related to the skill area manding and/or the skill requesting something by pointing, and annotate the video scene 1120b to be related to the skill area listener responding 1120b and/or the skill responding to someone's speaking. In some cases, the expert clinicians can also annotate the video scene, with reference to the information of the typical looking behavior group 1130, e.g., the distribution map 1132 and the modified video scene 1134. In some examples, the expert clinicians can annotate a video related to a specific skill area, and a first series of video scenes are related to a first skill associated with the specific skill area, and a second series of video scenes are related to a second skill associated with the specific skill area. In some examples, the expert clinicians can annotate a first series of video scenes in a video to be related to a first specific skill area and a second series of video scenes in the video to be related to a second specific skill area. The expert clinicians can further annotate individual video scenes in the first series of video scenes to respective skills associated with the first specific skill area and individual video scenes in the second series of video scenes to respective skills associated with the second specific skill area. The annotations of the expert clinicians can be respectively associated with the video scenes and stored, together with the video scenes 1120 and the information of the reference group's typical looking behavior 1130, can be stored in a network-connected server, e.g., the network-connected server 110 of FIG. 1A such as in platform subsystem 112 of FIG. 1A or 220 of FIG. 2A, or a library or cloud storage.

If a patient's looking area is closer (or convergent) to the highlighted areas in the map 1132 or the highlighted video scene 1134 for a specific skill area, it can indicate that the patient is more normal in the specific skill area. If a patient's looking area is farther (or divergent) to the highlighted areas in the map 1132 or the highlighted video scene 1134 for a specific skill, it can indicate that the patient may be abnormal in the specific skill. In some implementations, a cutoff threshold is determined for evaluating patients' looking behavior for a video scene annotated with a specific skill area, e.g., a contour around one or more highlighted areas in the map 1132, for example, contour 1133a in the map 1132a or contour 1133b in the map 1132b. If a patient's looking area is within the contour, e.g., a map value higher than the cutoff threshold, it can be determined that the patient is normal with respect to the specific skill area at that moment. If a patient's looking area is out of the contour, e.g., a map value lower than the cutoff threshold, it can be determined that the patient is abnormal at that moment or has development disorder with respect to the specific skill area, e.g., if abnormal over a number of moments. Note that a patient's looking area being in or outside the contour corresponding to the cutoff threshold at a single moment does not indicate an overall normal/abnormality for the patient, but rather normal/abnormality of his/her behavior at that moment (or frame) only. An overall abnormality/disorder can be indicated from the full session, e.g., if abnormal over a threshold number of moments. The cutoff threshold and/or the contour can be determined by the AI or ML model analyzing the looking behavior of the typical group, e.g., based on looking behaviors of known normal children, or by the expert clinicians with reference to the analysis of the model.

In some implementations, a skill-specific metric for evaluating a patient's development disorder in a specific skill area is defined as a percentage of a number of moments a patient is determined to be normal over a total number of moments related to the specific skill area in a data collection playlist while the patient is watching. The skill-specific metric can be also called convergent looking percentage or attendance percentage. As an example, during a data collection playlist in a session for a patient Ben, there are 200 video scenes annotated with the skill area manding. Over the 200 video scenes, there are 100 moments (corresponding to 100 video scenes) the patient is looking at the screen of the patient-side computing device, e.g., based on captured eye-collection data of the patient during the session. That is, there can be another 100 moments that the patient is not looking at the screen of the patient-side computing device. Over the 100 moments, there are 29 moments that the patient's looking area is within the contour or has a map value higher than the cutoff threshold, that is, the patient is normal in the 29 moments. There can be other 71 moments that the patient is looking at the video scene but not within the contour or has a map value lower than the cutoff threshold. Thus, the skill-specific metric for manding of the patient is 29% for the session. For example, as illustrated in FIG. 11, the information of Ben's looking behavior 1140 includes a representative video scene 1142a and a manding-specific metric 1144a noting that Ben attended to 29% of moments relevant to manding in the session. Similarly, the information of Ben's looking behavior 1140 includes a representative video scene 1142b and a skill-specific metric 1144b noting that Ben attended to 37% of moments relevant to listener responding, which indicates that Ben is determined to be normal in the skill area listener responding in 37% of the moments while Ben is watching the video scenes related to the listener responding. In some implementations, alternatively or additionally, the information of Ben's looking behavior 1140 is compared to reference data of the reference group. For example, an attendance percentage for the reference group can be used as a baseline for determining how much attendance percentage is normal or expected or typical. The attendance percentage of the patient can be compared to the attendance percentage of the reference group, and the information of the patient's looing behavior can include a result of the comparison as a metric to indicate expected/goal/typical attendance percentage and/or normative percentile. As an example, an attendance percentage for the reference group in listener responding is 40%, while the attendance percentage of the patient (e.g., Ben) is 37%. The information of the patient's behavior can note that "37% is in the 92.5 percentile for the listener responding skill area" or "$^{37}$% is within the expected 90-94% attendance percentage of typical age-matched peers for the listener responding skill area".

As discussed with further details below, video scenes with annotations made by the expert clinicians in view of the looking behaviors of the reference group enable to accurately identify specific skill areas/skills for patient's diagnostics and/or treatment, to effectively adjust data collection playlist for patients on selected skill areas/skills, and to monitor patients' improvements or treatment effects on the selected skill areas/skills.

FIG. 12A illustrates an example illustrative user interface 1200 presented on an operator device for session launch, according to one or more embodiments of the present disclosure. The operator device can be an operator-side computing device such as the computing device 140 of FIGS. 1A-1B, or the operator-side computing device described with respect to FIGS. 4A-4J.

For example, an operator (e.g., a medical assistant, a medical professional, or any other representative of the treatment provider) can log in a web portal (e.g., the web portal 222 of FIG. 2A) running on a network-connected server (e.g., the cloud server 110 of FIG. 1A or platform subsystem 220 220 of FIG. 2A) for device management, patient management, and data management. The operator can have a corresponding user role and permission, e.g., as discussed in FIG. 2D. The user interface (UI) 1200 can be presented on a display screen of the operator-side computing device after the operator logs in the web portal using the operator-side computing device. The UI 1200 can be a user interface of an operator application (e.g., the operator application 216 of FIG. 2A) running on the network-connected server or on the operator-side computing device.

As shown in FIG. 12A, the UI 1200 includes a menu 1210 showing buttons "Home", "Patients", and "Appointments." By clicking a button, corresponding information (e.g., patient information, device information, or appointment information) can be presented in the UI 1200. As discussed in FIGS. 4A-4B, the operator-side computing device can establish a communication with a patient-side computing device (e.g., the patient-side computing device 130 of FIG. 1A or the patient-side computing device discussed with respect to FIGS. 4A-4J), e.g., through the network-connected server. After the communication is established, the operator can select a patient (or create a new patient) to start a session for the patient. When choosing to launch a session from the web portal, the operator can be presented with the UI 1200 showing session launch 1220 for session setup.

As illustrated in FIG. 12A, under the session launch 1220, the operator can select a session type 1230 that can include a diagnostic session 1232, a monitoring session 1234, and a targeted monitoring session 1236. The diagnostic session 1232 is configured to run a session, e.g., as illustrated in FIGS. 4C-4J, and generate a diagnostic report, e.g., as illustrated in FIG. 8A. The diagnostic report can include diagnostic results, e.g., whether the patient is ASD or non-ASD and/or scores of three indexes (social disability index, verbal ability index, and nonverbal ability index). The monitoring session 1234 is configured to monitor a behavior (or performance) change over a series of sessions for an existing patient by running a session, e.g., as described in FIGS. 4C-4J, and generate a monitoring report, e.g., as described with further details in FIGS. 13A-13D. In some examples, e.g., as illustrated in FIG. 12A, the UI 1200 can show a time (e.g., a date) where a last run was performed for the monitoring session 1234 and/or the diagnostic session 1232.

In some implementations, the diagnostic session 1232 and the monitoring session 1234 have a same data collection playlist of visual stimuli. In some implementations, the monitoring session 1234 can have a different data collection playlist of visual stimuli from the diagnostic session 1232. The monitoring session 1234 can run a default playlist that can be same as a playlist performed in a last session for the patient. The playlist performed in the last session can be customized for one or more specific skill areas, e.g., the last session can be a targeted monitoring session.

If the targeted monitoring session 1236 is selected, when the operator clicks a "continue" button 1238 in the UI 1200, a window 1250 can be prompted on the UI 1200 for the operator to select a set of skill areas that the operator would like to target, e.g., as illustrated in FIG. 12B. The window 1250 can be overlaid on the user interface 1200, be side by side with the user interface 1200, or have an overlap with the user interface 1200. The user interface 1200 can be changed to the new window 1250.

The set of skill areas can include, but not limited to, manding, listener responding, turn-taking, joint attention, tact, and play. A default selection can be any skill areas selected in a prior targeted monitoring session. The network-connected server can recommend consistent skill area selections over multiple sequential monitoring sessions. In some cases, the network-connected server stores previously selected targeted skill areas and/or personalized playlist, then the operator can repeat the same targeted monitoring session at a next session without reselecting targeted skill areas if desired. The window 1250 can also present a note "Auto-select from previous Targeted Monitoring Session," which the operator can click to automatically select targeted skill areas to be same as those in a previous targeted monitoring session. The operator can choose to keep the same selected targeted skill areas or change one or more targeted skill areas. In some implementations, there is a maximum number of targeted skill areas set for the selection, e.g., up to 4. The maximum number can be determined, for example, by a time length of videos in the data collection playlist. After the targeted skill areas are selected or confirmed, the operator can click a button 1260 in the window 1250 to run the session for the targeted skill areas.

Based on the selected targeted skill areas, a personalized playlist of videos can be built and enriched for the targeted skill areas, e.g., by including and prioritizing videos that are determined or known to best monitor the targeted skill areas. The network-connected server can optimize the playlist to maximize video contents related to the targeted skill areas. In some implementations, the playlist of videos is reordered to arrange videos (or video scenes) annotated relevant to the targeted skill areas at the beginning of the session where the patient has more attention to watch videos. In some implementations, new videos that have been specifically enriched for one or more selected skill areas are added to the playlist. In some implementations, to keep a reasonable time length of videos for a session, videos that are unrelated to the selected skill areas are reduced or removed from the playlist. In some implementations, the visual scenes related to the selected one or more targeted skill areas are in an order of weighted correlation values to the selected one or more targeted skill areas. In some implementations, only the visual scenes related to the selected one or more targeted skill areas are selected in the data collection playlist.

The playlist of videos can be personalized by the network-connected server or the operator-side computing device or the patient-side computing device, e.g., for example, when the targeted skill areas are selected in the window 1250 or when the button 1260 for running session for targeted skill areas are clicked. In some implementations, the network-connected server receives the input from the operator through the web portal, personalizes the playlist of videos, and transmits information of the personalized playlist (e.g., a sequence of videos in the playlist) to the patient-side computing device that can be configured to adjust the playlist according to the information of the personalized playlist. In some cases, the patient-side computing device can download new videos from the network-connected server, if the new videos are not previously installed on the patient-side computing device. In some implementations, a command can be transmitted from the network-connected server to the patient-side computing device that is configured to personalize the playlist on the patient-side computing device based on the command.

FIGS. 13A-13D illustrate user interfaces for reviewing session information on a user device by a user through a web portal (e.g., the web portal 222 of FIG. 2A) of a network-connected server (e.g., the cloud server 110 of FIG. 1A or platform subsystem 220 220 of FIG. 2A). The user can be, for example, a treatment provider, a clinician, or a patient's guardian, or any other suitable person that has a permission or authority to access the patient's information. The user device can be any suitable computing device, and can be same as or different from the operator-side computing device 140 of FIGS. 1A-1B or the operator-side computing device as discussed in FIGS. 4A-4J.

FIG. 13A illustrates an example illustrative user interface 1300 for reviewing session information on the user device, according to one or more embodiments of the present disclosure. The user interface 1300 includes a menu 1302 (e.g., the menu 1210 of FIG. 12A) showing buttons "Home," "Patients," and "Appointments." By clicking one of the buttons, corresponding information (e.g., patient information, device information, or appointment information) can be presented in the user interface 1300. Th user can select a patient to review information of the patient. The user interface 1300 also includes another menu 1304 showing buttons "Information," "Sessions," and "History." By clicking one of the buttons, corresponding information (e.g., patient or appointment information, session information, or history information) can be presented in the user interface 1300.

For example, by selecting "Sessions" in the menu 1304, session information 1306 associated with the patient is presented in the user interface 1300. The session information 1306 include session background information 1308 that can include session date, patient name, session age (months) indicating how long the session had been performed, session status (uploaded or not), quality checks passed (yes or no), device (which patient-side computing device is used to capture session data), and/or operator (who runs the session using an operator-side computing device).

Besides the session background information 1308, the session information 1306 further includes button 1310 for reviewing session results (e.g., as described with details in FIG. 8A, FIGS. 8B-8C, FIG. 13B-1, and/or FIG. 13B-2), button 1312 for customizing diagnostics/monitoring report (e.g., as described with details in FIG. 13C), and button 1314 for launching interactive results dashboard (e.g., as described with details in FIG. 13D).

FIG. 13B-1 illustrates an example portion 1320 of an evaluation report, showing comparisons between annotated video scenes, information of typical looking behavior group, and information of patient's looking behavior for different specific skill areas, according to one or more embodiments of the present disclosure. FIG. 13B-2 illustrates another example portion 1330 of an evaluation report, showing monitoring of treatment-specific skills in section 1332 and information of features skills in section 1334, according to one or more embodiments of the present disclosure.

In some implementations, the evaluation report is a diagnostic report that can include the example portion 1320, and/or the information presented in FIGS. 8A, 8B, and/or 8C. As noted above, the diagnostic report can be generated by running a diagnostic session as described in FIG. 12A. In some implementations, the evaluation report is a monitoring report that can include the example portion 1320, the example portion 1330, and/or the information presented in FIGS. 8A, 8B, and/or 8C. As noted above, the monitoring report can be generated by running a monitoring session or a targeted monitoring session as described in FIGS. 12A-12B.

In some implementations, e.g., as illustrated in FIG. 13A, the example portion 1330 of the evaluation report can include an introduction section 1322 and a chart section 1324. The introduction section 1322 describes information of the chart section 1324, for example, including "An individual's looking behavior metrics quantify how much of their looking behavior aligned with age expected looking behavior during moments that have been identified by expert clinicians as being relevant to a special skill area . . . "

The chart section 1324 can be similar to the example 1100 of FIG. 11, including relevant skill areas, example video scenes, information of a typical group looking behavior (distribution map and highlighted video scenes), and information of a patient's looking behavior (highlighted video scenes and statistics score or convergent looking percentage). The relevant skill areas can be automatically selected by the network-connected server, or selected for those with the greatest amount of reliable data or those with the most popularly requested skills/skill areas, or selected for those with a particularly high, low, or representative score, or selected in a previous evaluation report for the patient, or selected when launching a targeted monitoring session, or a combination thereof. For example, as illustrated in FIG. 13B-1, the chart section 1324 includes information of the skill areas "Manding," "Listener responding," and "Joint Attention" that can be annotated for video scenes of expert clinicians. It is shown that the patient Ben attended to 29% of moments relevant to manding, 37% of moments relevant to listener responding, and 32% of moments relevant to joint attention.

If there are previously monitoring sessions for the patient, the example portion 1330 of the evaluation report can indicate change from last sessions. As illustrated in FIG. 13B-2, the example portion 1330 includes a monitoring section 1332 showing changes of the relevant skill areas, including a chart showing the convergent looking percentage changing over a series of sessions for each relevant skill area (e.g., manding, listener responding, and joint attention). The monitoring section 1332 can note a comparison of the convergent looking percentages between a current section and a previous section, e.g., Ben attended to 29% of moment relevant to manding, up from 21% last session; Ben attended to 37% of moment relevant to listener responding, no change from last session; Ben attended to 14% of moment relevant to joint attention, up from 13% last session. In such a way, the user can easily tell whether the patient has any improvement in each of the relevant skill areas and/or whether the current treatment is effective or helpful. The example portion 1330 can also include information 1334 on featured skills/skill areas, which can include definitions of the relevant skill areas (e.g., manding, listener responding, and joint attention).

If the user selects the button 1310 for reviewing results in the user interface 1300, a default report with automatically selected skill areas, e.g., the evaluation report as described in FIGS. 8A-8C, 13B-1, and/or 13B-2, can be provided to the user. In contrast, if the user selects button 1312 for viewing customized report, instead of generating the default report, the network-connected server can present a new window 1340, e.g., as illustrated in FIG. 13C, for the user to select targeted skill areas (e.g., Manding, Listener Responding, Joint Attention, and Play) to customize the evaluation report. There can be a maximum number of targeted skill areas (e.g., up to 4) to be selected for customization. After the user selects the targeted skill areas, the user can click the button "view custom report" 1342 to generate a customized report. The customized report can be similar to the evaluation report, e.g., as illustrated in FIG. 13B-1 and/or 13B-2. The relevant skill areas in the customized report are the selected targeted skill areas through the window 1340. In some examples, if the user selects the target monitoring session, the network-connected server (e.g., an operator application running on the network-connected server) can automatically customize the monitoring report of the targeted monitoring session to select the same targeted skill areas as chosen for the playlist for the targeted monitoring session. The new window 1340 can be overlaid on the user interface 1300, side by side with the user interface 1300, or have an overlap with the user interface 1300. The user interface 1300 can be changed to the new window 1340.

Referring back to FIG. 13A, if the user selects button 1314 for launching interactive results dashboard, an example interactive results dashboard 1360, e.g., as illustrated in FIG. 13D, can be shown in a user interface 1350 presented on a display screen of the user device. The dashboard 1360 can include section 1362 for the user to select a targeted skill area (e.g., manding) to interact, section 1364 for the user to select a particular session among a series of sequential sessions, and section 1366 showing the patient's looking behavior in comparison with a reference group's looking behavior, e.g., moment-by-moment (or frame-by-frame). For example, the section 1366 can show the comparisons of highlighted video scenes 1370 of the reference group (e.g., the highlighted video scene 1134 of FIG. 11) and highlighted video scenes 1372 of the patient (e.g., the highlighted video scene 1142 of FIG. 11). The section 1366 can also include a play sliding bar 1368 that allows the user to watch the video or pause or select particular moments/frames (still images) to compare or view. The section 1366 can also include convergent looking percentage information of the current session and the previous session.

FIG. 14 is a flowchart of an example process 1400 for managing specific skills for developmental disorder assessment, according to one or more embodiments of the present disclosure. The process 1400 can be performed by a network-connected server that can be a cloud server in a cloud environment, e.g., the cloud server 110 of FIG. 1A or the cloud server as described in FIGS. 2A-2G. For example, the network-connected server can include a platform, e.g., 112 of FIG. 1A or 220 of FIGS. 2A-2G, and a data pipeline system, e.g., 114 of FIG. 1A or 230 of FIGS. 2A-2G. The platform can include a web portal (e.g., 222 of FIGS. 2A-2G), an application data database (e.g., 224 of FIGS. 2A-2G), and a database (e.g., 226 of FIGS. 2A-2G). The data pipeline system can include one or more data processing modules (e.g., 232 of FIGS. 2A-2G) and one or more data analysis modules (e.g., 234 of FIGS. 2A-2G).

At step 1402, a request is received at the network-connected server. The request is for an assessment result of a patient based on session data of the patient. The session data is collected during presentation of a data collection playlist of visual stimuli to the patient in a session. At least one visual scene of the data collection playlist is annotated with at least one of a plurality of skill areas associated with visual scenes of the data collection playlist.

At step 1404, the assessment result of the patient is output by the network-collected server. The assessment result includes, for each of one or more specific skill areas of the plurality of skill areas, behavior data of the patient with respect to moments relevant to the specific skill area in the session, each of the moments corresponding to a respective visual scene of the visual scenes of the data collection playlist.

In some embodiments, the behavior data includes an attendance percentage defined as a ratio between a number of moments which the patient attends to relevant scene content and a total number of moments which the patient is watching the visual stimuli, e.g., as discussed in FIG. 11.

In some embodiments, the session data includes eye-tracking data of the patient. The network-connected server can determine the total number of moments which the patient is watching the visual stimuli based on the eye-tracking data of the patient, and determine the number of moments which the patient attends to relevant scene content based on the eye-tracking data of the patient.

In some embodiments, the process 1400 further includes: determining, at a moment in the session, an attendance area of the patient to be within a predetermined region and determining the moment to be one of the number of moments which the patient attends to relevant scene content. The predetermined region corresponds to a contour (e.g., contour 1133a or 1133b of FIG. 11) of a distribution map (e.g., the map 1132 of FIG. 11) of behavior data of a reference group. The behavior data of the reference group can be based on reference session data collected during presentation of the data collection playlist of visual stimuli to each person of the reference group. A value of the contour of the distribution map can correspond to a cutoff threshold.

In some embodiments, e.g., as illustrated in FIG. 13B-1, the assessment result further includes the distribution map of the behavior data of the reference group. The assessment result can further includes at least one of: for each of the one or more specific skill areas, a representative visual scene, the representative visual scene highlighting one or more attendance areas in the predetermined region for the reference group, or the representative visual scene highlighting the attendance area of the patient in the session.

In some embodiments, e.g., as illustrated in FIG. 13B-2, the assessment result further includes at least one of: for each of the one or more specific skill areas, behavior data of one or more preceding sessions of the patient, or a comparison between the behavior data of the session and the behavior data of the one or more preceding sessions of the patient. The assessment result can include a graph showing, for each of the one or more specific skill areas, the behavior data of the session and the behavior data of the one or more preceding sessions of the patient.

In some embodiments, the process 1400 further includes: selecting the one or more specific skill areas from the plurality of skill areas for the assessment result of the patient. The selecting of the one or more specific skill areas from the plurality of skill areas includes at least one of: selecting a specific skill area with reliable data among the plurality of skill areas, selecting a popularly requested skill area among the plurality of skill areas, selecting a skill area with a particularly high, low, or representative score among the plurality of skill areas, wherein a score represents an attendance percentage of the patient, selecting a skill area that is previously selected as a targeted skill area in the session, selecting a skill area that is selected for customizing the assessment result, or selecting a skill area that is previously selected in a previous session of the patient or a previous assessment result of the patient.

In some embodiments, e.g., as illustrated in FIG. 12A, the process 1400 includes: receiving, through a web portal on the network-connected server, a session request to launch the session, presenting a list of sessions on a user interface (e.g., the user interface 1200 of FIG. 12A) of the web portal, and receiving a selection of the session from the list of sessions on the user interface.

In some embodiments, e.g., as illustrated in FIG. 12B, the process 1400 further includes: in response to receiving the selection of the session, popping up a window (e.g., the window 1250 of FIG. 12B) for selecting targeted skill areas from the plurality of skill areas listed in the window, receiving a user input to select one or more targeted skill areas in the window, and running the session based on the selected one or more targeted skill areas. The selected one or more targeted skill areas can include the one or more specific skill areas in the assessment result.

In some embodiments, the network-connected server adjusts the data collection playlist of visual stimuli based on the selected one or more targeted skill areas, e.g., by at least one of prioritizing visual scenes annotated to monitor the selected one or more targeted skill areas in the data collection playlist, enriching additional visual scenes related to the selected one or more targeted skill areas in the data collection playlist, or reducing or removing visual scenes unrelated to the selected targeted skill areas in the data collection playlist.

In some embodiments, prioritizing the visual scenes annotated to monitor the selected one or more targeted skill areas includes at least one of: arranging the visual scenes annotated to monitor the selected one or more targeted skill areas at a beginning of the data collection playlist, arranging the visual scenes related to the selected one or more targeted skill areas in an order of weighted correlation values to the selected one or more targeted skill areas, or selecting only the visual scenes related to the selected one or more targeted skill areas in the data collection playlist. The user input can be received from an operator-side computing device in communication with the network-connected server through the web portal. The network-connected server can establish a communication between the operator-side computing device with a patient-side computing device through the network-connected server, and transmit information of the adjusted data collection playlist of visual stimuli to the patient-side computing device, such that the adjusted data collection playlist of visual stimuli is presented on a display screen of the patient-side computing device to the patient in the session. The operator-side computing device can be the computing device 140 of FIGS. 1A-1B or the operator-side computing device with respect to FIGS. 4A-4J and/or 12A-12B and 13A-13D. The patient-side computing device can be the computing device 130 of FIG. 1A or the patient-side computing device with respect to FIGS. 4A-4J.

In some embodiments, the process 1400 further includes: receiving the session data of the patient from the patient-side computing device for the patient once the session is completed. The session data of the patient is collected by the patient-side computing device during the session and generating the behavior data of the patient by processing the session data of the patient based on reference data of a reference group and the one or more specific skill areas.

In some embodiments, the process 1400 further includes loading the reference data of the reference group, e.g., from a library or cloud storage. The reference data can be based on behavior data of the reference group that is based on reference session data collected during presentation of the data collection playlist of visual stimuli and the one or more specific skill areas.

In some embodiments, the reference data includes at least one of: for each of the one or more specific skill areas, specific visual scenes relevant to the specific skill area, each of the specific visual scenes highlighting one or more attendance areas of the reference group, or a distribution map of the behavior data of the reference group for each of the specific visual scenes, e.g., as illustrated in FIG. 11 and FIG. 13B-1.

In some embodiments, the reference data includes: for each of the one or more specific skill areas and for each of the specific visual scenes, a contour in the distribution map representing a threshold for determining whether or not the patient attends to relevant scene content the specific visual scene. The process 1400 can further include at least one of: determining that the patient attends to relevant scene content the specific visual scene if an attendance area of the patient is within a predetermined region corresponding to the contour, or determining that the patient fails to attend to the specific visual scene if an attendance area of the patient is out of the predetermined region.

In some embodiments, the behavior data of the patient includes an attendance percentage defined as a ratio between a number of moments which the patient attends to relevant scene content and a total number of moments which the patient is watching the visual stimuli. The process 1400 can further include: determining, at a moment in the session, an attendance area of the patient to be within the predetermined region, and determining the moment to be one of the number of moments which the patient attends to relevant scene content. In some embodiments, the behavior data of the patient includes a result of comparison between an attendance percentage of the patient and a threshold attendance percentage of the reference group. For example, the result of comparison can include at least one of: a ratio between the attendance percentage of the patient and the threshold attendance percentage of the reference group, or a relationship between the attendance percentage of the patient and the threshold attendance percentage of the reference group.

In some embodiments, receiving the request includes: receiving, from a user device, a user input on a user interface (e.g., the user interface 1300 of FIG. 13A) of a web portal of the network-connected server, the user input indicating the request, the user interface being presented on a display screen of the user device.

In some embodiments, e.g., as illustrated in FIG. 13A, the user interface includes at least one of a first user interface element (e.g., button 1310 of FIG. 13A) for viewing a default evaluation report, a second user interface element (e.g., button 1312 of FIG. 13A) for customizing an evaluation report, or a third user interface element (e.g., button 1314 of FIG. 13A) for launching an interactive dashboard (e.g., the dashboard 360 of FIG. 13D) with the assessment result.

In some embodiments, e.g., as illustrated in FIG. 13C, the process 1400 further includes: in response to a selection for the second user interface element, popping up a window on the user interface for selecting targeted skill areas in the evaluation report, receiving a second user input for selecting one or more targeted skill areas in the window, and generating the evaluation report based on the selected one or more targeted skill areas, wherein the one or more targeted skill areas comprise the one or more specific skill areas in the assessment result.

In some embodiments, e.g., as illustrated in FIG. 13D, the process 1400 further includes: in response to a selection for the third user interface element, presenting the interactive dashboard in the user interface. The interactive dashboard can include a sub-window for selecting one of a list of skill areas for interaction. In response to receiving a selection of a particular targeted skill area from the list of skill areas, the process 1400 can present at least one of: a change of an attendance percentage of the patient for the particular targeted skill area over a series of sequential sessions, a change of a ratio between the attendance percentage of the patient and the threshold attendance percentage of the reference group, a change of a relationship between the attendance percentage of the patient and the threshold attendance percentage of the reference group, or for each of a plurality of visual scenes relevant to the particular target skill area, a first scene highlighting one or more attendance areas of a reference group in the visual scene and a second scene highlighting an attendance area of the patient in the visual scene.

In some embodiments, the plurality of visual scenes are overlaid with each other in the user interface, and the interactive dashboard includes a sliding user interface element (e.g., the sliding bar 1368 of FIG. 13D) for selecting each of the plurality of visual scenes.

In some embodiments, the network-connected server is configured to: store annotation data of visual scenes of the data collection playlist of visual stimuli, the annotation data specifying respective specific skill areas associated with the visual scenes, and store reference data of a reference group, the reference data being based on behavior data that is based on reference session data collected during presentation of the data collection playlist of visual stimuli. The annotation data and the reference data can be stored in a library or cloud storage.

In some embodiments, the session data comprises at least one of: eye-tracking data collected by an eye-tracking device (e.g., the eye-tracking device 134 of FIG. 1A) assembled in a patient-side computing device in communication with the network-connected server, or at least one of image data, audio data, or video data collected by one or more recording device (e.g., the recording device 138 of FIG. 1A). The one or more recording devices can be assembled in at least one of the patient-side computing device (e.g., as illustrated in FIG. 1A) or external to the patient-side computing device.

In some embodiments, the operator-side computing device is configured to: access a web portal at the network-connected server, receiving a user input on a user interface of the web portal, the user input for requesting an assessment result of a patient based on session data of the patient, the session data being collected during presentation of a data collection playlist of visual stimuli to the patient in a session. Each visual scene of the data collection playlist is annotated with at least one of a plurality of skill areas associated with visual scenes of the data collection playlist. The operator-side computing device can be configured to: present the assessment result on a display screen of the operator-side computing device. The assessment result can include, for each of one or more specific skill areas of the plurality of skill areas, behavior data of the patient with respect to moments relevant to the specific skill area in the session, each of the moments corresponding to a respective visual scene of the visual scenes of the data collection playlist.

In some embodiments, the patient-side computing device is configured to: initiate a session for a patient by establishing a communication with the operator-side computing device and the patient-side portable tablet computing device, the patient-side portable tablet computing device being integrated with an eye-tracking device (e.g., the eye-tracking device 134 of FIG. 1A); sequentially presenting visual scenes of a data collection playlist of visual stimuli on a screen of the patient-side portable tablet computing device to the patient while collecting eye-tracking data of the patient using the eye-tracking device, each visual scene of the data collection playlist being annotated with at least one of a plurality of skill areas associated with the visual scenes of the data collection playlist; and transmitting session data of the session to the network-connected server the session data comprising the eye-tracking data of the patient collected in the session. The data collection playlist can include visual scenes relevant to one or more specific skill area of the plurality of skill areas that are prioritized in the data collection playlist.

In some embodiments, the patient-side computing device is configured to: collecting at least one of image data, audio data, or video data collected by one or more recording devices while the visual scenes of the data collection playlist of visual stimuli are sequentially presented. The one or more recording device can be assembled in at least one of the patient-side computing device or external to the patient-side computing device. The session data can include the at least one of image data, audio data, or video data.

Example Management of Treatment Plans

An evaluation system disclosed herein can be configured for evaluation of developmental disorders, e.g., Austim Spectrum Disorder (ASD). The evaluation system can be the system 200 of FIGS. 2A-2G and can be implemented in the environment 100 of FIG. 1A. The evaluation system can include a cloud server (or a network-connected server), e.g., the cloud server 110 of FIGS. 1A-1D or the cloud server with respect to FIGS. 2A-2G. In some examples, the evaluation system disclosed herein is represented as EarliPoint.

As discussed with details above (e.g., FIGS. 1A to 14), the evaluation system can perform one or more evaluation sessions (e.g., diagnostic session or monitoring session) to evaluate a patient's developmental disorder and generate a corresponding evaluation report (e.g., as illustrated in FIGS. 8A-8C, FIGS. 13A-13D, or FIGS. 16A-16F). As discussed with further details in FIGS. 15A-15H, the evaluation system can also generate a specific prescriptive treatment plan for the patient based on at least one of treatment plan data, patient data, or reference data.

In some implementations, the cloud server includes a cloud platform (e.g., the cloud platform 112 of FIG. 1A or the platform subsystem 220 of FIGS. 2A-2G) and a data pipeline system (e.g., the data pipeline system 114 of FIG. 1A or the data pipeline subsystem 230 of FIGS. 2A-2G). The cloud platform can be configured to provide a web portal, store application data associated with treatment providers, and store data, e.g., raw eye-tracking data, processed data, analytical and/or diagnostic results, and/or treatment plan data. The data pipeline system can be configured to perform data processing and data analysis. As discussed with details in FIGS. 6 and 7A-7B, the cloud server can automatically receive, process, and analyze session data from multiple computing systems, and process and analyze session data of a number of sessions from a large number of computing systems in parallel.

In some implementations, during the processing and analysis process (e.g., by the data pipeline system), a patient's individual data can be compared (e.g., using artificial intelligence algorithms or models) to reference data which were previously generated from historical eye-tracking data of patients belonging to a same or similar group and/or having similar ages, backgrounds, and/or conditions. The result of the comparison can be a diagnosis of a neurodevelopmental disorder including but not limited to ASD, a measure of the patient's developmental/cognitive functioning and/or prescriptive recommendation for a treatment plan. Alternatively or additionally, the collected data is compared and/or reviewed for a given patient over multiple sessions (and over a predetermined time period) to identify a potential change in visual fixation (e.g., a decline in visual fixation). Those results may be condensed into a diagnostic report, for use by the patient's physician. Once a diagnostic result is ready, the evaluation system can transfer the diagnostic result to a computing device for review (e.g., the operator-side computing device 140 of FIG. 1), and the diagnostic result can be presented on a user interface of the operator-side computing device 140, e.g., as discussed in FIGS. 8A-8C and FIGS. 13B-1, 13B-2, 13C, and 13D, and FIGS. 16A-16F. In some implementations, a large amount of model data, including data related to patients at similar ages, similar backgrounds, and/or similar situations, can be used with processed session data for a patient to generate a diagnosis result for the patient and/or a prescriptive treatment plan for the patient, e.g., using comparison or inference via statistical models, algorithms, artificial intelligence (AI) models such as machine learning or artificial neural network models, which can greatly increase accuracy of the diagnosis results.

For patients having developmental disorders (e.g., ASD), there can be different treatment plans for the patients, depending on the patients' ages, backgrounds, situations, evaluation reports, developmental stage, demography, geography, and/or available resources/practitioners. Also, a same patient may have experienced different treatment plans. In the following, example treatment plans are described, and the example treatment plans include, but not limited to, at least one of EarliPoint, the Early Start Denver Model (ESDM), Early Social Interaction (ESI), Discrete Trial Training (DTT), Joint Attention Symbolic Play Engagement Regulation (JASPER), or Project of Improving Parents As Communication Teachers (Project ImPACT). It is noted that the above treatment plans are just examples, and any other suitable treatment plans can be also implemented in the present disclosure.

EarliPoint evaluation system evaluates patients' developmental disorders using three developmental disorder indexes including social disability index, verbal ability index, and nonverbal learning index (e.g., as illustrated in FIGS. 8A and 16A-16E) and specific skill areas including manding, listener responding, turn-taking, joint attention or responding to joint attention (RJA), tact, and/or play (e.g., as illustrated in FIGS. 11-14 and 16F). As noted above, a skill area can include a number of specific skills (e.g., over 10, 20, 50, or 100 more). The EarliPoint evaluation system can generate treatment plans based on scores of the developmental disorder indexes and skill areas/skills.

The Early Start Denver Model (ESDM) is a behavioral therapy for children with autism between the ages of 12-48 months. It is based on the methods of applied behavior analysis (ABA). Parents and therapists use play to build positive and fun relationships. Through play and joint activities, a child is encouraged to boost language, social and cognitive skills. The ESDM treatment is based on understanding of normal toddler learning and development, focused on building positive relationships, teaching occurs during natural play and everyday activities, and uses play to encourage interaction and communication. ESDM can help children make progress in their social skills, language skills, and cognitive skills.

Early Social Interaction (ESI) provides early intervention for toddlers with autism spectrum disorders (ASD) and their families. ESI teaches parents how to support their child's social communication, emotional regulation, and play in everyday activities and settings.

Discrete Trial Training (DTT) is an intensive treatment program used to help children with developmental disabilities such as Autism. DTT involves training a child with autism a variety of skills that they may not pick up on their own. This method focuses on teaching a skill through a step-by-step process, rather than teaching the desired skill all at once. DTT uses a basic process to teach a new skill or behaviour and repeats it until children learn. The process involves giving an instruction like 'Pick up the cup'. If needed, a child follows up the instruction with a physical or verbal prompt like pointing at the cup.

JASPER is a treatment approach based on a combination of developmental and behavioral principles. This intervention model targets the foundations of social-communication (joint attention, imitation, play), uses naturalistic strategies to increase the rate and complexity of social-communication, and includes parents and teachers as implementers of the intervention to promote generalization across settings and activities and to ensure maintenance over time.

Project ImPACT is a parent-mediated intervention for young children with autism spectrum disorder (ASD) and related social communication delays. Parent-mediated means that a Project ImPACT coach teaches the parent techniques to be used with their child. The Project ImPACT coach uses systematic instruction to increase the parent's responsiveness to the child's behavior and teaches the parent how to use prompting and reinforcement to teach the child to use new communication, imitation, and play skills within child-led interactions. It is a naturalistic developmental behavioral intervention (NDBI). An NDBI is a newer class of intervention that has been informed by the fields of developmental and communication sciences and applied behavior analysis (ABA). Project ImPACT can be implemented in an individual or group coaching model and can be adapted for telehealth.

Different treatment plans can have different names for skill areas, different prompting approaches, different treatment/training materials, different reinforcement approaches, and/or different data collection methods. For example, Discrete Trial Training (DTT) is more rigid in structure, materials, location, delivery method. Naturalistic Developmental Behavioral Interventions (NDBI) like ESDM, JASPER, etc, maintain the core principles of ABA but are less rigid, more naturalistic and flexible in location and materials. There are also different subgroups in both of these ABA categories that use their own specific vocabulary, prompt structure, data collection sheet, etc. Some primary differences between treatment approaches can include: a) exact names of skills (e.g., "requesting" vs "manding", "listener responding" vs "following directions"), b) prompting approaches (e.g., most to least, least to most, how and when to adjust prompt, and level of verbal or nonverbal communication in prompt), c) materials (e.g., preordered and intentional for use in treatment setting or naturalistic to what is in child's environment), and d) reinforcement approaches that can be physical rewards, intrinsic rewards, screen time, edibles, etc.

For illustration, Table 1 shows two examples treatment curriculum plans (ESDM and DTT) for a same skill area. Note that clincians can have flexibility in creating specific curriculum plans for patients.

TABLE 1

Comparisons of treatment curriculum plans for ESDM and DTT

| | Early Start Denver Model (NDBI) | Discrete Trial Training (DTT) |
|---|---|---|
| Skill area | Requesting | Manding |
| Goal | Child will request a preferred item with gestures or gaze three or more times in a 15 minute period across three sessions | Child will mand 10 preferred items or activities with 90% accuracy across three days, by x date |
| Method | Lay out a big amount of toys in the room, let the child move and play. When they get to an activity they like, focus on this skill (requesting) alternating with other skills (e.g. turn taking, retrieving from point) as feels natural to playing. Capture eye contact, present the SD, and prompt least to most to occasion the correct response. | Put out 3 flashcards in front of the kid. Present the command. Wait 1 second, then do prompt sequence, if correct give X, if incorrect, do error correction. Use these words: x y z. |
| Materials | Any objects, toys or materials in treatment or home space. | Preordered ABA flashcards and objects |
| SD (discriminative stimulus) | "What do you want?" or similar, may start with gesture only | "What do you want?" or similar |
| Prerequisites | Developmentally able to control body, control eye gaze, track objects, understand basic instructions | N/A |

TABLE 1-continued

Comparisons of treatment curriculum plans for ESDM and DTT

| | Early Start Denver Model (NDBI) | Discrete Trial Training (DTT) |
|---|---|---|
| Prompting | Least to Most prompting (starts with least additional prompting and increases at incorrect responses) | Most to Least (starts with most additional prompting and decreases at correct responses) |
| Correct Response | Child uses verbal communication, physical gestures, or eye gaze to indicate a request for any of the objects presented for choice | Child mands for one of the presented flashcards within one second of prompt |
| Incorrect Response | Ignores prompt or makes no requests | Child ignores prompt, mands for something other than presented, plays with other toy, or is otherwise disengaged |
| Reinforcement | Child has an opportunity to play with or hold the toy/object they requested | Child gets an edible reward (e.g. skittle) or preferred break activity (e.g. one minute on iPad) |
| Error Correction Procedure | Ignore, move to another skill, return and repeat prompt at next natural opportunity | Repeat prompt until 5 incorrect responses, then break |
| Data Collection Method | Number of opportunities, scale 0-5 correctness and level of independence in response | Number of trials, correct/incorrect/no response, rate of correct response, duration of trials |

As described with further details in FIGS. 15A-15H, implementations of the present disclosure provide techniques for integrating treatment data (e.g., in a different treatment plan format), patient data, and reference data to generate specific treatment plans for patients.

FIGS. 15A-15H illustrate example illustrative user interfaces presented on a computing device, according to one or more embodiments of the present disclosure. The computing device can be an operator device or an operator-side computing device such as the computing device 140 of FIGS. 1A-1B, or the operator-side computing device described with respect to FIGS. 4A-4J. For example, an operator (e.g., a medical assistant, a medical professional, or any other representative of the treatment provider) can log in the web portal (e.g., the web portal 222 of FIG. 2A) running on the cloud server for device management, patient management, and data management. The operator can have a corresponding user role and permission, e.g., as discussed in FIG. 2D. The user interfaces (UIs) can be presented on a display screen of the operator-side computing device after the operator logs in the web portal using the operator-side computing device. The UIs can be user interfaces of an operator application (e.g., the operator application 216 of FIG. 2A) running on the cloud server or on the operator-side computing device.

FIG. 15A illustrates an example illustrative user interface 1500 presented on the computing device when the cloud server runs a data aggregator application. The data aggregator application can be configured to connect with one or more third party tools to ingest (e.g., by parsing) a patient's treatment data, including data from EHR (Electronic Health Records)/EMR (Electronic Medical Record) and ABA (Applied Behavior Analysis) practice management tools, and optionally reference patients' data, ingest (e.g., by parsing) the patient's (and/or other patients') treatment plans, goals, behavioral presses, patient responses over time, and other relevant clinical or treatment data. The data aggregator application can be configured to, combined with assessment data by the evaluation system, build a massive and unique data repository of clinical treatment and patient trajectories.

As FIG. 15A shows, the data aggregator application enables an operator to upload a patient's most recent treatment plan. The treatment plan can be in a different format from a default treatment plan format (e.g., EarliPoint) associated with the evaluation system (e.g., EarliPoint). As FIG. 15A shows, the user interface 1500 includes a selection element 1502 for the operator to select a plan format of the treatment plan to be uploaded, a drop-down list 1504 showing a list of treatment plan formats (e.g., EarliPoint, ESDM, ESI, DTT, JASPER, and Project ImPACT), and an uploading document element 1506 for uploading a document of the treatment plan. The data aggregator application can upload the document of the treatment plan from a repository (e.g., in the platform 220 of FIG. 2A) storing data of the patient in the cloud server, from the computing device, or from a storage medium (e.g., a USB, a disk, or a storage disk) coupled to the computing device.

After the document of the treatment plan is uploaded, the data aggregrator application can automatically parse the document of the treatment plan to retrieve relevant information based on the plan format of the treatment plan. As noted above, different treatment plans can have different names for a same skill area. The data aggregrator application can convert the different skill area names to a same skill area name (e.g., a default skill area name) used in the evaluation system. For example, the skill area name "requesting" in ESDM can be converted to "manding" in EarliPoint. The data aggregrator application can also summarize the treatment plan in view of the skill areas, e.g., how many hours have each treatment-specific skill area been trained per week? What are the impact of the treatment plan on the treatment-specific skill areas? In some examples, the impact of the treatment plan can be determined based on the patient's convergence looking percentage.

Figure 15E:
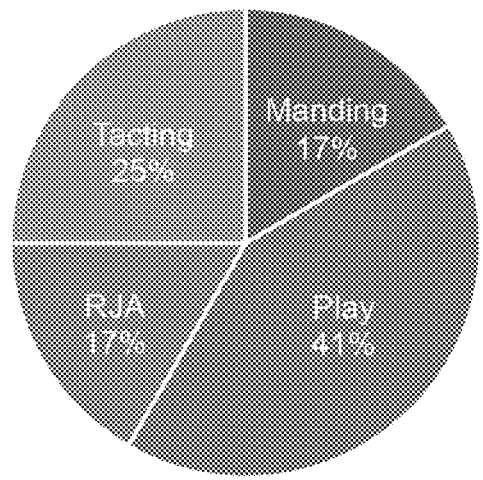
FIG. 15E illustrates a breakdown graph showing efforts of example treatment-specific skill areas in a treatment plan for a patient, according to one or more embodiments of the present disclosure.

FIG. 15E illustrates a breakdown graph 1540 showing efforts of example treatment-specific skill areas in a treatment plan for a patient. The example treatment-specific skill areas include manding, play, tacting, and RJA. The treatment plan can include hours for the example treatment-specific skill areas (e.g., per week) after a last evaluation report is generated for the patient. The efforts can be determined based on percentages of corresponding hours of the treatment-specific skill areas with respect to a total number of hours in the treatment plan. For example, the graph 1540 shows breakdown percentages of different treatment-specific skill areas in the treatment plan, including 41% for Play, 25% for Tacting, 17% for Manding, and 17% for RJA.

Figure 15F:
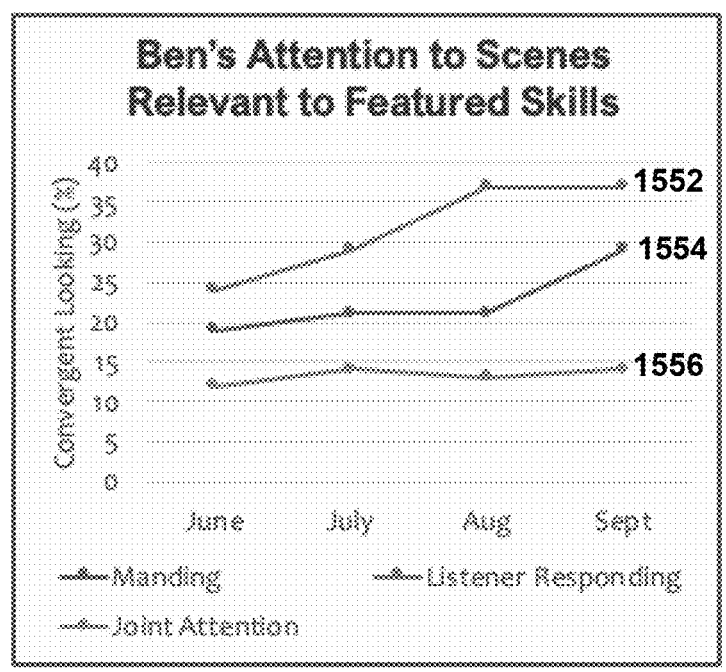
FIG. 15F illustrates a graph showing a patient's attention to scenes relevant to feature skills over sessions during a period of time, according to one or more embodiments of the present disclosure.

As noted above, a patient's looking behavior reflects how well the patient is good at a treatment-specific skill area. Thus, monitoring a change of convergent looking percentage for a treatment-specific skill area over a series of subsequent sessions (or a period of time) can show an impact of the treatment plan on a skill area. FIG. 15F illustrates a graph 1550 showing a patient's attention to scenes (represented by convergent looking percentage) relevant to feature skills over four sessions during a period of time, e.g., as illustrated in FIG. 13B-2. Based on the graph 1150, a comparison of the convergent looking percentages between a current session and one or more previous sessions can be determined. For example, as illustrated in FIG. 15F, Ben attended to 29% of moments relevant to manding, up from 21% last session; Ben attended to 37% of moments relevant to listener responding, no change from last session; and Ben attended to 14% of moments relevant to joint attention, up from 13% last session. Based on the changes of the convergent looking percentages of the skill areas, it can be referred the impact of the treatment plan between adjacent sessions or over multiple sessions on these treatment-specific skill areas.

Figure 15G:
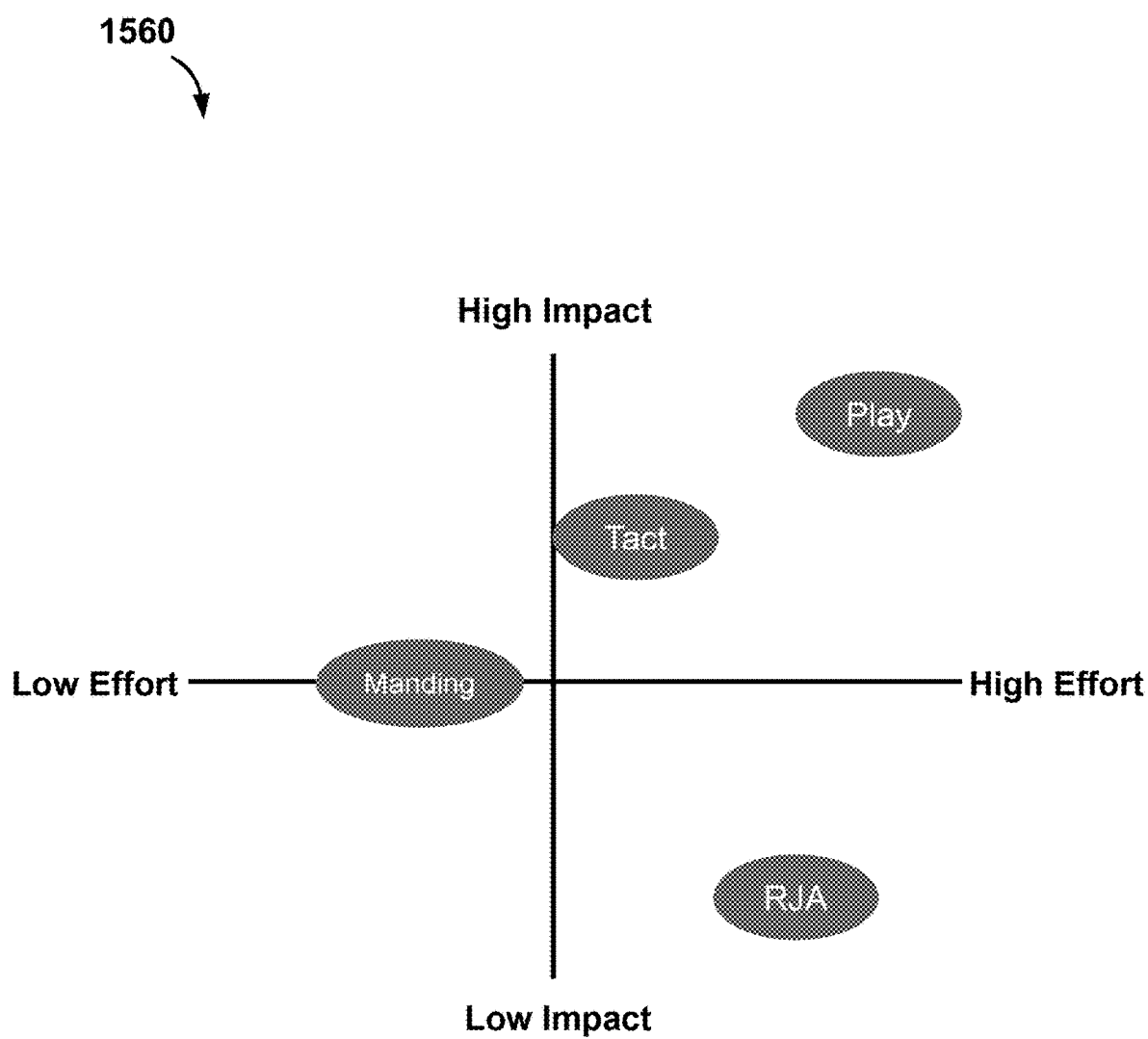
FIG. 15G illustrates a graph showing relationships between efforts and impacts for different skill areas, according to one or more embodiments of the present disclosure.

FIG. 15G illustrates a graph 1560 showing relationships between efforts and impacts for different skill areas. It is shown that: i) for the skill area of RJA, high effort causes low impact, which may indicate that the treatment plan has no or little effect on RJA and need to be changed (e.g., no treatment on RJA for a while); ii) for the skill area of Play, high effort causes high impact, which may indicate that the treatment plan has effect on Play with high effort; iii) for the skill area of Tact, medium effort causes high impact, which may indicate that the treatment plan can increase the effort on Tact to get higher impact; and iv) for the skill area of Manding, low effort causes medium impact, which may indicate that the treatment plan can increase the effort on Manding to get a higher impact.

Referring back to FIG. 15A, by parsing the treatment plan, the cloud server (e.g., the data aggregator application) can retrieve and/or determine information of the treatment plan (or treatment data). The data aggregator application can also parse multiple previous treatment plans for a patient to determine the relationship between efforts and impacts of the treatment plans on treatment-specific skill areas, e.g., as illustrated in FIG. 15E, 15F, and/or 15G, which can be presented on user interfaces of the computing device for the operator to review. For example, based on the relationship, the operator can consider when selecting a playlist of visual stimuli for the patient, e.g., to select more visual scenes on a skill area with high impact and low or medium effort like Tact and Manding as shown in FIG. 15G.

In some implementations, besides aggregating data from the patient's treatment plans, the data aggregator application is configured to aggregate data from treatment plans of other patients that are identified to have similar age, background, developmental stage, geography, and/or conditions, e.g., based on information of the patient.

In some implementations, the data aggregator application is configured to aggregate patient data and/or reference data from one or more third party tools for use. For example, the data aggregator can connect with the one or more third party tools to ingest (e.g., by parsing) a patient's treatment data, including data from EHR (Electronic Health Records)/EMR (Electronic Medical Record) and ABA (Applied Behavior Analysis) practice management tools, and optionally reference patients' data, ingest (e.g., by parsing) the patient's (and/or other patients') treatment plans, goals, behavioral presses, patient responses over time, and other relevant clinical or treatment data. The data aggregator can be configured to, combined with assessment data by the evaluation system, build a massive and unique data repository of clinical treatment and patient trajectories.

FIG. 15B illustrates an example illustrative user interface 1510 presented on the computing device when the cloud server runs the data aggregator application to aggregate data from an external tool. The user interface 1510 is configured to connect the external tool to aggregate data from third party electronic records and/or practice management tools. As FIG. 15B shows, the user interface 1510 includes a selection element 1512 for the operator to select a third party tool to connect, a drop-down list 1514 showing a list of third party tools (e.g., Cerner, EPIC EHR, Motivity, NextGen, and Spectrum AI), and a connection element 1516 for connecting a selected third party tool. After a third party tool (e.g., EPIC EHR shown in FIG. 15B) is selected and the connection element 1516 is clicked, the cloud server (e.g., the data aggregrator application) can connect to the selected third party tool to build a connection and retrieve data from the third party electronic records and/or practice management tools. e.g., based on information of the patient.

The information of the patient can include patient's age, background, condition, demographic information, geographical information, previous evaluation data, previous/current treatment data and/or treatment plans, and/or impacts of treatment plans on different skill areas. The information of the patient can help the cloud server (e.g., the data aggregrator application) to retrieve relevant data to the patient, including the patient's own data and/or data of reference patients having similar age, background, condition, developmental stage, demography, and/or geography. The cloud server can process these relevant data, e.g., using artificial intelligence (AI) model(s) running on the cloud server or an external computing system coupled to the cloud server.

In some implementations, the cloud server (e.g., the data aggregrator application) is configured to enable the operator to manually enter patient information. FIG. 15C illustrates an example illustrative user interface (UI) 1520 presented on the computing device when the cloud server runs the data aggregator application for the operator to manually enter the patient information. The user interface 1520 includes input fields of the patient's most recent treatment plan 1522, including Hours per week, Treatment Delivery location (e.g., center, home, school), Treatment Delivery Professional (e.g., BCBA, registered behavior technican—RBT, behavior analyst—BA), and Treatment Manual Type. The operator can click corresponding elements to select or input corresponding information. The user interface 1520 can also include area 1528 for inputting Goals, UI element 1525 for deleting Goal, and UI element for Adding Next Goal 1527.

In some implementations, the user interface 1520 includes a UI element 1524 for customizing input fields of the treatment plan. For example, the data aggregator application can automatically fill input fields of the treatment plan (e.g., the input fields shown in area 1528) based on the uploaded treatment plan for the patient (e.g., as illustrated in FIG. 15A). After the UI element 1524 is clicked, the data aggregator application can present a user interface for the operator to customize individual input fields of the treatment plan, e.g., based on a conversation with the patient's caregiver or previous treatment practioner or a performance of the patient during the treatment or evaluation session.

In some implementations, the user interface 1520 includes a UI element 1526 for in-treatment data entry. After the UI element 1526 is clicked, the data aggregator application can present a user interface to the operator to input data associated with the patient, e.g., based on a live performance of the patient during the treatment.

FIG. 15D illustrates example illustrative user interface 1530 presented on the computing device for session launch, according to one or more embodiments of the present disclosure. The user interface 1530 can be similar to the user interface 1200 of FIG. 12A.

As shown in diagram (a) of FIG. 15D, the UI 1530 includes a menu 1532 showing buttons "Home", "Patients", and "Appointments." By clicking a button, corresponding information (e.g., patient information, device information, or appointment information) can be presented in the UI 1530. As discussed in FIGS. 4A-4B, the computing device (e.g., operator-side computing device) can establish a communication with a patient-side computing device (e.g., the patient-side computing device 130 of FIG. 1A or the patient-side computing device discussed with respect to FIGS. 4A-4J), e.g., through the cloud server. After the communication is established, the operator can select a patient (or create a new patient) to start a session for the patient. When choosing to launch a session from the web portal, the operator can be presented with the UI 1530 showing session launch 1534 for session setup.

As illustrated in diagram (a) of FIG. 15D, under the session launch 1534, the operator can select a session type 1536 that can include a diagnostic session 1531 (e.g., the diagnostic session 1232 of FIG. 12A), a monitoring session 1533 (e.g., the monitoring session 1234 of FIG. 12A), and a targeted monitoring session 1535 (e.g., the targeted monitoring session 1236 of FIG. 12A). The diagnostic session 1531 is configured to run a session, e.g., as illustrated in FIGS. 4C-4J, and generate a diagnostic report, e.g., as illustrated in FIG. 8A or FIGS. 16A-16F. The diagnostic report can include diagnostic results, e.g., whether the patient is ASD or non-ASD and/or scores of three indexes (social disability index, verbal ability index, and nonverbal ability index) and/or correlations with other developmental measures. The monitoring session 1533 is configured to monitor a behavior (or performance) change over a series of sessions for an existing patient by running a session, e.g., as described in FIGS. 4C-4J, and generate a monitoring report, e.g., as described with further details in FIGS. 13A-13D. In some examples, e.g., as illustrated in diagram (a) of FIG. 15D, the UI 1530 can show a time (e.g., a date) where a last run was performed for the monitoring session 1533 and/or the diagnostic session 1531.

In some implementations, the diagnostic session 1531 and the monitoring session 1533 have a same data collection playlist of visual stimuli. In some implementations, the monitoring session 1533 can have a different data collection playlist of visual stimuli from the diagnostic session 1531. The monitoring session 1533 can run a default playlist that can be same as a playlist performed in a last session for the patient. The playlist performed in the last session can be customized for one or more specific skill areas, e.g., the last session can be a targeted monitoring session.

If the targeted monitoring session 1535 is selected, when the operator clicks a "continue" button 1537 in the UI 1530, a window 1538 can be prompted on the UI 1530 for the operator to select a set of skill areas that the operator would like to target, e.g., as illustrated in diagram (b) of FIG. 15D. The window 1538 can be overlaid on the user interface 1530, be side by side with the user interface 1530, or have an overlap with the user interface 1530. The user interface 1530 can be changed to the new window 1538.

If the targeted monitoring session 1535 is selected, when the operator clicks a "continue" button 1537 in the UI 1530, a window 1538 can be prompted on the UI 1530 for the operator to select a set of skill areas that the operator would like to target, e.g., as illustrated in diagram (b) of FIG. 15D. The window 1538 can be overlaid on the user interface 1530, be side by side with the user interface 1530, or have an overlap with the user interface 1530. The user interface 1530 can be changed to the new window 1538.

The set of skill areas can include, but not limited to, manding, listener responding, turn-taking, joint attention, tact, and play. A default selection can be any skill areas selected in a prior targeted monitoring session. The network-connected server can recommend consistent skill area selections over multiple sequential monitoring sessions. In some cases, the network-connected server stores previously selected targeted skill areas and/or personalized playlist, then the operator can repeat the same targeted monitoring session at a next session without reselecting targeted skill areas if desired.

Different from the window 1250 of FIG. 12B which presents a note "Auto-select from previous Targeted Monitoring Session" that the operator can click to automatically select targeted skill areas to be same as those in a previous targeted monitoring session, in diagram (b) of FIG. 15D, the window 1538 includes a note "Auto-select from Treatment Plan" that the operator can click to automatically select targeted skill areas to be same as those in a treatment plan that is predetermined for the patient. The treatment plan can be the uploaded most recent treatment plan (e.g., as illustrated in FIG. 15A), or predetermined based on manual input or customized by the operator (e.g., as illustrated in FIG. 15C). The operator can choose to keep the same selected targeted skill areas or change one or more targeted skill areas. In some implementations, there is a maximum number of targeted skill areas set for the selection, e.g., up to 4. The maximum number can be determined, for example, by a time length of videos in the data collection playlist. After the targeted skill areas are selected or confirmed, the operator can click a button 1539 in the window 1538 to run the session for the targeted skill areas, e.g., as illustrated in FIG. 12B.

The cloud server can receive and process session data o the targeted monitoring session, e.g., as described with details in FIGS. 1-14, and generate an evaluation report for the patient, e.g., as illustrated in FIG. 8A-8C, 13A-13D, or 16A-16F. As noted above, the cloud server can also generate a new treatment plan for the patient based on at least one of the evaluation report, the most recent treatment plan uploaded (e.g., as illustrated in FIG. 15A), one or more previous treatment plans, or reference data relevant to the patient (e.g., treatment plans of patients belonging to a same group as the patient, having a similar age, background, condition, developmental stage, demography or geography), by artificial intelligence (AI) algorithms and/or models.

Figure 15H:
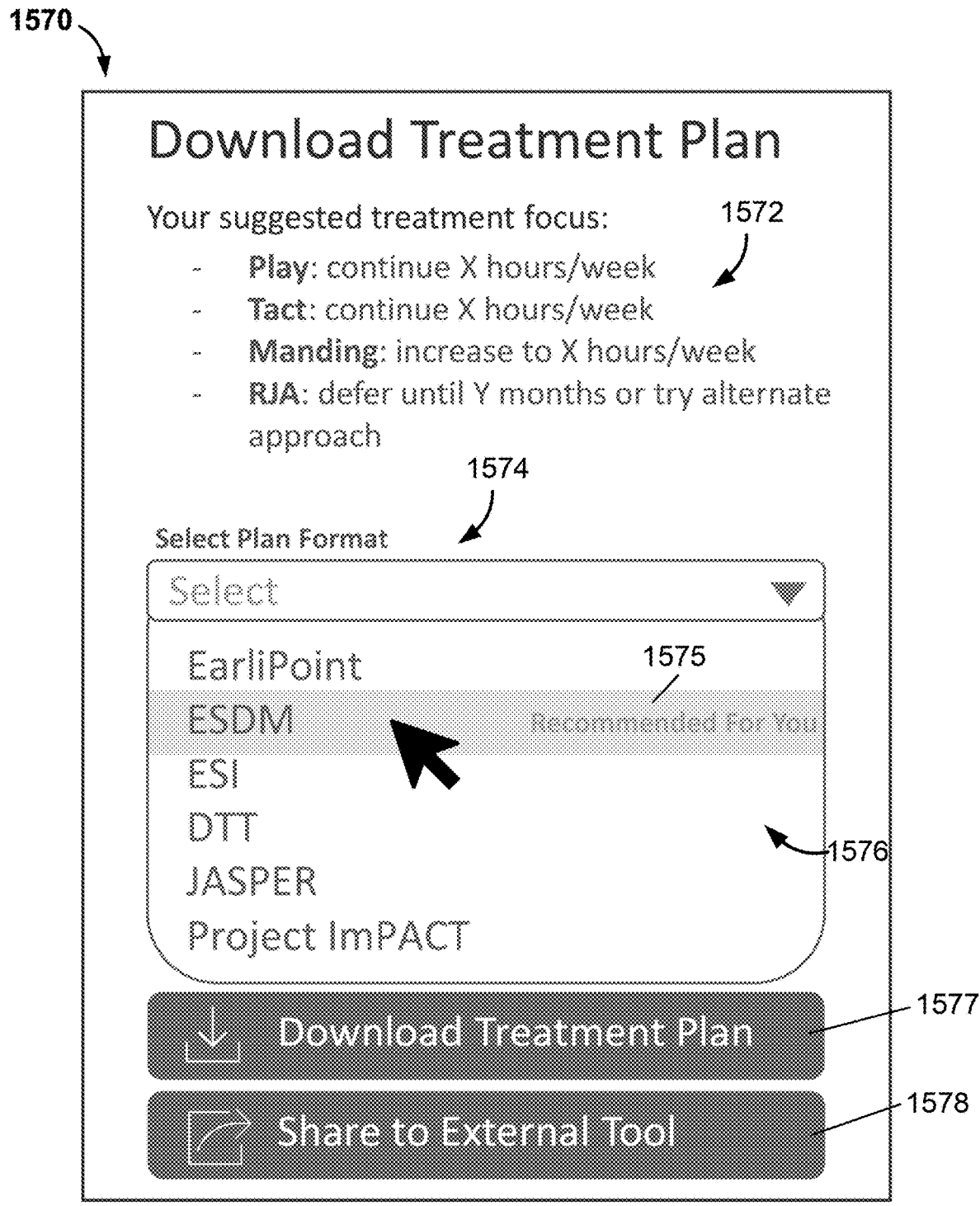
FIG. 15H illustrates an example illustrative user interface presented on a computing device when a cloud server outputs a treatment plan, according to one or more embodiments of the present disclosure.

FIG. 15H illustrates an example illustrative user interface 1570 presented on the computing device when the cloud server outputs a treatment plan. As noted above, the cloud server can determine the treatment plan. The user interface 1570 can present the suggested treatment focus 1572 showing the treatment on different skill areas, e.g., compared to the previous or most recent treatment plan. The suggested treatment focus 1572 can include, e.g., Play: continue X hours/week, Tact: continue X hours/week, Manding: increase to X hours/week, RJA: defer until Y months or try alternate approach.

As noted above, different treatment plan formats can have different names for skill areas, different prompting approaches, different treatment/training materials, different reinforcement approaches, and/or different data collection methods. Further, different treatment plan formats can have different impacts/effectiveness on different patients. The user interface 1570 can include a selection element 1574 to present a drop-down list 1576 of treatment plan formats (e.g., EarliPoint, ESDM, ESI, DTT, JASPER, and/or Project ImPACT). In some implementations, e.g., as illustrated in FIG. 15H, the cloud server provides a recommendation 1575 for a treatment plan format for the patient. The cloud server can use AI models and/or algorithms to select the recommended treatment plan format based on the patient's evaluation report, the patient's previous treatment plans, and/or treatment plans with different treatment plan formats of reference patients that belong to a same group as the patient or have a similar age, background, condition, developmental stage, demography, or geography. For example, patients in a same group as the patient have improved their specific skills more using ESDM format than those using other formats. The cloud server can then recommend ESDM format for the patient.

The operator can select a specific treatment plan format to download a specific treatment plan for the patient by clicking UI element 1577. The specific treatment plan format can be the recommended treatment plan format (e.g., ESDM) or another treatment plan format. The cloud server can generate the specific treatment plan based on the selected specific treatment plan format and information of the new treatment plan determined by the cloud server (e.g., as discussed above). For example, the cloud server can use AI algorithms or models to generate the specific treatment plan with the specific treatment plan format based on a number of treatment plans with the specific treatment plan format and/or the default treatment plan format for the evaluation system (e.g., EarliPoint). The operator can also share the specific treatment plan with the specific treatment plan format to an external third party tool (e.g., Cerner, EPIC EHR, Motivity, NextGen, or Spectrum AI as illustrated in FIG. 15B) by clicking UI element 1578.

In some implementations, as noted above, besides the specific treatment plan with the specific treatment plan format, the cloud server can also provide content-specific tutorials for the specific treatment plan. The cloud server can select the content-specific tutorials from a large number of tutorials. The content-specific tutorials can provide guidance or instruction on how to understand, interpret, and execute the specific treatment plan, without referring to the large number of tutorials, which can greatly save time and improve efficiency. The content-specific tutorials can also enable unexperienced treatment providers or treatment provides with little experience (e.g., providers in rural areas) to understand, interpret, and/or execute the specific treatment plan. The content-specific tutorials also enable experienced providers to use the selected tutorials as references or support to understand, interpret, and/or execute the specific treatment plan.

Example Evaluation Reports

FIGS. 16A to 16F illustrate example result interfaces of an example evaluation report of an evaluation system. The evaluation system can be implemented using the techniques disclosed herein and can be configured for evaluation of developmental disorders, e.g., Austim Spectrum Disorder (ASD). The evaluation system can be the system 200 of FIGS. 2A-2G. The evaluation system can include a cloud server, e.g., the cloud server 110 of FIGS. 1A-1D or the cloud server with respect to FIGS. 2A-2G. In some examples, the evaluation system is represented as EarliPoint.

The evaluation report can include a series of pages that can be individually displayed on the result interfaces of a computing device of a viewer. The viewer can be an operator, a clinician, a caregiver of a parent, a therapist, or a treatment practioner, or anyone that has authority to view the evaluation report of the patient. The computing device can include a graphical user interface (GUI) to present these result interfaces, e.g., one by one. As an example, the evaluation report includes 6 pages that are individually displayed on six result interfaces, e.g., as illustrated with details in FIGS. 16A-16F.

FIG. 16A illustrates an example result interface 1600 showing page 1 of the evaluation report. As illustrated in FIG. 16A, the result interface 1600 shows a title 1601 of the evaluation report, e.g., including a name of the evaluation system such as EarliPoint and a name of development disorders such as ASD. The result interface 1600 also shows patient information 1602 (e.g., patient name, data of birth, and age at evaluation) and session information 1604 (e.g., testing organization, prescribing clinician, session date, results prepared time, device operator, and device name).

The result interface 1600 can further show narrative results summary 1606, which includes assessment results 1607. For example, as shown in FIG. 16A, the summary recites "Ben is a 24-month-old child referred for an EarliPoint Evaluation for Austim Spectrum Disorder. Ben's evaluation took place on XX/XX/XX at CHOA where his results are consistent with a diagnosis of ASD." The assessment results 1607 recites a conclusion "1. Results are consistent with a diagnosis of Austim Spectrum Disorder," and scores of a series of development disorder indexes and associated indication information. For example, the assessment results 1607 show that a social disability index (e.g., EarliPoint social disability index for EarliPoint evaluation system) with a score of −7.2 indicates a high concern for social disability, a verbal ability index (e.g., EarliPoint verbal ability index for EarliPoint evaluation system) with a score of 23 indicates less advanced verbal ability than typical age-matched peers, and a nonverbal learning index (e.g., EarliPoint nonverbal learning index for EarliPoint evaluation system) with a score of 78 indicates more advanced nonverbal learning skills than typical age-matched peers. The result interface 1600 can also include a space for clinical comments and clinical signature.

FIG. 16B illustrates an example result interface 1610 showing page 2 of the evaluation report. As illustrated in FIG. 16B, the result interface 1610 shows a diagnostic assessment results 1612 (e.g., ASD or Non-ASD) and Severity Measures 1614. The diagnostic assessment results 1612 can be determined by the evaluation system, e.g., the cloud server, based on the severity measures 1614. The severity measures 1614 can include social disability index information 1614*a*, verbal ability index information 1614*b*, and nonverbal learning index information 1614*c*. The social disability index information 1614*a* can include the patient's actual score (e.g., −7.2) for social disability index over a score bar and associated indication information (e.g., a high concern for social disability). The verbal ability index information 1614*b* can include the patient's actual score (e.g., 23) for verbal ability index over a score bar and associated indication information with respect to peers (e.g., less advanced verbal ability than typical age-matched peers). The nonverbal learning index information 1614*c* can include the patient's actual score (e.g., 78) for nonverbal learning index over a score bar and associated indication information with respect to peers (e.g., more advanced nonverbal learning skills than typical age-matched peers).

The result interface 1610 further shows correlations between the Severity Measures 1614 and at least one reference assessment measure, with two such correlations depicted in this example (e.g., ADOS-2 Measures and Mullen Scales of Early Learning Measures). In some examples, correlation 1616 shows a correlation between EarliPoint Social Disability Index score and ADOS-2 Measures, and refers to page 3 of the evaluation report for details. Correlation 1618 shows: i) a correlation between with EarliPoint Verbal Ability Index score and a Mullen verbal age equivalent that is compared to the patient's chronological age; and ii) a correlation between with EarliPoint Nonverbal Learning Index score and a Mullen nonverbal age equivalent that is compared to the patient's chronological age. The correlation 1618 also refers to pages 4 and 5 of the evaluation report for details.

The EarliPoint test executed by the evaluation system is clinically validated as a tool to aid clinicians in the diagnosis and assessment of young children with ASD and to measure an individual child's strengths and vulnerabilities on three indices, e.g., EarliPoint Social Disability Index, EarliPoint verbal ability index, and EarliPoint nonverbal learning index.

The EarliPoint Social Disability Index quantifies how a child looks at social information in the environment. The EarliPoint Social Disability index can serve as a proxy to (e.g., be correlated to) a measure on the ADOS-2 scale, e.g., as illustrated in FIG. 16C. The Autism Diagnostic Observation Schedule-Second Edition (ADOS-2) is a standardized assessment tool that helps providers diagnose autism spectrum disorders (ASD) in children and adults. The ADOS provides standardized activities and questions that give the examiner opportunities to observe behaviors that are directly relevant to the diagnosis of ASD. The ADOS-2 incorporates the use of planned social activities designed for different developmental levels and chronological ages that provide situations in which social interactions, communication and particular types of behaviors are likely to appear.

A young child's language skills are acquired through interaction: through paying attention to what other people are doing, saying, and feeling. The EarliPoint Verbal Ability Index is clinically validated as a tool to measure a child's strengths and vulnerabilities in verbal abilities, quantifying how a child looks at communicative cues and language-related information in the environment. The EarliPoint Verbal Ability Index can serve as a proxy to (e.g., be correlated to) a verbal age equivalent score on the Mullen Scales of Early Learning (MSEL), e.g., as illustrated in FIG. 16D. MSEL is used to measure gross motor, visual reception, fine motor, expressive language, and receptive language skills in children from birth to 5 years old. The MSEL is an evaluation that helps to assess early intellectual development and school readiness. It measures overall cognitive ability and motor development by identifying and targeting a child's strengths and weaknesses in a quick and reliable manner. The MSEL is an important psychological assessment in the diagnostic process of young children suspected of having an autism spectrum disorder (ASD).

When a young child pays attention to the way in which events and actions happen over time, they acquire problem-solving skills, and their looking behavior reflects these skills. The EarliPoint Nonverbal Learning Index is clinically validated as a tool to measure a child's strengths and vulnerabilities in early learning and cognitive skills, quantifying how a child looks at cause-and-effect sequences over time. The EarliPoint Nonverbal Learning index proxies nonverbal age equivalent scores on the Mullen Scales of Early Learning (MSEL), e.g., as illustrated in FIG. 16E.

FIGS. 16C-16E illustrate detailed individual test results in the evaluation report. FIG. 16C illustrates an example result interface 1620 showing page 3 of the evaluation report, where information 1622 related to EarliPoint social disability index in the detailed individual test results is shown. The information 1622 includes a description of the EarliPoint social disability index and its corresponding reference assessment measure—ADOS-2. The result interface 1620 includes section 1624 showing EarliPoint social disability index correlation to ADOS-2 total score. The section 1624 includes two figures 1626, 1628 showing how the EarliPoint social disability Index correlates to the ADOS-2 total score.

FIG. 1626 shows a correlation curve between EarliPoint social disability index score and ADOS-2 total score, with 95% confidential interval (CI). FIG. 1626 also shows a line 1625 with the patient's social disability index score (e.g., −7.2), which corresponds to an ADOS-2 total score (e.g, 24 with 95% confidence interval of 23-25) according to the correlation curve. The ADOS-2 categorizes scores in terms of level of concern, from "moderate-to-severe," to "mild-to-moderate," or "little-to-no." While higher scores on the ADOS-2 indicate more concern about social disability, lower and more negative EarliPoint Social Disability Scores indicate more concern about social disability. The ADOS-2 concern ranges are dependent on the child's age and whether the child is nonverbal (e.g., has less than five words) or has some words (e.g., five or more).

FIG. 1628 shows a relationship between ADOS-2 level of concern and ADOS-2 total score. FIG. 1628 includes the level of concerns for different groups, e.g., diagram 1628*a* associated with a group of age 16-20 months OR nonverbal and diagram 1628*b* associated with a group of age 21+ months or with 5+words. As an example, based on FIG. 1626, the corresponding ADOS-2 total score of the patient (e.g., 24) can be determined based on EarliPoint social disability index (e.g., −7.2). Based on FIG. 1628, the corresponding ADOS-2 total score corresponds to moderate-to-Severe level of concern.

The result interface 1620 can also show a test result 1623 including the EarliPoint social disability index score (e.g., −7.2), associated indication information (e.g., indicating a high concern for social disability), and associated correlation information with ADOS-2 (e.g., this score correlates to a moderate-to-severe level of concern on the ADOS-2).

FIG. 16D illustrates an example result interface 1630 showing page 4 of the evaluation report, where information 1632 related to EarliPoint verbal ability index in the detailed individual test results is shown. The information 1632 includes a description of the EarliPoint verbal ability index and its corresponding reference assessment measure—Mullen Scales of Early Learning (MSEL). The result interface 1630 includes section 1634 showing EarliPoint verbal ability index correlation to Mullen verbal age equivalent. The section 1634 includes two figures 1636, 1638 showing how the EarliPoint verbal ability Index correlates to the MSEL age equivalent. Higher scores indicate more advance verbal abilities.

FIG. 1636 shows a correlation curve between EarliPoint verbal ability index score and MSEL age equivalent (months), with 95% confidential interval (CI). FIG. 1636 also shows a line 1635 with the patient's verbal ability index score (e.g., 23), which corresponds to a Mullen verbal age equivalent (e.g, 6 months with 95% confidence interval of 5-7 months) according to the correlation curve. FIG. 1638 shows a comparison between the patient's actual age 1638a (e.g., 24 months) and the Mullen verbal age equivalent 1638b (e.g., 6 months). For example, the patient's verbal age equivalent is less than his actual age, indicating less advanced verbal ability than typical age-matched peers.

The result interface 1630 can also show a test result 1633 including the EarliPoint verbal ability index score (e.g., 23), associated indication information (e.g., indicating less advanced verbal ability than typical age-matched peers), and associated correlation information with Mullen verbal age equivalent (e.g., this score correlates to a Mullen verbal age equivalent of approximately 6 months).

FIG. 16E illustrates an example result interface 1640 showing page 5 of the evaluation report, where information 1642 related to EarliPoint nonverbal learning index in the detailed individual test results is shown. The information 1642 includes a description of the EarliPoint nonverbal learning index and its corresponding reference assessment measure—Mullen Scales of Early Learning (MSEL). The result interface 1640 includes section 1644 showing EarliPoint nonverbal learning index correlation to Mullen verbal age equivalent. The section 1644 includes two figures 1646, 1648 showing how the EarliPoint nonverbal learning index correlates to the MSEL age equivalent. Higher scores indicate more advanced nonverbal learning skills.

FIG. 1646 shows a correlation curve between EarliPoint nonverbal learning index score and mullen nonverbal age equivalent (months), with 95% confidential interval (CI). FIG. 1646 also shows a line 1645 with the patient's nonverbal learning index score (e.g., 78), which corresponds to a Mullen nonverbal age equivalent (e.g, 29 months with 95% confidence interval of 27-30 months) according to the correlation curve. FIG. 1648 shows a comparison between the patient's actual age 1648a (e.g., 24 months) and the Mullen nonverbal age equivalent 1638b (e.g., 29 months). For example, the patient's verbal age equivalent is greater than his actual age, indicating more advanced nonverbal learning skills than typical age-matched peers.

The result interface 1640 can also show a test result 1643 including the EarliPoint nonverbal learning index score (e.g., 78), associated indication information (e.g., indicating more advanced nonverbal learning skills than typical age-matched peers), and associated correlation information with Mullen nonverbal age equivalent (e.g., this score correlates to a Mullen nonverbal age equivalent of approximately 29 months).

FIG. 16F illustrates an example result interface 1650 showing page 6 of the evaluation report, including an introduction 1652 of visualizing individual test results and visualized FIG. 1654. The introduction 1652 notes that "when watching video scenes of social interaction, typically developing children spend the majority of their time focusing on the same scene content at the same moments in time. This behavior—when different individual children look at the same content at the same time, responding in the same way to salient social information—is known as entrainment: children's looking behavior is entrained to salient social information. The EarliPoint test compares an individual child's looking behavior to clinically validated reference standards at each moment." The visualized FIG. 1654 shows a comparison of reference standard looking behavior with patient data, e.g., as illustrated in FIG. 11. The visualized FIG. 1654 includes images showing a still image of the social content 1654a, the age-expected reference standard typical looking behavior 1654b, and the patient's looking behavior data 1654c.

The result interface 1650 can also include the EarliPoint attentional funnel 1656 that includes a description 1657 and related figures 1658. In some examples, the figures 1658 includes: moment-by-moment eye-Gaze measurement (FIG. 2), attentional funnel for typically developing children (FIG. 3), and a patient's deviation data from the attentional funnel (FIG. 4). the description 1657 notes that "compiling moment-by-moment looking behavior over many social scenes (FIG. 2) shows the focus of typically developing children largely converging on the same content at the same moments in time. Represented by the narrow, red area on the salience map, these points of convergence create Attentional Funnel (FIG. 3). During the test, a child's attention, whether inside or outside of the funnel (FIG. 4), is analyzed to determine the presence or absence of ASD together with individual measures of social disability, verbal ability, and nonverbal learning."

Example Processes

Figure 17A:
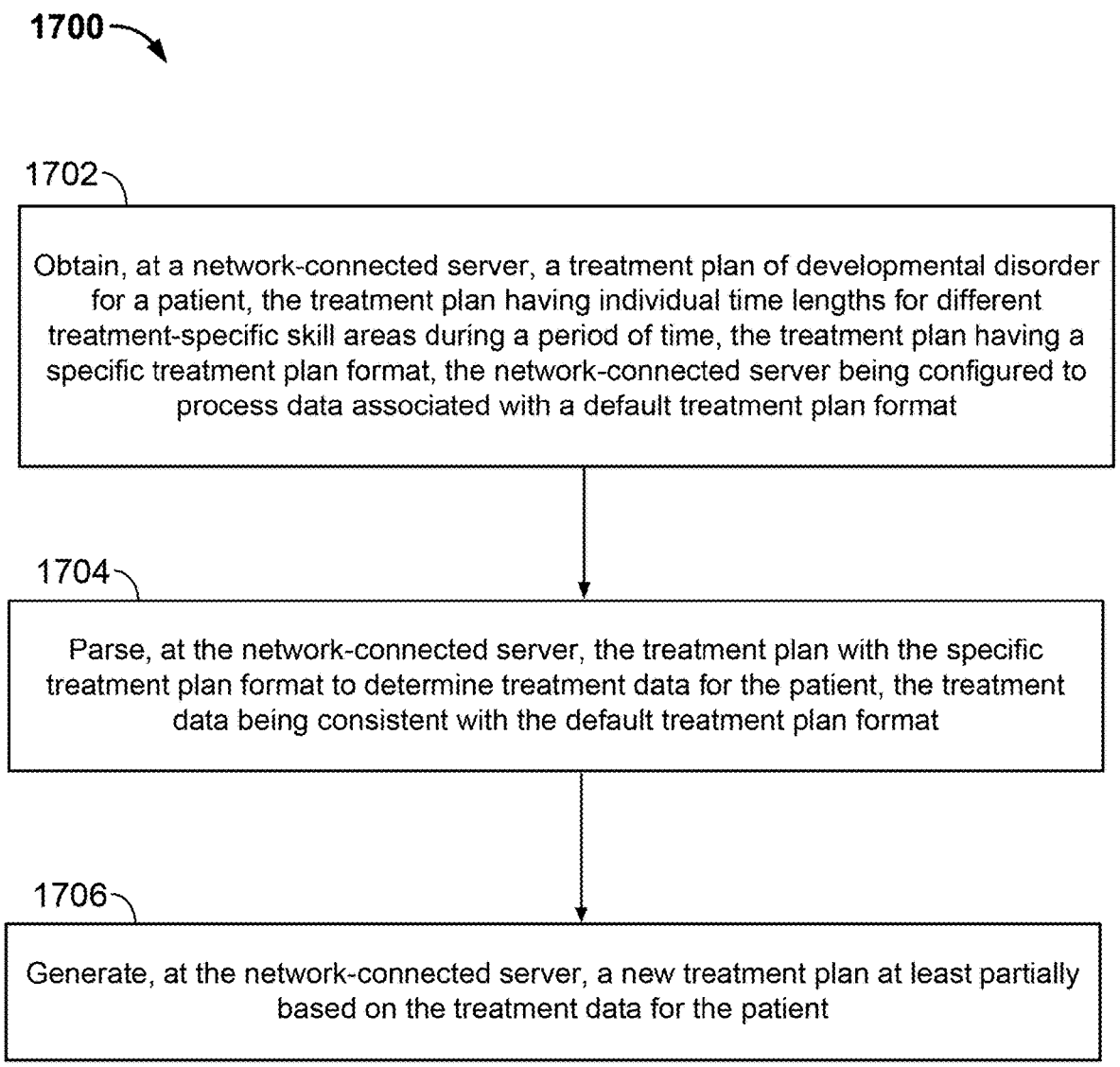
FIG. 17A is a flowchart of an example process for managing treatment plans for development disorder assessment, according to one or more embodiments of the present disclosure.

FIG. 17A is a flowchart of an example process 1700 for managing treatment plans for developmental disorder assessment, according to one or more embodiments of the present disclosure. FIG. 17B is a flowchart of an example process 1750 for managing evaluation reports, according to one or more embodiments of the present disclosure. Each of the processes 1700 and 1750 can be performed by a network-connected server of an evaluation system. The evaluation system can be the system 200 of FIGS. 2A-2G. In some examples, the evaluation system is represented as EarliPoint. The network-connected server can be a cloud server in a cloud environment, e.g., the cloud server 110 of FIG. 1A, the cloud server as described in FIGS. 2A-2G or the cloud server as described in FIGS. 15A-15H. The network-connected server can be included in an evaluation system For example, the network-connected server can include a platform, e.g., 112 of FIG. 1A or 220 of FIGS. 2A-2G, and a data pipeline system, e.g., 114 of FIG. 1A or 230 of FIGS. 2A-2G. The platform can include a web portal (e.g., 222 of FIGS. 2A-2G), an application data database (e.g., 224 of FIGS. 2A-2G), and a database (e.g., 226 of FIGS. 2A-2G). The data pipeline system can include one or more data processing modules (e.g., 232 of FIGS. 2A-2G) and one or more data analysis modules (e.g., 234 of FIGS. 2A-2G).

Referring to FIG. 17A, at step 1702, the network-connected server obtains a treatment plan of developmental disorder for a patient. The treatment plan has individual time lengths for different treatment-specific skill areas during a period of time, e.g., as illustrated in FIG. 15H. The treatment plan can have a specific treatment plan format (e.g., EarliPoint, ESDM, ESI, DTT, JASPER, or Project ImPACT).

The network-connected server is configured to process data associated with a default treatment plan format (e.g., EarliPoint).

At step 1704, the network-connected server parses the treatment plan with the specific treatment plan format to determine treatment data for the patient. The treatment data is consistent with the default treatment plan format.

In some embodiments, the network-connected server receives an input for selecting a treatment plan format from a plurality of treatment plan formats presented on a user interface, e.g., as illustrated in FIG. 15A. The plurality of treatment plan formats can be different from each other in at least one of skill area names, prompting approaches, treatment or training materials, reinforcement approaches, or data collection approaches. In some examples, the plurality of treatment plan formats include two or more of EarliPoint, the Early Start Denver Model (ESDM), Early Social Interaction (ESI), Discrete Trial Training (DTT), Joint Attention Symbolic Play Engagement Regulation (JASPER), and Project of Improving Parents As Communication Teachers (Project ImPACT).

In some embodiments, parsing the treatment plan with the specific treatment plan format includes: parsing the treatment plan with the specific treatment plan format based on the selected treatment plan format and the default treatment plan format. In such a way, the treatment plan can be converted to the treatment data consistent with the default treatment plan format, such that the treatment data can be recognized and/or processed by the network-connected server.

In some embodiments, obtaining the treatment plan of developmental disorder for the patient includes: uploading the treatment plan with the specific treatment plan format from a repository at the network-connected server or a storage medium, e.g., as illustrated in FIG. 15A.

In some embodiments, the treatment data includes at least one of: i) respective time lengths of the different treatment-specific skill areas during the period of time, ii) respective percentages of time lengths of the different treatment-specific skill areas during the period of time, iii) respective attendance percentages of the different treatment-specific skill areas over a series of sessions, iv) respective attendance percentage changes of the different treatment-specific skill areas between at least two most recent sessions, or v) relationships between the respective percentages of time lengths and the respective attendance percentage changes of the different treatment-specific skill areas, e.g., as illustrated in FIGS. 15E, 15F, and 15G. Attendance percentage can be defined as a ratio between a number of moments which the patient attends to relevant scene contents in visual stimuli and a total number of moments which the patient is watching the visual stimuli.

At step 1706, the network-connected server generates a new treatment plan at least partially based on the treatment data for the patient. The new treatment plan can be customized. In some embodiments, the network-connected server receives an input for selecting a treatment plan format from a plurality of treatment plan formats presented on a user interface, e.g., as illustrated in FIG. 15H. The network-connected server can then generate the new treatment plan based on the treatment data for the patient and the selected treatment plan format. Similarly, the plurality of treatment plan formats can include one or more of EarliPoint, ESDM, ESI, DTT, JASPER, and Project ImPACT.

In some embodiments, the network-connected server transmits the new treatment plan with the selected treatment plan format to a computing device (e.g., by clicking a download element 1577 of FIG. 15H) or an external server (e.g., by clicking the sharing element 1578 of FIG. 15H.

In some embodiments, the network-connected server generates evaluation data of developmental disorder for the patient based on eye-tracking session data of the patient, e.g., as illustrated in FIGS. 1A to 14. The new treatment plan can be generated based on the evaluation data of developmental disorder for the patient, together with the treatment data for the patient.

In some embodiments, the network-connected server determines a particular treatment plan format for the new treatment plan for the patient among the plurality of treatment plan formats and presents a visual indication (e.g., the recommendation 1575 of FIG. 15H) on the particular treatment plan format among the plurality of treatment plan formats in the user interface, the visual indication indicating a recommendation of the particular treatment plan format for the new treatment plan for the patient, e.g., as illustrated in FIG. 15H.

In some embodiments, the network-connected server receives a selection of a targeted session from a list of sessions on a user interface of a web portal on the network-connected server, e.g., as illustrated in diagram (a) of FIG. 15D. In response to receiving the selection of the targeted session, a window can be popped up for selecting targeted skill areas from a plurality of skill areas listed in the window, e.g., as illustrated in diagram (b) of FIG. 15D. The network-connected server can automatically select one or more targeted skill areas from the plurality of skill areas based on the treatment data, e.g., by AI algorithms or models. In some examples, the one or more targeted skill areas can be same as the treatment-specific skill areas in the treatment plan. In some examples, the one or more targeted skill areas can be different from the treatment-specific skill areas in the treatment plan. For example, the network-connected server can adjust the selection of the targeted skill areas based on the treatment data parsed from the treatment plan. The network-connected server can run the targeted session based on the selected one or more targeted skill areas.

In some embodiments, the network-connected server presents input fields of the treatment plan on a user interface of a web portal on the network-connected server, e.g., as illustrated in FIG. 15C. The network-connected server can receive an input for one of the input fields of the treatment plan on the user interface, and update the treatment plan based on the input for the one of the input fields.

In some examples, the different treatment-specific skill areas include one or more of manding, listener responding, turn-taking, joint attention, tact, and play.

In some embodiments, the network-connected server receives an input for selecting a third party system from a plurality of third party systems presented on a user interface, e.g., as illustrated in FIG. 15B. The network-connected server can retrieve data relevant to the patient from the selected third party system after establishing a connection between the network-connected server and the selected third party system. The data relevant to the patient can include at least one of previous clinical data of the patient, previous treatment data of the patient, or reference data of other patients. The network-connected server can generate a new treatment plan for the patient based on the treatment data and the data relevant to the patient.

Referring to FIG. 17B, at step 1752, the network-connected server receives a request for an evaluation result of a patient based on session data of the patient. The session data are collected during presentation of a data collection playlist of visual stimuli to the patient in a session for evaluating a development disorder of the patient, e.g., as illustrated in FIG. 1A-1D. At step 1754, the network-connected server outputs the evaluation result of the patient, e.g., as illustrated in FIGS. 8A-8C, 13A-13D, or FIGS. 16A-16F. The evaluation result can include: respective scores of developmental disorder indexes associated with the development disorder for the patient, e.g., as illustrated in FIG. 16B. The evaluation result can also include: for each of the developmental disorder indexes, a result of a correlation between the respective score of the developmental disorder index and a corresponding reference assessment measure, e.g., FIGS. 16C-16E. The corresponding reference assessment measure can include, but not limited to, ADOS-2 measure, MSEL measure, ADI-R measure, CARS measure, VABS measure, DAS-II measure, WISC measure, WASI measure, or VB-MAPP measure.

In some embodiments, the result of the correlation includes at least one of: a summary describing the correlation (e.g., 1623 of FIG. 16C, 1633 of FIG. 16D, or 1643 of FIG. 16E) or a graphical presentation of the correlation (e.g., 1626 and 1628 of FIG. 16C, 1636 and 1638 of FIG. 16D, or 1646, 1648 of FIG. 16E).

In some embodiments, the evaluation result further includes at least one of: an assessment result indicating whether the patient has the developmental disorder (e.g., 1606 of FIG. 16A or 1612 of FIG. 16B) or indication information of each of the respective scores of the developmental disorder indexes (e.g., 1607 of FIG. 16A).

In some examples, the developmental disorder indexes include at least one of social disability index, verbal ability index, or nonverbal learning index. In some examples, the corresponding measure for the respective score of the social disability index includes ADOS-2 measure (e.g., as illustrated in FIG. 16C), the corresponding measure for the respective score of the verbal ability index comprises Mullen Verbal Age Equivalent (e.g., as illustrated in FIG. 16D), and the corresponding measure for the respective score of the nonverbal learning index comprises Mullen Nonverbal Age Equivalent (e.g., as illustrated in FIG. 16E). The evaluation result can also include descriptions or definitions of the developmental disorder indexes and the corresponding measures, e.g., as illustrated by 1622 of FIG. 16C, 1632 of FIG. 16D, 1642 of FIG. 16E.

In some embodiments, at least one visual scene of the data collection playlist is annotated with at least one of a plurality of skill areas associated with visual scenes of the data collection playlist. The evaluation result includes, for each of one or more specific skill areas of the plurality of skill areas, behavior data of the patient with respect to moments relevant to the specific skill area in the session, each of the moments corresponding to a respective visual scene of the visual scenes of the data collection playlist.

In some embodiments, the behavior data includes an attendance percentage defined as a ratio between a number of moments which the patient attends to relevant scene contents in the visual stimuli and a total number of moments which the patient is watching the visual stimuli, e.g., as illustrated in FIG. 11.

In some embodiments, the evaluation result includes: a contour of a distribution map of behavior data of a reference group, the behavior data of the reference group being based on reference session data collected during presentation of the data collection playlist of visual stimuli to each person of the reference group. The evaluation result also includes at least one of: for each of the one or more specific skill areas, a representative visual scene, the representative visual scene highlighting one or more attendance areas in a predetermined region for the reference group, or the representative visual scene highlighting the attendance area of the patient in the session, e.g., as illustrated in FIG. 16F.

In some embodiments, the evaluation result includes at least one of: a first graphical presentation of moment-by-moment measurement of the patient's looking behavior during the session, or a second graphical presentation of attentional funnel of a reference group and the patient's attention during the session, e.g., as illustrated in FIG. 16F.

Example Cloud Computing System Architecture

FIG. 18 is an example architecture 1800 for a cloud computing system (e.g., the cloud server 110 described in reference to FIG. 1A or the cloud server described in reference to FIGS. 2A-2G), according to one or more embodiments of the present disclosure. Other architectures are possible, including architectures with more or fewer components. In some implementations, architecture 1800 includes one or more processor(s) 1802 (e.g., dual-core Intel® Xeon® Processors), one or more network interface(s) 1806, one or more storage device(s) 1804 (e.g., hard disk, optical disk, flash memory) and one or more computer-readable medium(s) 1808 (e.g., hard disk, optical disk, flash memory, etc.). These components can exchange communications and data over one or more communication channel(s) 1810 (e.g., buses), which can utilize various hardware and software for facilitating the transfer of data and control signals between components.

The term "computer-readable medium" refers to any medium that participates in providing instructions to processor(s) 1802 for execution, including without limitation, non-volatile media (e.g., optical or magnetic disks), volatile media (e.g., memory) and transmission media. Transmission media includes, without limitation, coaxial cables, copper wire and fiber optics.

Computer-readable medium(s) 1808 can further include instructions 1812 for an operating system (e.g., Mac OS® server, Windows® NT server, Linux Server), instructions 1814 for network communications module, data processing instructions 1816, and interface instructions 1818.

Operating system can be multi-user, multiprocessing, multitasking, multithreading, real time, etc. Operating system performs basic tasks, including but not limited to: recognizing input from and providing output to devices 1802, 1804, 1806 and 1808; keeping track and managing files and directories on computer-readable medium(s) 1808 (e.g., memory or a storage device); controlling peripheral devices; and managing traffic on the one or more communication channel(s) 1810. Network communications module includes various components for establishing and maintaining network connections (e.g., software for implementing communication protocols, such as TCP/IP, HTTP, etc.) and for creating a distributed streaming platform using, for example, Apache Kafka™. Data processing instructions 1816 include server-side or backend software for implementing the server-side operations, as described in reference to FIG. 1. Interface instructions 1818 includes software for implementing a web server and/or portal for sending and receiving data to and from user side computing devices and service side computing devices.

Architecture 1800 can be implemented by a cloud computing system and can be included in any computer device, including one or more server computers in a local or distributed network each having one or more processing cores. Architecture 1800 can be implemented in a parallel processing or peer-to-peer infrastructure or on a single device with one or more processors. Software can include multiple software components or can be a single body of code.

Example Computing Devices

FIG. 19 illustrates an architecture for a computing device, according to one or more embodiments of the present disclosure. Referring now to FIG. 19, illustrated is a schematic diagram of a device 1900. Device 1900 includes processor 1904, memory 1906, storage component 1908, input interface 1910, output interface 1916, communication interface 1914, and bus 1902. In some embodiments, device 1900 corresponds to at least one of the patient-side computing device 130 or the operator-side computing device 140 of FIG. 1.

Bus 1902 includes a component that permits communication among the components of device 1900. In some embodiments, processor 1904 is implemented in hardware, software, or a combination of hardware and software. In some examples, processor 1904 includes a processor (e.g., a central processing unit (CPU), a graphics processing unit (GPU), an accelerated processing unit (APU), and/or the like), a microphone, a digital signal processor (DSP), and/or any processing component (e.g., a field-programmable gate array (FPGA), an application specific integrated circuit (ASIC), and/or the like) that can be programmed to perform at least one function. Memory 1906 includes random access memory (RAM), read-only memory (ROM), and/or another type of dynamic and/or static storage device (e.g., flash memory, magnetic memory, optical memory, and/or the like) that stores data and/or instructions for use by processor 1904.

Storage component 1908 stores data and/or software related to the operation and use of device 1900. In some examples, storage component 1908 includes a hard disk (e.g., a magnetic disk, an optical disk, a magneto-optic disk, a solid state disk, and/or the like), a compact disc (CD), a digital versatile disc (DVD), a floppy disk, a cartridge, a magnetic tape, a CD-ROM, RAM, PROM, EPROM, FLASH-EPROM, NV-RAM, and/or another type of computer readable medium, along with a corresponding drive.

Input interface 1910 includes a component that permits device 1900 to receive information, such as via user input (e.g., a touchscreen display, a keyboard, a keypad, a mouse, a button, a switch, a microphone, a camera, and/or the like). Additionally or alternatively, in some embodiments input interface 1910 includes a sensor that senses information (e.g., a global positioning system (GPS) receiver, an accelerometer, a gyroscope, an actuator, and/or the like). Output interface 1916 includes a component that provides output information from device 1900 (e.g., a display, a speaker, one or more light-emitting diodes (LEDs), and/or the like).

In some embodiments, communication interface 1914 includes a transceiver-like component (e.g., a transceiver, a separate receiver and transmitter, and/or the like) that permits device 1900 to communicate with other devices via a wired connection, a wireless connection, or a combination of wired and wireless connections. In some examples, communication interface 1914 permits device 1900 to receive information from another device and/or provide information to another device. In some examples, communication interface 1914 includes an Ethernet interface, an optical interface, a coaxial interface, an infrared interface, a radio frequency (RF) interface, a universal serial bus (USB) interface, a Wi-Fi® interface, a cellular network interface, and/or the like.

In some embodiments, device 1900 performs one or more processes described herein. Device 1900 performs these processes based on processor 1904 executing software instructions stored by a computer-readable medium, such as memory 1906 and/or storage component 1908. A computer-readable medium (e.g., a non-transitory computer readable medium) is defined herein as a non-transitory memory device. A non-transitory memory device includes memory space located inside a single physical storage device or memory space spread across multiple physical storage devices.

In some embodiments, software instructions are read into memory 1906 and/or storage component 1908 from another computer-readable medium or from another device via communication interface 1914. When executed, software instructions stored in memory 1906 and/or storage component 1908 cause processor 1904 to perform one or more processes described herein. Additionally or alternatively, hardwired circuitry is used in place of or in combination with software instructions to perform one or more processes described herein. Thus, embodiments described herein are not limited to any specific combination of hardware circuitry and software unless explicitly stated otherwise.

Memory 1906 and/or storage component 1908 includes data storage or at least one data structure (e.g., a database and/or the like). Device 1900 is capable of receiving information from, storing information in, communicating information to, or searching information stored in the data storage or the at least one data structure in memory 1906 or storage component 1908. In some examples, the information includes network data, input data, output data, or any combination thereof.

In some embodiments, device 1900 is configured to execute software instructions that are either stored in memory 1906 and/or in the memory of another device (e.g., another device that is the same as or similar to device 1900). As used herein, the term "module" refers to at least one instruction stored in memory 1906 and/or in the memory of another device that, when executed by processor 1904 and/or by a processor of another device (e.g., another device that is the same as or similar to device 1900) cause device 1900 (e.g., at least one component of device 1900) to perform one or more processes described herein. In some embodiments, a module is implemented in software, firmware, hardware, and/or the like.

The number and arrangement of components illustrated in FIG. 19 are provided as an example. In some embodiments, device 1900 can include additional components, fewer components, different components, or differently arranged components than those illustrated in FIG. 19. Additionally or alternatively, a set of components (e.g., one or more components) of device 1900 can perform one or more functions described as being performed by another component or another set of components of device 1900.

The disclosed and other examples can be implemented as one or more computer program products, for example, one or more modules of computer program instructions encoded on a computer readable medium for execution by, or to control the operation of, data processing apparatus. The computer readable medium can be a machine-readable storage device, a machine-readable storage substrate, a memory device, or a combination of one or more them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A system may encompass all apparatus, devices, and machines for processing data, including by way of example a programmable processor, a computer, or multiple processors or computers. A system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed for execution on one computer or on multiple computers that are located at one site or distributed across multiple sites and interconnected by a communications network.

The processes and logic flows described in this document can be performed by one or more programmable processors executing one or more computer programs to perform the functions described herein. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer can include a processor for performing instructions and one or more memory devices for storing instructions and data. Generally, a computer can also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data can include all forms of nonvolatile memory, media and memory devices, including by way of example semiconductor memory devices, e.g., EPROM, EEPROM, and flash memory devices; magnetic disks. The processor and the memory can be supplemented by, or incorporated in, special purpose logic circuitry.

While this document may describe many specifics, these should not be construed as limitations on the scope of an invention that is claimed or of what may be claimed, but rather as descriptions of features specific to particular embodiments. Certain features that are described in this document in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination in some cases can be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

The foregoing is merely illustrative of the principles of the disclosure, and the systems, devices, and methods can be practiced by other than the described embodiments, which are presented for purposes of illustration and not of limitation. Although the embodiments and features herein are specifically described for use in connection with collecting and analyzing eye-tracking data of patients for the assessment, screening, monitoring, or diagnosis of autism spectrum disorders (ASD), it will be understood that the systems, devices, and methods may also apply to other developmental, cognitive social or mental abilities or disabilities, as well as other conditions, including but not limited to language disorders, intellectual disabilities, developmental disabilities with or without the presence of known genetic disorders, as well as attention deficit hyperactivity disorder (ADHD), attention deficit disorder (ADD), post-traumatic stress disorder (PTSD), head trauma, concussion, sports injuries, and dementia. It will be understood that such data, if not indicating measures for a disorder, may provide a measure of the degree of typicality of normative development, providing an indication of variability in typical development. Further, all of the components and other features outlined herein may be combined with one another in any suitable manner and may be adapted and applied to systems outside of medical diagnosis. For example, the interactive visual stimuli of the present disclosure may be used as a therapeutic tool. Further, the collected data may yield measures of certain types of visual stimuli that patients attend to preferentially. Such measures of preference have applications both in and without the fields of medical diagnosis and therapy, including, for example advertising or other industries where data related to visual stimuli preference is of interest.

A number of implementations have been described. Nevertheless, it will be understood that various modifications may be made without departing from the spirit and scope of the techniques and devices described herein. For example, phase perturbation or variation methods discussed above may be implemented in diffractive structures to remove high frequency artifacts or medium frequency artifacts in inference patterns. Features shown in each of the implementations may be used independently or in combination with one another. Additional features and variations may be included in the implementations as well. Accordingly, other implementations are within the scope of the following claims.

What is claimed is:

1. A system using at least one portable computing device with eye-tracking capability, the system comprising:
   a portable eye-tracker console comprising a display screen and an eye-tracker device mounted adjacent to the display screen such that both the display screen and the eye-tracker device are oriented toward a patient, wherein the eye-tracker device is configured to collect eye-tracking coordinate data of the patient while a predetermined sequence of stimulus videos is presented on the display screen during a session;

a portable computing device having a touchscreen display interface and being spaced apart from, and portable to different locations relative to, the portable eye-tracker console; and a network-connected server that wirelessly receives session data of the session from the portable eye-tracker console and comprises a web portal that exports an evaluation result including a graphic correlation of a numeric disability index score correlated to a reference assessment measure, wherein the network-connected server is configured to wirelessly connect with both the portable eye-tracker console and the portable computing device such that, subsequent to the portable computing device wirelessly communicating with the portable eye-tracker console via the network-connected server to control activation of the session present the predetermined sequence of stimulus videos on the display screen of the portable eye-tracker console, the portable eye-tracker console wirelessly communicates to the network-connected server the session data comprising the eye-tracking coordinate data in timestamp relationship with information of the predetermined sequence of stimulus videos displayed by the portable eye-tracker console during the session.

2. The system of claim 1, comprising multiple portable eye-tracker consoles that contemporaneously wirelessly communicate with the network-connected server.

3. The system of claim 1, wherein the eye-tracker device comprises one or more eye-tracking sensors mechanically assembled adjacent to a periphery of the display screen.

4. The system of claim 3, wherein each of the one or more eye-tracking sensors comprises:
an illumination source configured to emit detection light, and
a camera configured to capture eye movement data comprising at least one of pupil or corneal reflection or reflex of the detection light from the illumination source, and
wherein the eye-tracking sensor is configured to convert the eye movement data into a data stream that contains information of at least one of pupil position, a gaze vector for each eye, or gaze point, wherein eye-tracking data of the patient comprises a corresponding data stream of the patient.

5. The system of claim 4, wherein the detection light comprises an infrared light, and the camera comprises an infrared-sensitive camera, and
wherein, while the predetermined sequence of stimulus videos is presented on the display screen oriented to the patient during the session, a caregiver that carries the patient wears a pair of eyeglasses having a filter configured to filter the infrared light, such that the camera captures only eye movement data of the patient.

6. The system of claim 1, wherein the eye-tracker device comprises at least one image acquisition device configured to capture images of at least one eye of the patient, while the predetermined sequence of stimulus videos is presented on the display screen oriented to the patient during the session, and
wherein the eye-tracker device is configured to generate corresponding eye-tracking data of the patient based on the captured images of the at least one eye of the patient.

7. The system of claim 1, further comprising at least one recording device assembled on the portable eye-tracker console and configured to collect at least one of image data, audio data, or video data associated with the patient while the predetermined sequence of stimulus videos is presented on the display screen oriented to the patient during the session, and
wherein the session data comprises the at least one of image data, audio data, or video data.

8. The system of claim 1, wherein the portable eye-tracker console comprises:
a housing configured to hold the display screen and the eye-tracker device, and
a base coupled to the housing through one or more joints, wherein the base is rotatable around the one or more joints to adjust a relative position or angle between the display screen and the patient during the session.

9. The system of claim 1, wherein the network-connected server provides the web portal accessible by the portable computing device, and
wherein the network-connected server is configured to output a developmental analysis report comprising developmental analysis data of the patient on a user interface of the web portal to the portable computing device.

10. The system of claim 1, wherein the network-connected server is configured to:
receive treatment data associated with the patient, the treatment data comprising at least one of previous developmental analysis data of the patient, previous treatment plans for the patient, or reference treatment data of other patients; and
generate a prescriptive treatment plan for the patient based on the treatment data associated with the patient and developmental analysis data of the patient using artificial intelligence.

11. A computer-implemented method, comprising:
obtaining, at a network-connected server, a treatment plan of developmental disorder for a patient, the treatment plan having individual time lengths for different treatment-specific skill areas during a period of time, the treatment plan having a specific treatment plan format, wherein the network-connected server is configured to process data associated with a default treatment plan format;
parsing, at the network-connected server, the treatment plan with the specific treatment plan format to determine treatment data for the patient, the treatment data being consistent with the default treatment plan format;
wirelessly receiving, at the network-connected server, eye-tracking session data of the patient from a portable eye-tracker console;
generating, at the network-connected server, evaluation data of developmental disorder for the patient based on the eye-tracking session data of the patient; and
generating, at the network-connected server, a new treatment plan based on the treatment data for the patient and the evaluation data of developmental disorder for the patient.

12. The computer-implemented method of claim 11, further comprising:
receiving, at the network-connected server, an input for selecting a treatment plan format from a plurality of treatment plan formats presented on a user interface, wherein the plurality of treatment plan formats are different from each other,
wherein parsing the treatment plan with the specific treatment plan format comprises:
parsing the treatment plan with the specific treatment plan format based on the selected treatment plan format and the default treatment plan format.

13. The computer-implemented method of claim 12, wherein the plurality of treatment plan formats are different from each other in at least one of skill area names, prompting approaches, treatment or training materials, reinforcement approaches, or data collection approaches.

14. The computer-implemented method of claim 11, wherein the treatment data comprises at least one of
respective time lengths of the different treatment-specific skill areas during the period of time,
respective percentages of time lengths of the different treatment-specific skill areas during the period of time,
respective attendance percentages of the different treatment-specific skill areas over a series of sessions,
respective attendance percentage changes of the different treatment-specific skill areas between at least two most recent sessions, or
relationships between the respective percentages of time lengths and the respective attendance percentage changes of the different treatment-specific skill areas.

15. The computer-implemented method of claim 11, further comprising:
receiving, at the network-connected server, an input for selecting a treatment plan format from a plurality of treatment plan formats presented on a user interface, wherein the plurality of treatment plan formats are different from each other;
generating, at the network-connected server, the new treatment plan based on the treatment data for the patient and the selected treatment plan format; and
transmitting, by the network-connected server, the new treatment plan with the selected treatment plan format to a computing device or an external server.

16. The computer-implemented method of claim 15, further comprising:
determining, at the network-connected server, a particular treatment plan format for the new treatment plan for the patient among the plurality of treatment plan formats; and
presenting a visual indication on the particular treatment plan format among the plurality of treatment plan formats in the user interface, the visual indication indicating a recommendation of the particular treatment plan format for the new treatment plan for the patient.

17. The computer-implemented method of claim 11, further comprising:
receiving, at the network-connected server, a selection of a targeted session from a list of sessions on a user interface of a web portal on the network-connected server;
in response to receiving the selection of the targeted session, popping up a window for selecting targeted skill areas from a plurality of skill areas listed in the window;
automatically selecting one or more targeted skill areas from the plurality of skill areas based on the treatment data, wherein the different treatment-specific skill areas comprise the one or more targeted skill areas; and
running the targeted session based on the selected one or more targeted skill areas.

18. The computer-implemented method of claim 11, further comprising:
presenting, at the network-connected server, input fields of the treatment plan on a user interface of a web portal on the network-connected server;
receiving, at the network-connected server, an input for one of the input fields of the treatment plan on the user interface; and
updating, at the network-connected server, the treatment plan based on the input for the one of the input fields.

19. The computer-implemented method of claim 11, further comprising:
receiving, at the network-connected server, an input for selecting a third party system from a plurality of third party systems presented on a user interface;
retrieving, by the network-connected server, data relevant to the patient from the selected third party system after establishing a connection between the network-connected server and the selected third party system, wherein the data relevant to the patient comprises at least one of previous clinical data of the patient, previous treatment data of the patient, or reference data of other patients; and
generating, at the network-connected server, the new treatment plan for the patient based on the treatment data and the data relevant to the patient.

20. An apparatus, comprising:
one or more processors; and
one or more memories storing instructions for execution by the one or more processors to perform operations comprising:
obtaining a treatment plan of developmental disorder for a patient, the treatment plan having individual time lengths for different treatment-specific skill areas during a period of time, the treatment plan having a specific treatment plan format, wherein the one or more processors are configured to process data associated with a default treatment plan format;
parsing the treatment plan with the specific treatment plan format to determine treatment data for the patient, the treatment data being consistent with the default treatment plan format;
wirelessly receiving eye-tracking session data of the patient from a portable eye-tracker console;
generating evaluation data of developmental disorder for the patient based on the eye-tracking session data of the patient; and
generating a new treatment plan based on the treatment data for the patient and the evaluation data of developmental disorder for the patient.

* * * * *